United States Patent
Chari et al.

(10) Patent No.: US 11,229,639 B2
(45) Date of Patent: Jan. 25, 2022

(54) CAMPTOTHECIN DERIVATIVES

(71) Applicant: IMMUNOGEN, INC., Waltham, MA (US)

(72) Inventors: Ravi V. J. Chari, Newton, MA (US); Wayne C. Widdison, Belmont, MA (US); Wei Li, Acton, MA (US); David P. Pleynet, Newton, MA (US)

(73) Assignee: IMMUNOGEN, INC., Waltham, MA (US)

(*) Notice: Subject to any disclaimer, the term of this patent is extended or adjusted under 35 U.S.C. 154(b) by 0 days.

(21) Appl. No.: 17/032,219

(22) Filed: Sep. 25, 2020

(65) Prior Publication Data

US 2021/0077482 A1 Mar. 18, 2021

Related U.S. Application Data

(63) Continuation of application No. PCT/US2020/027831, filed on Apr. 10, 2020.

(60) Provisional application No. 62/978,159, filed on Feb. 18, 2020, provisional application No. 62/875,169, filed on Jul. 17, 2019, provisional application No. 62/839,440, filed on Apr. 26, 2019.

(51) Int. Cl.

| | |
|---|---|
| *A61K 31/4745* | (2006.01) |
| *A61K 47/68* | (2017.01) |
| *A61P 35/00* | (2006.01) |
| *A61K 39/395* | (2006.01) |
| *C07D 491/22* | (2006.01) |

(52) U.S. Cl.
CPC ...... *A61K 31/4745* (2013.01); *A61K 39/3955* (2013.01); *A61K 47/6803* (2017.08); *A61P 35/00* (2018.01); *C07D 491/22* (2013.01)

(58) Field of Classification Search
CPC ........ A61K 47/06; A61K 47/22; A61K 47/50; A61K 47/545; A61K 47/68; A61K 47/6817; A61K 47/6803; A61K 47/6819; A61K 47/6835; A61K 47/6889; A61K 47/65
See application file for complete search history.

(56) References Cited

U.S. PATENT DOCUMENTS

| 5,559,235 A | 9/1996 | Luzzio et al. |
| 2004/0266803 A1 | 12/2004 | Wani et al. |
| 2006/0193865 A1 | 8/2006 | Govindan |

FOREIGN PATENT DOCUMENTS

| DE | 19640207 A1 | 4/1998 |
| EP | 0325247 A1 | 7/1989 |
| EP | 3088419 A1 | 11/2016 |
| WO | 200149291 A1 | 7/2001 |
| WO | 2019195665 A1 | 10/2019 |

OTHER PUBLICATIONS

Nakada etal (Bioorganic & Medicinal Chemistry, 2016, vol. 26, pp. 1542-1545) (Year: 2016).*
Venditto and Simanek (Molecular Pharmaceutics, 2010, vol. 7, p. 307-349) (Year: 2010).*
Lau et al (Molecular Pharmaceutics, 2018 vol. 15, pp. 4063-4072) (Year: 2018).*
Singh etal, Pharmaceutical Research, 2015, vol. 32, pp. 3541-3571 (Year: 2015).*
The abstract of Chemuturi etal (Proceedings of the AACR, Apr. 2017, abstract 4075) (Year: 2017).*
Hansch et al., 20-(S)-camptothecin analogues as DNA topoisomerase I inhibitors: a QSAR study ChemMedChem. Dec. 2007;2(12):1807-13.
Wani et al., Plant antitumor agents. 25. Total synthesis and antileukemic activity of ring A substituted camptothecin analogues. Structure-activity correlations. J Med Chem. Oct. 1987;30(10):1774-9.
International Search Report for Application No. PCT/US2020/027831, dated Jun. 15, 2020, 21 pages.
Cochran et al., Characterization of Payload Release From an Improved Camptothecin Drug-Linker. Abstract No. 2895 AACR Virtual Annual Meeting II. Jun. 22-24. 1 page.
Li et al., Synthesis and Evaluation of Camptothecin Antibody-Drug Conjugates. ACS Med Chem Lett. Sep. 6, 2019;10(10):1386-1392.
Lyski et al., Discovery of a tripeptide-based camptothecin drug-linker for antibody-drug conjugates with potent antitumor activity and a broad therapeutic window. Abstract No. 2885/2. AACR Virtual Annual Meeting II. Jun. 22-24, 2020. 1 page.
Ryan et al., SGN-CD30C, a new CD30-directed camptothecin antibody-drug conjugate (ADC), shows strong anti-tumor activity and superior tolerability in preclinical studies. Abstract No. 2889, AACR Virtual Annual Meeting II. Jun. 22-24, 2020. 1 page.

* cited by examiner

*Primary Examiner* — Karen A. Canella
(74) *Attorney, Agent, or Firm* — McCarter & English, LLP; Xin Zhang

(57) ABSTRACT

Disclosed herein are novel cytotoxic compounds, and cytotoxic conjugates comprising these cytotoxic compounds and cell-binding agents. More specifically, this disclosure relates to novel camptothecin derivatives thereof, intermediates thereof, conjugates thereof, and pharmaceutically acceptable salts thereof, which are useful as medicaments, in particular as anti-proliferative agents (anticancer agents).

7 Claims, 16 Drawing Sheets

Specification includes a Sequence Listing.

SEQUENCE LISTING

<160> NUMBER OF SEQ ID NOS: 114

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 1

Arg Ala Ser Gln Asp Ile Asn Ser Tyr Leu Ser
1               5                   10

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 2

Arg Val Asn Arg Leu Val Asp

```
1               5

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Leu Gln Tyr Asp Ala Phe Pro Tyr Thr
1               5

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Ser Ile Met His
1               5

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Tyr Ile Lys Pro Tyr Asn Asp Gly Thr Lys Tyr Asn Glu Lys Phe Lys
1               5                   10                  15

Gly

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Glu Gly Gly Asn Asp Tyr Tyr Asp Thr Met Asp Tyr
1               5                   10

<210> SEQ ID NO 7
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120

<210> SEQ ID NO 8
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
```

```
                       245                 250                 255
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Cys Leu Ser
        435                 440                 445

Pro Gly
    450

<210> SEQ ID NO 9
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg
            100                 105

<210> SEQ ID NO 10
<211> LENGTH: 214
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic polypeptide"

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Lys Ser Ser Gln Ser Val Phe Phe Ser Ser Gln Lys Asn Tyr Leu
1               5                   10                  15

Ala

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Trp Ala Ser Thr Arg Glu Ser

<210> SEQ ID NO 13
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

His Gln Tyr Leu Ser Ser Arg Thr
1               5

<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ser Tyr Tyr Ile His
1               5

<210> SEQ ID NO 15
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Val Ile Tyr Pro Gly Asn Asp Asp Ile Ser Tyr Asn Gln Lys Phe Gln
1               5                   10                  15

Gly

<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Glu Val Arg Leu Arg Tyr Phe Asp Val
1               5

<210> SEQ ID NO 17
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
            35                  40                  45

Gly Val Ile Tyr Pro Gly Asn Asp Asp Ile Ser Tyr Asn Gln Lys Phe
 50                  55                  60

Gln Gly Lys Ala Thr Leu Thr Ala Asp Lys Ser Ser Thr Thr Ala Tyr
65                   70                  75                  80

Met Gln Leu Ser Ser Leu Thr Ser Glu Asp Ser Ala Val Tyr Tyr Cys
            85                  90                  95

Ala Arg Glu Val Arg Leu Arg Tyr Phe Asp Val Trp Gly Gln Gly Thr
            100                 105                 110

Thr Val Thr Val Ser Ser
            115

<210> SEQ ID NO 18
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
            35                  40                  45

Gly Val Ile Tyr Pro Gly Asn Asp Asp Ile Ser Tyr Asn Gln Lys Phe
 50                  55                  60

Gln Gly Lys Ala Thr Leu Thr Ala Asp Lys Ser Ser Thr Thr Ala Tyr
65                   70                  75                  80

Met Gln Leu Ser Ser Leu Thr Ser Glu Asp Ser Ala Val Tyr Tyr Cys
            85                  90                  95

Ala Arg Glu Val Arg Leu Arg Tyr Phe Asp Val Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg

```
                    245                 250                 255

Thr Pro Glu Val Thr Cys Val Val Asp Val Ser His Glu Asp Pro
        260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 19
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg

<210> SEQ ID NO 20
<211> LENGTH: 219
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 20

```
Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 21
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

```
Lys Ala Ser Gln Ser Val Asp Tyr Ser Gly Asp Ser Tyr Met Asn
1               5                   10                  15
```

<210> SEQ ID NO 22
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

```
Ala Ala Ser Asp Leu Glu Ser
1               5
```

```
<210> SEQ ID NO 23
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gln Gln Ser His Glu Asp Pro Phe Thr
1               5

<210> SEQ ID NO 24
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ser Tyr Trp Met His
1               5

<210> SEQ ID NO 25
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Glu Ile Ile Pro Ile Phe Gly His Thr Asn Tyr Asn Glu Lys Phe Lys
1               5                   10                  15

Ser

<210> SEQ ID NO 26
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gly Gly Tyr Tyr Tyr Tyr Pro Arg Gln Gly Phe Leu Asp Tyr
1               5                   10

<210> SEQ ID NO 27
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30
```

Trp Met His Trp Val Arg Gln Ala Pro Gly Lys Gly Leu Glu Trp Val
            35                  40                  45

Gly Glu Ile Ile Pro Ile Phe Gly His Thr Asn Tyr Asn Glu Lys Phe
 50                  55                  60

Lys Ser Arg Phe Thr Ile Ser Leu Asp Asn Ser Lys Asn Thr Leu Tyr
 65                  70                  75                  80

Leu Gln Met Gly Ser Leu Arg Ala Glu Asp Thr Ala Val Tyr Tyr Cys
            85                  90                  95

Ala Arg Gly Gly Tyr Tyr Tyr Pro Arg Gln Gly Phe Leu Asp Tyr
            100                 105                 110

Trp Gly Gln Gly Thr Thr Val Thr Val Ser Ser
            115                 120

<210> SEQ ID NO 28
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Ile Val Met Thr Gln Ser Pro Asp Ser Leu Ala Val Ser Leu Gly
 1               5                  10                  15

Glu Arg Ala Thr Ile Ser Cys Lys Ala Ser Gln Ser Val Asp Tyr Ser
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Thr Tyr Tyr Cys Gln Gln Ser His
            85                  90                  95

Glu Asp Pro Phe Thr Phe Gly Gln Gly Thr Lys Leu Glu Ile Lys
            100                 105                 110

<210> SEQ ID NO 29
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
            35                  40                  45

Gly Glu Ile Ile Pro Ile Phe Gly His Thr Asn Tyr Asn Glu Lys Phe
 50                  55                  60

Lys Ser Arg Phe Thr Ile Ser Leu Asp Asn Ser Lys Asn Thr Leu Tyr
 65                  70                  75                  80

Leu Gln Met Gly Ser Leu Arg Ala Glu Asp Thr Ala Val Tyr Tyr Cys

```
                85                  90                  95
Ala Arg Gly Gly Tyr Tyr Tyr Pro Arg Gln Gly Phe Leu Asp Tyr
            100                 105                 110
Trp Gly Gln Gly Thr Thr Val Thr Val Ser Ser Ala Ser Thr Lys Gly
            115                 120                 125
Pro Ser Val Phe Pro Leu Ala Pro Ser Ser Lys Ser Thr Ser Gly Gly
            130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Arg Val Glu Pro Lys
                210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Tyr Ile Thr Arg Glu Pro Glu Val Thr Cys Val Val Val Asp Val
                260                 265                 270
Ser His Glu Asp Pro Glu Val Lys Phe Asn Trp Tyr Val Asp Gly Val
                275                 280                 285
Glu Val His Asn Ala Lys Thr Lys Pro Arg Glu Glu Gln Tyr Asn Ser
            290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Glu Glu Met Thr Lys Asn Gln
                355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Cys
                435                 440                 445
Leu Ser Pro Gly
        450

<210> SEQ ID NO 30
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 30

Asp Ile Val Met Thr Gln Ser Pro Asp Ser Leu Ala Val Ser Leu Gly
1               5                   10                  15

Glu Arg Ala Thr Ile Ser Cys Lys Ala Ser Gln Ser Val Asp Tyr Ser
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln Gln Ser His
                85                  90                  95

Glu Asp Pro Phe Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 31
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Lys Ala Ser Gln Ser Val Ser Phe Ala Gly Thr Ser Leu Met His
1               5                   10                  15

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Arg Ala Ser Asn Leu Glu Ala
1               5

<210> SEQ ID NO 33
<211> LENGTH: 9
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 33

Gln Gln Ser Arg Glu Tyr Pro Tyr Thr
1               5

<210> SEQ ID NO 34
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Tyr Phe Met Asn
1               5

<210> SEQ ID NO 35
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Arg Ile His Pro Tyr Asp Gly Asp Thr Phe Tyr Asn Gln Lys Phe Gln
1               5                   10                  15

Gly

<210> SEQ ID NO 36
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Tyr Asp Gly Ser Arg Ala Met Asp Tyr
1               5

<210> SEQ ID NO 37
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gly Tyr Thr Phe Thr Gly Tyr Phe Met Asn
1               5                   10

<210> SEQ ID NO 38
<211> LENGTH: 10
<212> TYPE: PRT
<213> ORGANISM: Artificial Sequence
<220> FEATURE:
<221> NAME/KEY: source
```

<223> OTHER INFORMATION: /note="Description of Artificial Sequence:
       Synthetic peptide"

<400> SEQUENCE: 38

Arg Ile His Pro Tyr Asp Gly Asp Thr Phe
1               5                   10

<210> SEQ ID NO 39
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 39

Gln Val Gln Leu Val Gln Ser Gly Ala Glu Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
                100                 105                 110

Thr Val Thr Val Ser Ser
            115

<210> SEQ ID NO 40
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 40

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
                100                 105                 110

<210> SEQ ID NO 41

```
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 42
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 43
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
```

```
                   100                 105                 110
Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 44
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 45
```

```
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg Ser Ser Arg Ser Leu Leu His Ser Asp Gly Phe Thr Tyr Leu Tyr
1               5                   10                  15

<210> SEQ ID NO 46
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gln Thr Ser Asn Leu Ala Ser
1               5

<210> SEQ ID NO 47
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ala Gln Asn Leu Glu Leu Pro Asn Thr
1               5

<210> SEQ ID NO 48
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Asn Tyr Tyr Ile His
1               5

<210> SEQ ID NO 49
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Trp Ile Tyr Pro Gly Asn Val Tyr Ile Gln Tyr Asn Glu Lys Phe Lys
1               5                   10                  15

Gly

<210> SEQ ID NO 50
<211> LENGTH: 7
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Asp Gly Pro Trp Phe Ala Tyr
1               5

<210> SEQ ID NO 51
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Asp Ile Val Leu Thr Gln Thr Pro Leu Ser Leu Ser Val Thr Pro Gly
1               5                   10                  15

Gln Pro Ala Ser Ile Ser Cys Arg Ser Ser Arg Ser Leu Leu His Ser
            20                  25                  30

Asp Gly Phe Thr Tyr Leu Tyr Trp Phe Leu Gln Lys Pro Gly Gln Ser
        35                  40                  45

Pro Gln Leu Leu Ile Tyr Gln Thr Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Asn Thr Phe Gly Gln Gly Thr Lys Leu Glu Ile Lys
            100                 105                 110

<210> SEQ ID NO 52
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Arg Leu Glu Tyr Ile
        35                  40                  45

Gly Trp Ile Tyr Pro Gly Asn Val Tyr Ile Gln Tyr Asn Glu Lys Phe
    50                  55                  60

Lys Gly Arg Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Pro Trp Phe Ala Tyr Trp Gly Gln Gly Thr Leu Val
            100                 105                 110

Thr Val Ser Ser
            115

<210> SEQ ID NO 53
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Asp Ile Val Leu Thr Gln Thr Pro Leu Ser Leu Ser Val Thr Pro Gly
1               5                   10                  15

Gln Pro Ala Ser Ile Ser Cys Arg Ser Ser Arg Ser Leu Leu His Ser
            20                  25                  30

Asp Gly Phe Thr Tyr Leu Tyr Trp Phe Leu Gln Lys Pro Gly Gln Ser
        35                  40                  45

Pro Gln Leu Leu Ile Tyr Gln Thr Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Asn Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 54
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Arg Leu Glu Tyr Ile
        35                  40                  45

Gly Trp Ile Tyr Pro Gly Asn Val Tyr Ile Gln Tyr Asn Glu Lys Phe
    50                  55                  60

```
Lys Gly Arg Ala Thr Leu Thr Ala Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Pro Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Cys Leu Ser Pro Gly
        435                 440                 445

<210> SEQ ID NO 55
<211> LENGTH: 7
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 55

Asp Gly Pro Trp Phe Ala Tyr
1               5

<210> SEQ ID NO 56
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Trp Ile Tyr Pro Gly Asn Val Tyr Ile Gln Tyr Ser Gln Lys Phe Gln
1               5                   10                  15

Gly

<210> SEQ ID NO 57
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ser Tyr Tyr Ile His
1               5

<210> SEQ ID NO 58
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Asn Tyr Asn Ile His
1               5

<210> SEQ ID NO 59
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Trp Ile Tyr Pro Gly Asp Val Tyr Ile Gln Tyr Asn Glu Lys Phe Lys
1               5                   10                  15

Gly

<210> SEQ ID NO 60
<211> LENGTH: 5
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 60

Asn Tyr Phe Ile His
1               5

<210> SEQ ID NO 61
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Asn Tyr Ser Ile His
1               5

<210> SEQ ID NO 62
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Asn Tyr Trp Ile His
1               5

<210> SEQ ID NO 63
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Trp Phe Tyr Pro Gly Asn Val Tyr Ile Gln Tyr Asn Glu Lys Phe Lys
1               5                   10                  15

Gly

<210> SEQ ID NO 64
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Trp Ile Asn Pro Gly Asn Val Tyr Ile Gln Tyr Asn Glu Lys Phe Lys
1               5                   10                  15

Gly

<210> SEQ ID NO 65
<211> LENGTH: 7
<212> TYPE: PRT
<213> ORGANISM: Artificial Sequence
<220> FEATURE:
<221> NAME/KEY: source
```

```
-continued

<223> OTHER INFORMATION: /note="Description of Artificial Sequence:
      Synthetic peptide"

<400> SEQUENCE: 65

Glu Gly Pro Trp Phe Ala Tyr
1               5

<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Asp Gly Pro Tyr Phe Ala Tyr
1               5

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Asp Gly Ala Trp Phe Ala Tyr
1               5

<210> SEQ ID NO 68
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Asn Tyr Tyr Met His
1               5

<210> SEQ ID NO 69
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Asn Tyr His Ile His
1               5

<210> SEQ ID NO 70
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70
```

-continued

```
Asn Tyr Asp Ile His
1               5

<210> SEQ ID NO 71
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Asp Gly Tyr Trp Phe Ala Tyr
1               5

<210> SEQ ID NO 72
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Asp Gly Ser Trp Phe Ala Tyr
1               5

<210> SEQ ID NO 73
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Asp Gly Phe Trp Phe Ala Tyr
1               5

<210> SEQ ID NO 74
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Asp Gly Gly Trp Phe Ala Tyr
1               5

<210> SEQ ID NO 75
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Asp Gly Thr Trp Phe Ala Tyr
1               5
```

<210> SEQ ID NO 76
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Asp Gly Val Trp Phe Ala Tyr
1               5

<210> SEQ ID NO 77
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Asn Tyr Ile Ile His
1               5

<210> SEQ ID NO 78
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Arg Ser Ser Lys Ser Leu Leu His Ser Asp Gly Phe Thr Tyr Leu Tyr
1               5                   10                  15

<210> SEQ ID NO 79
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Arg Ser Ser Arg Ser Leu Leu His Ser Asn Gly Phe Thr Tyr Leu Tyr
1               5                   10                  15

<210> SEQ ID NO 80
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Arg Ser Ser Arg Ser Leu Leu His Ser Asp Gly Ile Thr Tyr Leu Tyr
1               5                   10                  15

<210> SEQ ID NO 81
<211> LENGTH: 9
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Ala Gln Asn Leu Glu Leu Pro Trp Thr
1               5

<210> SEQ ID NO 82
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Arg Ser Ser Arg Ser Leu Leu His Ser Asp Gly Phe Thr Tyr Leu Ser
1               5                   10                  15

<210> SEQ ID NO 83
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Gln Gln Asn Leu Glu Leu Pro Asn Thr
1               5

<210> SEQ ID NO 84
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Leu Gln Asn Leu Glu Leu Pro Asn Thr
1               5

<210> SEQ ID NO 85
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Ala Gln Tyr Leu Glu Leu Pro Asn Thr
1               5

<210> SEQ ID NO 86
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 86

Ala Gln Gly Leu Glu Leu Pro Asn Thr
1               5

<210> SEQ ID NO 87
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Ala Gln Ser Leu Glu Leu Pro Asn Thr
1               5

<210> SEQ ID NO 88
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Asn Tyr Leu Ile His
1               5

<210> SEQ ID NO 89
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Ala Leu Ala Leu
1

<210> SEQ ID NO 90
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Leu Ala Leu Ala
1

<210> SEQ ID NO 91
<211> LENGTH: 4
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: Xaa
<222> LOCATION: (1)..(1)
<223> OT HER INFORMATION: beta-Ala

<400> SEQUENCE: 91

Xaa Leu Ala Leu
1

<210> SEQ ID NO 92
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Gly Phe Leu Gly
1

<210> SEQ ID NO 93
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gly Leu Phe Gly
1

<210> SEQ ID NO 94
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Ala Ala Ala Ala
1

<210> SEQ ID NO 95
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Gly Ala Gly Gly
1

<210> SEQ ID NO 96
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Gly Ala Gly
1

<210> SEQ ID NO 97
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gly Val Gly Gly
1

<210> SEQ ID NO 98
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gly Gly Val Gly
1

<210> SEQ ID NO 99
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Gly Phe Gly Gly
1

<210> SEQ ID NO 100
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Gly Gly Phe Gly
1

<210> SEQ ID NO 101
<211> LENGTH: 4
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: Xaa
<222> LOCATION: (2)..(2)
<223> OTHER INFORMATION: D-Ala

<400> SEQUENCE: 101

Ala Xaa Ala Ala

```
<210> SEQ ID NO 102
<211> LENGTH: 4
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: Xaa
<222> LOCATION: (3)..(3)
<223> OTHER INFORMATION: D-Ala

<400> SEQUENCE: 102

Ala Ala Xaa Ala
1

<210> SEQ ID NO 103
<211> LENGTH: 4
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: Xaa
<222> LOCATION: (4)..(4)
<223> OTHER INFORMATION: D-Ala

<400> SEQUENCE: 103

Ala Ala Ala Xaa
1

<210> SEQ ID NO 104
<211> LENGTH: 4
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: Xaa
<222> LOCATION: (2)..(2)
<223> OTHER INFORMATION: D-Ala

<400> SEQUENCE: 104

Gly Xaa Gly Gly
1

<210> SEQ ID NO 105
<211> LENGTH: 4
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: Xaa
<222> LOCATION: (3)..(3)
<223> OTHER INFORMATION: D-Ala

<400> SEQUENCE: 105

Gly Gly Xaa Gly
1

<210> SEQ ID NO 106
<211> LENGTH: 4
<212> TYPE: PRT
<213> ORGANISM: Artificial Sequence
```

```
<220> FEATURE:
<223> OTHER INFORMATION: /note="Description of Artificial Sequence:
      Synthetic peptide"
<220> FEATURE:
<221> NAME/KEY: Xaa
<222> LOCATION: (2)..(2)
<223> OTHER INFORMATION: D-Val

<400> SEQUENCE: 106

Gly Xaa Gly Gly
1

<210> SEQ ID NO 107
<211> LENGTH: 4
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: Xaa
<222> LOCATION: (3)..(3)
<223> OTHER INFORMATION: D-Val

<400> SEQUENCE: 107

Gly Gly Xaa Gly
1

<210> SEQ ID NO 108
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Gly Gly Ser Gly
1

<210> SEQ ID NO 109
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Gly Gly Ser Gly Gly
1               5

<210> SEQ ID NO 110
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Gly Ser Gly Ser Gly
1               5

<210> SEQ ID NO 111
<211> LENGTH: 5
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Gly Ser Gly Gly Gly
1               5

<210> SEQ ID NO 112
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Gly Gly Gly Ser Gly
1               5

<210> SEQ ID NO 113
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Gly Ser Ser Ser Gly
1               5

<210> SEQ ID NO 114
<211> LENGTH: 4
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: Xaa
<222> LOCATION: (2)..(2)
<223> OTHER INFORMATION: D-Ala

<400> SEQUENCE: 114

Ala Xaa Ala Gly
1
```

CAMPTOTHECIN DERIVATIVES

This application is a continuation application of International Application No. PCT/US2020/027831, filed Apr. 10, 2020, which claims the benefit of and priority from U.S. Provisional Patent Applications 62/839,440, filed Apr. 26, 2019, 62/875,169, filed Jul. 17, 2019, and 62/978,159, filed Feb. 18, 2020. The entire content of each of the foregoing applications is incorporated by reference herein in its entirety.

SEQUENCE LISTING

The instant application contains a Sequence Listing which has been submitted electronically in ASCII format and is hereby incorporated by reference in its entirety. Said ASCII copy, created on Mar. 27, 2020, is named 000219-0002-WO1_-_Sequence_Listing.txt and is 61,926 bytes in size. A corrected Sequence Listing, named 121162-05504_ST25, is submitted herewith electronically in ASCII format and is hereby incorporated by reference in its entirety.

FIELD OF THE APPLICATION

Disclosed herein are novel compounds, and conjugates thereof. More specifically, this disclosure relates to novel camptothecin derivatives, intermediates, metabolites and conjugates thereof, and pharmaceutically acceptable salts thereof, which are useful as medicaments, in particular as anti-proliferative agents (anticancer agents).

BACKGROUND

Cell binding agent-drug conjugates, including antibody-drug conjugates (ADC) are emerging as a powerful class of agents with efficacy across a range of abnormal cell growth or proliferative diseases (e.g., cancers). Cell binding agent-drug conjugates (such as ADCs) are commonly composed of three distinct elements: a cell-binding agent (e.g., an antibody); a linker; and a cytotoxic moiety.

Camptothecin (CPT) is a pentacyclic alkaloid isolated from the bark and stem of *Camptotheca acuminata* (*Camptotheca*, Happy tree), a tree native to China. Camptothecin inhibits topoisomerase I, which leads to cell death. Because of its cytotoxic mechanism and broad-spectrum antitumor activity, there have been substantial efforts towards developing clinical analogues of camptothecin. Poor solubility and inactivity at physiological conditions,
however, have limited the clinical development of suitable camptothecin analogues. Camptothecin and most of its derivatives are not soluble in aqueous buffers. Further, camptothecin is in equilibrium in an active lactone form and inactive hydrolyzed carboxylate form, thereby limiting its therapeutic efficacy.

There exists a need for therapeutically effective camptothecin derivatives that have increased solubility, potency, lactone stability, and bioavailability.

SUMMARY

In one aspect, the invention provides a compound of Formula I, or a pharmaceutically acceptable salt, thereof:

$$Z\text{-}L^1\text{-}D \qquad \text{(Formula I)}$$

wherein:
D is represented by the following structural formula:

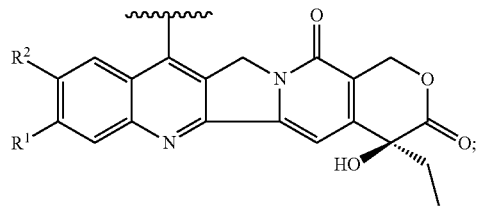

$R^1$ is —F, —CH$_3$, or —CF$_3$;
$R^2$ is —H, —F, —OR$^3$, —SR$^3$, —S(O)R$^4$, —S(O)$_2$R$^4$, C$_1$-C$_6$ alkyl, or C$_1$-C$_6$ fluoroalkyl; or $R^1$ and $R^2$ taken together with the carbon atoms to which they are attached form a methylenedioxy or a difluoromethylenedioxy ring;
$R^3$ is H or C$_1$-C$_6$ alkyl;
$R^4$ is C$_1$-C$_6$ alkyl;
$L^1$ is absent, —(C$_1$-C$_6$ alkylene)-, —(C$_1$-C$_6$ alkylene)-X$^1$—(C$_1$-C$_6$ alkylene)-, —X$^{1'}$—(C$_1$-C$_6$ alkylene)-*, or —(C$_1$-C$_6$ alkylene)-X$^1$-L$^2$-*; where * is the site covalently attached to Z;
$X^1$ is —O—, —S—, —S(O)—, —S(O)$_2$—, —C(=O)—, —NR$^5$—, —NR$^5$C(=O)—, or —C(=O)NR$^5$—;
$X^{1'}$ is —O—, —S—, —S(O)—, or —S(O)$_2$—;
$L^2$ is phenylene;
each $R^5$ is independently —H, C$_1$-C$_6$ alkyl, C$_1$-C$_6$ fluoroalkyl, C$_3$-C$_6$ cycloalkyl, aryl, heteroaryl, or benzyl;
Z is —H or —X$^2$;
$X^2$ is —OR$^6$, —SR$^6$, —S(O)R$^6$, —S(O)$_2$R$^6$, —SSR$^6$, or —N(R$^6$)$_2$;
each $R^6$ is independently —H, C$_1$-C$_6$ alkyl, C$_1$-C$_6$ fluoroalkyl, C$_3$-C$_6$ cycloalkyl, aryl, heteroaryl, or benzyl;
$L^1$ and $L^2$ are each independently optionally substituted with 1-4 substituents selected from halogen, —CN, —OR$^7$, —SR$^7$, —N(R$^7$)$_2$, C$_1$-C$_6$ alkyl, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, or heteroaryl; and
each $R^7$ is independently H, C$_1$-C$_6$ alkyl, C$_1$-C$_6$ fluoroalkyl, C$_3$-C$_6$ cycloalkyl, aryl, heteroaryl, or benzyl;
with the proviso that if $R^1$ is F, then $L^1$ is —(C$_1$-C$_6$ alkylene)-, —(C$_1$-C$_6$ alkylene)-X$^1$—(C$_1$-C$_6$ alkylene)-, —X$^{1'}$—(C$_1$-C$_6$ alkylene)-*, or —(C$_1$-C$_6$ alkylene)-X$^1$-L$^2$-*; where * is the site covalently attached to Z; and Z is —X$^2$; and
with the proviso that if $R^1$ is F and $R^2$ is —OMe, then -L$^1$-Z cannot be —NH$_2$.
In some embodiments, the compound of Formula I has the further proviso that if $R^1$ is F and $R^2$ is -Me, then -L$_1$-Z cannot be —CH$_2$OH.
In some embodiments, $R^1$ is —H or —F. In some embodiments, $R^1$ is —F. In some embodiments, $R^2$ is —H, —F, —OCF$_3$, —CF$_3$, —OMe, —OEt, —SMe, —S(O)Me, —S(O)$_2$Me, —SEt, —S(O)Et, —S(O$_2$)Et, methyl, or ethyl. In some embodiments, $R^2$ is —F. In some embodiments, $R^2$ is —OMe, —SMe, —S(O)Me, or methyl. In some embodiments, $R^2$ is methyl. In some embodiments, $R^1$ is —F and $R^2$ is —F. In some embodiments, $R^1$ is methyl and $R^2$ is —F. In some embodiments, $R^1$ is —F and $R^2$ is -methyl.
In some embodiments, -L$^1$-Z is —H. In some embodiments, -L$^1$-Z is —(C$_1$-C$_6$ alkylene)-H, or —(C$_1$-C$_6$ alkylene)-X$^2$. In some embodiments, -L$^1$-Z is —(C$_1$-C$_6$ alkylene)-H. In some embodiments, -L$^1$-Z is —(C$_1$-C$_6$ alkylene)-X$^2$. In some embodiments, -L$^1$-Z is —(C$_1$-C$_6$ alkylene)-X$^2$. In some embodiments, -L$^1$-Z is methyl, ethyl, propyl, or butyl.

In some embodiments, -L$^1$-Z is —(C$_1$-C$_4$ alkylene)-OR$^6$, —(C$_1$-C$_4$ alkylene)-SR$^6$, or —(C$_1$-C$_4$ alkylene)-N(R$^6$)$_2$. In some embodiments, -L$^1$-Z is —(C$_1$-C$_4$ alkylene)-OR$^6$. In some embodiments, -L$^1$-Z is —(C$_1$-C$_4$ alkylene)-SR$^6$. In some embodiments, -L$^1$-Z is —(C$_1$-C$_4$ alkylene)-N(R$^6$)$_2$.

In some embodiments, -L$^1$-Z is —CH$_2$OH, —(CH$_2$)$_2$OH, —(CH$_2$)$_3$OH, —(CH$_2$)$_4$OH, —CH$_2$OMe, —(CH$_2$)$_2$OMe, —(CH$_2$)$_3$OMe, —(CH$_2$)$_4$OMe, —CH$_2$SH, —(CH$_2$)$_2$SH, —(CH$_2$)$_3$SH, —(CH$_2$)$_4$SH, —CH$_2$SMe, —(CH$_2$)$_2$SMe, —(CH$_2$)$_3$SMe, —(CH$_2$)$_4$SMe, —CH$_2$NH$_2$, —(CH$_2$)$_2$NH$_2$, —(CH$_2$)$_3$NH$_2$, or —(CH$_2$)$_4$NH$_2$.

In some embodiments, -L$^1$-Z is —(C$_1$-C$_5$ alkylene)-NR$^5$C(=O)—(C$_1$-C$_5$ alkylene)-OR$^6$, —(C$_1$-C$_5$ alkylene)-NR$^5$C(=O)—(C$_1$-C$_5$ alkylene)-SR$^6$, —(C$_1$-C$_5$ alkylene)-S—(C$_1$-C$_5$ alkylene)-SR$^6$, or —(C$_1$-C$_5$ alkylene)-S—(C$_1$-C$_5$ alkylene)-SSR$^6$. In some embodiments, -L$^1$-Z is —(C$_1$-C$_5$ alkylene)-NR$^5$C(=O)—(C$_1$-C$_5$ alkylene)-OR$^6$. In some embodiments, -L$^1$-Z is —(C$_1$-C$_5$ alkylene)-NR$^5$C(=O)—(C$_1$-C$_5$ alkylene)-SR$^6$. In some embodiments, -L$^1$-Z is —(C$_1$-C$_5$ alkylene)-S—(C$_1$-C$_5$ alkylene)-SR$^6$. In some embodiments, -L$^1$-Z is —(C$_1$-C$_5$ alkylene)-S—(C$_1$-C$_5$ alkylene)-SSR$^6$.

In some embodiments, -L$^1$-Z is —CH$_2$NHC(=O)CH$_2$OH, —CH$_2$NHC(=O)(CH$_2$)$_2$OH, —CH$_2$NHC(=O)(CH$_2$)$_3$OH, —CH$_2$NHC(=O)(CH$_2$)$_4$OH, —CH$_2$NHC(=O)(CH$_2$)$_5$OH, —CH$_2$NHC(=O)CH$_2$OMe, —CH$_2$NHC(=O)(CH$_2$)$_2$OMe, —CH$_2$NHC(=O)(CH$_2$)$_3$OMe, —CH$_2$NHC(=O)(CH$_2$)$_4$OMe, —CH$_2$NHC(=O)(CH$_2$)$_5$OMe, —CH$_2$NHC(=O)CH$_2$SH, —CH$_2$NHC(=O)(CH$_2$)$_2$SH, —CH$_2$NHC(=O)(CH$_2$)$_3$SH, —CH$_2$NHC(=O)(CH$_2$)$_4$SH, —CH$_2$NHC(=O)(CH$_2$)$_5$SH, —CH$_2$NHC(=O)CH$_2$SMe, —CH$_2$NHC(=O)(CH$_2$)$_2$SMe, —CH$_2$NHC(=O)(CH$_2$)$_3$SMe, —CH$_2$NHC(=O)(CH$_2$)$_4$SMe, —CH$_2$NHC(=O)(CH$_2$)$_5$SMe, —CH$_2$SCH$_2$OH, —CH$_2$S(CH$_2$)$_2$OH, —CH$_2$S(CH$_2$)$_3$OH, —CH$_2$S(CH$_2$)$_4$OH, —CH$_2$S(CH$_2$)$_5$OH, —CH$_2$SCH$_2$OMe, —CH$_2$S(CH$_2$)$_2$OMe, —CH$_2$S(CH$_2$)$_3$OMe, —CH$_2$S(CH$_2$)$_4$OMe, —CH$_2$S(CH$_2$)$_5$OMe, —CH$_2$SCH$_2$SH, —CH$_2$S(CH$_2$)$_2$SH, —CH$_2$S(CH$_2$)$_3$SH, —CH$_2$S(CH$_2$)$_4$SH, —CH$_2$S(CH$_2$)$_5$SH, —CH$_2$SCH$_2$SMe, —CH$_2$S(CH$_2$)$_2$SMe, —CH$_2$S(CH$_2$)$_3$SMe, —CH$_2$S(CH$_2$)$_4$SMe, or —CH$_2$S(CH$_2$)$_5$SMe.

In some embodiments, each R$^5$ is independently —H, methyl, or benzyl. In some embodiments, each R$^5$ is independently —H. In some embodiments, each R$^5$ is methyl. In some embodiments, each R$^5$ is benzyl.

In some embodiments, each R$^6$ is independently —H, methyl, or benzyl. In some embodiments, each R$^6$ is independently —H. In some embodiments, each R$^6$ is methyl. In some embodiments, each R$^6$ is benzyl.

In some embodiments, -L$^1$-Z is —X$^{1'}$—(C$_1$-C$_4$ alkylene)-X$^2$. In some embodiments, -L$^1$-Z is —OCH$_2$OH, —O(CH$_2$)$_2$OH, —O(CH$_2$)$_3$OH, —O(CH$_2$)$_4$OH, —SCH$_2$OH, —S(CH$_2$)$_2$OH, —S(CH$_2$)$_3$OH, —S(CH$_2$)$_4$OH, —S(O)CH$_2$OH, —S(O)(CH$_2$)$_2$OH, —S(O)(CH$_2$)$_3$OH, —S(O)(CH$_2$)$_4$OH, —S(O)$_2$CH$_2$OH, —S(O)$_2$(CH$_2$)$_2$OH, —S(O)$_2$(CH$_2$)$_3$OH, —S(O)$_2$(CH$_2$)$_4$OH, —OCH$_2$SMe, —O(CH$_2$)$_2$SMe, —O(CH$_2$)$_3$SMe, —O(CH$_2$)$_4$SMe, —SCH$_2$SMe, —S(CH$_2$)$_2$SMe, —S(CH$_2$)$_3$SMe, —S(CH$_2$)$_4$SMe, —S(O)CH$_2$SMe, —S(O)(CH$_2$)$_2$SMe, —S(O)(CH$_2$)$_3$SMe, —S(O)(CH$_2$)$_4$SMe, —S(O)$_2$CH$_2$SMe, —S(O)$_2$(CH$_2$)$_2$SMe, —S(O)$_2$(CH$_2$)$_3$SMe, or —S(O)$_2$(CH$_2$)$_4$SMe.

In some embodiments, -L$^1$-Z is —(C$_1$-C$_6$ alkylene)-X$^1$-L$^1$-X$^2$. In some embodiments, -L$^1$-Z is

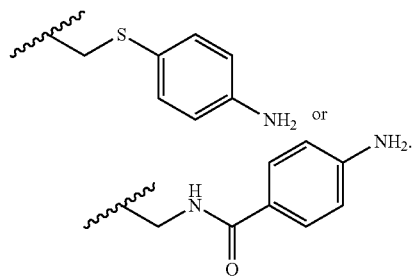

In some embodiments, -L$^1$-Z is

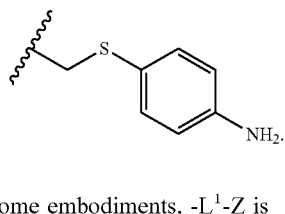

In some embodiments, -L$^1$-Z is

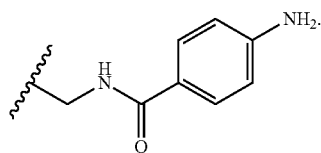 [SMILES: *CNC(=O)c1ccc(N)cc1]

In some embodiments, the compound is any one of the compounds selected from the following:

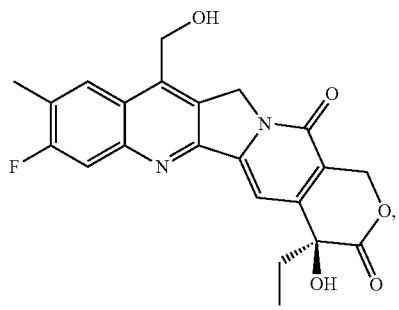

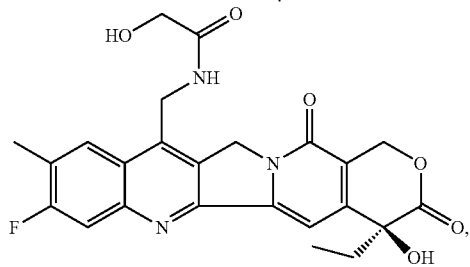

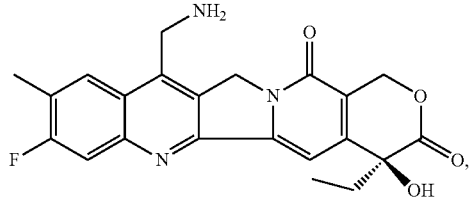

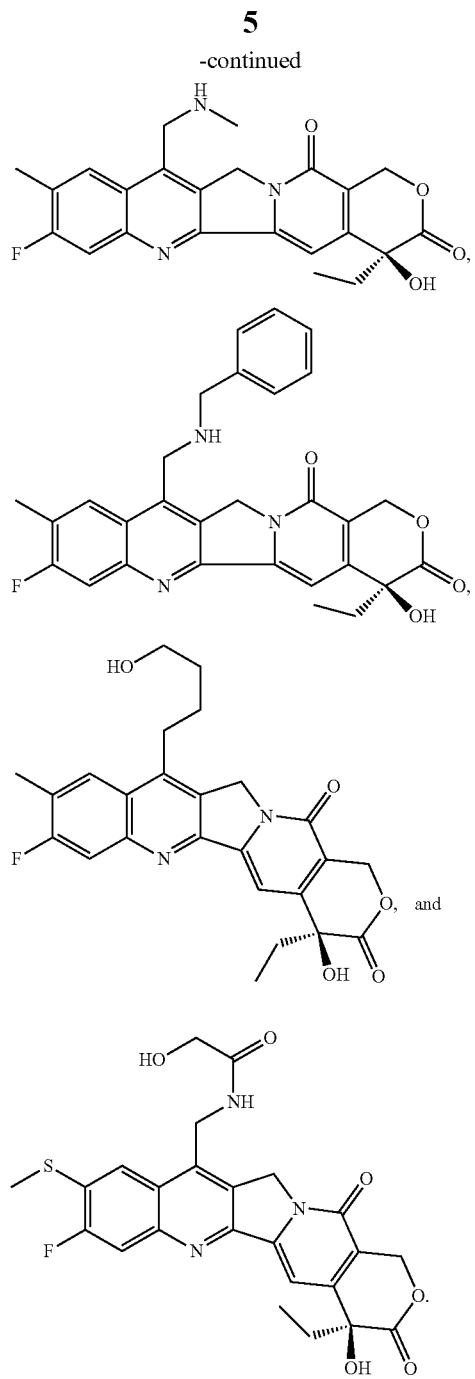
In some embodiments, the compound is any one of the compounds selected from the following:
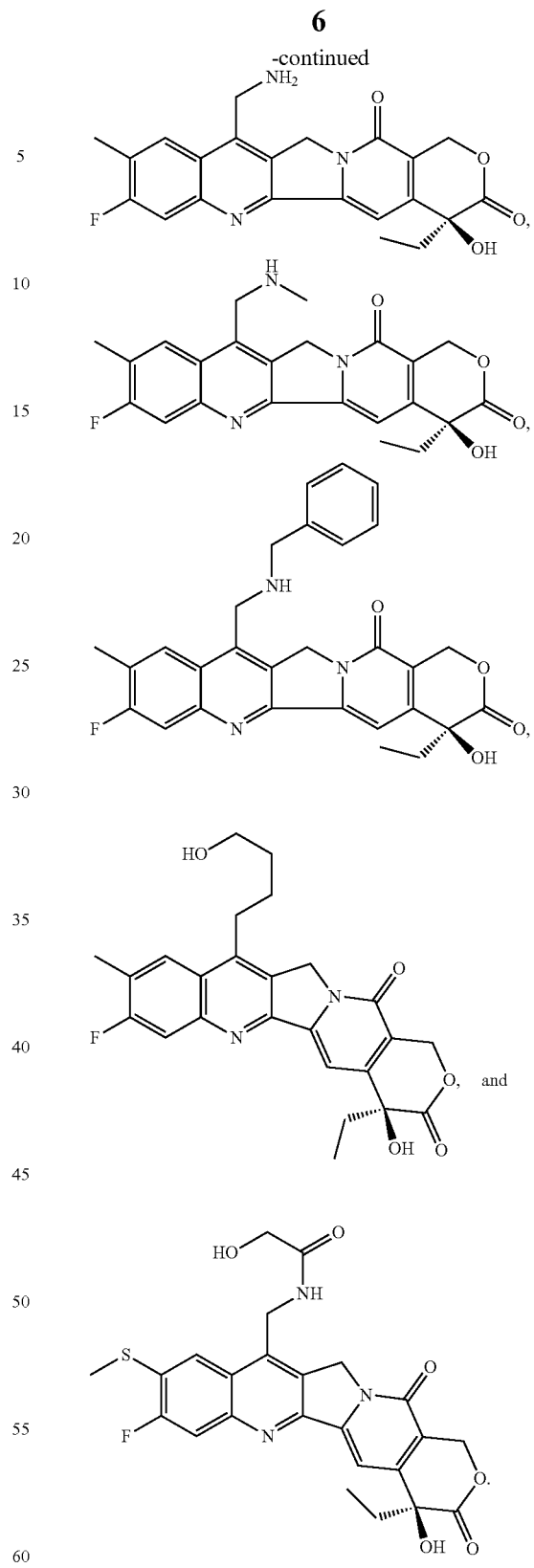
In some embodiments, the compound is any one of the compounds selected from Table 1B.
In another aspect, the invention provides a compound of Formula II, or a pharmaceutically acceptable salt thereof:
$$E\text{-}A\text{-}Z'\text{-}L^1\text{-}D \qquad \text{(Formula II)}$$
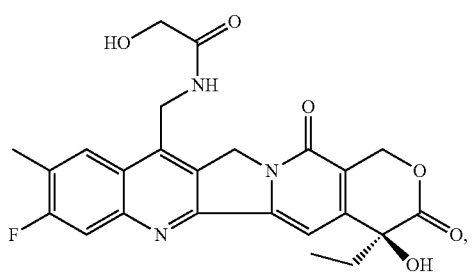

wherein:

D is represented by the following structural formula:

$R^1$ is —H, —F, —CH$_3$, or —CF$_3$;
$R^2$ is —H, —F, —OR$^3$, —SR$^3$, —S(O)R$^4$, —S(O)$_2$R$^4$, C$_1$-C$_6$ alkyl, or C$_1$-C$_6$ fluoroalkyl; or $R^1$ and $R^2$ taken together with the carbon atoms to which they are attached form a methylenedioxy or a difluoromethylenedioxy ring; with the proviso that both $R^1$ and $R^2$ cannot be —H;
$R^3$ is H or C$_1$-C$_6$ alkyl;
$R^4$ is C$_1$-C$_6$ alkyl;
$L^1$ is absent, —(C$_1$-C$_6$ alkylene)-, —(C$_1$-C$_6$ alkylene)-X$^1$—(C$_1$-C$_6$ alkylene)-, X$^{1'}$—(C$_1$-C$_6$ alkylene)-*, or —(C$_1$-C$_6$ alkylene)-X$^1$-L$^2$-*; where * is the site covalently attached to Z';
$X^1$ is —O—, —S—, —S(O)—, —S(O)$_2$—, —C(=O)—, —NR$^5$—, —NR$^5$C(=O)—, or —C(=O)NR$^5$—;
$X^{1'}$ is —O—, —S—, —S(O)—, or —S(O)$_2$—;
$L^2$ is phenylene;
each $R^5$ is independently —H, C$_1$-C$_6$ alkyl, C$_1$-C$_6$ fluoroalkyl, C$_3$-C$_6$ cycloalkyl, aryl, heteroaryl, or benzyl;
Z' is —O—CH$_2$—NR$^8$—*, —S—CH$_2$—NR$^8$—*, —NR$^8$—*; where * is the site covalently attached to A;
each $R^8$ is independently —H, C$_1$-C$_6$ alkyl, C$_1$-C$_6$ fluoroalkyl, C$_3$-C$_6$ cycloalkyl, aryl, heteroaryl, or benzyl;
$L^1$ and $L^2$ are each independently optionally substituted with 1-4 substituents selected from halogen, —CN, —OR$^7$, —SR$^7$, —N(R$^7$)$_2$, C$_1$-C$_6$ alkyl, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, or heteroaryl; and
each $R^7$ is independently H, C$_1$-C$_6$ alkyl, C$_1$-C$_6$ fluoroalkyl, C$_3$-C$_6$ cycloalkyl, aryl, heteroaryl, or benzyl;
A is a peptide comprising 2 to 10 amino acids; wherein A is optionally substituted with one or more polyol; and
E is —C(=O)-L$^3$-X$^3$;
$L^3$ is —(C$_1$-C$_{10}$ alkylene)- or —Y$^1$—(C$_1$-C$_{10}$ alkylene)-X$^4$—Y$^2$—(C$_1$-C$_{10}$ alkylene)-*; where * is the site covalently attached to X$^3$;
$Y^1$ is absent, —(CR$^a$R$^b$O)$_n$—, or —(CR$^a$R$^b$CR$^{a'}$R$^{b'}$O)$_m$—;
$X^4$ is —NR$^9$C(=O)— or —C(=O)NR$^9$—;
$Y^2$ is absent, —(CR$^c$R$^d$O)$_o$—, or —(CR$^c$R$^d$CR$^{c'}$R$^{d'}$O)$_p$—;
n, m, o, and p are each independently 1-10;
each $R^a$, $R^b$, $R^{a'}$, $R^{b'}$, $R^c$, $R^d$, $R^{c'}$, and $R^{d'}$ are independently —H, C$_1$-C$_6$ alkyl, C$_1$-C$_6$ fluoroalkyl, C$_3$-C$_6$ cycloalkyl, aryl, heteroaryl, or benzyl;
wherein $L^3$ is optionally substituted with 0-4 substituents selected from halogen, —CN, —OR$^{11}$, —SR$^{11}$, —N(R$^{u}$)$_2$, C$_1$-C$_6$ alkyl, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, heteroaryl, and polyol;
each $R^{11}$ is independently H, C$_1$-C$_6$ alkyl, C$_1$-C$_6$ fluoroalkyl, C$_3$-C$_6$ cycloalkyl, aryl, heteroaryl, or benzyl;

$X^3$ is

—C(=O)—CR$^{bb}$R$^{cc}$—W', —NR$^{ee}$—C(=O)—CR$^{bb}$R$^{cc}$—W', or —SR$^{10}$;
each W' is independently —H, —N(R$^{gg}$)$_2$, C$_1$-C$_{10}$ alkyl, C$_1$-C$_{10}$ alkenyl, C$_1$-C$_{10}$ alkynyl, C$_3$-C$_6$ cycloalkyl, aryl, heteroaryl, or —(CH2CH$_2$O)$_q$—R$^{ff}$;
q is 1 to 24;
each $R^{aa}$, $R^{bb}$, $R^{cc}$, $R^{ee}$, and $R^{ff}$ are independently —H or optionally substituted C$_1$-C$_6$ alkyl;
each $R^{YY}$ and $R^{XX}$ are independently —H or C$_1$-C$_6$ alkyl;
$R^{gg}$ are each independently —H or C$_1$-C$_6$ alkyl; and
$R^9$ and $R^{10}$ are each independently —H, C$_1$-C$_6$ alkyl, C$_1$-C$_6$ fluoroalkyl, C$_3$-C$_6$ cycloalkyl, aryl, heteroaryl, or benzyl.

In some embodiments, $R^1$ is —H or —F. In some embodiments, $R^1$ is —F. In some embodiments, $R^2$ is —H, —F, —OCF$_3$, —CF$_3$, —OMe, —OEt, —SMe, —S(O)Me, —S(O)$_2$Me, —SEt, —S(O)Et, —S(O)$_2$Et, methyl, or ethyl. In some embodiments, $R^2$ is —F. In some embodiments, $R^2$ is —OMe, —SMe, —S(O)Me, or methyl. In some embodiments, $R^2$ is methyl. In some embodiments, $R^1$ is —F and $R^2$ is —F. In some embodiments, $R^1$ is methyl and $R^2$ is —F. In some embodiments, $R^1$ is —F and $R^2$ is -methyl.

In some embodiments, -$L^1$-$Z'$—* is —($C_1$-$C_4$ alkylene)-O—$CH_2$—$NR^8$—*, —($C_1$-$C_4$ alkylene)-S—$CH_2$—$NR^8$—*, or —($C_1$-$C_4$ alkylene)-$NR^8$—*. In some embodiments, -$L^1$-$Z'$—* is —($C_1$-$C_4$ alkylene)-O—$CH_2$—$NR^8$—*. In some embodiments, -$L^1$-$Z'$—* is —($C_1$-$C_4$ alkylene)-S—$CH_2$—$NR^8$—*. In some embodiments, -$L^1$-$Z'$—* is —($C_1$-$C_4$ alkylene)-$NR^8$—*.

In some embodiments, -$L^1$-$Z'$—* is —$CH_2$O—$CH_2$NH—*, —$(CH_2)_2$O—$CH_2$NH—*, —$(CH_2)_3$O—$CH_2$NH—*, —$(CH_2)_4$O—$CH_2$NH—*, —$CH_2$S—$CH_2$NH—*, —$(CH_2)_2$S—$CH_2$NH—*, —$(CH_2)_3$S—$CH_2$NH—*, —$(CH_2)_4$S—$CH_2$NH—*, —$CH_2$NH—*, —$(CH_2)_2$NH—*, —$(CH_2)_3$NH—*, or —$(CH_2)_4$NH—*.

In some embodiments, -$L^1$-$Z'$—* is —($C_1$-$C_5$ alkylene)-$NR^5$C(=O)—($C_1$-$C_5$ alkylene)-O—$CH_2$—$NR^8$—*, —($C_1$-$C_5$ alkylene)-$NR^5$C(=O)—($C_1$-$C_5$ alkylene)-S—$CH_2$—$NR^8$—*, —($C_1$-$C_5$ alkylene)-S—($C_1$-$C_5$ alkylene)-S—$CH_2$—$NR^8$—*, or —($C_1$-$C_5$ alkylene)-S—($C_1$-$C_5$ alkylene)-SS—$CH_2$—$NR^8$—*. In some embodiments, -$L^1$-$Z'$—* is —($C_1$-$C_5$ alkylene)-$NR^5$C(=O)—($C_1$-$C_5$ alkylene)-O—$CH_2$—$NR^8$—*. In some embodiments, -$L^1$-$Z'$—* is —($C_1$-$C_5$ alkylene)-$NR^5$C(=O)—($C_1$-$C_5$ alkylene)-S—$CH_2$—$NR^8$—*. In some embodiments, -$L^1$-$Z'$—* is -($C_1$-$C_5$ alkylene)-S—($C_1$-$C_5$ alkylene)-S—$CH_2$—$NR^8$—*. In some embodiments, -$L^1$-$Z'$—* is —($C_1$-$C_5$ alkylene)-S—($C_1$-$C_5$ alkylene)-SS—$CH_2$—$NR^8$—*.

In some embodiments, -$L^1$-$Z'$—* is —$CH_2$NHC(=O)$CH_2$O—$CH_2$—NH—*, —$CH_2$NHC(=O)$(CH_2)_2$O—$CH_2$—NH—*, —$CH_2$NHC(=O)$(CH_2)_3$O—$CH_2$—NH—*, —$CH_2$NHC(=O)$(CH_2)_4$O—$CH_2$—NH—*, —$CH_2$NHC(=O)$(CH_2)_5$O—$CH_2$—NH—*, —$CH_2$NHC(=O)$CH_2$S—$CH_2$—NH—*, —$CH_2$NHC(=O)$(CH_2)_2$S—$CH_2$—NH—*, —$CH_2$NHC(=O)$(CH_2)_3$S—$CH_2$—NH—*, —$CH_2$NHC(=O)$(CH_2)_4$S—$CH_2$—NH—*, —$CH_2$NHC(=O)$(CH_2)_5$S—$CH_2$—NH—*, —$CH_2$S$CH_2$O—$CH_2$—NH—*, —$CH_2$S$(CH_2)_2$O—$CH_2$—NH—*, —$CH_2$S$(CH_2)_3$O—$CH_2$—NH—*, —$CH_2$S$(CH_2)_4$O—$CH_2$—NH—*, —$CH_2$S$(CH_2)_5$O—$CH_2$—NH—*, —$CH_2$S$CH_2$S—$CH_2$—NH—*, —$CH_2$S$(CH_2)_2$S—$CH_2$—NH—*, —$CH_2$S$(CH_2)_3$S—$CH_2$—NH—*, —$CH_2$S$(CH_2)_4$S—$CH_2$—NH—*, or —$CH_2$S$(CH_2)_5$S—$CH_2$—NH—*.

In some embodiments, each $R^5$ is independently —H, methyl, or benzyl. In some embodiments, each $R^5$ is independently —H. In some embodiments, each $R^5$ is methyl. In some embodiments, each $R^5$ is benzyl. In some embodiments, each $R^8$ is independently —H, methyl, or benzyl. In some embodiments, each $R^8$ is independently —H. In some embodiments, each $R^8$ is methyl. In some embodiments, each $R^8$ is benzyl.

In some embodiments, -$L^1$-$Z'$—* is —$X^{1'}$—($C_1$-$C_4$ alkylene)-O—$CH_2$—$NR^8$—*, —$X^{1'}$—($C_1$-$C_4$ alkylene)-S—$CH_2$—$NR^8$—*, or —$X^{1'}$—($C_1$-$C_4$ alkylene)-$NR^8$—*. In some embodiments, -$L^1$-$Z'$—* is —$X^1$—($C_1$-$C_4$ alkylene)-O—$CH_2$—$NR^8$—*. In some embodiments, -$L^1$-$Z'$—* is —$X^1$—($C_1$-$C_4$ alkylene)-S—$CH_2$—$NR^8$—*. In some embodiments, -$L^1$-$Z'$—* is —$X^1$—($C_1$-$C_4$ alkylene)-$NR^8$—*.

In some embodiments, -$L^1$-$Z'$—* is —O$CH_2$O—$CH_2$—NH—*, —O$(CH_2)_2$O—$CH_2$—NH—*, —O$(CH_2)_3$O—$CH_2$—NH—*, —O$(CH_2)_4$O—$CH_2$—NH—*, —S$CH_2$O—$CH_2$—NH—*, —S$(CH_2)_2$O—$CH_2$—NH—*, —S$(CH_2)_3$O—$CH_2$—NH—*, —S$(CH_2)_4$O—$CH_2$—NH—*, —S(O)$CH_2$O—$CH_2$—NH—*, —S(O)$(CH_2)_2$O—$CH_2$—NH—*, —S(O)$(CH_2)_3$O—$CH_2$—NH—*, —S(O)$(CH_2)_4$O—$CH_2$—NH—*, —S(O)$_2$$CH_2$O—$CH_2$—NH—*, —S(O)$_2$$(CH_2)_2$O—$CH_2$—NH—*, —S(O)$_2$$(CH_2)_3$O—$CH_2$—NH—*, —S(O)$_2$$(CH_2)_4$O—$CH_2$—NH—*, —O$CH_2$S—$CH_2$—NH—*, —O$(CH_2)_2$S—$CH_2$—NH—*, —O$(CH_2)_3$S—$CH_2$—NH—*, —O$(CH_2)_4$S—$CH_2$—NH—*, —S$CH_2$S—$CH_2$—NH—*, —S$(CH_2)_2$S—$CH_2$—NH—*, —S$(CH_2)_3$S—$CH_2$—NH—*, —S$(CH_2)_4$S—$CH_2$—NH—*, —S(O)$CH_2$S—$CH_2$—NH—*, —S(O)$(CH_2)_2$S—$CH_2$—NH—*, —S(O)$(CH_2)_3$S—$CH_2$—NH—*, —S(O)$(CH_2)_4$S—$CH_2$—NH—*, —S(O)$_2$$CH_2$S—$CH_2$—NH—*, —S(O)$_2$$(CH_2)_2$S—$CH_2$—NH—*, —S(O)$_2$$(CH_2)_3$S—$CH_2$—NH—*, —S(O)$_2$$(CH_2)_4$S—$CH_2$—NH—*, —O$CH_2$—NH—*, —O$(CH_2)_2$—NH—*, —O$(CH_2)_3$—NH—*, —O$(CH_2)_4$S—NH—*, —S$CH_2$—NH—*, —S$(CH_2)_2$—NH—*, —S$(CH_2)_3$—NH—*, —S$(CH_2)_4$—NH—*, —S(O)$CH_2$—NH—*, —S(O)$(CH_2)_2$—NH—*, —S(O)$(CH_2)_3$—NH—*, —S(O)$(CH_2)_4$—NH—*, —S(O)$_2$$CH_2$—NH—*, —S(O)$_2$$(CH_2)_2$—NH—*, —S(O)$_2$$(CH_2)_3$—NH—*, or —S(O)$_2$$(CH_2)_4$—NH—*.

In some embodiments, -$L^1$-$Z'$—* is —($C_1$-$C_6$ alkylene)-$X^1$-$L^2$-$Z'$—*. In some embodiments, -$L^1$-$Z'$—* is

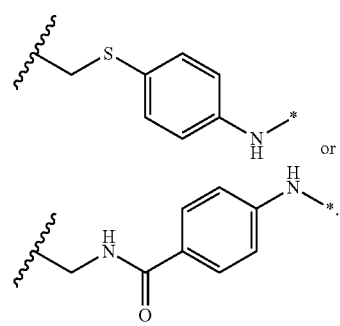

In some embodiments, -$L^1$-$Z'$—* is

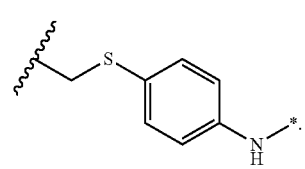

In some embodiments, -$L^1$-$Z'$—* is

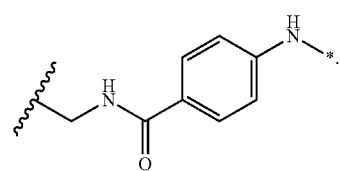

In the various embodiments disclosing -$L^1$-$Z'$—* herein, * is the site covalently attached to A.

In some embodiments, A is a peptide comprising 2 to 8 amino acids. In some embodiments, A is a peptide comprising 2 to 4 amino acids. In some embodiments, at least one amino acid in said peptide is a L amino acid. In some embodiments, each amino acid in said peptide is a L amino acid. In some embodiments, at least one amino acid in said peptide is a D amino acid.

In some embodiments, A is -(AA$^1$)-(AA$^2$)$_{a1}$-*, where * is the site covalently attached to E; AA$^1$ and AA$^2$ are each independently an amino acid residue; and a1 is an integer from 1-9.

In some embodiments, -AA$^1$-(AA$^2$)$_{a1}$-* is -Gly-Gly-Gly-*, -Ala-Val-*, -Val-Ala-*, -Val-Cit-*, -Val-Lys-*, -Lys-Val-*, -Phe-Lys-*, -Lys-Phe-*, -Lys-Lys-*, -Ala-Lys-*, -Lys-Ala-*, -Phe-Cit-*, -Cit-Phe-*, -Leu-Cit-*, -Cit-Leu-*, -Ile-Cit-*, -Phe-Ala-*, -Ala-Phe-*, -Phe-N$^9$-tosyl-Arg-*, —N$^9$-tosyl-Arg-Phe-*, -Phe-N$^9$-nitro-Arg-*, —N$^9$-nitro-Arg-Phe*, -Phe-Phe-Lys-*, -Lys-Phe-Phe-*, -Gly-Phe-Lys-*, Lys-Phe-Gly-*, -Leu-Ala-Leu-*, -lie-Ala-Leu-*, -Leu-Ala-Ile-*, -Val-Ala-Val-*, -Ala-Leu-Ala-Leu-(SEQ ID NO: 89)*, -Leu-Ala-Leu-Ala-(SEQ ID NO: 90)*, -p-Ala-Leu-Ala-Leu- (SEQ ID NO: 91)*, -Gly-Phe-Leu-Gly- (SEQ ID NO: 92)*, -Gly-Leu-Phe-Gly- (SEQ ID NO: 93)*, -Val-Arg-*, -Arg-Val-*, -Arg-Arg-*, -Ala-Ala-*, -Ala-Met-*, -Met-Ala-*, -Thr-Thr-*, -Thr-Met-*, -Met-Thr-*, -Leu-Ala-*, -Ala-Leu-*, -Cit-Val-*, -Gln-Val-*, -Val-Gln-*, —Ser-Val-*, -Val-Ser-*, —Ser-Ala-*, —Ser-Gly-*, -Ala-Ser-*, -Gly-Ser-*, -Leu-Gin-*, -Gin-Leu-*, -Phe-Arg-*, -Arg-Phe-*, -Tyr-Arg-*, -Arg-Tyr-*, -Phe-Gln-*, -Gln-Phe-*, -Val-Thr-*, -Thr-Val-*, -Met-Tyr-*, and -Tyr-Met-*.

In some embodiments, -AA$^1$-(AA$^2$)$_{a1}$-* is -Val-D-Lys-*, -Val-D-Arg-*, -L-Val-Cit-*, -L-Val-Lys-*, -L-Val-Arg-*, -L-Val-D-Cit-*, -L-Phe-Phe-Lys-*, -L-Val-D-Lys-*, -L-Val-D-Arg-*, -L-Arg-D-Arg-*, -L-Ala-Ala-*, -L-Ala-D-Ala-*, -Ala-D-Ala-*, -Val-D-Cit-*, -L-Ala-L-Ala-*, -L-Ala-L-Val-*, -L-Gln-L-Val-*, -L-Gln-L-Leu-*, or -L-Ser-L-Val-*.

In some embodiments, -AA$^1$-(AA$^2$)$_{a1}$-* is: -Ala-Ala-*, -Ala-Val-*, -Val-Ala-*, -Gin-Leu-*, -Leu-Gin-*, -Ala-Ala-Ala-*, -Ala-Ala-Ala-Ala- (SEQ ID NO: 94)*, -Gly-Ala-Gly-Gly- (SEQ ID NO: 95)*, -Gly-Gly-Ala-Gly- (SEQ ID NO: 96)*, -Gly-Val-Gly-Gly- (SEQ ID NO: 97)*, -Gly-Gly-Val-Gly- (SEQ ID NO: 98)*, -Gly-Phe-Gly-Gly- (SEQ ID NO: 99)*, or -Gly-Gly-Phe-Gly- (SEQ ID NO: 100)*.

In some embodiments, -AA$^1$-(AA$^2$)$_{a1}$-* is: -L-Ala-L-Ala-*, -L-Ala-D-Ala-*, -L-Ala-L-Val-*, -L-Ala-D-Val-*, -L-Val-L-Ala-*, -L-Val-D-Ala-*, -L-Gln-L-Leu-*, -L-Gln-D-Leu-*, -L-Leu-L-Gln-*, -L-Leu-D-Gln-*, -L-Ala-L-Ala-L-Ala-*, -L-Ala-D-Ala-L-Ala-*, -L-Ala-L-Ala-D-Ala-*, -L-Ala-L-Ala-L-Ala-L-Ala- (SEQ ID NO: 94)*, -L-Ala-D-Ala-L-Ala-L-Ala- (SEQ ID NO: 101)*, -L-Ala-L-Ala-D-Ala-L-Ala- (SEQ ID NO: 102)*, -L-Ala-L-Ala-L-Ala-D-Ala- (SEQ ID NO: 103)*, -Gly-L-Ala-Gly-Gly- (SEQ ID NO: 95)*, -Gly-Gly-L-Ala-Gly- (SEQ ID NO: 96)*, -Gly-D-Ala-Gly-Gly- (SEQ ID NO: 104)*, Gly-Gly-D-Ala-Gly- (SEQ ID NO: 105)*, -Gly-L-Val-Gly-Gly- (SEQ ID NO: 97)*, Gly-Gly-L-Val-Gly-(SEQ ID NO: 98)*, -Gly-D-Val-Gly-Gly- (SEQ ID NO: 106)*, Gly-Gly-D-Val-Gly- (SEQ ID NO: 107)*, -Gly-L-Phe-Gly-Gly- (SEQ ID NO: 99)*, or Gly-Gly-L-Phe-Gly- (SEQ ID NO: 100)*.

In some embodiments, -AA$^1$-(AA$^2$)$_{a1}$-* is: -L-Ala-L-Ala-*, -L-Ala-D-Ala-LAla-*, -L-Ala-L-Ala-L-Ala-*, or -L-Ala-L-Ala-L-Ala-L-Ala- (SEQ ID NO: 94)*.

In the various embodiments disclosing -AA$^1$-(AA$^2$)$_{a1}$-* herein, * is the site covalently attached to E.

In some embodiments, A is substituted with one or more polyol. In some embodiments, E is substituted with one or more polyol. In some embodiments, polyol is —(C$_1$-C$_6$ alkylene)-X$^5$—Y$^3$; wherein: X$^5$ is —NR$^{12}$C(=O)— or —C(=O)NR$^{12}$—; Y$^3$ is —C$_1$-C$_{10}$ alkyl, where Y$^3$ is substituted with 0-10 OH groups; and R$^{12}$ is —H, C$_1$-C$_6$ alkyl, C$_1$-C$_6$ fluoroalkyl, C$_3$-C$_6$ cycloalkyl, aryl, heteroaryl, or benzyl.

In some embodiments, wherein polyol is

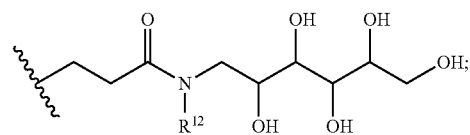

wherein R$^{12}$ is H or methyl.

In some embodiments, E is —C(=O)—(C$_1$-C$_{10}$ alkylene)-X$^3$. In some embodiments, E is

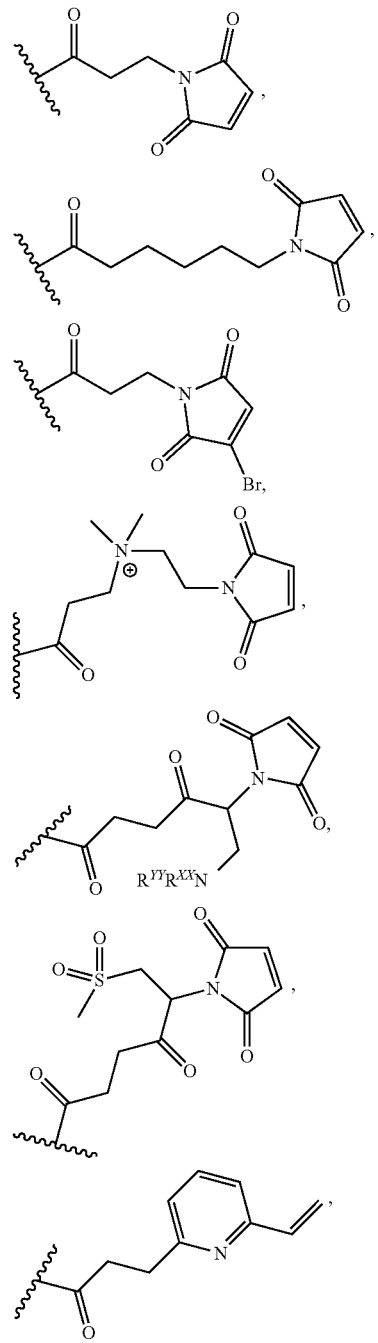

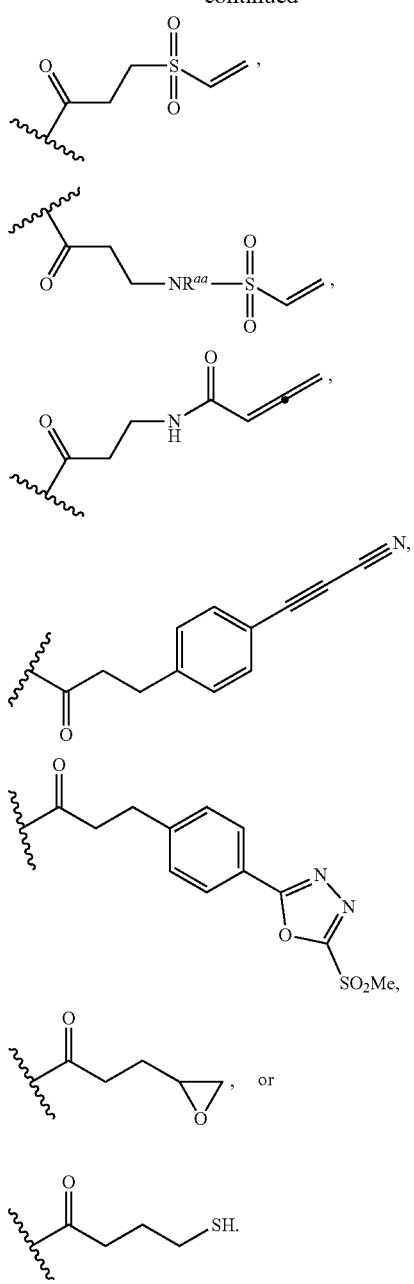
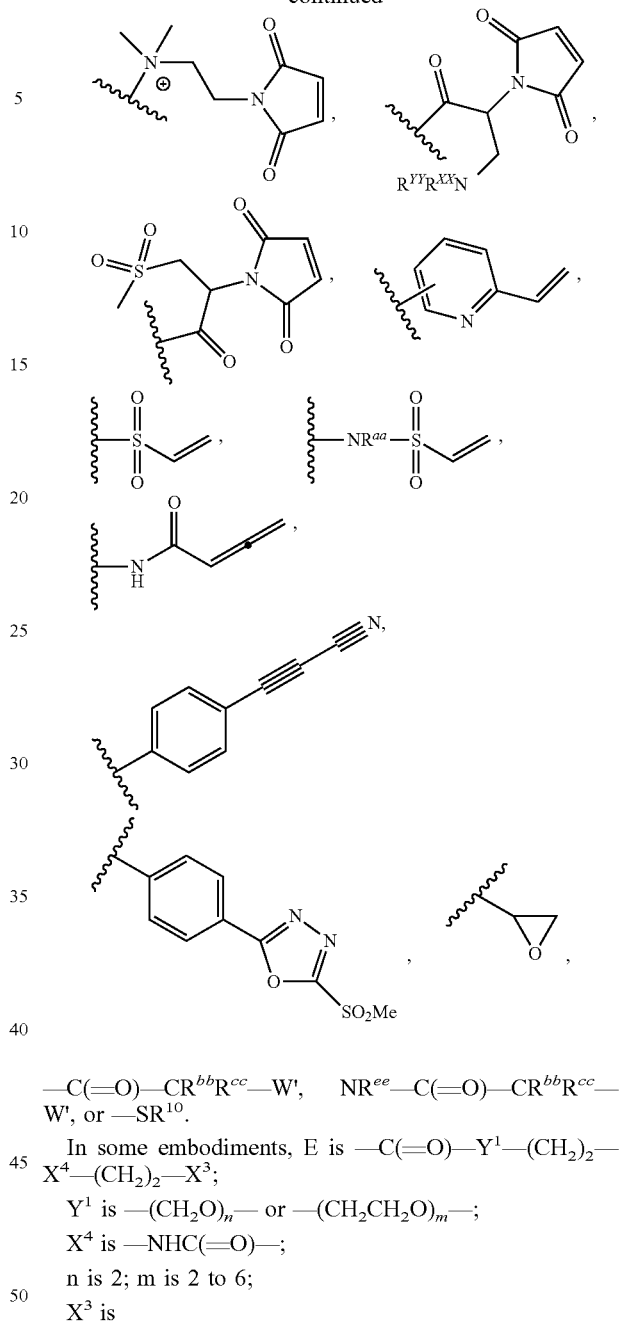
In some embodiments, E is —C(=O)—Y$^1$—(C$_1$-C$_{10}$ alkylene)-X$^4$—(C$_1$-C$_{10}$ alkylene)-X$^3$;
Y$^1$ is —(CR$^a$R$^b$O)$_n$—, or —(CR$^a$R$^b$CR$^{a'}$R$^{b'}$O)$_m$—;
X$^4$ is —NR$^9$C(=O)—; and
X$^3$ is
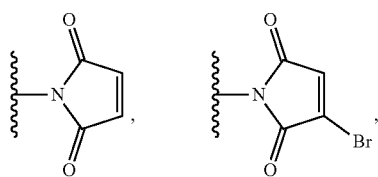
—C(=O)—CR$^{bb}$R$^{cc}$—W', NR$^{ee}$—C(=O)—CR$^{bb}$R$^{cc}$—W', or —SR$^{10}$.
In some embodiments, E is —C(=O)—Y$^1$—(CH$_2$)$_2$—X$^4$—(CH$_2$)$_2$—X$^3$;
Y$^1$ is —(CH$_2$O)$_n$— or —(CH$_2$CH$_2$O)$_m$—;
X$^4$ is —NHC(=O)—;
n is 2; m is 2 to 6;
X$^3$ is -continued —C(=O)—CR$^{bb}$R$^{cc}$—W', NR$^{ee}$—C(=O)—CR$^{bb}$R$^{cc}$—W', or —SR$^{10}$.

In some embodiments, the compound is any one of the compounds selected from Table 2.

In another aspect, the invention provides a compound of Formula III, or a pharmaceutically acceptable salt thereof:

CBA-E'-A-Z'-L$^1$-D     (Formula III)

wherein:

D is represented by the following structural formula:

R$^1$ is —H, —F, —CH$_3$, or —CF$_3$;

R$^2$ is —H, —F, —OR$^3$, —SR$^3$, —S(O)R$^4$, —S(O)$_2$R$^4$, C$_1$-C$_6$ alkyl, or C$_1$-C$_6$ fluoroalkyl; or R$^1$ and R$^2$ taken together with the carbon atoms to which they are attached form a methylenedioxy or a difluoromethylenedioxy ring; with the proviso that both R$^1$ and R$^2$ cannot be —H;

R$^3$ is H or C$_1$-C$_6$ alkyl;

R$^4$ is C$_1$-C$_6$ alkyl;

L$^1$ is absent, —(C$_1$-C$_6$ alkylene)-, —(C$_1$-C$_6$ alkylene)-X$^1$—(C$_1$-C$_6$ alkylene)-, X$^{1'}$—(C$_1$-C$_6$ alkylene)-*, or —(C$_1$-C$_6$ alkylene)-X$^1$-L$^2$-*; where * is the site covalently attached to Z';

X$^1$ is —O—, —S—, —S(O)—, —S(O)$_2$—, —C(=O)—, —NR$^5$—, —NR$^5$C(=O)—, or —C(=O)NR$^5$—;

X$^{1'}$ is —O—, —S—, —S(O)—, or —S(O)$_2$—;

L$^2$ is phenylene;

each R$^5$ is independently —H, C$_1$-C$_6$ alkyl, C$_1$-C$_6$ fluoroalkyl, C$_3$-C$_6$ cycloalkyl, aryl, heteroaryl, or benzyl;

Z' is —O—CH$_2$—NR$^8$—*, —S—CH$_2$—NR$^8$—*, —NR$^8$—*; where * is the site covalently attached to A;

each R$^8$ is independently —H, C$_1$-C$_6$ alkyl, C$_1$-C$_6$ fluoroalkyl, C$_3$-C$_6$ cycloalkyl, aryl, heteroaryl, or benzyl;

L$^1$ and L$^2$ are each independently optionally substituted with 1-4 substituents selected from halogen, —CN, —OR$^7$, —SR$^7$, —N(R$^7$)$_2$, C$_1$-C$_6$ alkyl, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, or heteroaryl; and each R$^7$ is independently H, C$_1$-C$_6$ alkyl, C$_1$-C$_6$ fluoroalkyl, C$_3$-C$_6$ cycloalkyl, aryl, heteroaryl, or benzyl;

A is a peptide comprising 2 to 10 amino acids; wherein A is optionally substituted with one or more polyol;

E' is —C(=O)-L$^3$-X$^6$—*; where * is the site covalently linked to CBA;

L$^3$ is —(C$_1$-C$_{10}$ alkylene)- or —Y$^1$—(C$_1$-C$_{10}$ alkylene)-X$^4$—Y$^2$—(C$_1$-C$_{10}$ alkylene)-*; where * is the site covalently attached to X$^6$;

Y$^1$ is absent, —(CR$^a$R$^b$O)$_n$— or —(CR$^a$R$^b$CR$^a$R$^b$O)$_m$—;

X$^4$ is —NR$^9$C(=O)— or —C(=O)NR$^9$—;

Y$^2$ is absent, —(CR$^c$R$^d$O)$_o$—, or —(CR$^c$R$^d$CR$^{c'}$R$^{d'}$O)$_p$—;

n, m, o, and p are each independently 1-10;

each R$^a$, R$^b$, R$^{a'}$, R$^{b'}$, R$^c$, R$^d$, R$^{c'}$, and R$^{d'}$ are independently —H, C$_1$-C$_6$ alkyl, C$_1$-C$_6$ fluoroalkyl, C$_3$-C$_6$ cycloalkyl, aryl, heteroaryl, or benzyl;

wherein L$^3$ is optionally substituted with 0-4 substituents selected from halogen, —CN, —OR$^{11}$, —SR$^{11}$, —N(R$^u$)$_2$, C$_1$-C$_6$ alkyl, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, heteroaryl, and polyol;

each R$^{11}$ is independently H, C$_1$-C$_6$ alkyl, C$_1$-C$_6$ fluoroalkyl, C$_3$-C$_6$ cycloalkyl, aryl, heteroaryl, or benzyl;

X$^6$ is

-continued

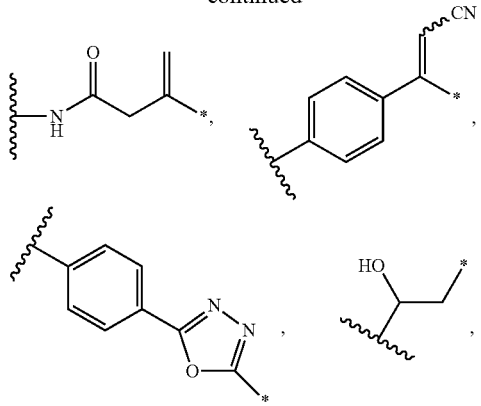

—C(=O)—CR$^{bb}$R$^{cc}$—*, or —NR$^{ee}$—C(=O)—CR$^{bb}$R$^{cc}$—*; where * is the site covalently attached to CBA;
each R$^{aa}$, R$^{bb}$, R$^{cc}$, and R$^{ee}$ are independently —H or optionally substituted $C_1$-$C_6$ alkyl;
each R$^{YY}$ and R$^{XX}$ are independently —H or $C_1$-$C_6$ alkyl;
R$^9$ is independently —H, $C_1$-$C_6$ alkyl, $C_1$-$C_6$ fluoroalkyl, $C_3$-$C_6$ cycloalkyl, aryl, heteroaryl, or benzyl; and
CBA is a cell binding agent.

In some embodiments, R$^1$ is —H or —F. In some embodiments, R$^1$ is —F. In some embodiments, R$^2$ is —H, —F, —OCF$_3$, —CF$_3$, —OMe, —OEt, —SMe, —S(O)Me, —S(O)$_2$Me, —SEt, —S(O)Et, —S(O$_2$)Et, methyl, or ethyl. In some embodiments, R$^2$ is —F. In some embodiments, R$^2$ is —OMe, —SMe, —S(O)Me, or methyl. In some embodiments, R$^2$ is methyl. In some embodiments, R$^1$ is —F and R$^2$ is —F. In some embodiments, R$^1$ is methyl and R$^2$ is —F. In some embodiments, R$^1$ is —F and R$^2$ is -methyl.

In some embodiments, -L$^1$-Z'—* is —($C_1$-$C_4$ alkylene)-O—CH$_2$—NR$^8$—*, —($C_1$-$C_4$ alkylene)-S—CH$_2$—NR$^8$—*, or —($C_1$-$C_4$ alkylene)-NR$^8$—*. In some embodiments, -L$^1$-Z'—* is —($C_1$-$C_4$ alkylene)-O—CH$_2$—NR$^8$—*. In some embodiments, -L$^1$-Z'—* is —($C_1$-$C_4$ alkylene)-S—CH$_2$—NR$^8$—*. In some embodiments, -L$^1$-Z'—* is —($C_1$-$C_4$ alkylene)-NR$^8$—*.

In some embodiments, -L$^1$-Z'—* is —CH$_2$O—CH$_2$NH—*, —(CH$_2$)$_2$O—CH$_2$NH—*, —(CH$_2$)$_3$O—CH$_2$NH—*, —(CH$_2$)$_4$O—CH$_2$NH—*, —CH$_2$S—CH$_2$NH—*, —(CH$_2$)$_2$S—CH$_2$NH—*, —(CH$_2$)$_3$S—CH$_2$NH—*, —(CH$_2$)$_4$S—CH$_2$NH—*, —CH$_2$NH—*, —(CH$_2$)$_2$NH—*, —(CH$_2$)$_3$NH—*, or —(CH$_2$)$_4$NH—.

In some embodiments, -L$^1$-Z'—* is —($C_1$-$C_5$ alkylene)-NR$^5$C(=O)—($C_1$-$C_5$ alkylene)-O—CH$_2$—NR$^8$—*, —($C_1$-$C_5$ alkylene)-NR$^5$C(=O)—($C_1$-$C_5$ alkylene)-S—CH$_2$—NR$^8$—*, —($C_1$-$C_5$ alkylene)-S—($C_1$-$C_5$ alkylene)-S—CH$_2$—NR$^8$—*, or —($C_1$-$C_5$ alkylene)-S—($C_1$-$C_5$ alkylene)-SS—CH$_2$—NR$^8$—*. In some embodiments, -L$^1$-Z'—* is —($C_1$-$C_5$ alkylene)-NR$^5$C(=O)—($C_1$-$C_5$ alkylene)-O—CH$_2$—NR$^8$—*. In some embodiments, -L$^1$-Z'—* is —($C_1$-$C_5$ alkylene)-NR$^5$C(=O)—($C_1$-$C_5$ alkylene)-S—CH$_2$—NR$^8$—*. In some embodiments, -L$^1$-Z'—* is —($C_1$-$C_5$ alkylene)-S—($C_1$-$C_5$ alkylene)-S—CH$_2$—NR$^8$—*. In some embodiments, -L$^1$-Z'—* is —($C_1$-$C_5$ alkylene)-S—($C_1$-$C_5$ alkylene)-SS—CH$_2$—NR$^8$—*.

In some embodiments, -L$^1$-Z'—* is —CH$_2$NHC(=O)CH$_2$O—CH$_2$—NH—*, —CH$_2$NHC(=O)(CH$_2$)$_2$O—CH$_2$—NH—*, —CH$_2$NHC(=O)(CH$_2$)$_3$O—CH$_2$—NH—*, —CH$_2$NHC(=O)(CH$_2$)$_4$O—CH$_2$—NH—*, —CH$_2$NHC(=O)(CH$_2$)$_5$O—CH$_2$—NH—*, —CH$_2$NHC(=O)CH$_2$S—CH$_2$—NH—*, —CH$_2$NHC(=O)(CH$_2$)$_2$S—CH$_2$—NH—*, —CH$_2$NHC(=O)(CH$_2$)$_3$S—CH$_2$—NH—*, —CH$_2$NHC(=O)(CH$_2$)$_4$S—CH$_2$—NH—*, —CH$_2$NHC(=O)(CH$_2$)$_5$S—CH$_2$—NH—*, —CH$_2$SCH$_2$O—CH$_2$—NH—*, —CH$_2$S(CH$_2$)$_2$O—CH$_2$—NH—*, —CH$_2$S(CH$_2$)$_3$O—CH$_2$—NH—*, —CH$_2$S(CH$_2$)$_4$O—CH$_2$—NH—*, —CH$_2$S(CH$_2$)$_5$O—CH$_2$—NH—*, —CH$_2$SCH$_2$S—CH$_2$—NH—*, —CH$_2$S(CH$_2$)$_2$S—CH$_2$—NH—*, —CH$_2$S(CH$_2$)$_3$S—CH$_2$—NH—*, —CH$_2$S(CH$_2$)$_4$S—CH$_2$—NH—*, or —CH$_2$S(CH$_2$)$_5$S—CH$_2$—NH—*.

In some embodiments, each R$^5$ is independently —H, methyl, or benzyl. In some embodiments, each R$^5$ is independently —H. In some embodiments, each R$^5$ is methyl. In some embodiments, each R$^5$ is benzyl. In some embodiments, each R$^8$ is independently —H, methyl, or benzyl. In some embodiments, each R$^8$ is independently —H. In some embodiments, each R$^8$ is methyl. In some embodiments, each R$^8$ is benzyl.

In some embodiments -L$^1$-Z'—* is —X$^{1'}$—($C_1$-$C_4$ alkylene)-O—CH$_2$—NR$^8$—*, —X$^{1'}$—($C_1$-$C_4$ alkylene)-S—CH$_2$—NR$^8$—*, or —X$^1$—($C_1$-$C_4$ alkylene)-NR$^8$—*. In some embodiments -L$^1$-Z'—* is —X$^1$—($C_1$-$C_4$ alkylene)-O—CH$_2$—NR$^8$—*. In some embodiments -L$^1$-Z'—* is —X$^{1'}$—($C_1$-$C_4$ alkylene)-S—CH$_2$—NR$^8$—*. In some embodiments -L$^1$-Z'—* is —X$^1$—($C_1$-$C_4$ alkylene)-NR$^8$—*.

In some embodiments -L$^1$-Z'—* is —OCH$_2$O—CH$_2$—NH—*, —O(CH$_2$)$_2$O—CH$_2$—NH—*, —O(CH$_2$)$_3$O—CH$_2$—NH—*, —O(CH$_2$)$_4$O—CH$_2$—NH—*, —SCH$_2$O—CH$_2$—NH—*, —S(CH$_2$)$_2$O—CH$_2$—NH—*, —S(CH$_2$)$_3$O—CH$_2$—NH—*, —S(CH$_2$)$_4$O—CH$_2$—NH—*, —S(O)CH$_2$O—CH$_2$—NH—*, —S(O)(CH$_2$)$_2$O—CH$_2$—NH—*, —S(O)(CH$_2$)$_3$O—CH$_2$—NH—*, —S(O)(CH$_2$)$_4$O—CH$_2$—NH—*, —S(O)$_2$CH$_2$O—CH$_2$—NH—*, —S(O)$_2$(CH$_2$)$_2$O—CH$_2$—NH—*, —S(O)$_2$(CH$_2$)$_3$O—CH$_2$—NH—*, —S(O)$_2$(CH$_2$)$_4$O—CH$_2$—NH—*, —OCH$_2$S—CH$_2$—NH—*, —O(CH$_2$)$_2$S—CH$_2$—NH—*, —O(CH$_2$)$_3$S—CH$_2$—NH—*, —O(CH$_2$)$_4$S—CH$_2$—NH—*, —SCH$_2$S—CH$_2$—NH—*, —S(CH$_2$)$_2$S—CH$_2$—NH—*, —S(CH$_2$)$_3$S—CH$_2$—NH—*, —S(CH$_2$)$_4$S—CH$_2$—NH—*, —S(O)CH$_2$S—CH$_2$—NH—*, —S(O)(CH$_2$)$_2$S—CH$_2$—NH—*, —S(O)(CH$_2$)$_3$S—CH$_2$—NH—*, —S(O)(CH$_2$)$_4$S—CH$_2$—NH—*, —S(O)$_2$CH$_2$S—CH$_2$—NH—*, —S(O)$_2$(CH$_2$)$_2$S—CH$_2$—NH—*, —S(O)$_2$(CH$_2$)$_3$S—CH$_2$—NH—*, —S(O)$_2$(CH$_2$)$_4$S—CH$_2$—NH—*, —OCH$_2$—NH—*, —O(CH$_2$)$_2$—NH—*, —O(CH$_2$)$_3$—NH—*, —O(CH$_2$)$_4$S—NH—*, —SCH$_2$—NH—*, —S(CH$_2$)$_2$—NH—*, —S(CH$_2$)$_3$—NH—*, —S(CH$_2$)$_4$—NH—*, —S(O)CH$_2$—NH—*, —S(O)(CH$_2$)$_2$—NH—*, —S(O)(CH$_2$)$_3$—NH—*, —S(O)(CH$_2$)$_4$—NH—*, —S(O)$_2$CH$_2$—NH—*, —S(O)$_2$(CH$_2$)$_2$—NH—*, —S(O)$_2$(CH$_2$)$_3$—NH—*, or —S(O)$_2$(CH$_2$)$_4$—NH—*.

In some embodiments, -L$^1$-Z'—* is —($C_1$-$C_6$ alkylene)-X$^1$-L$^2$-Z'—*. In some embodiments, -L$^1$-Z'—* is

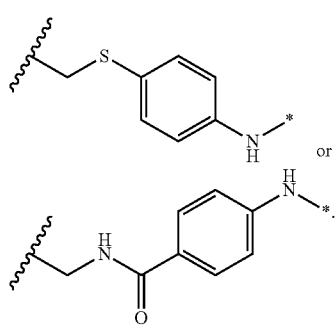

In some embodiments, -L¹-Z'—* is

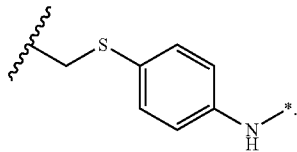

In some embodiments, -L¹-Z'—* is

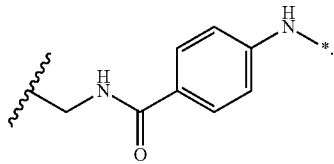

In the various embodiments disclosing -L¹-Z'—* herein, * is the site covalently attached to A.

In some embodiments, A is a peptide comprising 2 to 8 amino acids. In some embodiments, A is a peptide comprising 2 to 4 amino acids. In some embodiments, at least one amino acid in said peptide is a L amino acid. In some embodiments, each amino acid in said peptide is a L amino acid. In some embodiments, at least one amino acid in said peptide is a D amino acid.

In some embodiments, A is -(AA¹)-(AA²)$_{a1}$-*, where * is the point of attachment to E', AA¹ and AA² are each independently an amino acid residue; and a1 is an integer from 1-9.

In some embodiments, -AA¹-(AA²)$_{a1}$-* is -Gly-Gly-Gly-*, -Ala-Val-*, -Val-Ala-*, -Val-Cit-*, -Val-Lys-*, -Lys-Val-*, -Phe-Lys-*, -Lys-Phe-*, -Lys-Lys-*, -Ala-Lys-*, -Lys-Ala-*, -Phe-Cit-*, -Cit-Phe-*, -Leu-Cit-*, -Cit-Leu-*, -Ile-Cit-*, -Phe-Ala-*, -Ala-Phe-*, -Phe-N⁹-tosyl-Arg-*, —N⁹-tosyl-Arg-Phe-*, -Phe-N⁹-nitro-Arg-*, —N⁹-nitro-Arg-Phe*, -Phe-Phe-Lys-*, -Lys-Phe-Phe-*, -Gly-Phe-Lys-*, Lys-Phe-Gly-*, -Leu-Ala-Leu-*, -Ile-Ala-Leu-*, -Leu-Ala-Ile-*, -Val-Ala-Val-*, -Ala-Leu-Ala-Leu-(SEQ ID NO: 89)*, -Leu-Ala-Leu-Ala- (SEQ ID NO: 90)*, -p-Ala-Leu-Ala-Leu- (SEQ ID NO: 91)*, -Gly-Phe-Leu-Gly-(SEQ ID NO: 92)*, -Gly-Leu-Phe-Gly- (SEQ ID NO: 93)*, -Val-Arg-*, -Arg-Val-*, -Arg-Arg-*, -Ala-Ala-*, -Ala-Met-*, -Met-Ala-*, -Thr-Thr-*, -Thr-Met-*, -Met-Thr-*, -Leu-Ala-*, -Ala-Leu-*, -Cit-Val-*, -Gln-Val-*, -Val-Gln-*, —Ser-Val-*, -Val-Ser-*, —Ser-Ala-*, —Ser-Gly-*, -Ala-Ser-*, -Gly-Ser-*, -Leu-Gln-*, -Gln-Leu-*, -Phe-Arg-*, -Arg-Phe-*, -Tyr-Arg-*, -Arg-Tyr-*, -Phe-Gln-*, -Gln-Phe-*, -Val-Thr-*, -Thr-Val-*, -Met-Tyr-*, and -Tyr-Met-*.

In some embodiments, -AA¹-(AA²)$_{a1}$-* is -Val-D-Lys-*, -Val-D-Arg-*, -L-Val-Cit-*, -L-Val-Lys-*, -L-Val-Arg-*, -L-Val-D-Cit-*, -L-Phe-Phe-Lys-*, -L-Val-D-Lys-*, -L-Val-D-Arg-*, -L-Arg-D-Arg-*, -L-Ala-Ala-*, -L-Ala-D-Ala-*, -Ala-D-Ala-*, -Val-D-Cit-*, -L-Ala-L-Ala-*, -L-Ala-L-Val-*, -L-Gln-L-Val-*, -L-Gln-L-Leu-*, or -L-Ser-L-Val-*.

In some embodiments, -AA¹-(AA²)$_{a1}$-* is: -Ala-Ala-*, -Ala-Val-*, -Val-Ala-*, -Gln-Leu-*, -Leu-Gln-*, -Ala-Ala-Ala-*, -Ala-Ala-Ala-Ala- (SEQ ID NO: 94)*, -Gly-Ala-Gly-Gly- (SEQ ID NO: 95)*, -Gly-Gly-Ala-Gly- (SEQ ID NO: 96)*, -Gly-Val-Gly-Gly- (SEQ ID NO: 97)*, -Gly-Gly-Val-Gly- (SEQ ID NO: 98)*, -Gly-Phe-Gly-Gly- (SEQ ID NO: 99)*, or -Gly-Gly-Phe-Gly- (SEQ ID NO: 100)*.

In some embodiments, -AA¹-(AA²)$_{a1}$-* is: -L-Ala-L-Ala-*, -L-Ala-D-Ala-*, -L-Ala-L-Val-*, -L-Ala-D-Val-*, -L-Val-L-Ala-*, -L-Val-D-Ala-*, -L-Gln-L-Leu-*, -L-Gln-D-Leu-*, -L-Leu-L-Gln-*, -L-Leu-D-Gln-*, -L-Ala-L-Ala-L-Ala-*, -L-Ala-D-Ala-L-Ala-*, -L-Ala-L-Ala-D-Ala-*, -L-Ala-L-Ala-L-Ala-L-Ala- (SEQ ID NO: 94)*, -L-Ala-D-Ala-L-Ala-L-Ala- (SEQ ID NO: 101)*, -L-Ala-L-Ala-D-Ala-L-Ala- (SEQ ID NO: 102)*, -L-Ala-L-Ala-L-Ala-D-Ala- (SEQ ID NO: 103)*, -Gly-L-Ala-Gly-Gly- (SEQ ID NO: 95)*, -Gly-Gly-L-Ala-Gly- (SEQ ID NO: 96)*, -Gly-D-Ala-Gly-Gly- (SEQ ID NO: 104)*, Gly-Gly-D-Ala-Gly- (SEQ ID NO: 105)*, -Gly-L-Val-Gly-Gly- (SEQ ID NO: 97)*, Gly-Gly-L-Val-Gly-(SEQ ID NO: 98)*, -Gly-D-Val-Gly-Gly- (SEQ ID NO: 106)*, Gly-Gly-D-Val-Gly- (SEQ ID NO: 107)*, -Gly-L-Phe-Gly-Gly- (SEQ ID NO: 99)*, or Gly-Gly-L-Phe-Gly- (SEQ ID NO: 100)*.

In some embodiments, -AA¹-(AA²)$_{a1}$-* is: -L-Ala-L-Ala-*, -L-Ala-D-Ala-L-Ala-*, -L-Ala-L-Ala-L-Ala-*, or -L-Ala-L-Ala-L-Ala-L-Ala- (SEQ ID NO: 94)*.

In the various embodiments disclosing -AA¹-(AA²)$_{a1}$-* herein, * is the site covalently attached to E'.

In some embodiments, A is substituted with one or more polyol. In some embodiments, E' is substituted with one or more polyol. In some embodiments, polyol is —(C₁-C₆ alkylene)-X⁵—Y³; wherein: X⁵ is —NR¹²C(=O)— or —C(=O)NR¹²—; Y³ is —C₁-C₁₀ alkyl, where Y³ is substituted with 0-10 OH groups; and R¹² is —H, C₁-C₆ alkyl, C₁-C₆ fluoroalkyl, C₃-C₆ cycloalkyl, aryl, heteroaryl, or benzyl.

In some embodiments, polyol is

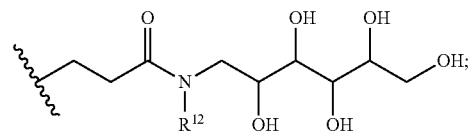

wherein R¹² is H or methyl.

In some embodiments, E' is —C(=O)—(C₁-C₁₀ alkylene)-X⁶—*. In some embodiments, E' is

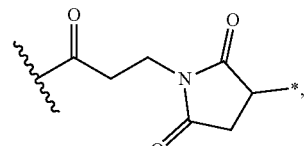

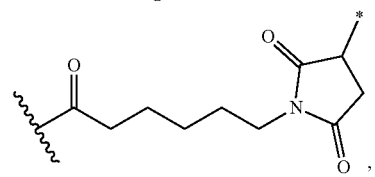

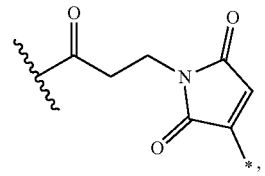

-continued
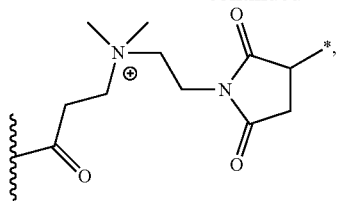
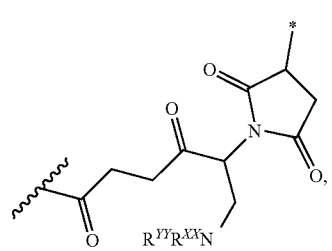
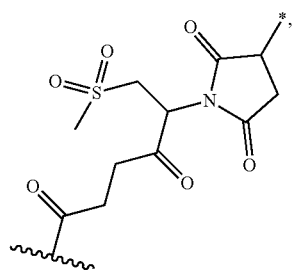
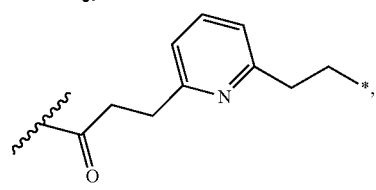
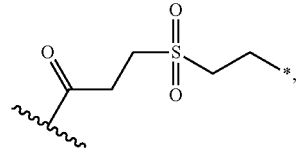
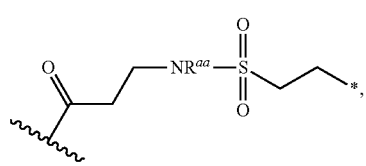
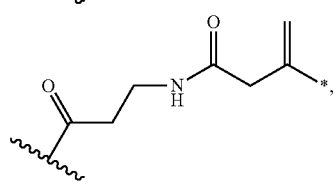
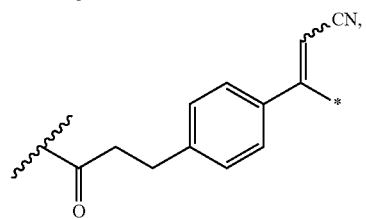
-continued
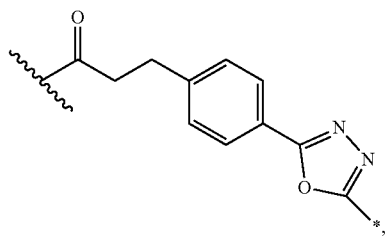
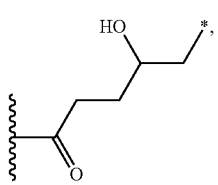
—C(=O)CH$_2$CH$_2$—C(=O)—CR$^{bb}$R$^{cc}$—*, or —C(=O)CH$_2$CH$_2$—NR$^{ee}$—C(=O)—CR$^{bb}$R$^{cc}$—*; where * is the site covalently attached to CBA.
In some embodiments, E' is —C(=O)—Y$^1$—(C$_1$-C$_{10}$ alkylene)-X$^4$—(C$_1$-C$_{10}$ alkylene)-X$^6$—*;
Y$^1$ is —(CR$^a$R$^b$O)$_n$—, or —(CR$^a$R$^b$CR$^{a'}$R$^{b'}$O)$_m$—;
X$^4$ is —NR$^9$C(=O)—; and
X$^6$ is
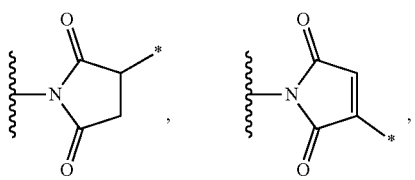
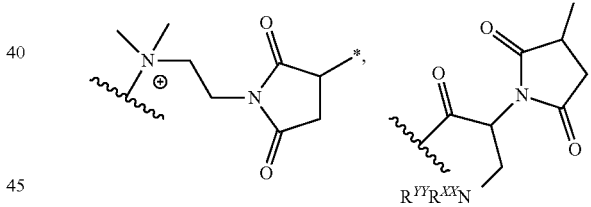
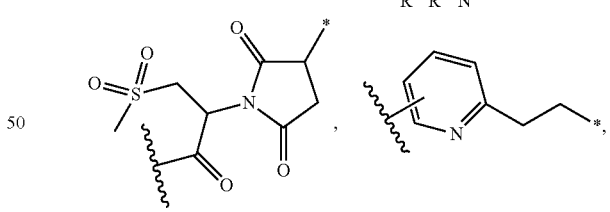
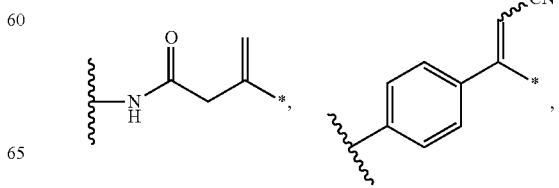

-continued

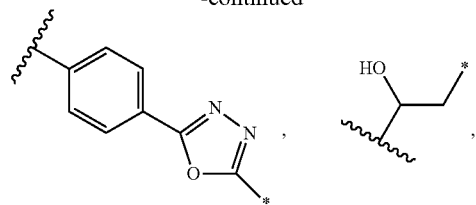

—C(=O)—CR$^{bb}$R$^{cc}$—*, or —NR$^{ee}$—C(=O)—CR$^{bb}$R$^{cc}$—*; where * is the site covalently attached to CBA.

In some embodiments, E' is —C(=O)—Y$^1$—(CH$_2$)$_2$—X$^4$—(CH$_2$)$_2$—X$^6$—*;

Y$^1$ is —(CH$_2$O)$_n$—, or —(CH$_2$CH$_2$O)$_m$—;

X$^4$ is —NHC(=O)—;

n is 2; m is 2 to 6;

X$^6$ is

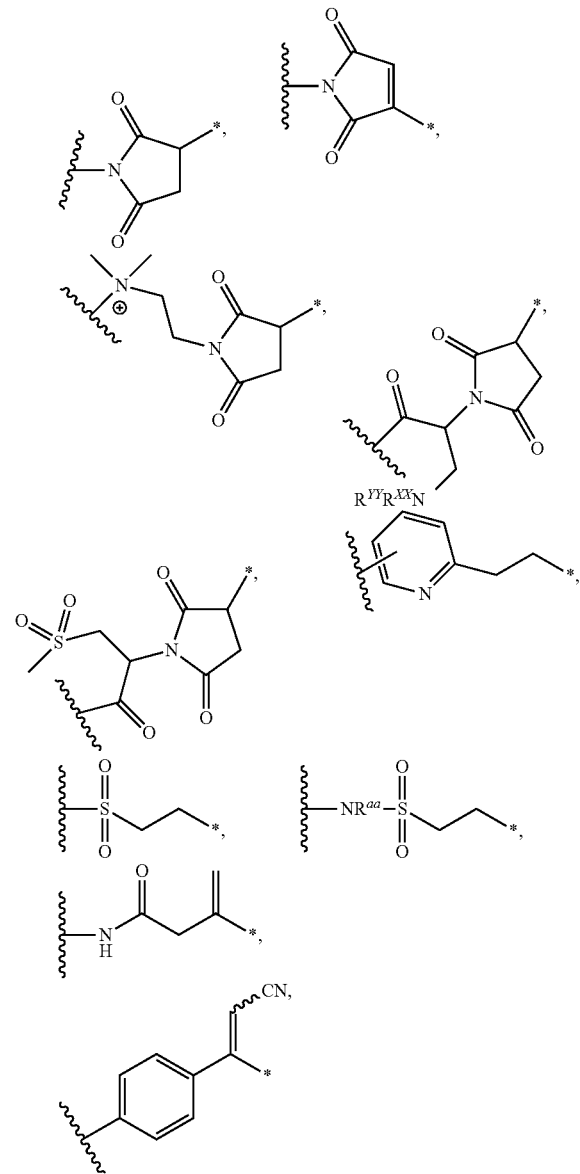

-continued

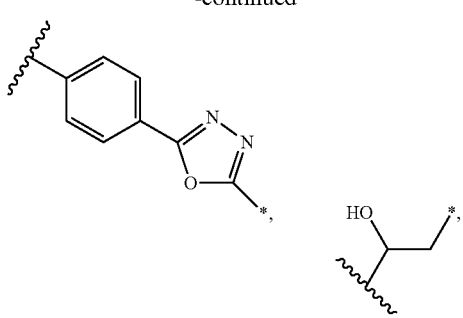

—C(=O)—CR$^{bb}$R$^{cc}$—*, or —NR$^{ee}$—C(=O)—CR$^{bb}$R$^{cc}$—*; where * is the site covalently attached to the CBA.

In some embodiments, the CBA comprises a —SH group that covalently links with E' to provide

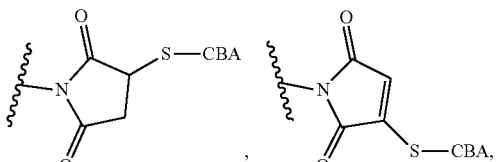

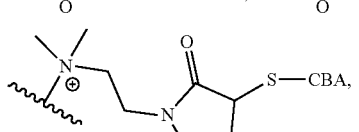

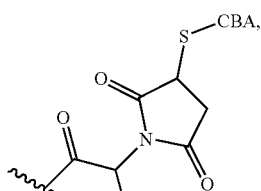

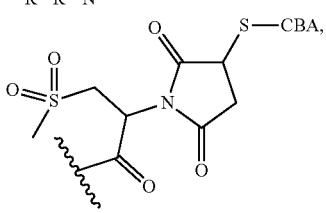

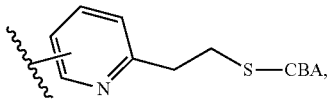

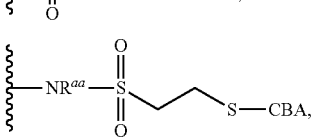

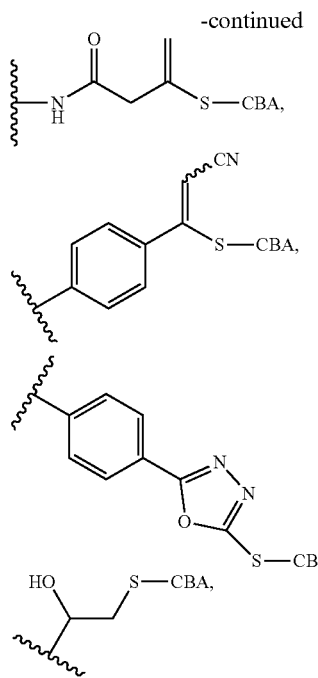

—C(=O)—CR$^{bb}$R$^{cc}$—S-CBA, or —NR$^{ee}$—C(=O)—CR$^{bb}$R$^{cc}$—S-CBA.

In some embodiments, the CBA is an antibody and E'-A-Z'-L$^1$-D is a drug-linker structure, the average number of drug-linker structures conjugated per antibody is in the range of from 2 to 10.

In some embodiments, the average number of drug-linker structures conjugated per antibody is in the range of from 2 to 10. In some embodiments, the average number of drug-linker structures conjugated per antibody is in the range of from 6 to 8. In some embodiments, the average number of drug-linker structures conjugated per antibody is 8.

In some embodiments, the CBA is an antibody, a single chain antibody, an antibody fragment that specifically binds to the target cell, a monoclonal antibody, a single chain monoclonal antibody, or a monoclonal antibody fragment that specifically binds to a target cell, a chimeric antibody, a chimeric antibody fragment that specifically binds to the target cell, a domain antibody, a domain antibody fragment that specifically binds to the target cell, a probody, a nanobody, a hexabody, a lymphokine, a hormone, a vitamin, a growth factor, a colony stimulating factor, or a nutrient-transport molecule.

In some embodiments, the CBA binds to target cells selected from tumor cells, virus infected cells, microorganism infected cells, parasite infected cells, autoimmune cells, activated cells, myeloid cells, activated T-cells, B cells, or melanocytes; cells expressing any one or more of 5T4, ADAM-9, ALK, AMHRII, ASCT2, Axl, B7-H3, BCMA, C4.4a, CA6, CA9, CanAg, CD123, CD138, CD142, CD166, CD184, CD19, CD20, CD205, CD22, CD248, CD25, CD3, CD30, CD33, CD352, CD37, CD38, CD40L, CD44v6, CD45, CD46, CD48, CD51, CD56, CD7, CD70, CD71, CD74, CD79b, CDH6, CEACAM5, CEACAM6, cKIT, CLDN18.2, CLDN6, CLL-1, c-MET, Cripto, CSP-1, CXCR5, DLK-1, DLL3, DPEP3, Dysadherin, EFNA4, EGFR, EGFRviii, ENPP3, EpCAM, EphA2, EphA3, ETBR, FGFR2, FGFR3, FLT3, FOLR-alpha, FSH, GCC, GD2, GD3, Globo H, GPC-1, GPC3, gpNMB, HER-2, HER-3, HLA-DR, HSP90, IGF-1R, IL-13R, IL1RAP, IL7R, Interleukin-4 Receptor (IL4R), KAAG-1, LAMP-1, Lewis Y antigen, LGALS3BP, LGRS, LH/hCG, LHRH, LIV-1, LRP-1, LRRC15, Ly6E, MAGE, Mesothelin (MSLN), MET, MHC class I chain-related protein A and B (MICA and MICB), MT1-MMP, MTX3, MTXS, MUC1, MUC16, NaPi2b, Nectin-4, NOTCH3, OAcGD2, OX001L, p-Cadherin, PD-L1, Phosphatidylserine (PS), Polymorphic epithelial mucin (PEM), Prolactin Receptor (PRLR), PSMA, PTK7, RNF43, ROR1, ROR2, SAIL, SLAMF7, SLC44A4, SLITRK6, SSTR2, STEAP-1, STING, STn, TIM-1, TM4SF1, TNF-alpha, TRA, TROP-2, Tumor-associated glycoprotein 72 (TAG-72), tumor-specific epitope of mucin-1 (TA-MUC1), CDS, TIM-3, UPK2, or UPK1b antigen.

In some embodiments, the cell-binding agent is an anti-folate receptor antibody or an antibody fragment thereof, an anti-EGFR antibody or an antibody fragment thereof, an anti-CD33 antibody or an antibody fragment thereof, an anti-EpCAM antibody or an antibody fragment thereof, an anti-CD19 antibody or an antibody fragment thereof, an anti-Muc1 antibody or an antibody fragment thereof, or an anti-CD37 antibody or an antibody fragment thereof.

The present invention also includes a composition (e.g., a pharmaceutical composition) comprising a cytotoxic compound or a conjugate of the present invention described herein, and a carrier (a pharmaceutically acceptable carrier). The present compounds, conjugates or compositions are useful for inhibiting abnormal cell growth or treating a proliferative disorder (e.g., cancer), an autoimmune disorder, destructive bone disorder, infectious disease, viral disease, fibrotic disease, neurodegenerative disorder, pancreatitis or kidney disease in a mammal (e.g., human).

The present compounds, conjugates or compositions are useful for treating cancer in a subject in need thereof. In some embodiments, the cancer is a lymphoma or a leukemia. In some embodiments, the cancer is acute myeloid leukemia (AML), chronic myelogenous leukemia (CML), myelodysplastic syndrome (MDS), acute lymphoblastic leukemia (ALL), acute B lymphoblastic leukemia or B-cell acute lymphoblastic leukemia (B-ALL), chronic lymphocytic leukemia (CLL), hairy cell leukemia (HCL), acute promyelocytic leukemia (APL), B-cell chronic lymphoproliferative disease (B-CLPD), atypical chronic lymphocytic leukemia, diffuse large B-cell lymphoma (DLBCL), blastic plasmacytoid dendritic cell neoplasm (BPDCN), non-Hodgkin lymphomas (NHL), mantel cell leukemia (MCL), small lymphocytic lymphoma (SLL), Hodgkin's lymphoma, systemic mastocytosis, and Burkitt's lymphoma. In some embodiments, the cancer is endometrial cancer, lung cancer, colorectal cancer, bladder cancer, gastric cancer, pancreatic cancer, renal cell carcinoma, prostate cancer, esophageal cancer, breast cancer, head and neck cancer, uterine cancer, ovarian cancer, liver cancer, cervical cancer, thyroid cancer, testicular cancer, myeloid cancer, melanoma, and lymphoid cancer. In some embodiments, the lung cancer is non-small cell lung cancer or small-cell lung cancer.

Also included in the present invention is the use of a cytotoxic compound, a conjugate, or a composition of the present invention for the manufacture of a medicament for inhibiting abnormal cell growth or treating a proliferative disorder (e.g., cancer), an autoimmune disorder, destructive bone disorder, infectious disease, viral disease, fibrotic disease, neurodegenerative disorder, pancreatitis or kidney disease in a mammal (e.g., human).

The present compounds, conjugates or compositions are useful for the manufacture of a medicament for treating cancer in a subject in need thereof. In some embodiments, the cancer is a lymphoma or a leukemia. In some embodiments, the cancer is acute myeloid leukemia (AML), chronic myelogenous leukemia (CML), myelodysplastic syndrome (MDS), acute lymphoblastic leukemia (ALL), acute B lymphoblastic leukemia or B-cell acute lymphoblastic leukemia (B-ALL), chronic lymphocytic leukemia (CLL), hairy cell leukemia (HCL), acute promyelocytic leukemia (APL), B-cell chronic lymphoproliferative disease (B-CLPD), atypical chronic lymphocytic leukemia, diffuse large B-cell lymphoma (DLBCL), blastic plasmacytoid dendritic cell neoplasm (BPDCN), non-Hodgkin lymphomas (NHL), mantel cell leukemia (MCL), small lymphocytic lymphoma (SLL), Hodgkin's lymphoma, systemic mastocytosis, and Burkitt's lymphoma. In some embodiments, the cancer is endometrial cancer, lung cancer, colorectal cancer, bladder cancer, gastric cancer, pancreatic cancer, renal cell carcinoma, prostate cancer, esophageal cancer, breast cancer, head and neck cancer, uterine cancer, ovarian cancer, liver cancer, cervical cancer, thyroid cancer, testicular cancer, myeloid cancer, melanoma, and lymphoid cancer. In some embodiments, the lung cancer is non-small cell lung cancer or small-cell lung cancer.

BRIEF DESCRIPTION OF THE DRAWINGS

FIG. 16 depicts the in vitro cytotoxicities of ADCs against Ag+ and Ag− cells. ADC standard in formulation (Standard) or blood serum (pooled) containing ADC taken at 2 min, 1 day or 3 days post administration into mice for ML66-22a.

DETAILED DESCRIPTION

Figure 1:
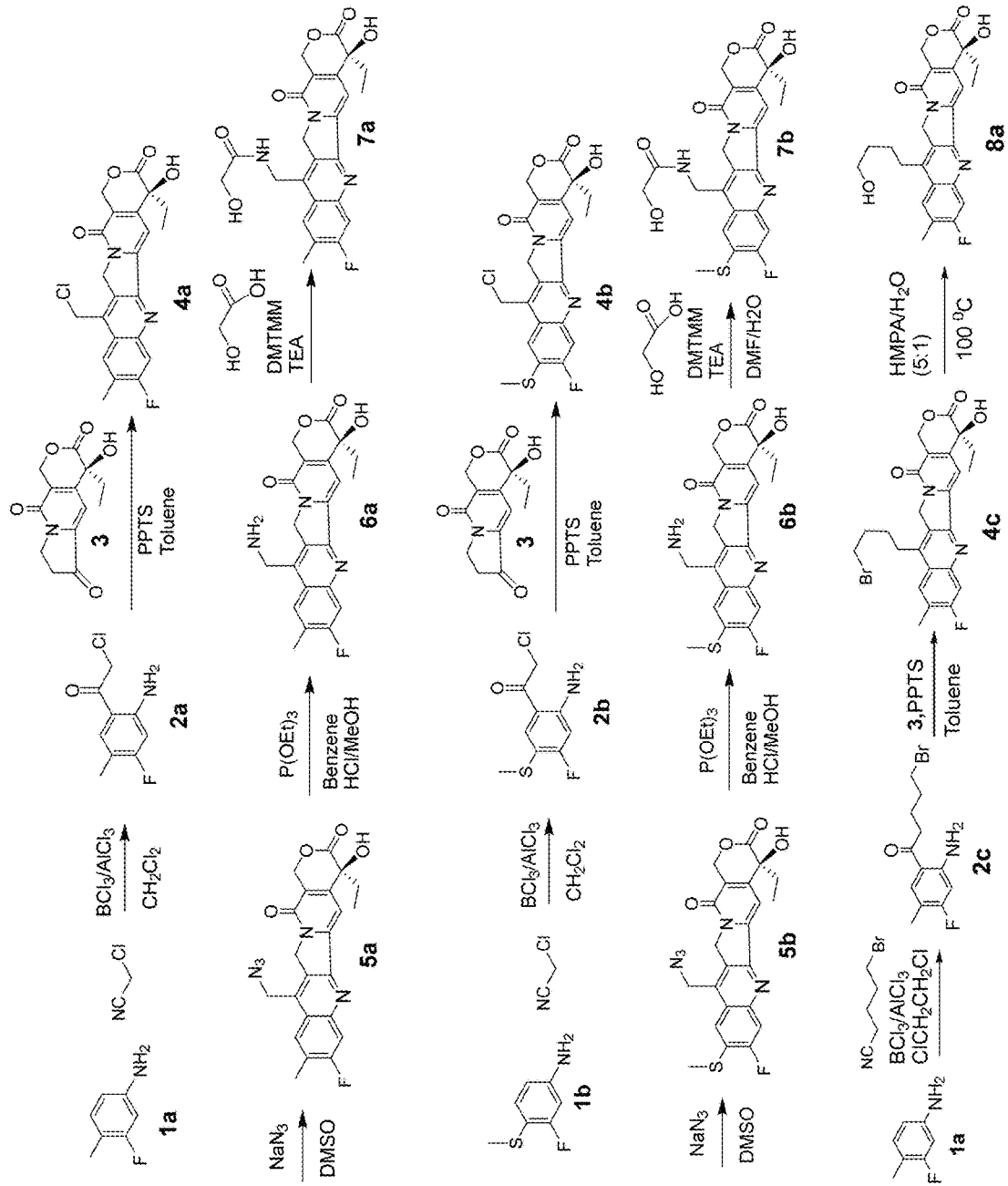
FIG. 1 depicts the first part of the synthesis of camptothecin building blocks.

In order that the invention described herein may be fully understood, the following detailed description is set forth. While the invention will be described in conjunction with the enumerated embodiments, it will be understood that they are not intended to limit the invention to those embodiments. On the contrary, the invention is intended to cover all alternatives, modifications, and equivalents that can be included within the scope of the present invention as defined by the claims. One skilled in the art will recognize many methods and materials similar or equivalent to those described herein, which could be used in the practice of the present invention.

The term "herein" means the entire application.

Unless otherwise defined herein, scientific and technical terms used in this application shall have the meanings that are commonly understood by those of ordinary skill in the art to which this invention belongs. Generally, nomenclature used in connection with the compounds, composition and methods described herein, are those well-known and commonly used in the art.

It should be understood that any of the embodiments described herein, including those described under different aspects of the invention and different parts of the specification (including embodiments described only in the Examples) can be combined with one or more other embodiments of the invention, unless explicitly disclaimed or improper. Combination of embodiments are not limited to those specific combinations claimed via the multiple dependent claims.

Chemistry terms used herein are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. Any information in any material that has been incorporated by reference herein, is only incorporated by reference to the extent that no conflict exists between such information and the other statements and drawings set forth herein. In the event of such conflict, any such conflicting information in such incorporated by reference material is specifically not incorporated by reference herein, and the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Throughout the specification, where compositions are described as having, including, or comprising (or variations thereof), specific components, it is contemplated that compositions also may consist essentially of, or consist of, the recited components. Similarly, where methods or processes are described as having, including, or comprising specific process steps, the processes also may consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "including" is used to mean "including but not limited to." "Including" and "including but not limited to" are used interchangeably.

As used herein, "about" or "approximately" means within an acceptable error range for the particular value as determined by one of ordinary skill in the art, which will depend in part on how the value is measured or determined, i.e., the limitations of the measurement system.

The use of the terms "a" and "an" and "the" and similar referents in the context of describing the elements (especially in the context of the following claims) are to be construed to cover both the singular and the plural, unless otherwise indicated herein or clearly contradicted by context.

The term "or" as used herein should be understood to mean "and/or," unless the context clearly indicates otherwise.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Definitions

The term "alkyl' or "linear or branched alkyl" as used herein refers to a saturated linear or branched monovalent hydrocarbon radical. In preferred embodiments, a straight chain or branched chain alkyl has thirty or fewer carbon atoms (e.g., $C_1$-$C_{30}$ for straight chain alkyl group and $C_3$-$C_{30}$ for branched alkyl), and more preferably twenty or fewer carbon atoms. Even more preferably, the straight chain or branched chain alkyl has ten or fewer carbon atoms (i.e., $C_1$-$C_{10}$ for straight chain alkyl group and $C_3$-$C_{10}$ for branched alkyl). In other embodiments, the straight chain or branched chain alkyl has six or fewer carbon atoms (i.e., $C_1$-$C_6$ for straight chain alkyl group or $C_3$-$C_6$ for branched chain alkyl). Examples of alkyl include, but are not limited to, methyl, ethyl, 1-propyl, 2-propyl, 1-butyl, 2-methyl-1-propyl, —CH$_2$CH(CH$_3$)$_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Moreover, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. As used herein, ($C_x$-$C_{xx}$)alkyl or means a linear or branched alkyl having x-xx number of carbon atoms.

The term "alkylene" as used herein refers to a saturated linear or branched divalent hydrocarbon radical. In preferred embodiments, a straight chain or branched chain alkylene has thirty or fewer carbon atoms (e.g., $C_1$-$C_{30}$ for straight chain alkylene group and $C_3$-$C_{30}$ for branched alkylene), and more preferably twenty or fewer carbon atoms. Even more preferably, the straight chain or branched chain alkylene has ten or fewer carbon atoms (i.e., $C_1$-$C_{10}$ for straight chain alkylene group and $C_3$-$C_{10}$ for branched alkylene). In other embodiments, the straight chain or branched chain alkylene has six or fewer carbon atoms (i.e., $C_1$-$C_6$ for straight chain alkylene group or $C_3$-$C_6$ for branched chain alkylene). As used herein, ($C_x$-$C_{xx}$)alkylene or $C_{x-xx}$alkylene means a linear or branched alkylene having x-xx number of carbon atoms.

The term "alkenyl" or "linear or branched alkenyl" refers to linear or branched-chain monovalent hydrocarbon radical of two to twenty carbon atoms with at least one site of unsaturation, i.e., a carbon-carbon double bond, wherein the alkenyl radical includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like. Preferably, the alkenyl has two to ten carbon atoms. More preferably, the alkyl has two to four carbon atoms.

The term "alkynyl" or "linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The terms "cyclic alkyl" and "cycloalkyl" can be used interchangeably. As used herein, the term refers to the radical of a saturated carbocyclic ring. In preferred embodiments, cycloalkyls have from 3 to 10 carbon atoms in their ring structure, and more preferably from 5 to 7 carbon atoms in the ring structure. In some embodiments, the two cyclic rings can have two or more atoms in common, e.g., the rings are "fused rings." Suitable cycloalkyls include, but are not limited to cycloheptyl, cyclohexyl, cyclopentyl, cyclobutyl and cyclopropyl. In some embodiments, the cycloalkyl is a monocyclic group. In some embodiments, the cycloalkyl is a bicyclic group. In some embodiments, the cycloalkyl is a tricyclic group.

The term "cycloalklalkyl" refers to an alkyl group described above that is substituted with a cycloalkyl group.

The term "cyclic alkenyl" refers to a carbocyclic ring radical having at least one double bond in the ring structure.

The term "cyclic alkynyl" refers to a carbocyclic ring radical having at least one triple bond in the ring structure.

The term "aryl" or "aromatic ring" as used herein, include substituted or unsubstituted single-ring aromatic groups in which each atom of the ring is carbon. Preferably the ring is a 5- to 7-membered ring, more preferably a 6-membered ring. Aryl groups include, but are not limited to, phenyl, phenol, aniline, and the like. The terms "aryl" also includes "polycyclyl", "polycycle", and "polycyclic" ring systems having two or more rings in which two or more atoms are common to two adjoining rings, e.g., the rings are "fused rings," wherein at least one of the rings is aromatic, e.g., the other cyclic rings can be cycloalkyls, cycloalkenyls, cycloalkynyls, or aromatic rings. In some preferred embodiments, polycycles have 2-3 rings. In certain preferred embodiments, polycyclic ring systems have two cyclic rings in which both of the rings are aromatic. Each of the rings of the polycycle can be substituted or unsubstituted. In certain embodiments, each ring of the polycycle contains from 3 to 10 carbon atoms in the ring, preferably from 5 to 7. For example, aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl, and the like. In some embodiments, the aryl is a single-ring aromatic group. In some embodiments, the aryl is a two-ring aromatic group. In some embodiments, the aryl is a three-ring aromatic group.

The term "heteroalkyl" refers to an alkyl group in which one or more skeletal atoms of the alkyl are selected from an atom other than carbon, e.g., O, S, N (e.g., —NH, —N(alkyl)-), or combinations thereof. A heteroalkyl is attached to the rest of the molecule at a carbon atom of the heteroalkyl. In one aspect, a heteroalkyl is a $C_1$-$C_{30}$heteroalkyl. A $C_1$-$C_{30}$heteroalkyl refers to an alkyl group having 1 to 30 carbon atoms and 1 to 15 heteroatoms. Examples of $C_1$-$C_{30}$heteroalkyl groups include, but are not limited to, ethers (e.g., —CH$_2$—O—CH$_3$, —(CH$_2$)$_2$—O—CH$_3$, —(CH2)$_3$—O—(CH$_2$)$_2$—O—CH$_3$, —(CH$_2$)$_2$—O—(CH$_2$)$_3$CH$_3$, CH$_2$—O—CH$_2$—O—CH$_3$, —CH$_2$—O—(CH$_2$)$_3$—O—CH$_3$), polyethylene glycol (PEG) derivatives (e.g., —[(CH$_2$)$_2$O]$_{10}$CH$_2$CH$_3$), thiothers (e.g., —CH$_2$—S—CH$_3$, —(CH$_2$)$_2$—S—CH$_3$, —(CH$_2$)$_3$—S—(CH$_2$)$_2$CH$_3$, —((CH$_2$)$_2$S)$_{10}$CH$_2$CH$_3$), —CH$_2$—S—S—CH$_2$, —(CH$_2$)$_2$—S—(CH$_2$)$_3$CH$_3$, CH$_2$—S—CH$_2$—S—CH$_3$, —CH$_2$—S—(CH$_2$)$_3$—S—CH$_3$), amines (e.g., —CH$_2$—NH—CH$_3$, —(CH$_2$)$_2$—N(alkyl)-CH$_3$, —(CH$_2$)$_3$—NH—(CH$_2$)$_2$CH$_3$, —(CH$_2$)$_2$—N(alkyl)-(CH$_2$)$_3$CH$_3$, CH$_2$—NH—CH$_2$—NH—CH$_3$, —CH$_2$—NH—(CH$_2$)$_3$—NH—CH$_3$), or combinations thereof. This disclosure also contemplates $C_1$-$C_{30}$heteroalkyl groups wherein one of the 1 to 15 heteroatoms occupies the terminal position of the alkyl group, resulting in, for example, an alcohol (i.e., OH), thiol (i.e., SH), or amine (e.g., —NH$_2$) in the terminal position of the moiety.

The term "heteroalkenyl" refers to an alkenyl group as defined herein, in which one or more of the carbon atoms have been replaced by a heteroatom, e.g., O, S, N (e.g., —NH, —N(alkyl)-). A heteroalkenyl is attached to the rest of the molecule at a carbon atom of the heteroalkenyl. In one aspect, a heteroalkenyl is a $C_1$-$C_{30}$heteroalkenyl. A $C_1$-$C_{30}$heteroalkenyl refers to an alkenyl group having 1 to 30 carbon atoms and 1 to 15 heteroatoms, for example, 1 to 10 heteroatoms or 1 to 5 heteroatoms. This disclosure also contemplates $C_1$-$C_{30}$heteroalkenyl groups wherein one of the 1 to 15 heteroatoms occupies the terminal position of the alkenyl group, resulting in, for example, an alcohol (i.e., OH), thiol (i.e., SH), amine (e.g., —NH$_2$), or imine (—C=N) in the terminal position of the moiety.

The term "heteroalkynyl" refers to an alkenyl group as defined herein, in which one or more of the carbon atoms have been replaced by a heteroatom, e.g., O, S, N (e.g., —NH, —N(alkyl)-). A heteroalkynyl is attached to the rest of the molecule at a carbon atom of the heteroalkynyl. In one aspect, a heteroalkynyl is a $C_1$-$C_{30}$heteroalkynyl. A $C_1$-$C_{30}$heteroalkenyl refers to an alkynyl group having 1 to 30 carbon atoms and 1 to 15 heteroatoms, for example, 1 to 10 heteroatoms or 1 to 5 heteroatoms. This disclosure also contemplates $C_1$-$C_{30}$heteroalkynyl groups wherein one of the 1 to 15 heteroatoms occupies the terminal position of the alkynyl group, resulting in, for example, an alcohol (i.e., OH), thiol (i.e., SH), amine (e.g., —NH$_2$), or nitrile (—CN) in the terminal position of the moiety.

The terms "heterocycle," "heterocyclyl," and "heterocyclic ring" as used herein, refers to substituted or unsubstituted non-aromatic ring structures of 3- to 18-membered rings, preferably 3- to 10-membered rings, more preferably 3- to 7-membered rings, whose ring structures include at least one heteroatom, preferably one to four heteroatoms, more preferably one or two heteroatoms. In certain embodiments, the ring structure can have two cyclic rings. In some embodiments, the two cyclic rings can have two or more atoms in common, e.g., the rings are "fused rings." Heterocyclyl groups include, for example, piperidine, piperazine, pyrrolidine, morpholine, lactones, lactams, and the like. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, tetrahydrofurane, dihydrofuran, tetrahydrothiene, tetrahydropyran, dihydropyran, tetrahydrothiopyran, thiomorpholine, thioxane, homopiperazine, azetidine, oxetane, thietane, homopiperidine, piperidine, piperazine, pyrrolidine, morpholine, oxepane, thiepane, oxazepine, diazepine, thiazepine, 2-pyrroline, 3-pyrroline, indoline, 2H-pyrane, 4H-pyrane, dioxane, 1,3-dioxolane, pyrazoline, dithiane, dithiolane, dihydropyrane, dihydrothiene, dihydrofurane, pyrazolidinylimidazoline, imidazolidine, 3-azabicyco[3.1.0]hexane, 3-azabicyclo[4.1.0]heptane, and azabicyclo[2.2.2]hexane. Spiro moieties are also included within the scope of this definition. Examples of a heterocyclic group wherein ring atoms are substituted with oxo (=O) moieties are pyrimidinone and 1,1-dioxo-thiomorpholine.

The term "heteroaryl" or "heteroaromatic ring" as used herein, refers to substituted or unsubstituted aromatic single ring structures, preferably 6- to 18-member rings, preferably 5- to 7-membered rings, more preferably 5- to 6-membered rings, whose ring structures include at least one heteroatom (e.g., O, N, or S), preferably one to four or one to three heteroatoms, more preferably one or two heteroatoms. When two or more heteroatoms are present in a heteroaryl ring, they may be the same or different. The term "heteroaryl" also includes "polycyclyl", "polycycle", and "polycyclic" ring systems having two or more cyclic rings in which two or more ring atoms are common to two adjoining rings, e.g., the rings are "fused rings," wherein at least one of the rings is heteroaromatic, e.g., the other cyclic rings can be cycloalkyls, cycloalkenyls, cycloalkynyls, aryls, heteroaromatics, and/or heterocyclyls. In some preferred embodiments, polycyclic heteroaryls have 2-3 rings. In certain embodiments, preferred polycyclic heteroaryls have two cyclic rings in which both of the rings are aromatic. In certain embodiments, each ring of the polycycle contains from 3 to 10 atoms in the ring, preferably from 5 to 7 atoms in the ring. For examples, heteroaryl groups include, but are not limited to, pyrrole, furan, thiophene, imidazole, oxazole, thiazole, pyrazole, pyridine, pyrazine, pyridazine, quinoline, pyrimidine, indolizine, indole, indazole, benzimidazole, benzothiazole, benzofuran, benzothiophene, cinnoline, phthalazine, quinazoline, carbazole, phenoxazine, quinoline, purine and the like. In some embodiments, the heteroaryl is a single-ring aromatic group. In some embodiments, the heteroaryl is a two-ring aromatic group. In some embodiments, the heteroaryl is a three-ring aromatic group.

The heterocycle or heteroaryl groups can be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclyl include the oxidized forms such as NO, SO, and $SO_2$.

In some embodiments, the heteroaromatic ring is a 5- to 18-membered ring.

The term "halo" or "halogen" refers to fluorine (F), chlorine (Cl), bromine (Br) or iodine (I). In some embodiments, the halogen is fluorine. In some embodiments, the halogen is chlorine. In some embodiments, the halogen is bromine. In some embodiments, the halogen is iodine. As used herein, the term "haloalkyl" refers to an alkyl, as defined herein, that is substituted by one or more halo groups as defined herein. The haloalkyl can be monohaloalkyl, dihaloalkyl or polyhaloalkyl. A monohaloalkyl can have one fluoro, chloro, bromo, or iodo substituent. Dihaloalkyl or polyhaloalkyl can be substituted with two or more of the same halo atoms or a combination of different halo groups. Examples of haloalkyl include, but are not limited to, fluoromethyl, difluoromethyl, trifluoromethyl, chloroamethyl, dichloromethyl, trichloromethyl, pentafluoroethyl, heptafluoropropyl, diflurochloromethyl, dichlorofluoromethyl, difluoroehthyl, diflosoropropyl, dichloroethyl and dichloropropyl.

The term "alkoxy" used herein refers to alkyl-O—, wherein alkyl is defined herein above. Examples of alkoxy include, not are not limited to, methoxy, ethoxy, propoxy, 2-propoxy, butoxy, tert-butoxy, pentyloxy, hexyloxy, and the like.

The alkyl, haloalkyl, alkoxy, alkenyl, alkynyl, cyclic alkyl, cyclic alkenyl, cyclic alkynyl, carbocyclyl, aryl, heterocyclyl and heteroaryl described above can be optionally substituted with one or more (e.g., 2, 3, 4, 5, 6 or more) substituents.

Unless specifically stated as "unsubstituted," references to chemical moieties herein are understood to also include substituted variants. For example, reference to an "alkyl" group or moiety implicitly includes both substituted and unsubstituted variants. Examples of substituents on chemical moieties includes but is not limited to, halogen, hydroxyl, carbonyl (such as carboxyl, alkoxycarbonyl, formyl, or acyl), thiocarbonyl (such as thioester, thioacetate, or thioformate), alkoxyl, alkylthio, acyloxy, phosphoryl, phosphate, phosphonate, amino, amido, amidine, imine, cyano, nitro, azido, sulfhydryl, alkylthio, sulfate, sulfonate, sulfamoyl, sulfonamido, sulfonyl, heterocyclyl, aralkyl, or aryl or heteroaryl moiety.

"Optional" or "optionally" means that the subsequently described circumstance may or may not occur, so that the application includes instances where the circumstance occurs and instances where it does not. For example, the phrase "optionally substituted" means that a nonhydrogen substituent may or may not be present on a given atom, and, thus, the application includes structures wherein a nonhydrogen substituent is present and structures wherein a nonhydrogen substituent is not present.

The term "substituted" refers to moieties having substituents replacing a hydrogen on one or more carbons, nitrogens, oxygens or sulfurs atoms. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a carbon of a substituent is described as being optionally substituted with one or more of a list of substituents, one or more of the hydrogens on the carbon (to the extent there are any) can separately and/or together be replaced with an independently selected optional substituent. If a nitrogen of a substituent is described as being optionally substituted with one or more of a list of substituents, one or more of the hydrogens on the nitrogen (to the extent there are any) can each be replaced with an independently selected optional substituent. One exemplary substituent can be depicted as —NR'R", wherein R' and R" together with the nitrogen atom to which they are attached, can form a heterocyclic ring. The heterocyclic ring formed from R' and R" together with the nitrogen atom to which they are attached can be partially or fully saturated. In some embodiments, the heterocyclic ring consists of 3 to 7 atoms. In other embodiments, the heterocyclic ring is selected from pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group can include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent can be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocyclyl, halogen, guanidinium [—NH(C=NH)NH$_2$], —OR$^{10}$, NR$^{101}$R$^{102}$, —NO$_2$, —NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—OCH$_2$CH$_2$)$_n$R$^{101}$ wherein M is H or a cation (such as Na$^+$ or K$^+$); R$^{101}$, R$^{102}$ and R$^{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyclyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, —CN, —NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —CF$_3$, —OR$^{101}$, aryl, heteroaryl, heterocyclyl, —SR$^{101}$, —SOR$^{101}$, —SO$_2$R$^{101}$ and —SO$_3$M.

For sulfoxides, represented by —SOR$^{101}$ as indicated in the preceding paragraph, both optical isomers (R and S configurations at the sulfur atom of the sulfoxide group) are encompassed.

The number of carbon atoms in a group can be specified herein by the prefix "C$_{x\text{-}xx}$" or "C$_x$-C$_{xx}$", wherein x and xx are integers. For example, "C$_{1\text{-}4}$alkyl" or "C$_1$-C$_4$ alkyl" is an alkyl group having from 1 to 4 carbon atoms.

The term "compound" or "cytotoxic compound," "cytotoxic dimer" and "cytotoxic dimer compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "conjugate" as used herein refers to a compound described herein or a derivative thereof that is linked to a cell binding agent.

The term "chiral" refers to molecules that have the property of non-superimposability of the mirror image partner, while the term "achiral" refers to molecules that are superimposable on their mirror image partner.

The term "stereoisomer" refers to compounds that have identical chemical constitution and connectivity, but different orientations of their atoms in space that cannot be interconverted by rotation about single bonds.

The term "diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as crystallization, electrophoresis and chromatography.

The term "enantiomers" refer to two stereoisomers of a compound that are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light.

In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies that are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt can involve the inclusion of another molecule such as an acetate ion, a succinate ion or other counter ion. The counter ion can be any organic or inorganic moiety that stabilizes the charge on the parent compound. Furthermore, a pharmaceutically acceptable salt can have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt can be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt can be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound that further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The phrase "pharmaceutically acceptable" indicates that the substance or composition must be compatible chemically and/or toxicologically, with the other ingredients comprising a formulation, and/or the mammal being treated therewith.

The term "leaving group" refers to a group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "reactive ester" refers to an ester having an easily displaceable leaving group that can readily react with an amine group to form an amide bond. Examples of reactive esters include, but are not limited to, N-hydroxysuccinimide ester, N-hydroxy sulfosuccinimide ester, nitrophenyl (e.g., 2 or 4-nitrophenyl) ester, dinitrophenyl (e.g., 2,4-dinitrophenyl) ester, sulfo-tetrafluorophenyl (e.g., 4 sulfo-2,3,5,6-tetrafluorophenyl) ester, or pentafluorophenyl ester.

The term "reactive group" refers to a group that can react with a moiety located on another molecule, such as the cell-binding agent or the cytotoxic compound, to form a covalent bond. The reactive group includes, but is not limited to an amine reactive group and a thiol reactive group.

The term "amine reactive group" refers to a group that can react with an amine group to form a covalent bond. Exemplary amine reactive groups include, but are not limited to, reactive ester groups, acyl halides, sulfonyl halide, imidoester, or a reactive thioester groups. In certain embodiments, the amine reactive group is a reactive ester group. In one embodiment, the amine reactive group is a N-hydroxysuccinimide ester or a N-hydroxy sulfo-succinimide ester.

The term "thiol-reactive group" refers to a group that can react with a thiol (—SH) group to form a covalent bond. Exemplary thiol-reactive groups include, but are not limited to, maleimide, haloacetyl, haloacetamide, vinyl sulfone, vinyl sulfonamide or vinyl pyridine. In one embodiment, the thiol-reactive group is maleimide.

The term "bifunctional crosslinking agent," "bifunctional linker" or "crosslinking agents" refers to modifying agents that possess two reactive groups; one of which is capable of reacting with a cell-binding agent while the other one reacts with the cytotoxic compound to link the two moieties together. Such bifunctional crosslinkers are well known in the art (see, for example, Isalm and Dent in *Bioconjugation* chapter 5, p 218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SLAB) to introduce iodoacetyl groups. Other bifunctional crosslinking agents that introduce maleimido groups or haloacetyl groups on to a cell binding agent are well known in the art (see US Patent Applications 2008/0050310, 20050169933, available from Pierce Biotechnology Inc. P.O. Box 117, Rockland, Ill. 61105, USA) and include, but not limited to, bis-maleimidopolyethyleneglycol (BMPEO), $BM(PEO)_2$, $BM(PEO)_3$, N-(β-maleimidopropyloxy)succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), κ-maleimidoundecanoic acid N-succinimidyl ester (KMUA), N-succinimidyl 4-(p-maleimidophenyl)-butyrate (SMPB), succinimidyl-6-(β-maleimidopropionamido) hexanoate (SMPH), succinimidyl-(4-vinyl sulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodo-acetyl)aminobenzoate (sulfo-SLAB), m-maleimidobenzoyl-N-hydroxysulfosuccinimide ester (sulfo-MBS), N-(γ-maleimidobutryloxy)sulfosuccinimide ester (sulfo-GMBS), N-(ε-maleimidocaproyloxy) sulfosuccimido ester (sulfo-EMCS), N-(κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA). Bifunctional crosslinking agents that enable the linkage of cell binding agent with cytotoxic compounds via disulfide bonds are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio) butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 20090274713 and 20100129314, all of which are incorporated herein by reference. Alternatively, crosslinking agents such as 2-iminothiolane, homocysteine thiolactone or S-acetylsuccinic anhydride that introduce thiol groups can also be used.

The term "linker," "linker moiety," or "linking group" as defined herein refers to a moiety that connects two groups, such as a cell binding agent and a cytotoxic compound, together. Typically, the linker is substantially inert under conditions for which the two groups it is connecting are linked. A bifunctional crosslinking agent can comprise two reactive groups, one at each ends of a linker moiety, such that one reactive group can be first reacted with the cytotoxic compound to provide a compound bearing the linker moiety and a second reactive group, which can then react with a cell binding agent. Alternatively, one end of the bifunctional crosslinking agent can be first reacted with the cell binding agent to provide a cell binding agent bearing a linker moiety and a second reactive group, which can then react with a cytotoxic compound. The linking moiety can contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in US 2009/0274713, US 2010/01293140 and WO 2009/134976, each of which is expressly incorporated herein by reference, each of which is expressly incorporated herein by reference.

The term "self-immolative linker" refers to a linker that will allow for release of the cytotoxic compound when a remote site is activated. In certain embodiments, the linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) Expert Opin. Ther. Patents (2005) 15:1087-1103). In some embodiments, the linker comprises p-aminobenzyloxycarbonyl (PAB). Other examples of self-immolative linkers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Linkage of a drug to the a-carbon of a glycine residue is another example of a self-immolative linker that may be useful in ADC (Kingsbury et al (1984) J. Med. Chem. 27:1447).

The term "amino acid" refers to naturally occurring amino acids or non-naturally occurring amino acid. In some embodiments, the amino acid is represented by $NH_2$—$(R^{aa'}R^{aa})$—$C(=O)OH$, wherein $R^{aa}$ and $R^{aa'}$ are each independently H, an optionally substituted linear, branched or cyclic alkyl, alkenyl or alkynyl having 1 to 10 carbon atoms, aryl, heteroaryl or heterocyclyl or $R^{aa}$ and the N-terminal nitrogen atom can together form a heterocyclic ring (e.g., as in proline). The term "amino acid residue" refers to the corresponding residue when one hydrogen atom is removed from the amine and/or carboxy end of the amino acid, such as —NH—$C(R^{aa'}R^{aa})$—$C(=O)$—.

The term "peptide" refers to short chains of amino acid monomers linked by peptide (amide) bonds. In some embodiments, the peptides contain 2 to 20 amino acid residues. In other embodiments, the peptides contain 2 to 10 or 2 to 8 amino acid residues. In yet other embodiments, the peptides contain 2 to 5 amino acid residues. As used herein, when a peptide is a portion of a cytotoxic agent or a linker described herein represented by a specific sequence of amino acids, the peptide can be connected to the rest of the cytotoxic agent or the linker in both directions.

The term "cation" refers to an ion with positive charge. The cation can be monovalent (e.g., $Na^+$, $K^+$, etc.), bi-valent (e.g., $Ca^{2+}$, $Mg^{2+}$, etc.) or multi-valent (e.g., $Al^{3+}$ etc.). Preferably, the cation is monovalent.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, and Fv fragments), single chain Fv (scFv) mutants, multispecific antibodies (e.g., bispecific antibodies, biparatopic antibodies, etc.), multivalent antibodies (e.g., trivalent, tetravalent, etc. antibodies that have three, four or more antigen binding sites) chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. As used herein "antibody" also includes is an activatable antibody (e.g., a probody). By activatable is meant that the activatable antibody, exhibits a first level of binding to a target when the activatable antibody, is in an inhibited, masked, intact or uncleaved state (i.e., a first conformation), and a second level of binding to the target in the uninhibited, unmasked and/or cleaved state (i.e., a second conformation), where the second level of target binding is greater than the first level of binding.

In some embodiments, an antibody is a non-naturally occurring antibody. In some embodiments, an antibody is purified from natural components. In some embodiments, an antibody is recombinantly produced. In some embodiments, an antibody is produced by a hybridoma.

The term "antibody fragment" refers to a portion of an intact antibody and refers to the antigenic determining variable regions of an intact antibody. Examples of antibody fragments include, but are not limited to, Fab, Fab', F(ab')$_2$, and $F_v$ fragments, linear antibodies, single chain antibodies, and multispecific antibodies (e.g., bispecific, biparatopic) formed from antibody fragments. The term "antigen-binding fragment" of an antibody includes one or more fragments of an antibody that retain the ability to specifically bind to an antigen. It has been shown that the antigen-binding function of an antibody can be performed by certain fragments of a full-length antibody. Examples of binding fragments encompassed within the term "antigen-binding fragment" of an antibody include (without limitation): (i) an Fab fragment, a monovalent fragment consisting of the $V_L$, $V_H$, $C_L$, and $C_{H1}$ domains (e.g., an antibody digested by papain yields three fragments: two antigen-binding Fab fragments, and one Fc fragment that does not bind antigen); (ii) a single chain Fab (scFab), a fragment consisting of the $V_L$, $V_H$, $C_L$, and $C_{H1}$ domains, wherein the $C_L$ and $V_H$ domains are linked via a linker peptide; (iii) a F(ab')$_2$ fragment, a bivalent fragment comprising two Fab fragments linked by a disulfide bridge at the hinge region (e.g., an antibody digested by pepsin yields two fragments: a bivalent antigen-binding F(ab')$_2$ fragment, and a pFc' fragment that does not bind antigen) and its related F(ab') monovalent unit; (iv) a $F_d$ fragment consisting of the $V_H$ and $C_{H1}$ domains (i.e., that portion of the heavy chain which is included in the Fab); (v) a $F_v$ fragment consisting of the $V_L$ and $V_H$ domains of a single arm of an antibody, and the related disulfide linked $F_v$; (vi) a dAb (domain antibody) or sdAb (single domain antibody) fragment (Ward et al., Nature 341:544-546, 1989), which consists of a $V_H$ domain; (vii) an isolated complementarity determining region (CDR); (viii) a single chain variable fragment (scFv), a fragment consisting of a $V_H$ and $V_L$ domain, connected via a linker peptide; and (ix) a tetravalent antibody, which may include various formats (structures) whereby the antibody comprises 4 antigen binding sites.

The term "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')$_2$, $F_v$), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability (Jones et al., Nature 321:522-525, 1986; Riechmann et al., Nature 332:323-327, 1988; Verhoeyen et al., Science 239:1534-1536, 1988).

In some instances, the $F_v$ framework region (FR) residues of a human immunoglobulin are replaced with the corresponding residues in an antibody from a non-human species that has the desired specificity, affinity, and capability. The humanized antibody can be further modified by the substitution of additional residues either in the $F_v$ framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain ($F_c$), typically that of a human immunoglobulin. Examples of methods used to generate humanized antibodies are described in U.S. Pat. Nos. 5,225,539 and 5,639,641, Roguska et al., Proc. Natl. Acad. Sci. USA 91(3):969-973, 1994; and Roguska et al., Protein Eng. 9(10):895-904, 1996 (all incorporated herein by reference). In some embodiments, a "humanized antibody" is a resurfaced antibody. In some embodiments, a "humanized antibody" is a CDR-grafted antibody.

The term "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. *Sequences of Proteins of Immunological Interest*, 5th ed., 1991, National Institutes of Health, Bethesda Md.); and (2) an approach based on crystallographic studies of antigen-antibody complexes (Al-lazikani et al., *J. Molec. Biol.* 273:927-948, 1997). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., *Sequences of Immunological Interest*, 5th Ed., Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., *Sequences of Proteins of Immunological Interest*, 5th Ed., Public Health Service, National Institutes of Health, Bethesda, Md. (1991) (incorporated herein by reference). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917,1987). The end of the Chothia CDR-H1 loop when numbered using the Kabat numbering convention varies between H32 and H34 depending on the length of the loop. This is because the Kabat numbering scheme places the insertions at H35A and H35B—if neither 35A nor 35B is present, the loop ends at 32; if only 35A is present, the loop ends at 33; if both 35A and 35B are present, the loop ends at 34. The AbM hypervariable regions represent a compromise between the Kabat CDRs and Chothia structural loops, and are used by Oxford Molecular's AbM antibody modeling software.

| Loop | Kabat   | AbM     | Chothia |
|------|---------|---------|---------|
| L1   | L24-L34 | L24-L34 | L24-L34 |
| L2   | L50-L56 | L50-L56 | L50-L56 |

-continued

| Loop | Kabat    | AbM                            | Chothia     |
|------|----------|--------------------------------|-------------|
| L3   | L89-L97  | L89-L97                        | L89-L97     |
| H1   | H31-H35B | H26-H35B<br>(Kabat Numbering)  | H26-H32..34 |
| H1   | H31H35   | H26-H35<br>(Chothia Numbering) | H26-H32     |
| H2   | H50-H65  | H50-H58                        | H52-H56     |
| H3   | H9S-H102 | H95-H102                       | H95-H102    |

The EU index or EU index as in Kabat or EU numbering scheme refers to the numbering system based on the human IgG1 Eu antibody of Edelman et al., 1969, Proc Natl Acad Sci USA 63:78-85, incorporated herein by reference.

The term "human antibody" means an antibody produced by a human or an antibody having an amino acid sequence corresponding to an antibody produced by a human made using any technique known in the art. In certain embodiments, the human antibody does not have non-human sequence. This definition of a human antibody includes intact or full-length antibodies, or antigen-binding fragments thereof.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid or reduce the chance of eliciting an immune response in that species (e.g., human). In certain embodiments, chimeric antibody may include an antibody or antigen-binding fragment thereof comprising at least one human heavy and/or light chain polypeptide, such as, for example, an antibody comprising murine light chain and human heavy chain polypeptides.

The terms "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$) or the half-maximal effective concentration ($EC_{50}$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described herein.

By "specifically binds," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

The term "immunoconjugate," "conjugate," or "ADC" as used herein refers to a compound or a derivative thereof that is linked to a cell binding agent (e.g., an antibody or antigen-binding fragment thereof).

The term "cysteine-engineered antibody" includes an antibody with at least one Cys that is not normally present at a given residue of the antibody light chain or heavy chain. Such Cys, which may also be referred to as "engineered Cys," can be engineered using any conventional molecular biology or recombinant DNA technology (e.g., by replacing the coding sequence for a non-Cys residue at the target residue with a coding sequence for Cys). For example, if the original residue is Ser with a coding sequence of 5'-UCU-3', the coding sequence can be mutated (e.g., by site-directed mutagenesis) to 5'-UGU-3', which encodes Cys. In certain embodiments, the Cys engineered antibody of the invention has an engineered Cys in the heavy chain. In certain embodiments, the engineered Cys is in or near the $CH_3$ domain of the heavy chain. In certain embodiments, the engineered Cys is at residue 442 of the heavy chain (EU/OU numbering). The C442 residue can be conjugated with a cytotoxic drug/agent through the free thiol group of the C442 residue, such as through reacting with a thiol-reactive agent of the cytotoxic drug (e.g., a maleimido group).

The terms "cancer" and "cancerous" refer to or describe the physiological condition in mammals in which a population of cells are characterized by unregulated cell growth. "Tumor" and "neoplasm" refer to one or more cells that result from excessive cell growth or proliferation, either benign (noncancerous) or malignant (cancerous) including pre-cancerous lesions.

Examples of cancer include endometrial cancer, lung cancer (e.g., non-small-cell lung cancer), colorectal cancer, bladder cancer, gastric cancer, pancreatic cancer, renal cell carcinoma, prostate cancer, esophageal cancer, breast cancer, head and neck cancer, uterine cancer, ovarian cancer, liver cancer, cervical cancer, thyroid cancer, testicular cancer, myeloid cancer, melanoma, and lymphoid cancer. In certain embodiments, the cancer is non-small-cell lung cancer, colorectal cancer, gastric cancer or pancreatic cancer. In certain embodiments, the cancer is non-small-cell lung cancer (squamous cell, nonsquamous cell, adenocarcinoma, or large-cell undifferentiated carcinoma), colorectal cancer (adenocarcinoma, gastrointestinal carcinoid tumors, gastrointestinal stromal tumors, primary colorectal lymphoma, leiomyosarcoma, or squamous cell carcinoma) or breast cancer (e.g., triple negative breast cancer (TNBC)). In certain embodiments, cancer is lymphoma and leukemia. In certain embodiments, examples of cancers include AML, CML, ALL (e.g., B-ALL), CLL, myelodysplastic syndrome, basic plasmacytoid DC neoplasm (BPDCN) leukemia, B-cell lymphomas including non-Hodgkin lymphomas (NHL), precursor B-cell lymphoblastic leukemia/lymphoma and mature B-cell neoplasms, such as B-cell chronic lymphocytic leukemia (B-CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia (HCL), diffuse large B-cell lymphoma (DLBCL), Burkitt's lymphoma, plasmacytoma, plasma cell myeloma, post-transplant lymphoproliferative disorder, Waldenstrom's macroglobulinemia, anaplastic large-cell lymphoma (ALCL), and Hodgkin's leukemia (HL). In certain embodiments, the cancer is BPDCN leukemia. In certain embodiments, the cancer is ALL. In other embodiments, the cancer is AML.

The term "subject" refers to any animal (e.g., a mammal), including, but not limited to humans, non-human primates, rodents, and the like, which is to be the recipient of a particular treatment. Typically, the terms "subject," "patient," and "individual" are used interchangeably herein in reference to a human subject.

The term "pharmaceutical composition" refers to a preparation which is in such form as to permit the biological activity of the active ingredient to be effective, and which contains no additional components which are unacceptably toxic to a subject to which the composition would be administered. Such composition can be sterile.

A "therapeutically effective amount" as used herein is an amount of a compound or composition sufficient to carry out a specifically stated purpose. The full therapeutic effect may not necessarily occur by administration of one dose, and may occur only after administration of a series of doses. The particular "therapeutically effective amount" will depend upon e.g., the age, weight and medical condition of the subject, as well as on the method of administration and the therapeutic or combination of therapeutics selected for administration. A "therapeutically effective amount" can be determined empirically and in a routine manner, in relation to the stated purpose.

As used herein, the term "treating," "treat," or "treatment" includes reversing, reducing, or arresting the symptoms, clinical signs or underlying pathology of a condition in a manner to improve, or stabilize the subject's condition. As used herein, and as well understood in the art, "treatment" is an approach for obtaining beneficial or desired results, including clinical results. Beneficial or desired results include, but are not limited to, prevention, alleviation, amelioration, or slowing the progression of one or more symptoms or conditions associated with a condition, diminishment of extent of disease, stabilized state of disease, delay or slowing of disease progression, amelioration or palliation of disease state, and remission (partial or total), whether detectable or undetectable. "Treatment" can also mean prolonging survival as compared to expected survival if not receiving treatment.

Compounds

In one aspect, the invention provides a compound of Formula I, or a pharmaceutically acceptable salt, thereof:

$$Z-L^1-D \quad \text{(Formula I)}$$

wherein:
D is represented by the following structural formula:

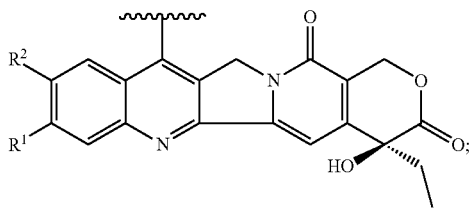

$R^1$ is —F, —CH$_3$, or —CF$_3$;
$R^2$ is —H, —F, —OR$^3$, —SR$^3$, —S(O)R$^4$, —S(O)$_2$R$^4$, C$_1$-C$_6$ alkyl, or C$_1$-C$_6$ fluoroalkyl; or R$^1$ and R$^2$ taken together with the carbon atoms to which they are attached form a methylenedioxy or a difluoromethylenedioxy ring;
$R^3$ is H or C$_1$-C$_6$ alkyl;
$R^4$ is C$_1$-C$_6$ alkyl;
$L^1$ is absent, —(C$_1$-C$_6$ alkylene)-, alkylene)-X$^1$—(C$_1$-C$_6$ alkylene)-, alkylene)-*, or —(C$_1$-C$_6$ alkylene)-X$^1$-L$^2$-*; where * is the site covalently attached to Z;
$X^1$ is —O—, —S—, —S(O)—, —S(O)$_2$—, —C(=O)—, —NR$^5$—, —NR$^5$C(=O)—, or —C(=O)NR$^5$—;
$X^{1'}$ is —O—, —S—, —S(O)—, or —S(O)$_2$—;
$L^2$ is phenylene;
each $R^5$ is independently —H, C$_1$-C$_6$ fluoroalkyl, C$_3$-C$_6$ cycloalkyl, aryl, heteroaryl, or benzyl;
Z is —H or —X$^2$;
$X^2$ is —OR$^6$, —SR$^6$, —S(O)R$^6$, —S(O)$_2$R$^6$, —SSR$^6$, or —N(R$^6$)$_2$;
each $R^6$ is independently —H, C$_1$-C$_6$ alkyl, C$_1$-C$_6$ fluoroalkyl, C$_3$-C$_6$ cycloalkyl, aryl, heteroaryl, or benzyl;
$L^1$ and $L^2$ are each independently optionally substituted with 1-4 substituents selected from halogen, —CN, —OR$^7$, —SR$^7$, —N(R$^7$)$_2$, C$_1$-C$_6$ alkyl, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, or heteroaryl; and
each $R^7$ is independently H, C$_1$-C$_6$ alkyl, C$_1$-C$_6$ fluoroalkyl, C$_3$-C$_6$ cycloalkyl, aryl, heteroaryl, or benzyl;
with the proviso that if R$^1$ is F, then L$^1$ is —(C$_1$-C$_6$ alkylene)-, —(C$_1$-C$_6$ alkylene)-X$^1$—(C$_1$-C$_6$ alkylene)-, —X$^{1'}$—(C$_1$-C$_6$ alkylene)-*, or —(C$_1$-C$_6$ alkylene)-X$^1$-L$^2$-*; where * is the site covalently attached to Z; and Z is —X$^2$; and
with the proviso that if R$^1$ is F and R$^2$ is —OMe, then -L$_1$-Z cannot be —NH$_2$.

In some embodiments, the invention provides a compound of Formula I, or a pharmaceutically acceptable salt, thereof:

Z-L$^1$-D          (Formula I)

wherein:
D is represented by the following structural formula:

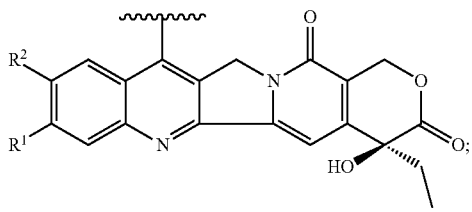

$R^1$ is —F, —CH$_3$, or —CF$_3$;
$R^2$ is —H, —F, —OR$^3$, —SR$^3$, —S(O)R$^4$, —S(O)$_2$R$^4$, C$_1$-C$_6$ alkyl, or C$_1$-C$_6$ fluoroalkyl; or R$^1$ and R$^2$ taken together with the carbon atoms to which they are attached form a methylenedioxy or a difluoromethylenedioxy ring;
$R^3$ is H or C$_1$-C$_6$ alkyl;
$R^4$ is C$_1$-C$_6$ alkyl;
$L^1$ is absent, —(C$_1$-C$_6$ alkylene)-, —(C$_1$-C$_6$ alkylene)-X$^1$—(C$_1$-C$_6$ alkylene)-, —X$^{1'}$—(C$_1$-C$_6$ alkylene)-*, or —(C$_1$-C$_6$ alkylene)-X$^1$-L$^2$-*; where * is the site covalently attached to Z;
$X^1$ is —O—, —S—, —S(O)—, —S(O)$_2$—, —C(=O)—, —NR$^5$—, —NR$^5$C(=O)—, or —C(=O)NR$^5$—;
$X^{1'}$ is —O—, —S—, —S(O)—, or —S(O)$_2$—;
$L^2$ is phenylene;
each $R^5$ is independently —H, C$_1$-C$_6$ alkyl, C$_1$-C$_6$ fluoroalkyl, C$_3$-C$_6$ cycloalkyl, aryl, heteroaryl, or benzyl;
Z is —H or —X$^2$;
$X^2$ is —OR$^6$, —SR$^6$, —S(O)R$^6$, —S(O)$_2$R$^6$, —SSR$^6$, or —N(R$^6$)$_2$;
each $R^6$ is independently —H, C$_1$-C$_6$ alkyl, C$_1$-C$_6$ fluoroalkyl, C$_3$-C$_6$ cycloalkyl, aryl, heteroaryl, or benzyl;
$L^1$ and $L^2$ are each independently optionally substituted with 1-4 substituents selected from halogen, —CN, —OR$^7$, —SR$^7$, —N(R$^7$)$_2$, C$_1$-C$_6$ alkyl, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, or heteroaryl; and
each $R^7$ is independently H, C$_1$-C$_6$ alkyl, C$_1$-C$_6$ fluoroalkyl, C$_3$-C$_6$ cycloalkyl, aryl, heteroaryl, or benzyl;
with the proviso that if R$^1$ is F, then L$^1$ is —(C$_1$-C$_6$ alkylene)-, —(C$_1$-C$_6$ alkylene)-X$^1$—(C$_1$-C$_6$ alkylene)-, —X$^{1'}$—(C$_1$-C$_6$ alkylene)-*, or —(C$_1$-C$_6$ alkylene)-X$^1$-L$^2$-*; where * is the site covalently attached to Z; and Z is —X$^2$;
with the proviso that if R$^1$ is F and R$^2$ is —OMe, then cannot be NH$_2$; and
with the proviso that if R$^1$ is F and R$^2$ is -Me, then -L$_1$-Z cannot be —CH$_2$OH.

In some embodiments, R$^1$ is F and -L$^1$-Z is —(C$_1$-C$_6$ alkylene)-X$^2$, —(C$_1$-C$_6$ alkylene)-X$^1$—(C$_1$-C$_6$ alkylene)-X$^2$, —X$^{1'}$—(C$_1$-C$_6$ alkylene)-X$^2$, or —(C$_1$-C$_6$ alkylene)-X$^1$-L$^2$-X$^2$. In some embodiments, R$^1$ is F and -L$^1$-Z is —(C$_1$-C$_6$ alkylene)-OR$^6$, —(C$_1$-C$_6$ alkylene)-SR$^6$, —(C$_1$-C$_6$ alkylene)-S(O)R$^6$, —(C$_1$-C$_6$ alkylene)-S(O)$_2$R$^6$, —(C$_1$-C$_6$ alkylene)-SSR$^6$, or —(C$_1$-C$_6$ alkylene)-N(R$^6$)$_2$. In some embodiments, R$^1$ is F and -L$^1$-Z is —(C$_1$-C$_6$ alkylene)-X$^1$—(C$_1$-C$_6$ alkylene)-OR$^6$, —(C$_1$-C$_6$ alkylene)-X$^1$—(C$_1$-C$_6$ alkylene)-SR$^6$, —(C$_1$-C$_6$ alkylene)-X$^1$—(C$_1$-C$_6$ alkylene)-S(O)R$^6$, —(C$_1$-C$_6$ alkylene)-X$^1$—(C$_1$-C$_6$ alkylene)-S(O)$_2$R$^6$, —(C$_1$-C$_6$ alkylene)-X$^1$—(C$_1$-C$_6$ alkylene)-SSR$^6$, or —(C$_1$-C$_6$ alkylene)-X$^1$—(C$_1$-C$_6$ alkylene)-N(R$^6$)$_2$. In some embodiments, R$^1$ is F and is —X$^{1'}$—(C$_1$-C$_6$ alkylene)-OR$^6$, —X$^{1'}$—(C$_1$-C$_6$ alkylene)-SR$^6$, —X$^{y}$—(C$_1$-C$_6$ alkylene)-S(O)R$^6$, —X$^{1'}$—(C$_1$-C$_6$ alkylene)-S(O)$_2$R$^6$, —X$^{1'}$—(C$_1$-C$_6$ alkylene)-SSR$^6$, or —X$^{1'}$—(C$_1$-C$_6$ alkylene)-N(R$^6$)$_2$. In some embodiments, R$^1$ is F and is —(C$_1$-C$_6$ alkylene)-X$^1$-L$^2$-OR$^6$, —(C$_1$-C$_6$ alkylene)-X$^1$-L$^2$-SR$^6$, —(C$_1$-C$_6$ alkylene)-X$^1$-L$^2$-S(O)R$^6$, —(C$_1$-C$_6$ alkylene)-X$^1$-L$^2$-S(O)$_2$R$^{6'}$—(C$_1$-C$_6$ alkylene)-X$^1$-L$^2$-SSR$^6$, or —(C$_1$-C$_6$ alkylene)-X$^1$-L$^2$-N(R$^6$)$_2$.

In some embodiments, R$^1$ is —H or —F. In some embodiments, R$^1$ is —F. In some embodiments, R$^2$ is —H, —F, —OCF$_3$, —CF$_3$, —OMe, —OEt, —SMe, —S(O)Me, —S(O)$_2$Me, —SEt, —S(O)Et, —S(O$_2$)Et, methyl, or ethyl. In some embodiments, R$^2$ is —F. In some embodiments, R$^2$ is —OMe, —SMe, —S(O)Me, or methyl. In some embodiments, R$^2$ is methyl. In some embodiments, R$^1$ is —F and R$^2$ is —F. In some embodiments, R$^1$ is methyl and R$^2$ is —F. In some embodiments, R$^1$ is —F and R$^2$ is -methyl.

In some embodiments, -L$^1$-Z is —H. In some embodiments, -L$^1$-Z is —(C$_1$-C$_6$ alkylene)-H, or —(C$_1$-C$_6$ alkylene)-X$^2$. In some embodiments, -L$^1$-Z is —(C$_1$-C$_6$ alkylene)-H. In some embodiments, -L$^1$-Z is —(C$_1$-C$_6$ alkylene)-X$^2$. In some embodiments, -L$^1$-Z is —(C$_1$-C$_6$ alkylene)-X$^2$. In some embodiments, -L$^{1'}$-Z is methyl, ethyl, propyl, or butyl.

In some embodiments, -L$^1$-Z is —(C$_1$-C$_4$ alkylene)-OR$^6$, —(C$_1$-C$_4$ alkylene)-SR$^6$, or —(C$_1$-C$_4$ alkylene)-N(R$^6$)$_2$. In some embodiments, -L$^1$-Z is —(C$_1$-C$_4$ alkylene)-OR$^6$. In some embodiments, -L$^1$-Z is —(C$_1$-C$_4$ alkylene)-SR$^6$. In some embodiments, -L$^1$-Z is —(C$_1$-C$_4$ alkylene)-N(R$^6$)$_2$.

In some embodiments, -L$^1$-Z is —CH$_2$OH, —(CH$_2$)$_2$OH, —(CH$_2$)$_3$OH, —(CH$_2$)$_4$OH, —CH$_2$OMe, —(CH$_2$)$_2$OMe, —(CH$_2$)$_3$OMe, —(CH$_2$)$_4$OMe, —CH$_2$SH, —(CH$_2$)$_2$SH, —(CH$_2$)$_3$SH, —(CH$_2$)$_4$SH, —CH$_2$SMe, —(CH$_2$)$_2$SMe, —(CH$_2$)$_3$SMe, —(CH$_2$)$_4$SMe, —CH$_2$NH$_2$, —(CH$_2$)$_2$NH$_2$, —(CH$_2$)$_3$NH$_2$, —(CH$_2$)$_4$NH$_2$.

In some embodiments, -L$^1$-Z is —(C$_1$-C$_5$ alkylene)-NR$^5$C(=O)—(C$_1$-C$_5$ alkylene)-OR$^6$, —(C$_1$-C$_5$ alkylene)-NR$^5$C(=O)—(C$_1$-C$_5$ alkylene)-SR$^6$, —(C$_1$-C$_5$ alkylene)-S—(C$_1$-C$_5$ alkylene)-SR$^6$, or —(C$_1$-C$_5$ alkylene)-S—(C$_1$-C$_5$ alkylene)-SSR$^6$. In some embodiments, -L$^1$-Z is —(C$_1$-C$_5$ alkylene)-NR$^5$C(=O)—(C$_1$-C$_5$ alkylene)-OR$^6$. In some embodiments, -L$^1$-Z is —(C$_1$-C$_5$ alkylene)-NR$^5$C(=O)—(C$_1$-C$_5$ alkylene)-SR$^6$. In some embodiments, -L$^1$-Z is —(C$_1$-C$_5$ alkylene)-S—(C$_1$-C$_5$ alkylene)-SR$^6$. In some embodiments, -L$^1$-Z is —(C$_1$-C$_5$ alkylene)-S—(C$_1$-C$_5$ alkylene)-SSR$^6$.

In some embodiments, -L$^1$-Z is —CH$_2$NHC(=O)CH$_2$OH, —CH$_2$NHC(=O)(CH$_2$)$_2$OH, —CH$_2$NHC(=O)(CH$_2$)$_3$OH, —CH$_2$NHC(=O)(CH$_2$)$_4$OH, —CH$_2$NHC(=O)(CH$_2$)$_5$OH, —CH$_2$NHC(=O)CH$_2$OMe, —CH$_2$NHC(=O)(CH$_2$)$_2$OMe, —CH$_2$NHC(=O)(CH$_2$)$_3$OMe, —CH$_2$NHC(=O)(CH$_2$)$_4$OMe, —CH$_2$NHC(=O)(CH$_2$)$_5$OMe, —CH$_2$NHC(=O)CH$_2$SH, —CH$_2$NHC(=O)(CH$_2$)$_2$SH, —CH$_2$NHC(=O)(CH$_2$)$_3$SH, —CH$_2$NHC(=O)(CH$_2$)$_4$SH, —CH$_2$NHC(=O)(CH$_2$)$_5$SH, —CH$_2$NHC(=O)CH$_2$SMe, —CH$_2$NHC(=O)(CH$_2$)$_2$SMe, —CH$_2$NHC(=O)(CH$_2$)$_3$SMe, —CH$_2$NHC(=O)(CH$_2$)$_4$SMe, —CH$_2$NHC(=O)(CH$_2$)$_5$SMe, —CH$_2$SCH$_2$OH, —CH$_2$S(CH$_2$)$_2$OH, —CH$_2$S(CH$_2$)$_3$OH, —CH$_2$S(CH$_2$)$_4$OH, —CH$_2$S(CH$_2$)$_5$OH, —CH$_2$SCH$_2$OMe, —CH$_2$S(CH$_2$)$_2$OMe, —CH$_2$S(CH$_2$)$_3$OMe, —CH$_2$S(CH$_2$)$_4$OMe, —CH$_2$S(CH$_2$)$_5$OMe, —CH$_2$SCH$_2$SH, —CH$_2$S(CH$_2$)$_2$SH, —CH$_2$S(CH$_2$)$_3$SH, —CH$_2$S(CH$_2$)$_4$SH, —CH$_2$S(CH$_2$)$_5$SH, —CH$_2$SCH$_2$SMe, —CH$_2$S(CH$_2$)$_2$SMe, —CH$_2$S(CH$_2$)$_3$SMe, —CH$_2$S(CH$_2$)$_4$SMe, or —CH$_2$S(CH$_2$)$_5$SMe.

In some embodiments, each R$^5$ is independently —H, methyl, or benzyl. In some embodiments, each R$^5$ is independently —H. In some embodiments, each R$^5$ is methyl. In some embodiments, each R$^5$ is benzyl.

In some embodiments, each R$^6$ is independently —H, methyl, or benzyl. In some embodiments, each R$^6$ is independently —H. In some embodiments, each R$^6$ is methyl. In some embodiments, each R$^6$ is benzyl.

In some embodiments, -L$^1$-Z is —X$^{1'}$—(C$_1$-C$_4$ alkylene)-X$^2$. In some embodiments, -L$^1$-Z is —OCH$_2$OH, —O(CH$_2$)$_2$OH, —O(CH$_2$)$_3$OH, —O(CH$_2$)$_4$OH, —SCH$_2$OH, —S(CH$_2$)$_2$OH, —S(CH$_2$)$_3$OH, —S(CH$_2$)$_4$OH, —S(O)CH$_2$OH, —S(O)(CH$_2$)$_2$OH, —S(O)(CH$_2$)$_3$OH, —S(O)(CH$_2$)$_4$OH, —S(O)$_2$CH$_2$OH, —S(O)$_2$(CH$_2$)$_2$OH, —S(O)$_2$(CH$_2$)$_3$OH, —S(O)$_2$(CH$_2$)$_4$OH, —OCH$_2$SMe, —O(CH$_2$)$_2$SMe, —O(CH$_2$)$_3$SMe, —O(CH$_2$)$_4$SMe, —SCH$_2$SMe, —S(CH$_2$)$_2$SMe, —S(CH$_2$)$_3$SMe, —S(CH$_2$)$_4$SMe, —S(O)CH$_2$SMe, —S(O)(CH$_2$)$_2$SMe, —S(O)(CH$_2$)$_3$SMe, —S(O)(CH$_2$)$_4$SMe, —S(O)$_2$CH$_2$SMe, —S(O)$_2$(CH$_2$)$_2$SMe, —S(O)$_2$(CH$_2$)$_3$SMe, or —S(O)$_2$(CH$_2$)$_4$SMe.

In some embodiments, -L$^1$-Z is —(C$_1$-C$_6$ alkylene)-X$^1$-L$^2$-X$^2$. In some embodiments, -L$^1$-Z is

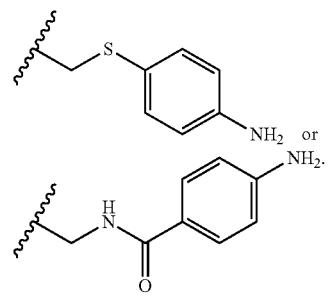

In some embodiments, -L$^1$-Z is

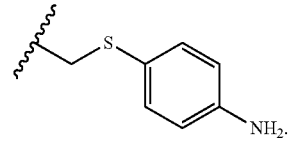 [SMILES: *CSc1ccc(N)cc1]

In some embodiments, -L$^1$-Z is

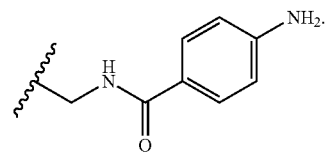 [SMILES: *CNC(=O)c1ccc(N)cc1]

In another aspect, the invention provides a compound of Formula II, or a pharmaceutically acceptable salt thereof:

E-A-Z'-L$^1$-D    (Formula II)

wherein:
D is represented by the following structural formula:

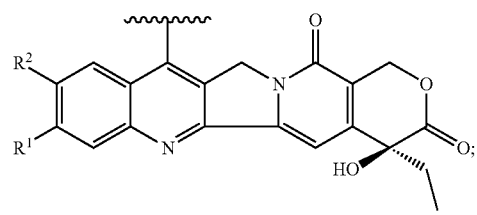

R$^1$ is —H, —F, —CH$_3$, or —CF$_3$;
R$^2$ is —H, —F, —OR$^3$, —SR$^3$, —S(O)R$^4$, —S(O)$_2$R$^4$, C$_1$-C$_6$ alkyl, or C$_1$-C$_6$ fluoroalkyl; or R$^1$ and R$^2$ taken together with the carbon atoms to which they are attached form a methylenedioxy or a difluoromethylenedioxy ring; with the proviso that both R$^1$ and R$^2$ cannot be —H;
R$^3$ is H or C$_1$-C$_6$ alkyl;
R$^4$ is C$_1$-C$_6$ alkyl;
L$^1$ is absent, —(C$_1$-C$_6$ alkylene)-, alkylene)-X$^1$—(C$_1$-C$_6$ alkylene)-, X$^{1'}$—(C$_1$-C$_6$ alkylene)-* or —(C$_1$-C$_6$ alkylene)-X$^1$-L$^2$-*; where * is the site covalently attached to Z';

$X^1$ is —O—, —S—, —S(O)—, —S(O)$_2$—, —C(=O)—, —NR$^5$C(=O)—, or —C(=O)NR$^5$—;

$X^{1'}$ is —O—, —S—, —S(O)—, or —S(O)$_2$—;

$L^2$ is phenylene;

each $R^5$ is independently —H, $C_1$-$C_6$ alkyl, $C_1$-$C_6$ fluoroalkyl, $C_3$-$C_6$ cycloalkyl, aryl, heteroaryl, or benzyl;

Z' is —O—CH$_2$—NR$^8$—*, —S—CH$_2$—NR$^8$—*, —NR$^8$—*; where * is the site covalently attached to A;

each $R^8$ is independently —H, $C_1$-$C_6$ alkyl, $C_1$-$C_6$ fluoroalkyl, $C_3$-$C_6$ cycloalkyl, aryl, heteroaryl, or benzyl;

$L^1$ and $L^2$ are each independently optionally substituted with 1-4 substituents selected from halogen, —CN, —OR$^7$, —SR$^7$, —N(R$^7$)$_2$, $C_1$-$C_6$ alkyl, $C_1$-$C_6$ fluoroalkyl, $C_1$-$C_6$ heteroalkyl, $C_3$-$C_6$ cycloalkyl, $C_2$-$C_{10}$ heterocycloalkyl, aryl, or heteroaryl; and each $R^7$ is independently H, $C_1$-$C_6$ alkyl, $C_1$-$C_6$ fluoroalkyl, $C_3$-$C_6$ cycloalkyl, aryl, heteroaryl, or benzyl;

A is a peptide comprising 2 to 10 amino acids; wherein A is optionally substituted with one or more polyol; and E is —C(=O)-L$^3$-X$^3$;

$L^3$ is —($C_1$-$C_{10}$ alkylene)- or —Y$^1$—($C_1$-$C_{10}$ alkylene)-X$^4$—Y$^2$—($C_1$-$C_{10}$ alkylene)-*; where * is the site covalently attached to $X^3$;

$Y^1$ is absent, —(CR$^a$R$^b$O)$_n$—, or —(CR$^a$R$^b$CR$^{a'}$R$^{b'}$O)$_m$—;

$X^4$ is —NR$^9$C(=O)— or —C(=O)NR$^9$—;

$Y^2$ is absent, —(CR$^c$R$^d$O)$_o$—, or —(CR$^c$R$^d$CR$^{c'}$R$^{d'}$O)$_p$—;

n, m, o, and p are each independently 1-10;

each R$^a$, R$^b$, R$^{a'}$, R$^{b'}$, R$^c$, R$^d$, R$^{c'}$, and R$^{d'}$ are independently —H, $C_1$-$C_6$ alkyl, $C_1$-$C_6$ fluoroalkyl, $C_3$-$C_6$ cycloalkyl, aryl, heteroaryl, or benzyl;

wherein $L^3$ is optionally substituted with 0-4 substituents selected from halogen, —CN, —OR$^{11}$, —SR$^{11}$, —N(R$^{11}$)$_2$, $C_1$-$C_6$ alkyl, $C_1$-$C_6$ fluoroalkyl, $C_1$-$C_6$ heteroalkyl, $C_3$-$C_6$ cycloalkyl, $C_2$-$C_{10}$ heterocycloalkyl, aryl, heteroaryl, and polyol;

each $R^{11}$ is independently H, $C_1$-$C_6$ alkyl, $C_1$-$C_6$ fluoroalkyl, $C_3$-$C_6$ cycloalkyl, aryl, heteroaryl, or benzyl;

$X^3$ is

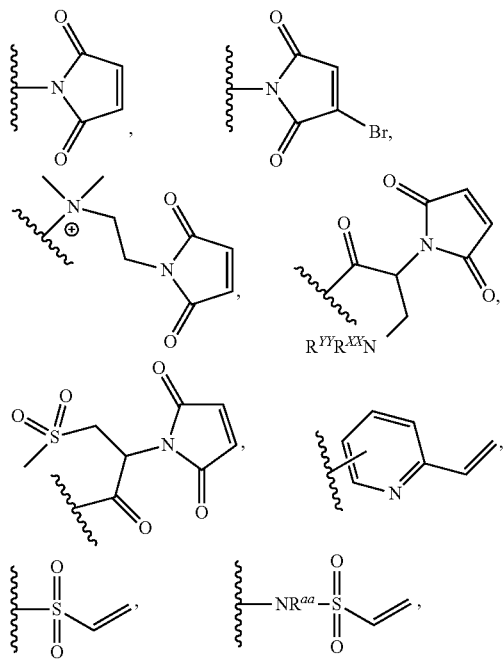

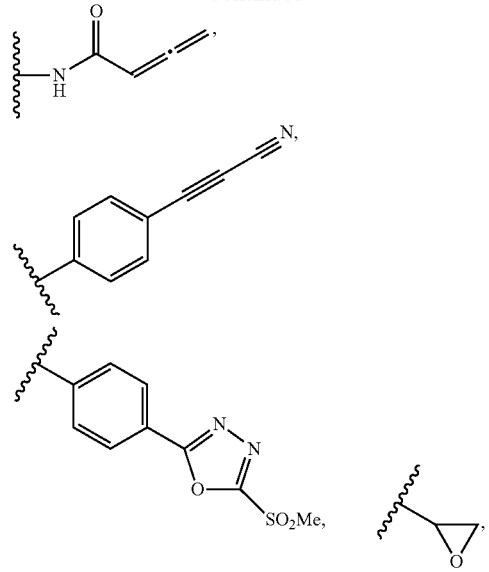

—C(=O)—CR$^{bb}$R$^{cc}$—W', —NR$^{ee}$—C(=O)—CR$^{bb}$R$^{cc}$—W', or —SR$^{10}$;

each W' is independently —H, —N(R$^{gg}$)$_2$, $C_1$-$C_{10}$ alkyl, $C_1$-$C_{10}$ alkenyl, $C_1$-$C_{10}$ alkynyl, $C_3$-$C_6$ cycloalkyl, aryl, heteroaryl, or —(CH$_2$CH$_2$O)$_q$—R$^{ff}$;

q is 1 to 24;

each R$^{aa}$, R$^{bb}$, R$^{cc}$, R$^{ee}$, and R$^{ff}$ are independently —H or optionally substituted $C_1$-$C_6$ alkyl;

each R$^{YY}$ and R$^o$ are independently —H or $C_1$-$C_6$ alkyl;

R$^{gg}$ are each independently —H or $C_1$-$C_6$ alkyl; and $R^9$ and $R^{10}$ are each independently —H, $C_1$-$C_6$ alkyl, $C_1$-$C_6$ fluoroalkyl, $C_3$-$C_6$ cycloalkyl, aryl, heteroaryl, or benzyl.

In some embodiments, $R^1$ is —H or —F. In some embodiments, $R^1$ is —F. In some embodiments, $R^2$ is H, —F, —OCF$_3$, —CF$_3$, —OMe, —OEt, —SMe, —S(O)Me, —S(O)$_2$Me, —SEt, —S(O)Et, —S(O$_2$)Et, methyl, or ethyl. In some embodiments, $R^2$ is —F. In some embodiments, $R^2$ is —OMe, —SMe, —S(O)Me, or methyl. In some embodiments, $R^2$ is methyl. In some embodiments, $R^1$ is —F and $R^2$ is —F. In some embodiments, $R^1$ is methyl and $R^2$ is —F. In some embodiments, $R^1$ is —F and $R^2$ is -methyl.

In some embodiments, -L$^1$-Z'—* is —($C_1$-$C_4$ alkylene)-O—CH$_2$—NR$^8$—*, —($C_1$-$C_4$ alkylene)-S—CH$_2$—NR$^8$—*, or —($C_1$-$C_4$ alkylene)-NR$^8$—*. In some embodiments, -L$^1$-Z'—* is —($C_1$-$C_4$ alkylene)-O—CH$_2$—NR$^8$—*. In some embodiments, -L$^1$-Z'—* is —($C_1$-$C_4$ alkylene)-S—CH$_2$—NR$^8$—*. In some embodiments, -L$^1$-Z'—* is —($C_1$-$C_4$ alkylene)-NR$^8$—*.

In some embodiments, -L$^1$-Z'—* is —CH$_2$O—CH$_2$NH—*, —(CH$_2$)$_2$O—CH$_2$NH—*, —(CH$_2$)$_3$O—CH$_2$NH—*, —(CH$_2$)$_4$O—CH$_2$NH—*, —CH$_2$S—CH$_2$NH—*, —(CH$_2$)$_2$S—CH$_2$NH—*, —(CH$_2$)$_3$S—CH$_2$NH—*, —(CH$_2$)$_4$S—CH$_2$NH—*, —CH$_2$NH—*, —(CH$_2$)$_2$NH—*, —(CH$_2$)$_3$NH—*, or —(CH$_2$)$_4$NH—*.

In some embodiments, -L$^1$-Z'—* is —($C_1$-$C_5$ alkylene)-NR$^5$C(=O)—($C_1$-$C_5$ alkylene)-O—CH$_2$—NR$^8$—*, —($C_1$-$C_5$ alkylene)-NR$^5$C(=O)—($C_1$-$C_5$ alkylene)-S—CH$_2$—NR$^8$—*, —($C_1$-$C_5$ alkylene)-S—($C_1$-$C_5$ alkylene)-S—CH$_2$—NR$^8$—*, or —($C_1$-$C_5$ alkylene)-S—($C_1$-$C_5$ alkylene)-SS—CH$_2$—NR$^8$—*. In some embodiments, -L$^1$-Z'—* is —($C_1$-$C_5$ alkylene)-NR$^5$C(=O)—($C_1$-$C_5$ alkylene)-O—CH$_2$—NR$^8$—*. In some embodiments, -L$^1$-

Z'—* is —(C₁-C₅ alkylene)-NR⁵C(=O)—(C₁-C₅ alkylene)-S—CH₂—NR⁸—*. In some embodiments, -L¹-Z'—* is —(C₁-C₅ alkylene)-S—(C₁-C₅ alkylene)-S—CH₂—NR⁸—*. In some embodiments, -L¹-Z'—* is —(C₁-C₅ alkylene)-S—(C₁-C₅ alkylene)-SS—CH₂—NR⁸—*.

In some embodiments, -L¹-Z'—* is —CH₂NHC(=O)CH₂O—CH₂—NH—*, —CH₂NHC(=O)(CH₂)₂O—CH₂—NH—*, —CH₂NHC(=O)(CH₂)₃O—CH₂—NH—*, —CH₂NHC(=O)(CH₂)₄O—CH₂—NH—*, —CH₂NHC(=O)(CH₂)₅O—CH₂—NH—*, —CH₂NHC(=O)CH₂S—CH₂—NH—*, —CH₂NHC(=O)(CH₂)₂S—CH₂—NH—*, —CH₂NHC(=O)(CH₂)₃S—CH₂—NH—*, —CH₂NHC(=O)(CH₂)₄S—CH₂—NH—*, —CH₂NHC(=O)(CH₂)₅S—CH₂—NH—*, —CH₂SCH₂O—CH₂—NH—*, —CH₂S(CH₂)₂O—CH₂—NH—*, —CH₂S(CH₂)₃O—CH₂—NH—*, —CH₂S(CH₂)₄O—CH₂—NH—*, —CH₂S(CH₂)₅O—CH₂—NH—*, —CH₂SCH₂S—CH₂—NH—*, —CH₂S(CH₂)₂S—CH₂—NH—*, —CH₂S(CH₂)₃S—CH₂—NH—*, —CH₂S(CH₂)₄S—CH₂—NH—*, or —CH₂S(CH₂)₅S—CH₂—NH—*.

In some embodiments, each R⁵ is independently —H, methyl, or benzyl. In some embodiments, each R⁵ is independently —H. In some embodiments, each R⁵ is methyl. In some embodiments, each R⁵ is benzyl. In some embodiments, each R⁸ is independently —H, methyl, or benzyl. In some embodiments, each R⁸ is independently —H. In some embodiments, each R⁸ is methyl. In some embodiments, each R⁸ is benzyl.

In some embodiments, -L¹-Z'—* is —X¹'—(C₁-C₄ alkylene)-O—CH₂—NR⁸—*, alkylene)-S—CH₂—NR⁸—*, or —X¹'—(C₁-C₄ alkylene)-NR⁸—*. In some embodiments, -L¹-Z'—* is —X¹'—(C₁-C₄ alkylene)-O—CH₂—NR⁸—*. In some embodiments, -L¹-Z'—* is —X¹'—(C₁-C₄ alkylene)-S—CH₂—NR⁸—*. In some embodiments, -L¹-Z'—* is —X¹'—(C₁-C₄ alkylene)-NR⁸—*.

In some embodiments, -L¹-Z'—* is —OCH₂O—CH₂—NH—*, —O(CH₂)₂O—CH₂—NH—*, —O(CH₂)₃O—CH₂—NH—*, —O(CH₂)₄O—CH₂—NH—*, —SCH₂O—CH₂—NH—*, —S(CH₂)₂O—CH₂—NH—*, —S(CH₂)₃O—CH₂—NH—*, —S(CH₂)₄O—CH₂—NH—*, —S(O)CH₂O—CH₁₂—NH—*, —S(O)(CH₂)₂O—CH₂—NH—*, —S(O)(CH₂)₃O—CH₂—NH—*, —S(O)(CH₂)₄O—CH₂—NH—*, —S(O)₂CH₂O—CH₂—NH—*, —S(O)₂(CH₂)₂O—CH₂—NH—*, —S(O)₂(CH₂)₃O—CH₂—NH—*, —S(O)₂(CH₂)₄O—CH₂—NH—*, —OCH₂S—CH₂—NH—*, —O(CH₂)₂S—CH₂—NH—*, —O(CH₂)₃S—CH₂—NH—*, —O(CH₂)₄S—CH₂—NH—*, —SCH₂S—CH₂—NH—*, —S(CH₂)₂S—CH₂—NH—*, —S(CH₂)₃S—CH₂—NH—*, —S(CH₂)₄S—CH₂—NH—*, S(O)CH₂S—CH₂—NH—*, —S(O)(CH₂)₂S—CH₂—NH—*, —S(O)(CH₂)₃S—CH₂—NH—*, —S(O)(CH₂)₄S—CH₂—NH—*, —S(O)₂CH₂S—CH₂—NH—*, —S(O)₂(CH₂)₂S—CH₂—NH—*, —S(O)₂(CH₂)₃S—CH₂—NH—*, —S(O)₂(CH₂)₄S—CH₂—NH—*, —OCH₂—NH—*, —O(CH₂)₂—NH—*, —O(CH₂)₃—NH—*, —O(CH₂)₄—NH—*, —SCH₂—NH—*, —S(CH₂)₂—NH—*, —S(CH₂)₃—NH—*, —S(CH₂)₄—NH—*, —S(O)CH₂—NH—*, —S(O)(CH₂)₂—NH—*, —S(O)(CH₂)₃—NH—*, —S(O)(CH₂)₄—NH—*, —S(O)₂CH₂—NH—*, —S(O)₂(CH₂)₂—NH—*, —S(O)₂(CH₂)₃—NH—*, or —S(O)₂(CH₂)₄—NH—*.

In some embodiments, -L¹-Z'—* is —(C₁-C₆ alkylene)-X¹-L²-Z'—*. In some embodiments, -L¹-Z'—* is

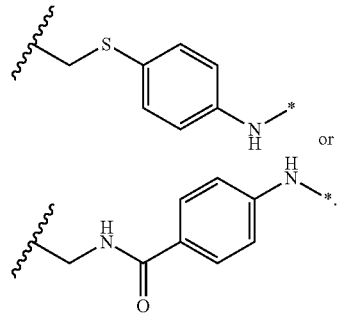

In some embodiments, -L¹-Z'—* is

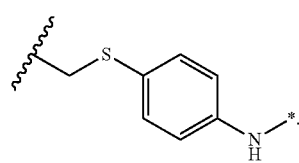

In some embodiments, -L¹-Z'—* is

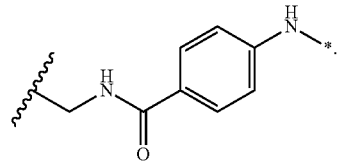

In the various embodiments disclosing -L¹-Z'—* herein, * is the site covalently attached to A.

In some embodiments, A is a peptide comprising 2 to 8 amino acids. In some embodiments, A is a peptide comprising 2 to 4 amino acids. In some embodiments, at least one amino acid in said peptide is a L amino acid. In some embodiments, each amino acid in said peptide is a L amino acid. In some embodiments, at least one amino acid in said peptide is a D amino acid.

In some embodiments, A is -(AA¹)-(AA²)ₐ₁-*, where * is the site covalently attached to E; AA¹ and AA² are each independently an amino acid residue; and a1 is an integer from 1-9.

In some embodiments, -AA¹-(AA²)ₐ₁-* is -Gly-Gly-Gly-*, -Ala-Val-*, -Val-Ala-*, -Val-Cit-*, -Val-Lys-*, -Lys-Val-*, -Phe-Lys-*, -Lys-Phe-*, -Lys-Lys-*, -Ala-Lys-*, -Lys-Ala-*, -Phe-Cit-*-Cit-Phe-*, -Leu-Cit-*, -Cit-Leu-*, -Ile-Cit-*, -Phe-Ala-*-Ala-Phe-*, -Phe-N⁹-tosyl-Arg-*, —N⁹-tosyl-Arg-Phe-*, -Phe-N⁹-nitro-Arg-*, —N⁹-nitro-Arg-Phe-*, -Phe-Phe-Lys-*, -Lys-Phe-Phe-*, -Gly-Phe-Lys-*, Lys-Phe-Gly-*, -Leu-Ala-Leu-*, -Ile-Ala-Leu-*, -Leu-Ala-Ile-*, -Val-Ala-Val-*, -Ala-Leu-Ala-Leu-(SEQ ID NO: 89)*, -Leu-Ala-Leu-Ala- (SEQ ID NO: 90)*, -β-Ala-Leu-Ala-Leu- (SEQ ID NO: 91)*, -Gly-Phe-Leu-Gly-(SEQ ID NO: 92)*, -Gly-Leu-Phe-Gly- (SEQ ID NO: 93)*, -Val-Arg-*, -Arg-Val-*, -Arg-Arg-*, -Ala-Ala-*, -Ala-Met-*, -Met-Ala-*, -Thr-Thr-*, -Thr-Met-*, -Met-Thr-*, -Leu-Ala-*, -Ala-Leu-*, -Cit-Val-*, -Gln-Val-*, -Val-Gln-*, —Ser-Val-*, -Val-Ser-*, —Ser-Ala-*, —Ser-Gly-*, -Ala-Ser-*, -Gly-Ser-*, -Leu-Gln-*, -Gln-Leu-*, -Phe-Arg-*, -Arg-Phe-*, -Tyr-Arg-*, -Arg-Tyr-*, -Phe-Gln-*, -Gln-Phe-*, -Val-Thr-*, -Thr-Val-*, -Met-Tyr-*, and -Tyr-Met-*.

In some embodiments, -AA$^1$-(AA$^2$)$_{a1}$-* is -Val-D-Lys-*, -Val-D-Arg-*, -L-Val-Cit-*, -L-Val-Lys-*, -L-Val-Arg-*, -L-Val-D-Cit-*, -L-Phe-Phe-Lys-*, -L-Val-D-Lys-*, -L-Val-D-Arg-*, -L-Arg-D-Arg-*, -L-Ala-Ala-*, -L-Ala-D-Ala-*, -Ala-D-Ala-*, -Val-D-Cit-*, -L-Ala-L-Ala-*, -L-Ala-L-Val-*, -L-Gln-L-Val-*, -L-Gln-L-Leu-*, or -L-Ser-L-Val-*.

In some embodiments, -AA$^1$-(AA$^2$)$_{a1}$-* is: -Ala-Ala-*, -Ala-Val-*, -Val-Ala-*, -Gln-Leu-*, -Leu-Gln-*, -Ala-Ala-Ala-*, -Ala-Ala-Ala-Ala- (SEQ ID NO: 94)*, -Gly-Ala-Gly-Gly- (SEQ ID NO: 95)*, -Gly-Gly-Ala-Gly- (SEQ ID NO: 96)*, -Gly-Val-Gly-Gly- (SEQ ID NO: 97)*, -Gly-Gly-Val-Gly- (SEQ ID NO: 98)*, -Gly-Phe-Gly-Gly- (SEQ ID NO: 99)*, or -Gly-Gly-Phe-Gly- (SEQ ID NO: 100)*.

In some embodiments, -AA$^1$-(AA$^2$)$_{a1}$-* is: -L-Ala-L-Ala-*, -L-Ala-D-Ala-*, -L-Ala-L-Val-*, -L-Ala-D-Val-*, -L-Val-L-Ala-*, -L-Val-D-Ala-*, -L-Gln-L-Leu-*, -L-Gln-D-Leu-*, -L-Leu-L-Gln-*, -L-Leu-D-Gln-*, -L-Ala-L-Ala-L-Ala-*, -L-Ala-D-Ala-L-Ala-*, -L-Ala-L-Ala-D-Ala-*, -L-Ala-L-Ala-L-Ala-L-Ala- (SEQ ID NO: 94)*, -L-Ala-D-Ala-L-Ala-L-Ala- (SEQ ID NO: 101)*, -L-Ala-L-Ala-D-Ala-L-Ala- (SEQ ID NO: 102)*, -L-Ala-L-Ala-L-Ala-D-Ala- (SEQ ID NO: 103)*, -Gly-L-Ala-Gly-Gly- (SEQ ID NO: 95)*, -Gly-Gly-L-Ala-Gly- (SEQ ID NO: 96)*, -Gly-D-Ala-Gly-Gly- (SEQ ID NO: 104)*, Gly-Gly-D-Ala-Gly- (SEQ ID NO: 105)*, -Gly-L-Val-Gly-Gly- (SEQ ID NO: 97)*, Gly-Gly-L-Val-Gly-(SEQ ID NO: 98)*, -Gly-D-Val-Gly-Gly- (SEQ ID NO: 106)*, Gly-Gly-D-Val-Gly- (SEQ ID NO: 107)*, -Gly-L-Phe-Gly-Gly- (SEQ ID NO: 99)*, or Gly-Gly-L-Phe-Gly- (SEQ ID NO: 100)*.

In some embodiments, -AA$^1$-(AA$^2$)$_{a1}$-* is: -L-Ala-L-Ala-*, -L-Ala-D-Ala-LAla-*, -L-Ala-L-Ala-L-Ala-*, or -L-Ala-L-Ala-L-Ala-L-Ala- (SEQ ID NO: 94)*.

In the various embodiments disclosing -AA$^1$-(AA$^2$)$_{a1}$-*herein, * is the site covalently attached to E.

In some embodiments, A is substituted with one or more polyol. In some embodiments, E is substituted with one or more polyol. In some embodiments, polyol is —(C$_1$-C$_6$ alkylene)-X$^5$—Y$^3$; wherein: X$^5$ is —NR$^{12}$C(=O)— or —C(=O)NR$^{12}$—; Y$^3$ is —C$_1$-C$_{10}$ alkyl, where Y$^3$ is substituted with 0-10 OH groups; and R$^{12}$ is —H, C$_1$-C$_6$ alkyl, C$_1$-C$_6$ fluoroalkyl, C$_3$-C$_6$ cycloalkyl, aryl, heteroaryl, or benzyl.

In some embodiments, wherein polyol is wherein R$^{12}$ is H or methyl.

In some embodiments, wherein polyol is wherein R$^{12}$ is H or methyl.

In some embodiments, E is —C(=O)—(C$_1$-C$_{10}$ alkylene)-X$^3$. In some embodiments, E is

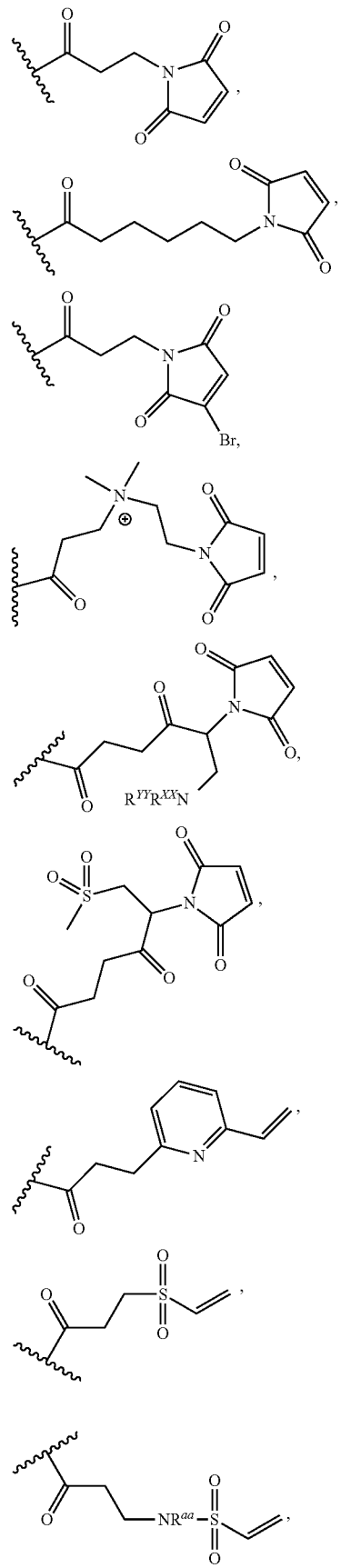

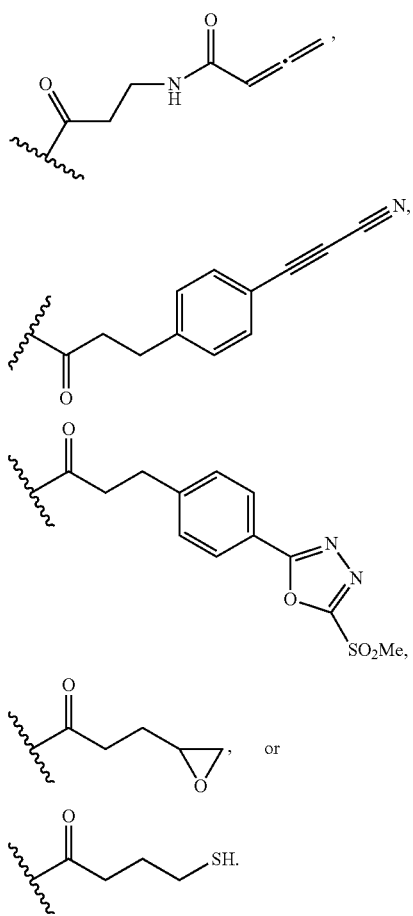
In some embodiments, E is —C(=O)—Y¹—(C₁-C₁₀ alkylene)-X⁴—(C₁-C₁₀ alkylene)-X³;
Y¹ is —(CRᵃRᵇO)ₙ—, or —(CRᵃRᵇCRᵃ'Rᵇ'O)ₘ—;
X⁴ is —NR⁹C(=O)—; and
X³ is
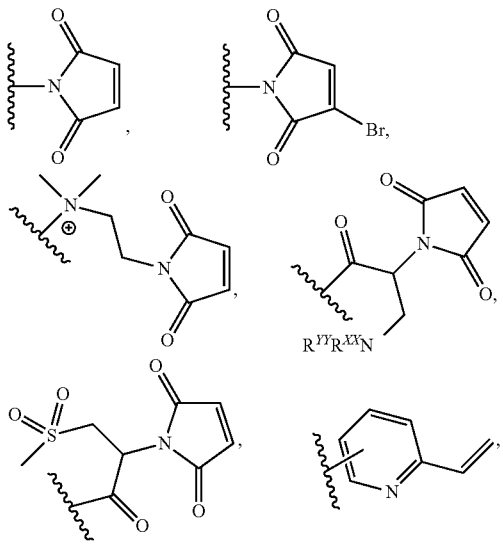
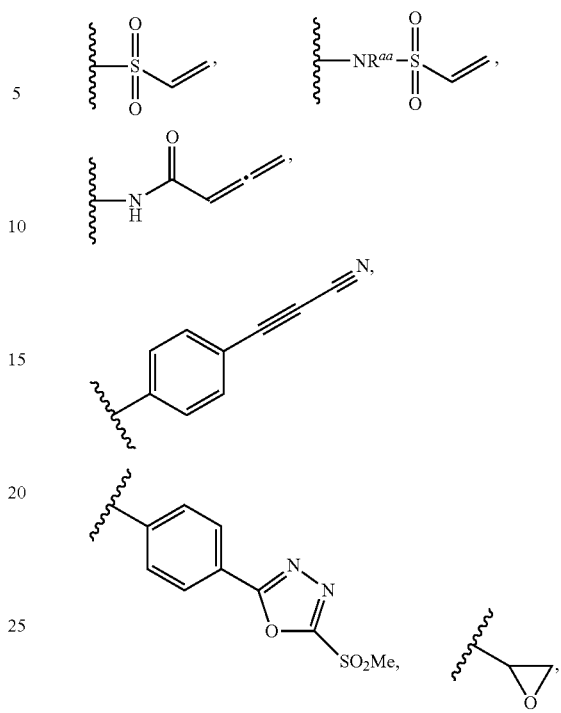
—C(=O)—CR^{bb}R^{cc}—W', NR^{ee}—C(=O)—CR^{bb}R^{cc}—W', or —SR^{m}.
In some embodiments, E is —C(=O)—Y¹—(CH₂)₂—X⁴—(CH₂)₂—X³;
Y¹ is —(CH₂O)ₙ— or —(CH₂CH₂O)ₘ—;
X⁴ is —NHC(=O)—;
n is 2; m is 2 to 6;
X³ is
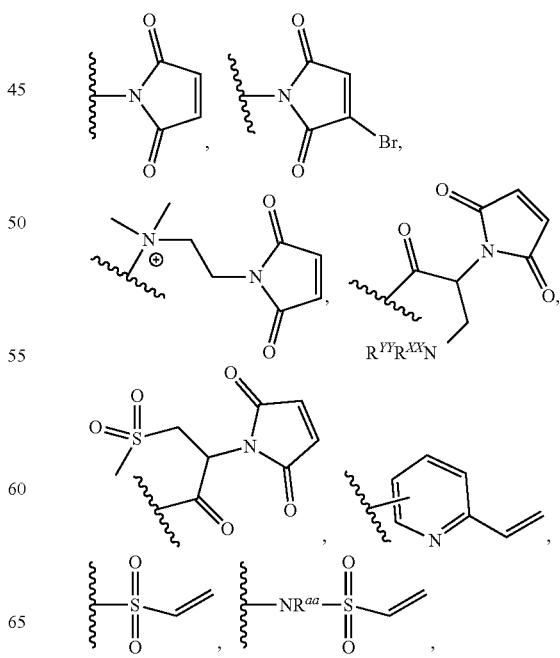

-continued

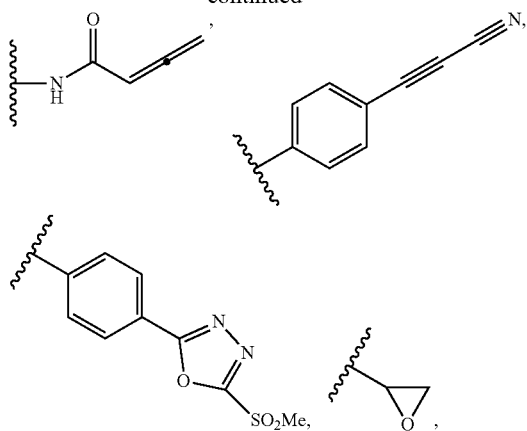

—C(=O)—CR$^{bb}$R$^{cc}$—W', NR$^{ee}$—C(=O)—CR$^{bb}$R$^{cc}$—W', or —SR$^m$.

In another aspect, the invention provides a compound of Formula III, or a pharmaceutically acceptable salt thereof:

CBA-E'-A-Z'-L$^1$-D   (Formula III)

wherein:

D is represented by the following structural formula:

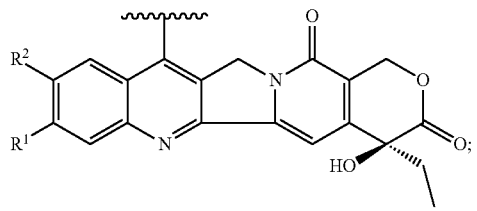

$R^1$ is —H, —F, —CH$_3$, or —CF$_3$;

$R^2$ is —H, —F, —OR$^3$, —SR$^3$, —S(O)R$^4$, —S(O)$_2$R$^4$, C$_1$-C$_6$ alkyl, or C$_1$-C$_6$ fluoroalkyl; or R$^1$ and R$^2$ taken together with the carbon atoms to which they are attached form a methylenedioxy or a difluoromethylenedioxy ring; with the proviso that both R$^1$ and R$^2$ cannot be —H;

$R^3$ is H or C$_1$-C$_6$ alkyl;

$R^4$ is C$_1$-C$_6$ alkyl;

$L^1$ is absent, —(C$_1$-C$_6$ alkylene)-, —(C$_1$-C$_6$ alkylene)-X$^1$—(C$_1$-C$_6$ alkylene)-, X$^{1'}$—(C$_1$-C$_6$ alkylene)-*, or —(C$_1$-C$_6$ alkylene)-X$^1$-L$^2$-*; where * is the site covalently attached to Z';

$X^1$ is —O—, —S—, —S(O)—, —S(O)$_2$—, —C(=O)—, —NR$^5$C(=O)—, or —C(=O)NR$^5$—;

$X^{1'}$ is —O—, —S—, —S(O)—, or —S(O)$_2$—;

$L^2$ is phenylene;

each $R^5$ is independently —H, C$_1$-C$_6$ alkyl, C$_1$-C$_6$ fluoroalkyl, C$_3$-C$_6$ cycloalkyl, aryl, heteroaryl, or benzyl;

Z' is —O—CH$_2$—NR$^8$—*, —NR$^8$—*; where * is the site covalently attached to A;

each $R^8$ is independently —H, C$_1$-C$_6$ alkyl, C$_1$-C$_6$ fluoroalkyl, C$_3$-C$_6$ cycloalkyl, aryl, heteroaryl, or benzyl;

$L^1$ and $L^2$ are each independently optionally substituted with 1-4 substituents selected from —CN, —SR$^7$, —N(R$^7$)$_2$, C$_1$-C$_6$ alkyl, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, or heteroaryl; and each $R^7$ is independently H, C$_1$-C$_6$ alkyl, C$_1$-C$_6$ fluoroalkyl, C$_3$-C$_6$ cycloalkyl, aryl, heteroaryl, or benzyl;

A is a peptide comprising 2 to 10 amino acids; wherein A is optionally substituted with one or more polyol;

E' is —C(=O)-L$^3$-X$^6$—*; where * is the site covalently linked to CBA;

$L^3$ is —(C$_1$-C$_{10}$ alkylene)- or —Y$^1$—(C$_1$-C$_{10}$ alkylene)-X$^4$—Y$^2$—(C$_1$-C$_{10}$ alkylene)-*; where * is the site covalently attached to X$^6$;

$Y^1$ is absent, —(CR$^a$R$^b$O)$_n$— or —(CR$^a$R$^b$CR$^{a'}$R$^{b'}$O)$_m$—;

$X^4$ is —NR$^9$C(=O)— or —C(=O)NR$^9$—;

$Y^2$ is absent, —(CR$^c$R$^d$O)$_o$—, or —(CR$^c$R$^d$CR$^{c'}$R$^{d'}$O)$_p$—;

n, m, o, and p are each independently 1-10;

each R$^a$, R$^b$, R$^{a'}$, R$^{b'}$, R$^c$, R$^d$, R$^{c'}$, and R$^{d'}$ are independently —H, C$_1$-C$_6$ alkyl, C$_1$-C$_6$ fluoroalkyl, C$_3$-C$_6$ cycloalkyl, aryl, heteroaryl, or benzyl;

wherein $L^3$ is optionally substituted with 0-4 substituents selected from halogen, —CN, —OR$^{11}$, —SR$^{11}$, —N(R$^{11}$)$_2$, C$_1$-C$_6$ alkyl, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, heteroaryl, and polyol;

each R" is independently H, C$_1$-C$_6$ alkyl, C$_1$-C$_6$ fluoroalkyl, C$_3$-C$_6$ cycloalkyl, aryl, heteroaryl, or benzyl;

$X^6$ is

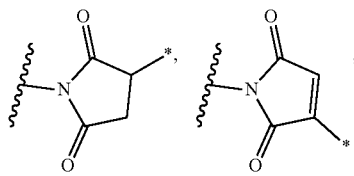

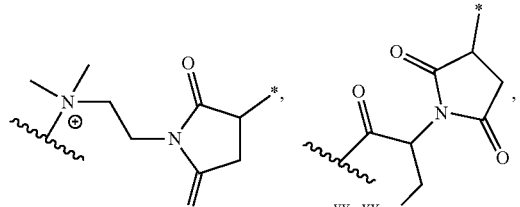

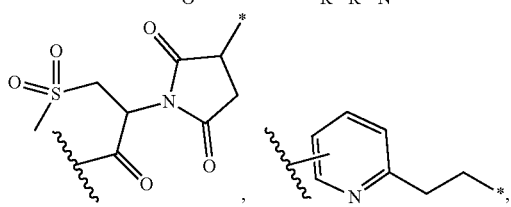

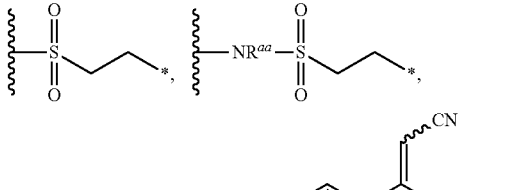

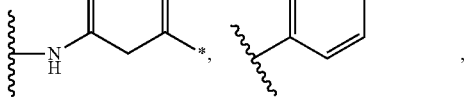

-continued

[structure: phenyl-oxadiazole fragment], [structure: HO-CH(CH₂CH₃)- fragment],

—C(=O)—CR$^{bb}$R$^{cc}$—*, or —NR$^{ee}$—C(=O)—CR$^{bb}$R$^{cc}$—*; where * is the site covalently attached to CBA;
each R$^{aa}$, R$^{bb}$, R$^{cc}$, and R$^{ee}$ are independently —H or optionally substituted $C_1$-$C_6$ alkyl;
each R$^{YY}$ and R$^{o}$ are independently —H or $C_1$-$C_6$ alkyl;
R$^9$ is independently —H, $C_1$-$C_6$ alkyl, $C_1$-$C_6$ fluoroalkyl, $C_3$-$C_6$ cycloalkyl, aryl, heteroaryl, or benzyl; and
CBA is a cell binding agent.

In some embodiments, R$^1$ is —H or —F. In some embodiments, R$^1$ is —F. In some embodiments, R$^2$ is H, —F, —OCF$_3$, —CF$_3$, —OMe, —OEt, —SMe, —S(O)Me, —S(O)$_2$Me, —SEt, —S(O)Et, —S(O$_2$)Et, methyl, or ethyl. In some embodiments, R$^2$ is —F. In some embodiments, R$^2$ is —OMe, —SMe, —S(O)Me, or methyl. In some embodiments, R$^2$ is methyl. In some embodiments, R$^1$ is —F and R$^2$ is —F. In some embodiments, R$^1$ is methyl and R$^2$ is —F. In some embodiments, R$^1$ is —F and R$^2$ is -methyl.

In some embodiments, -L$^1$-Z'—* is —($C_1$-$C_4$ alkylene)-O—CH$_2$—NR$^8$—*, alkylene)-S—CH$_2$—NR$^8$—*, or —($C_1$-$C_4$ alkylene)-NR$^8$—*. In some embodiments, -L$^1$-Z'—* is —($C_1$-$C_4$ alkylene)-O—CH$_2$—NR$^8$—*. In some embodiments, -L$^1$-Z'—* is —($C_1$-$C_4$ alkylene)-S—CH$_2$—NR$^8$—*. In some embodiments, -L$^1$-Z'—* is —($C_1$-$C_4$ alkylene)-NR$^8$—*.

In some embodiments, -L$^1$-Z'—* is —CH$_2$O—CH$_2$NH—*, —(CH$_2$)$_2$O—CH$_2$NH—*, —(CH$_2$)$_{30}$—CH$_2$NH—*, —(CH$_2$)$_4$O—CH$_2$NH—*, —CH$_2$S—CH$_2$NH—*, —(CH$_2$)$_2$S—CH$_2$NH—*, —(CH$_2$)$_3$S—CH$_2$NH—*, —(CH$_2$)$_4$S—CH$_2$NH—*, —CH$_2$NH—*, —(CH$_2$)$_2$NH—*, —(CH$_2$)$_3$NH—*, or —(CH$_2$)$_4$NH—.

In some embodiments, -L$^1$-Z'—* is —($C_1$-$C_5$ alkylene)-NR$^5$C(=O)—($C_1$-$C_5$ alkylene)-O—CH$_2$—NR$^8$—*, alkylene)-NR$^5$C(=O)—($C_1$-$C_5$ alkylene)-S—CH$_2$—NR$^8$—*, alkylene)-S—($C_1$-$C_5$ alkylene)-S—CH$_2$—NR$^8$—*, or —($C_1$-$C_5$ alkylene)-S—($C_1$-$C_5$ alkylene)-SS—CH$_2$—NR$^8$—*. In some embodiments, -L$^1$-Z'—* is —($C_1$-$C_5$ alkylene)-NR$^5$C(=O)—($C_1$-$C_5$ alkylene)-O—CH$_2$—NR$^8$—*. In some embodiments, -L$^1$-Z'—* is —($C_1$-$C_5$ alkylene)-NR$^5$C(=O)—($C_1$-$C_5$ alkylene)-S—CH$_2$—NR$^8$—*. In some embodiments, -L$^1$-Z'—* is —($C_1$-$C_5$ alkylene)-S—($C_1$-$C_5$ alkylene)-S—CH$_2$—NR$^8$—*. In some embodiments, -L$^1$-Z'—* is —($C_1$-$C_5$ alkylene)-S—($C_1$-$C_5$ alkylene)-SS—CH$_2$—NR$^8$—*.

In some embodiments, -L$^1$-Z'—* is —CH$_2$NHC(=O)CH$_2$O—CH$_2$—NH—*, —CH$_2$NHC(=O)(CH$_2$)$_2$O—CH$_2$—NH—*, —CH$_2$NHC(=O)(CH$_2$)$_3$O—CH$_2$—NH—*, —CH$_2$NHC(=O)(CH$_2$)$_4$O—CH$_2$—NH—*, —CH$_2$NHC(=O)(CH$_2$)$_5$O—CH$_2$—NH—*, —CH$_2$NHC(=O)CH$_2$S—CH$_2$—NH—*, —CH$_2$NHC(=O)(CH$_2$)$_2$S—CH$_2$—NH—*, —CH$_2$NHC(=O)(CH$_2$)$_3$S—CH$_2$—NH—*, —CH$_2$NHC(=O)(CH$_2$)$_4$S—CH$_2$—NH—*, —CH$_2$NHC(=O)(CH$_2$)$_5$S—CH$_2$—NH—*, —CH$_2$SCH$_2$O—CH$_2$—NH—*, —CH$_2$S(CH$_2$)$_2$O—CH$_2$—NH—*, —CH$_2$S(CH$_2$)$_3$O—CH$_2$—NH—*, —CH$_2$S(CH$_2$)$_4$O—CH$_2$—NH—*, —CH$_2$S(CH$_2$)$_5$O—CH$_2$—NH—*, —CH$_2$SCH$_2$S—CH$_2$—NH—*, —CH$_2$S(CH$_2$)$_2$S—CH$_2$—NH—*, —CH$_2$S(CH$_2$)$_3$S—CH$_2$—NH—*, —CH$_2$S(CH$_2$)$_4$S—CH$_2$—NH—*, or —CH$_2$S(CH$_2$)$_5$S—CH$_2$—NH—*.

In some embodiments, each R$^5$ is independently —H, methyl, or benzyl. In some embodiments, each R$^5$ is independently —H. In some embodiments, each R$^5$ is methyl. In some embodiments, each R$^5$ is benzyl. In some embodiments, each R$^8$ is independently —H, methyl, or benzyl. In some embodiments, each R$^8$ is independently —H. In some embodiments, each R$^8$ is methyl. In some embodiments, each R$^8$ is benzyl.

In some embodiments -L$^1$-Z'—* is —X$^{1'}$—($C_1$-$C_4$ alkylene)-O—CH$_2$—NR$^8$—*, alkylene)-S—CH$_2$—NR$^8$—*, or —X$^{1'}$—($C_1$-$C_4$ alkylene)-NR$^8$—*. In some embodiments -L$^1$-Z'—* is —X$^{1'}$—($C_1$-$C_4$ alkylene)-O—CH$_2$—NR$^8$—*. In some embodiments -L$^1$-Z'—* is —X$^{1'}$—($C_1$-$C_4$ alkylene)-S—CH$_2$—NR$^8$—*. In some embodiments -L$^1$-Z'—* is —X$^{1'}$—($C_1$-$C_4$ alkylene)-NR$^8$—*.

In some embodiments, -L$^1$-Z'—* is —OCH$_2$O—CH$_2$—NH—*, —O(CH$_2$)$_2$O—CH$_2$—NH—*, —O(CH$_2$)$_3$O—CH$_2$—NH—*, —O(CH$_2$)$_4$O—CH$_2$—NH—*, —SCH$_2$O—CH$_2$—NH—*, —S(CH$_2$)$_2$O—CH$_2$—NH—*, —S(CH$_2$)$_3$O—CH$_2$—NH—*, —S(CH$_2$)$_4$O—CH$_2$—NH—*, —S(O)CH$_2$O—CH$_2$—NH—*, —S(O)(CH$_2$)$_2$O—CH$_2$—NH—*, —S(O)(CH$_2$)$_3$O—CH$_2$—NH—*, —S(O)(CH$_2$)$_4$O—CH$_2$—NH—*, —S(O)$_2$CH$_2$O—CH$_2$—NH—*, —S(O)$_2$(CH$_2$)$_2$O—CH$_2$—NH—*, —S(O)$_2$(CH$_2$)$_3$O—CH$_2$—NH—*, —S(O)$_2$(CH$_2$)$_4$O—CH$_2$—NH—*, —OCH$_2$S—CH$_2$—NH—*, —O(CH$_2$)$_2$S—CH$_2$—NH—*, —O(CH$_2$)$_3$S—CH$_2$—NH—*, —O(CH$_2$)$_4$S—CH$_2$—NH—*, —SCH$_2$S—CH$_2$—NH—*, —S(CH$_2$)$_2$S—CH$_2$—NH—*, —S(CH$_2$)$_3$S—CH$_2$—NH—*, —S(CH$_2$)$_4$S—CH$_2$—NH—*, —S(O)CH$_2$S—CH$_2$—NH—*, —S(O)(CH$_2$)$_2$S—CH$_2$—NH—*, —S(O)(CH$_2$)$_3$S—CH$_2$—NH—*, —S(O)(CH$_2$)$_4$S—CH$_2$—NH—*, —S(O)$_2$CH$_2$S—CH$_2$—NH—*, —S(O)$_2$(CH$_2$)$_2$S—CH$_2$—NH—*, —S(O)$_2$(CH$_2$)$_3$S—CH$_2$—NH—*, —S(O)$_2$(CH$_2$)$_4$S—CH$_2$—NH—*, —OCH$_2$—NH—*, —O(CH$_2$)$_2$—NH—*, —O(CH$_2$)$_3$—NH—*, —O(CH$_2$)$_4$S—NH—*, —SCH$_2$—NH—*, —S(CH$_2$)$_2$—NH—*, —S(CH$_2$)$_3$—NH—*, —S(CH$_2$)$_4$—NH—*, —S(O)CH$_2$—NH—*, —S(O)(CH$_2$)$_2$—NH—*, —S(O)(CH$_2$)$_3$—NH—*, —S(O)(CH$_2$)$_4$—NH—*, —S(O)$_2$CH$_2$—NH—*, —S(O)$_2$(CH$_2$)$_2$—NH—*, —S(O)$_2$(CH$_2$)$_3$—NH—*, or —S(O)$_2$(CH$_2$)$_4$—NH—*.

In some embodiments, -L$^1$-Z'—* is —($C_1$-$C_6$ alkylene)-X$^1$-L$^2$-Z'—*. In some embodiments, -L$^1$-Z'—*

[structure: phenyl-S-linked NH fragment], or [structure: phenyl-C(=O)-NH fragment].

In some embodiments, -L¹-Z'—*

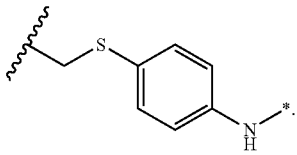

In some embodiments, -L¹-Z'—* is

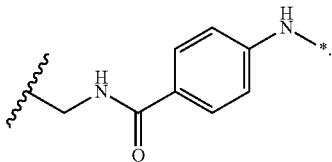

In the various embodiments disclosing -L¹-Z'—* herein, * is the site covalently attached to A.

In some embodiments, A is a peptide comprising 2 to 8 amino acids. In some embodiments, A is a peptide comprising 2 to 4 amino acids. In some embodiments, at least one amino acid in said peptide is an L amino acid. In some embodiments, each amino acid in said peptide is an L amino acid. In some embodiments, at least one amino acid in said peptide is a D amino acid.

In some embodiments, A is -(AA¹)-(AA²)$_{a1}$-*, where * is the point of attachment to E', AA¹ and AA² are each independently an amino acid residue; and a1 is an integer from 1-9.

In some embodiments, -AA¹-(AA²)$_{a1}$-* is -Gly-Gly-Gly-*, -Ala-Val-*, -Val-Ala-*, -Val-Cit-*, -Val-Lys-*, -Lys-Val-*, -Phe-Lys-*, -Lys-Phe-*, -Lys-Lys-*, -Ala-Lys-*, -Lys-Ala-*, -Phe-Cit-*-Cit-Phe-*, -Leu-Cit-*, -Cit-Leu-*, -Ile-Cit-*, -Phe-Ala-*-Ala-Phe-*, -Phe-N⁹-tosyl-Arg-*, —N⁹-tosyl-Arg-Phe-*, -Phe-N⁹-nitro-Arg-*, —N⁹-nitro-Arg-Phe-*, -Phe-Phe-Lys-*, -Lys-Phe-Phe-*, -Gly-Phe-Lys-*, Lys-Phe-Gly-*, -Leu-Ala-Leu-*, -Ile-Ala-Leu-*, -Leu-Ala-Ile-*, -Val-Ala-Val-*, -Ala-Leu-Ala-Leu-(SEQ ID NO: 89)*, -Leu-Ala-Leu-Ala- (SEQ ID NO: 90)*, -β-Ala-Leu-Ala-Leu- (SEQ ID NO: 91)*, -Gly-Phe-Leu-Gly-(SEQ ID NO: 92)*, -Gly-Leu-Phe-Gly- (SEQ ID NO: 93)*, -Val-Arg-*, -Arg-Val-*, -Arg-Arg-*, -Ala-Ala-*, -Ala-Met-*, -Met-Ala-*, -Thr-Thr-*, -Thr-Met-*, -Met-Thr-*, -Leu-Ala-*, -Ala-Leu-*, -Cit-Val-*, -Gln-Val-*, -Val-Gln-*, —Ser-Val-*, -Val-Ser-*, —Ser-Ala-*, —Ser-Gly-*, -Ala-Ser-*, -Gly-Ser-*, -Leu-Gln-*, -Gln-Leu-*, -Phe-Arg-*, -Arg-Phe-*, -Tyr-Arg-*, -Arg-Tyr-*, -Phe-Gln-*, -Gln-Phe-*, -Val-Thr-*, -Thr-Val-*, -Met-Tyr-*, and -Tyr-Met-*.

In some embodiments, -AA¹-(AA²)$_{a1}$-* is -Val-D-Lys-*, -Val-D-Arg-*, -L-Val-Cit-*, -L-Val-Lys-*, -L-Val-Arg-*, -L-Val-D-Cit-*, -L-Phe-Phe-Lys-*, -L-Val-D-Lys-*, -L-Val-D-Arg-*, -L-Arg-D-Arg-*, -L-Ala-Ala-*, -L-Ala-D-Ala-*, -Ala-D-Ala-*, -Val-D-Cit-*, -L-Ala-L-Ala-*, -L-Ala-L-Val-*, -L-Gln-L-Val-*, -L-Gln-L-Leu-*, or -L-Ser-L-Val-*.

In some embodiments, -AA¹-(AA²)$_{a1}$-* is: -Ala-Ala-*, -Ala-Val-*, -Val-Ala-*, -Gln-Leu-*, -Leu-Gln-*, -Ala-Ala-Ala-*, -Ala-Ala-Ala-Ala- (SEQ ID NO: 94)*, -Gly-Ala-Gly-Gly- (SEQ ID NO: 95)*, -Gly-Gly-Ala-Gly- (SEQ ID NO: 96)*, -Gly-Val-Gly-Gly- (SEQ ID NO: 97)*, -Gly-Gly-Val-Gly- (SEQ ID NO: 98)*, -Gly-Phe-Gly-Gly- (SEQ ID NO: 99)*, or -Gly-Gly-Phe-Gly- (SEQ ID NO: 100)*.

In some embodiments, -AA¹-(AA²)$_{a1}$-* is: -L-Ala-L-Ala-*, -L-Ala-D-Ala-*, -L-Ala-L-Val-*, -L-Ala-D-Val-*, -L-Val-L-Ala-*, -L-Val-D-Ala-*, -L-Gln-L-Leu-*, -L-Gln-D-Leu-*, -L-Leu-L-Gln-*, -L-Leu-D-Gln-*, -L-Ala-L-Ala-L-Ala-*, -L-Ala-D-Ala-L-Ala-*, -L-Ala-L-Ala-D-Ala-*, -L-Ala-L-Ala-L-Ala-L-Ala- (SEQ ID NO: 94)*, -L-Ala-D-Ala-L-Ala-L-Ala- (SEQ ID NO: 101)*, -L-Ala-L-Ala-D-Ala-L-Ala- (SEQ ID NO: 102)*, -L-Ala-L-Ala-L-Ala-D-Ala- (SEQ ID NO: 103)*, -Gly-L-Ala-Gly-Gly- (SEQ ID NO: 95)*, -Gly-Gly-L-Ala-Gly- (SEQ ID NO: 96)*, -Gly-D-Ala-Gly-Gly- (SEQ ID NO: 104)*, Gly-Gly-D-Ala-Gly- (SEQ ID NO: 105)*, -Gly-L-Val-Gly-Gly- (SEQ ID NO: 97)*, Gly-Gly-L-Val-Gly-(SEQ ID NO: 98)*, -Gly-D-Val-Gly-Gly- (SEQ ID NO: 106)*, Gly-Gly-D-Val-Gly- (SEQ ID NO: 107)*, -Gly-L-Phe-Gly-Gly- (SEQ ID NO: 99)*, or Gly-Gly-L-Phe-Gly- (SEQ ID NO: 100)*.

In some embodiments, -AA¹-(AA²)$_{a1}$-* is: -L-Ala-L-Ala-*, -L-Ala-D-Ala-L-Ala-*, -L-Ala-L-Ala-L-Ala-*, or -L-Ala-L-Ala-L-Ala-L-Ala- (SEQ ID NO: 94)*.

In the various embodiments disclosing -AA¹-(AA²)$_{a1}$-* herein, * is the site covalently attached to E'.

In some embodiments, A is substituted with one or more polyol. In some embodiments, E' is substituted with one or more polyol. In some embodiments, polyol is —(C₁-C₆ alkylene)-X⁵—Y³; wherein: X⁵ is —NR¹²C(=O)— or —C(=O)NR¹²—; Y³ is —C₁-C₁₀ alkyl, where Y³ is substituted with 0-10 OH groups; and R¹² is —H, C₁-C₆ alkyl, C₁-C₆ fluoroalkyl, C₃-C₆ cycloalkyl, aryl, heteroaryl, or benzyl.

In some embodiments, polyol is

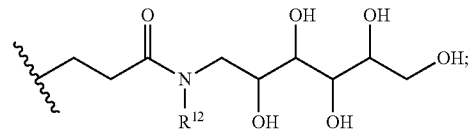

wherein R¹² is H or methyl.

In some embodiments, wherein polyol is

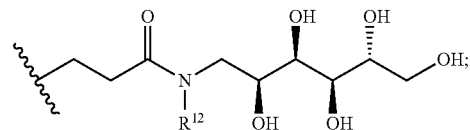

wherein R¹² is H or methyl.

In some embodiments, E' is —C(=O)—(C₁-C₁₀ alkylene)-X⁶—*. In some embodiments, E' is

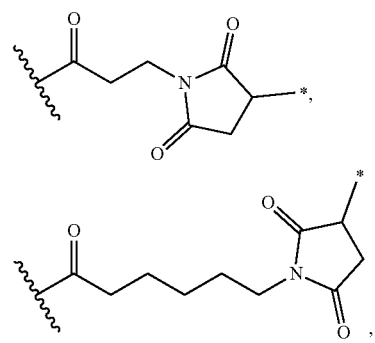

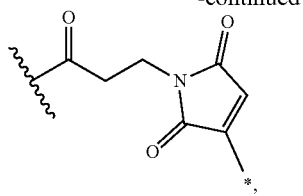

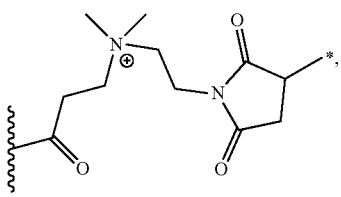

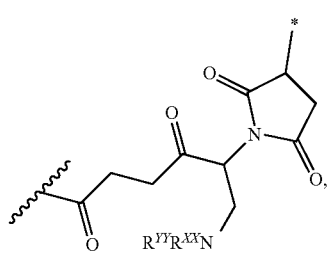

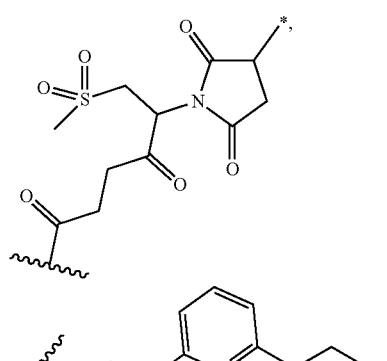

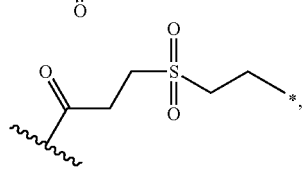

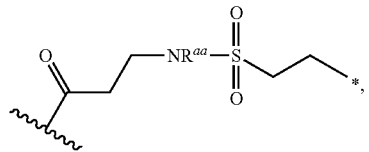

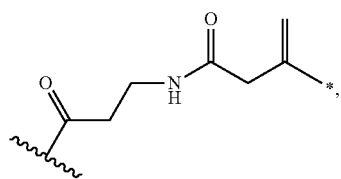

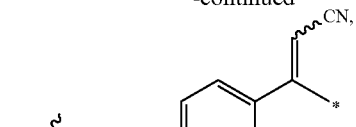

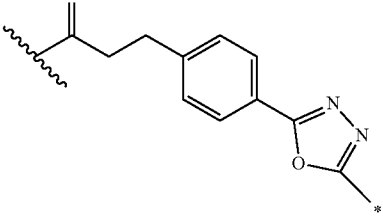

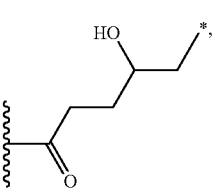

—C(=O)CH$_2$CH$_2$—C(=O)—CR$^{bb}$R$^{cc}$—*, or —C(=O)CH$_2$CH$_2$—NR$^{ee}$—C(=O)—CR$^{bb}$R$^{cc}$—*; where * is the site covalently attached to CBA. In some embodiments, R$^{YY}$, R$^{XX}$, R$^{aa}$, R$^{bb}$ are each independently —H or C$_1$-C$_6$ alkyl.

In some embodiments, E' is —C(=O)—Y$^1$—(C$_1$-C$_{10}$ alkylene)-X$^4$—(C$_1$-C$_{10}$ alkylene)-X$^6$—*

Y$^1$ is —(CR$^a$R$^b$O)$_n$—, or —(CR$^a$R$^b$CR$^a$'R$^b$'O)$_m$—;

X$^4$ is —NR$^9$C(=O)—; and

X$^6$ is

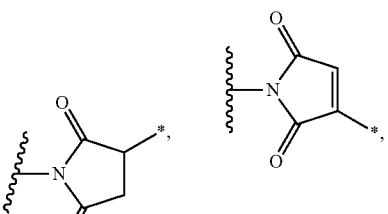

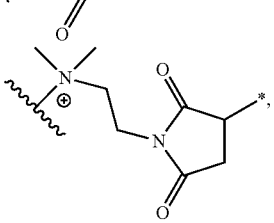

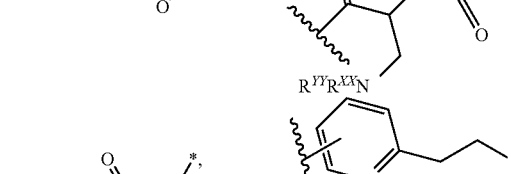

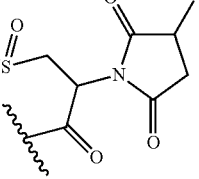

-continued

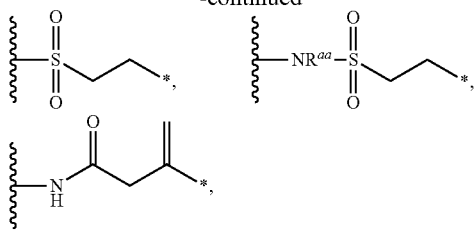
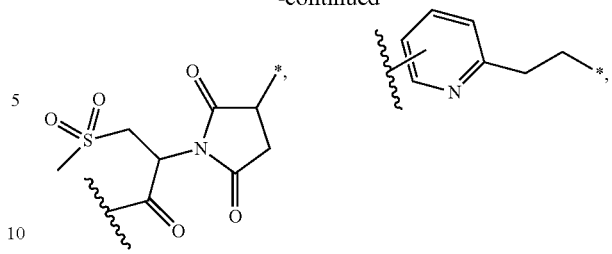

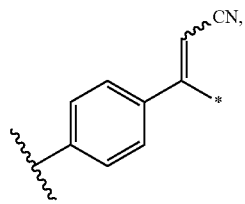

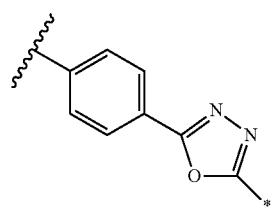

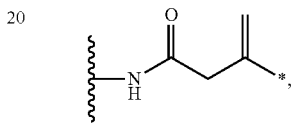

—C(=O)—CR$^{bb}$R$^{cc}$—*, or —NR$^{ee}$—C(=O)—CR$^{bb}$R$^{cc}$—*; where * is the site covalently attached to CBA.

In some embodiments, E' is —C(=O)—Y$^1$—(CH$_2$)$_2$—X$^4$—(CH$_2$)$_2$—X$^6$—*;

Y$^1$ is —(CH$_2$O)$_n$—, or —(CH$_2$CH$_2$O)$_m$—;

X$^4$ is —NHC(=O)—;

n is 2; m is 2 to 6;

X$^6$ is

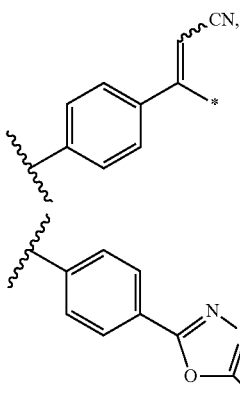
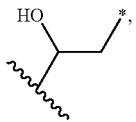
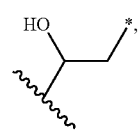
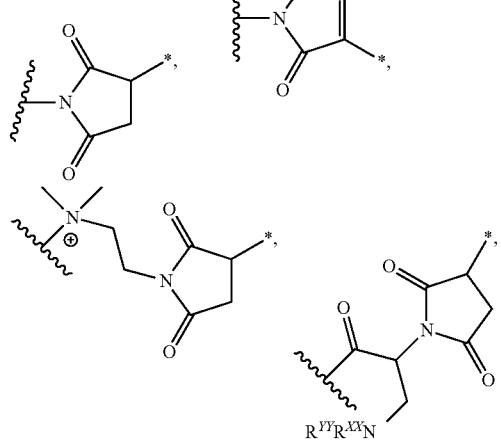

—C(=O)—CR$^{bb}$R$^{cc}$—*, or —NR$^{ee}$—C(=O)—CR$^{bb}$R$^{cc}$—*; where * is the site covalently attached to the CBA.

In some embodiments, the CBA comprises a —SH group that covalently links with E' to provide

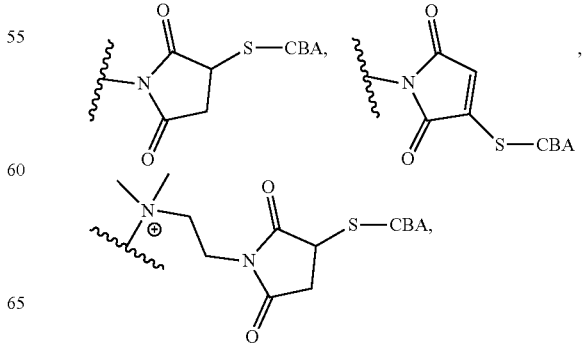

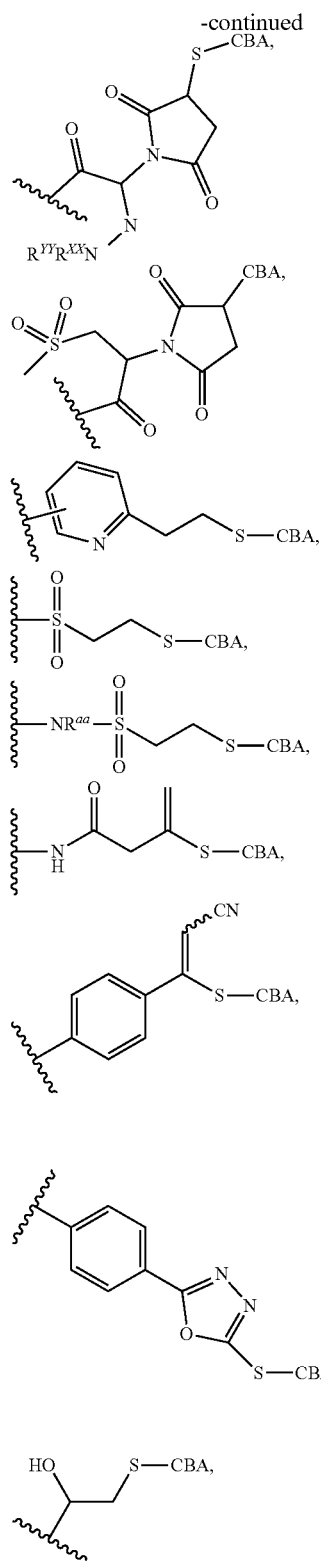

—C(=O)—CR$^{bb}$R$^{cc}$—S-CBA, or —NR$^{ee}$—C(=O)—CR$^{bb}$R$^{cc}$—S-CBA.

In another aspect, the invention provides a compound of Formula IV, or a pharmaceutically acceptable salt thereof:

E-A-Z'-L$^1$-D (Formula IV)

wherein:
D is represented by the following structural formula:

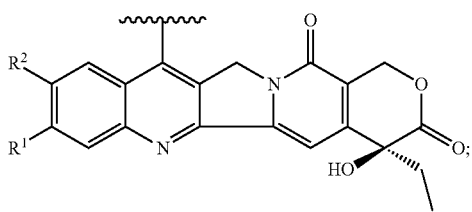

$R^1$ is —H, —F, —CH$_3$, or —CF$_3$;
$R^2$ is —H, —F, —OR$^3$, —SR$^3$, —S(O)R$^4$, —S(O)$_2$R$^4$, C$_1$-C$_6$ alkyl, or C$_1$-C$_6$ fluoroalkyl; or R$^1$ and R$^2$ taken together with the carbon atoms to which they are attached form a methylenedioxy or a difluoromethylenedioxy ring; with the proviso that both R$^1$ and R$^2$ cannot be —H;
$R^3$ is H or C$_1$-C$_6$ alkyl;
$R^4$ is C$_1$-C$_6$ alkyl;
$L^1$ is absent, —(C$_1$-C$_6$ alkylene)-, alkylene)-X$^1$—(C$_1$-C$_6$ alkylene)-, X$^{1'}$—(C$_1$-C$_6$ alkylene)-* or —(C$_1$-C$_6$ alkylene)-X$^1$-L$^2$-*; where * is the site covalently attached to Z';
$X^1$ is —O—, —S—, —S(O)—, —S(O)$_2$—, —C(=O)—, —NR$^5$C(=O)—, or —C(=O)NR$^5$—; X$^{1'}$ is —O—, —S—, —S(O)—, or —S(O)$_2$—;
$L^2$ is phenylene;
each $R^5$ is independently —H, C$_1$-C$_6$ fluoroalkyl, C$_3$-C$_6$ cycloalkyl, aryl, heteroaryl, or benzyl;
$Z'$ is —O—CH$_2$—NR$^8$—*, —S—CH$_2$—NR$^8$—*, —NR$^8$—*; where * is the site covalently attached to A;
each $R^8$ is independently —H, C$_1$-C$_6$ fluoroalkyl, C$_3$-C$_6$ cycloalkyl, aryl, heteroaryl, or benzyl;
$L^1$ and $L^2$ are each independently optionally substituted with 1-4 substituents selected from halogen, —CN, —OR$^7$, —SR$^7$, —N(R$^7$)$_2$, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, or heteroaryl;
each $R^7$ is independently H, C$_1$-C$_6$ fluoroalkyl, C$_3$-C$_6$ cycloalkyl, aryl, heteroaryl, or benzyl;
A is a peptide comprising 2 to 10 amino acids; wherein A is optionally substituted with one or more polyol;
E is —C(=O)O-L$^3$-X$^3$;
$L^3$ is —(C$_1$-C$_{10}$ alkylene)-;
wherein L$^3$ is optionally substituted with 0-4 substituents selected from halogen, —CN, —OR$^9$, —SR$^9$, —N(R$^9$)$_2$, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, heteroaryl, and polyol;
each $R^9$ is independently H, C$_1$-C$_6$ fluoroalkyl, C$_3$-C$_6$ cycloalkyl, aryl, heteroaryl, or benzyl; and
$X^3$ is

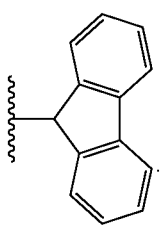 [SMILES: *C1c2ccccc2-c2ccccc21]

In some embodiments, E is —C(=O)O-L$^3$-X$^3$ and L$^3$ is —(C$_1$alkylene)-. In some embodiments, L$^3$ is —CH$_2$—.

In another aspect, the invention provides a compound of Formula V, or a pharmaceutically acceptable salt thereof:

A-Z'-L¹-D     (Formula V)

wherein:
D is represented by the following structural formula:

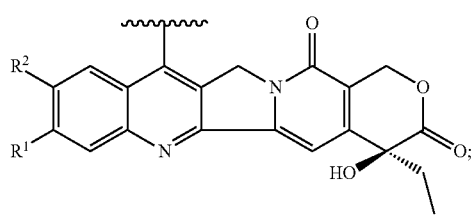

$R^1$ is —H, —F, —CH₃, or —CF₃;
$R^2$ is —H, —F, —OR³, —SR³, —S(O)R⁴, —S(O)₂R⁴, $C_1$-$C_6$ alkyl, or $C_1$-$C_6$ fluoroalkyl; or $R^1$ and $R^2$ taken together with the carbon atoms to which they are attached form a methylenedioxy or a difluoromethylenedioxy ring; with the proviso that both $R^1$ and $R^2$ cannot be —H;
$R^3$ is H or $C_1$-$C_6$ alkyl;
$R^4$ is $C_1$-$C_6$ alkyl;
$L^1$ is absent, —($C_1$-$C_6$ alkylene)-, —($C_1$-$C_6$ alkylene)-$X^1$—($C_1$-$C_6$ alkylene)-, $X^{1'}$—($C_1$-$C_6$ alkylene)-* or —($C_1$-$C_6$ alkylene)-$X^1$-$L^2$-*; where * is the site covalently attached to Z';
$X^1$ is —O—, —S—, —S(O)—, —S(O)₂—, —C(=O)—, —NR⁵C(=O)—, or —C(=O)NR⁵—;
$X^{1'}$ is —O—, —S—, —S(O)—, or —S(O)₂—;
$L^2$ is phenylene;
each $R^5$ is independently —H, $C_1$-$C_6$ alkyl, $C_1$-$C_6$ fluoroalkyl, $C_3$-$C_6$ cycloalkyl, aryl, heteroaryl, or benzyl;
Z' is —O—CH₂—NR⁸—*, —S—CH₂—NR⁸—*, —NR⁸—*; where * is the site covalently attached to A;
each $R^8$ is independently —H, $C_1$-$C_6$ alkyl, $C_1$-$C_6$ fluoroalkyl, $C_3$-$C_6$ cycloalkyl, aryl, heteroaryl, or benzyl;
$L^1$ and $L^2$ are each independently optionally substituted with 1-4 substituents selected from halogen, —CN, —OR⁷, —SR⁷, —N(R⁷)₂, $C_1$-$C_6$ alkyl, $C_1$-$C_6$ fluoroalkyl, $C_1$-$C_6$ heteroalkyl, $C_3$-$C_6$ cycloalkyl, $C_2$-$C_{10}$ heterocycloalkyl, aryl, or heteroaryl;
each $R^7$ is independently H, $C_1$-$C_6$ alkyl, C fluoroalkyl, $C_3$-$C_6$ cycloalkyl, aryl, heteroaryl, or benzyl; and
A is a peptide comprising 2 to 10 amino acids; wherein A is optionally substituted with one or more polyol.

In some embodiments, the compound is a compound of Formula I and is any one of the following compounds from the below table:

TABLE 1A

| Compound No. | Structure |
|---|---|
| a | |
| b | 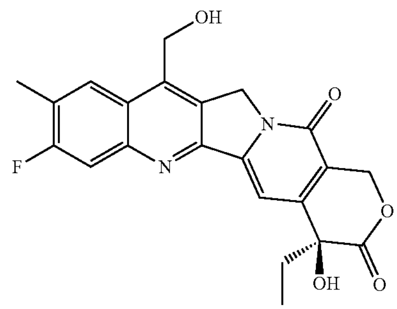 [SMILES: CC[C@@]1(O)C(=O)OCc2c1cc1n(c2=O)Cc2c-1nc1cc(F)c(C)cc1c2CO] |
| c | 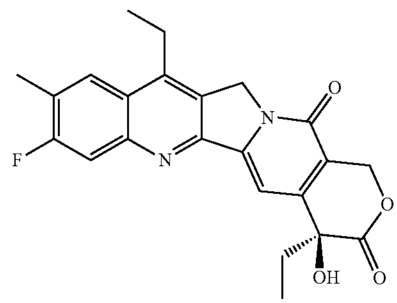 [SMILES: CCc1c2c(nc3cc(F)c(C)cc13)-c1cc3c(c(=O)n1C2)COC(=O)[C@]3(O)CC] |
| 7a | 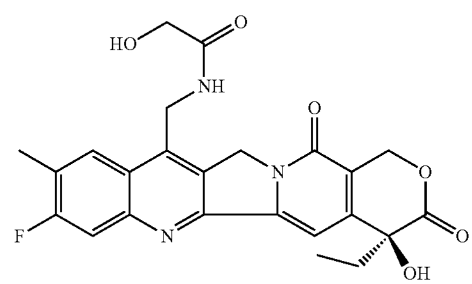 [SMILES: CC[C@@]1(O)C(=O)OCc2c1cc1n(c2=O)Cc2c-1nc1cc(F)c(C)cc1c2CNC(=O)CO] |
| 6a | 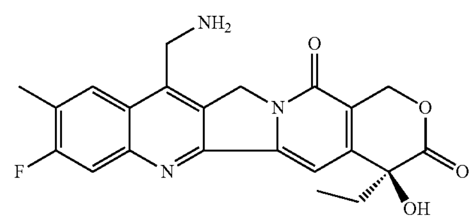 [SMILES: CC[C@@]1(O)C(=O)OCc2c1cc1n(c2=O)Cc2c-1nc1cc(F)c(C)cc1c2CN] |
| d | 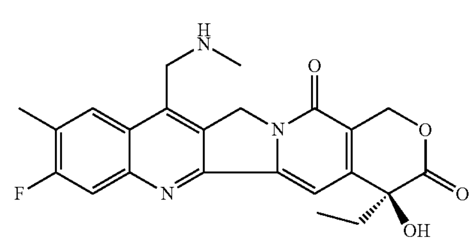 [SMILES: CC[C@@]1(O)C(=O)OCc2c1cc1n(c2=O)Cc2c-1nc1cc(F)c(C)cc1c2CNC] |

TABLE 1A-continued

| Compound No. | Structure |
|---|---|
| 6c | (structure) |
| e | (structure) |
| 8a | (structure) |
| 7b | (structure) |

TABLE 1B

| Compound No. | Structure |
|---|---|
| f | (structure) |
| g | (structure) |
| 35a | (structure) |
| h | (structure) |
| i | (structure) |

In some embodiments, the compound is a compound of Formula I and is a compound of any one of the following from the below table:

TABLE 1B-continued

| Compound No. | Structure |
|---|---|
| j | 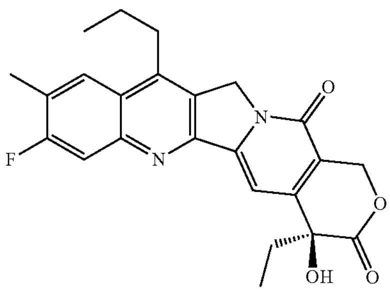 [SMILES: CCCc1c2c(nc3cc(F)c(C)cc13)-c1cc3c(c(=O)n1C2)COC(=O)[C@]3(O)CC] |
| 8p | 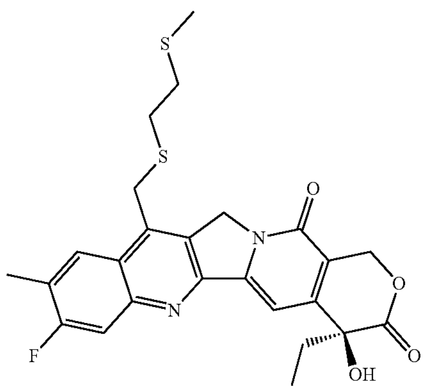 [SMILES: CC[C@@]1(O)C(=O)OCc2c1cc1n(c2=O)Cc2c-1nc1cc(F)c(C)cc1c2CSCCSC] |
| 7c | 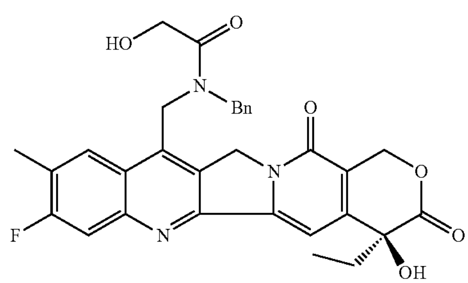 [SMILES: CC[C@@]1(O)C(=O)OCc2c1cc1n(c2=O)Cc2c-1nc1cc(F)c(C)cc1c2CN(Cc1ccccc1)C(=O)CO] |
| k | 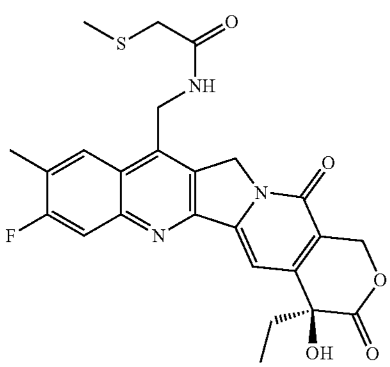 [SMILES: CC[C@@]1(O)C(=O)OCc2c1cc1n(c2=O)Cc2c-1nc1cc(F)c(C)cc1c2CNC(=O)CSC] |
| l | |
| m | |
| 8e | |
| 33a | |

TABLE 1B-continued
| Compound No. | Structure |
|---|---|
| 8b | 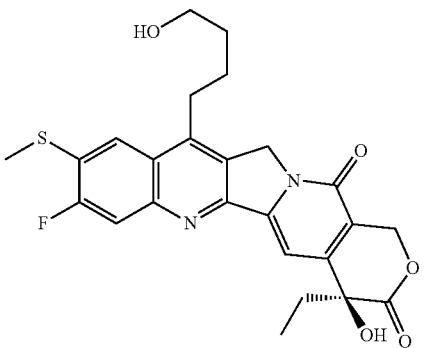 [SMILES: CC[C@@]1(O)C(=O)OCc2c1cc1n(c2=O)Cc2c-1nc1cc(F)c(SC)cc1c2CCCCO] |
| 8c | 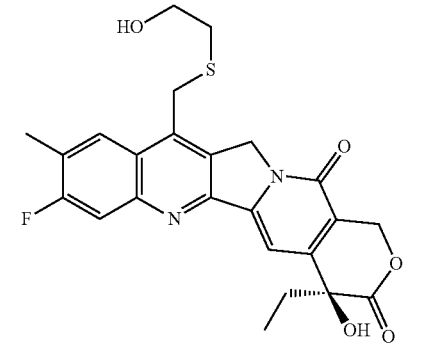 |
| 34a | 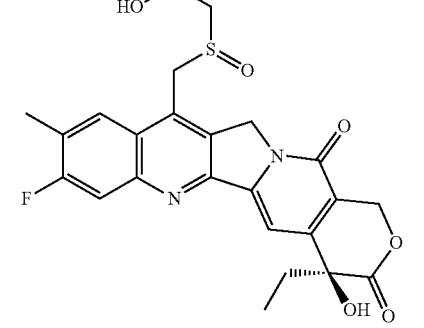 |
| 34b | 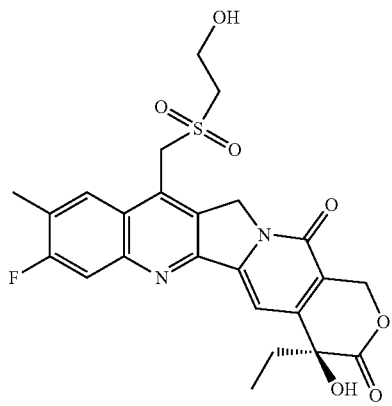 [SMILES: CC[C@@]1(O)C(=O)OCc2c1cc1n(c2=O)Cc2c-1nc1cc(F)c(C)cc1c2CS(=O)(=O)CCO] |
| n | 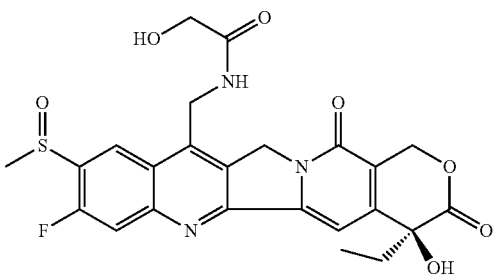 [SMILES: CC[C@@]1(O)C(=O)OCc2c1cc1n(c2=O)Cc2c-1nc1cc(F)c(S(C)=O)cc1c2CNC(=O)CO] |
In some embodiments, the compound is a compound of Formula II and is a compound of any one of the following from the below table:
TABLE 2
| Compound No. | Structure |
|---|---|
| o | 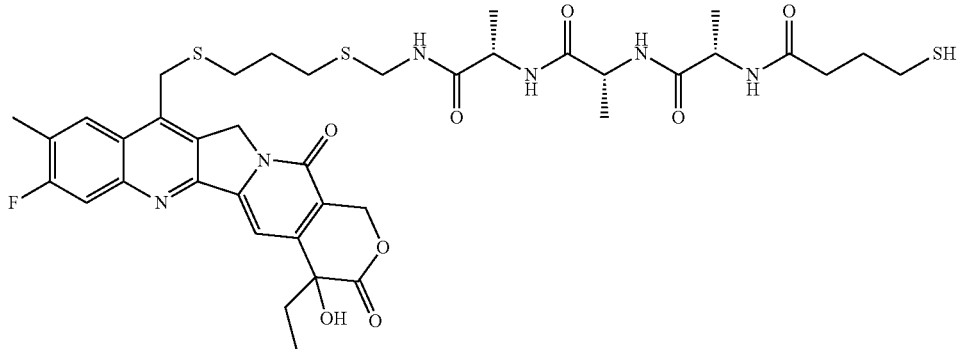 [SMILES: CCC1(O)C(=O)OCc2c1cc1n(c2=O)Cc2c-1nc1cc(F)c(C)cc1c2CSCCCSCNC(=O)[C@H](C)NC(=O)[C@@H](C)NC(=O)[C@H](C)NC(=O)CCCS] |

TABLE 2-continued

| Compound No. | Structure |
|---|---|
| p | 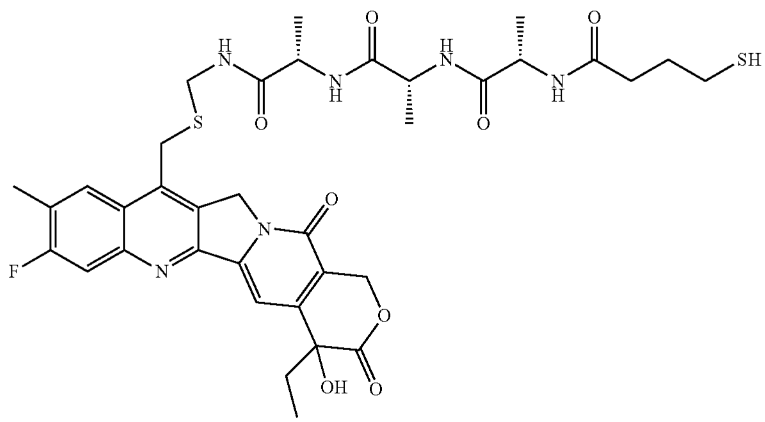 [SMILES: CCC1(O)C(=O)OCc2c1cc1n(c2=O)Cc2c-1nc1cc(F)c(C)cc1c2CSCNC(=O)[C@H](C)NC(=O)[C@@H](C)NC(=O)[C@H](C)NC(=O)CCCS] |
| q | 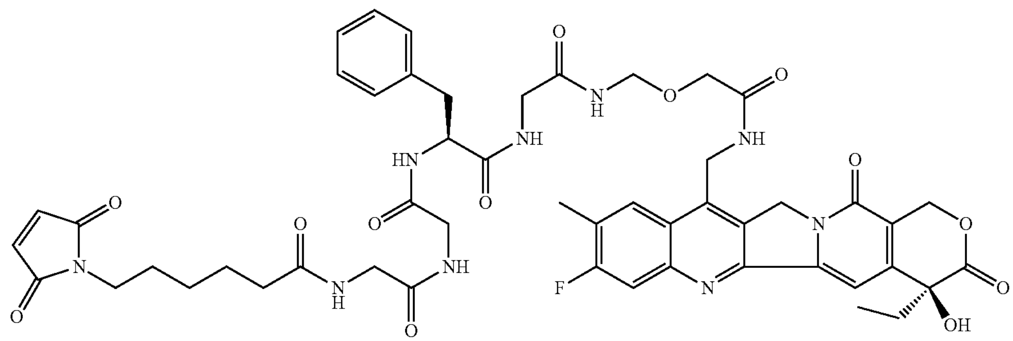 [SMILES: CC[C@@]1(O)C(=O)OCc2c1cc1n(c2=O)Cc2c-1nc1cc(F)c(C)cc1c2CNC(=O)COCNC(=O)CNC(=O)[C@H](Cc1ccccc1)NC(=O)CNC(=O)CNC(=O)CCCCCN1C(=O)C=CC1=O] |
| 25b | 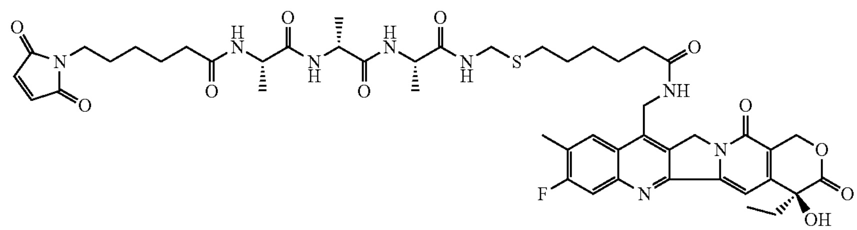 [SMILES: CC[C@@]1(O)C(=O)OCc2c1cc1n(c2=O)Cc2c-1nc1cc(F)c(C)cc1c2CNC(=O)CCCCCSCNC(=O)[C@H](C)NC(=O)[C@@H](C)NC(=O)[C@H](C)NC(=O)CCCCCN1C(=O)C=CC1=O] |
| 25a | 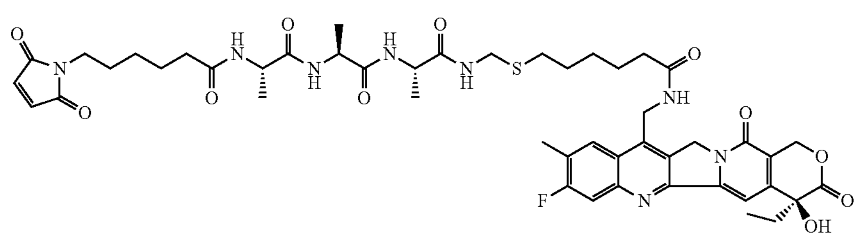 [SMILES: CC[C@@]1(O)C(=O)OCc2c1cc1n(c2=O)Cc2c-1nc1cc(F)c(C)cc1c2CNC(=O)CCCCCSCNC(=O)[C@H](C)NC(=O)[C@H](C)NC(=O)[C@H](C)NC(=O)CCCCCN1C(=O)C=CC1=O] |
| r | 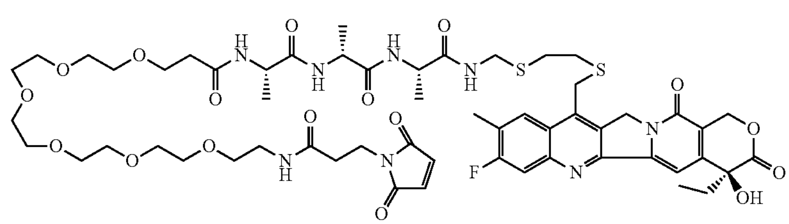 [SMILES: CC[C@@]1(O)C(=O)OCc2c1cc1n(c2=O)Cc2c-1nc1cc(F)c(C)cc1c2CSCCSCNC(=O)[C@H](C)NC(=O)[C@@H](C)NC(=O)[C@H](C)NC(=O)CCOCCOCCOCCOCCOCCOCCNC(=O)CCN1C(=O)C=CC1=O] |

TABLE 2-continued

| Compound No. | Structure |
|---|---|
| s | 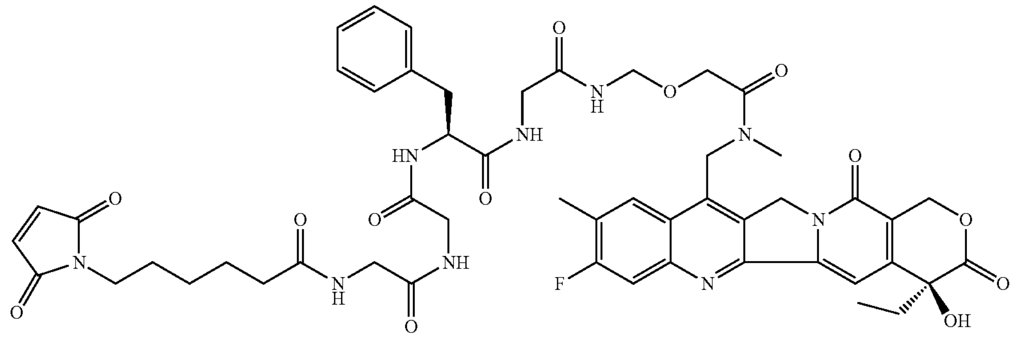 [SMILES: CC[C@@]1(O)C(=O)OCc2c1cc1n(c2=O)Cc2c-1nc1cc(F)c(C)cc1c2CN(C)C(=O)COCNC(=O)CNC(=O)[C@H](Cc1ccccc1)NC(=O)CNC(=O)CNC(=O)CCCCCN1C(=O)C=CC1=O] |
| t | 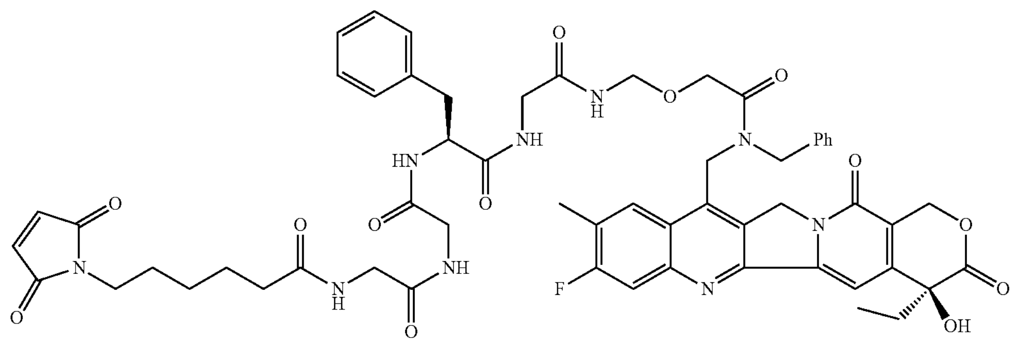 [SMILES: CC[C@@]1(O)C(=O)OCc2c1cc1n(c2=O)Cc2c-1nc1cc(F)c(C)cc1c2CN(Cc1ccccc1)C(=O)COCNC(=O)CNC(=O)[C@H](Cc1ccccc1)NC(=O)CNC(=O)CNC(=O)CCCCCN1C(=O)C=CC1=O] |
| 22a | 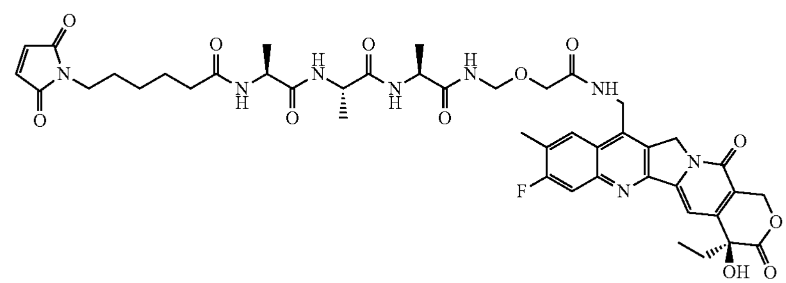 [SMILES: CC[C@@]1(O)C(=O)OCc2c1cc1n(c2=O)Cc2c-1nc1cc(F)c(C)cc1c2CNC(=O)COCNC(=O)[C@H](C)NC(=O)[C@H](C)NC(=O)[C@H](C)NC(=O)CCCCCN1C(=O)C=CC1=O] |
| u | 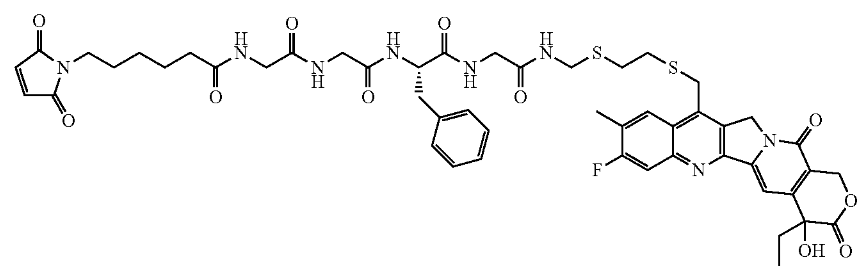 [SMILES: CCC1(O)C(=O)OCc2c1cc1n(c2=O)Cc2c-1nc1cc(F)c(C)cc1c2CSCCSCNC(=O)CNC(=O)[C@H](Cc1ccccc1)NC(=O)CNC(=O)CNC(=O)CCCCCN1C(=O)C=CC1=O] |
| v | 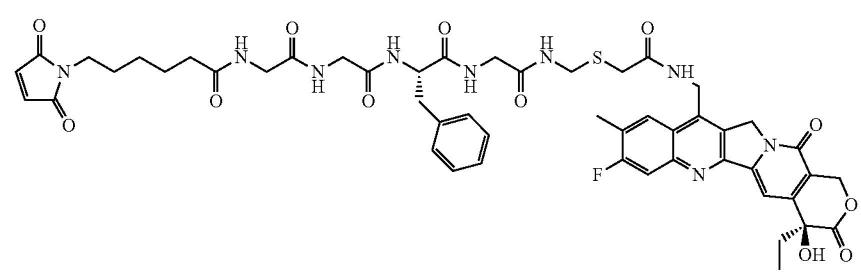 [SMILES: CC[C@@]1(O)C(=O)OCc2c1cc1n(c2=O)Cc2c-1nc1cc(F)c(C)cc1c2CNC(=O)CSCNC(=O)CNC(=O)[C@H](Cc1ccccc1)NC(=O)CNC(=O)CNC(=O)CCCCCN1C(=O)C=CC1=O] |

TABLE 2-continued

| Compound No. | Structure |
|---|---|
| w | 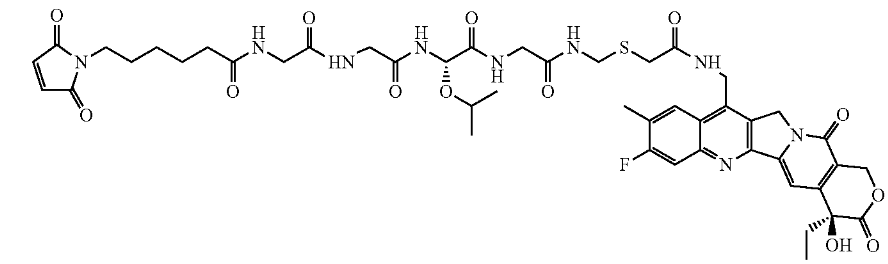 [SMILES: CC[C@@]1(O)C(=O)OCc2c1cc1n(c2=O)Cc2c-1nc1cc(F)c(C)cc1c2CNC(=O)CSCNC(=O)CNC(=O)[C@@H](NC(=O)CNC(=O)CNC(=O)CCCCCN1C(=O)C=CC1=O)OC(C)C] |
| x | 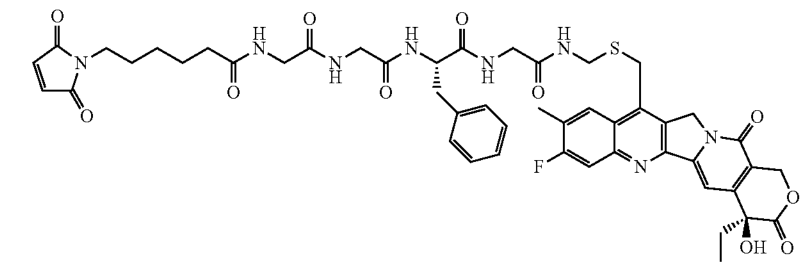 [SMILES: CC[C@@]1(O)C(=O)OCc2c1cc1n(c2=O)Cc2c-1nc1cc(F)c(C)cc1c2CSCNC(=O)CNC(=O)[C@H](Cc1ccccc1)NC(=O)CNC(=O)CNC(=O)CCCCCN1C(=O)C=CC1=O] |
| y | 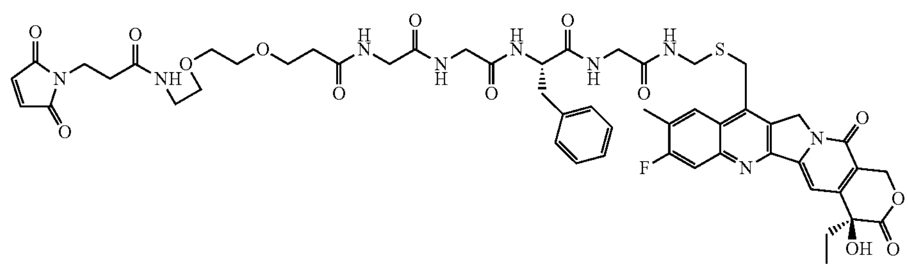 [SMILES: CC[C@@]1(O)C(=O)OCc2c1cc1n(c2=O)Cc2c-1nc1cc(F)c(C)cc1c2CSCNC(=O)CNC(=O)[C@H](Cc1ccccc1)NC(=O)CNC(=O)CNC(=O)CCOCCOCCNC(=O)CCN1C(=O)C=CC1=O] |
| z | 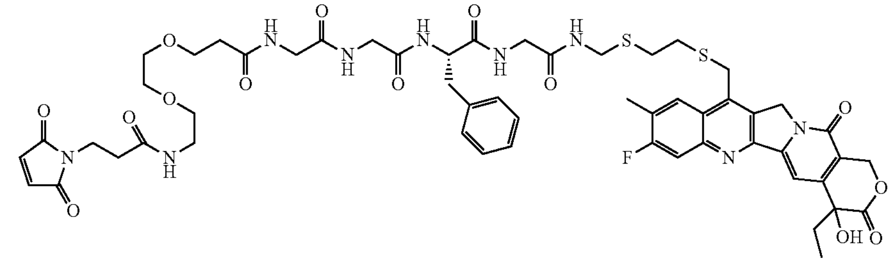 [SMILES: CCC1(O)C(=O)OCc2c1cc1n(c2=O)Cc2c-1nc1cc(F)c(C)cc1c2CSCCSCNC(=O)CNC(=O)[C@H](Cc1ccccc1)NC(=O)CNC(=O)CNC(=O)CCOCCOCCNC(=O)CCN1C(=O)C=CC1=O] |
| aa | 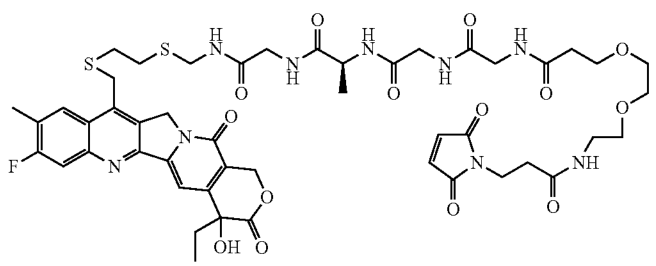 [SMILES: CCC1(O)C(=O)OCc2c1cc1n(c2=O)Cc2c-1nc1cc(F)c(C)cc1c2CSCCSCNC(=O)CNC(=O)[C@H](C)NC(=O)CNC(=O)CNC(=O)CCOCCOCCNC(=O)CCN1C(=O)C=CC1=O] |

TABLE 2-continued

| Compound No. | Structure |
|---|---|
| 22e | (structure) |
| 22c | (structure) |
| ab | (structure) |
| 22d | (structure) |
| ac | (structure) |
| 22b | (structure) |

TABLE 2-continued

| Compound No. | Structure |
| --- | --- |
| ad | (structure) |
| 32a | (structure) |
| ae | (structure) |
| 32b | (structure) |

TABLE 2-continued

| Compound No. | Structure |
|---|---|
| 28a | 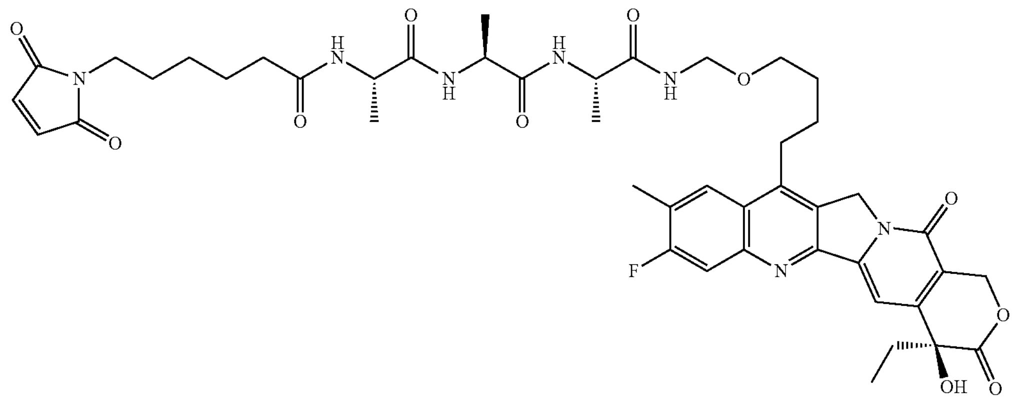 [SMILES: CC[C@@]1(O)C(=O)OCc2c1cc1n(c2=O)Cc2c-1nc1cc(F)c(C)cc1c2CCCCOCNC(=O)[C@H](C)NC(=O)[C@H](C)NC(=O)[C@H](C)NC(=O)CCCCCN1C(=O)C=CC1=O] |
| 28c | 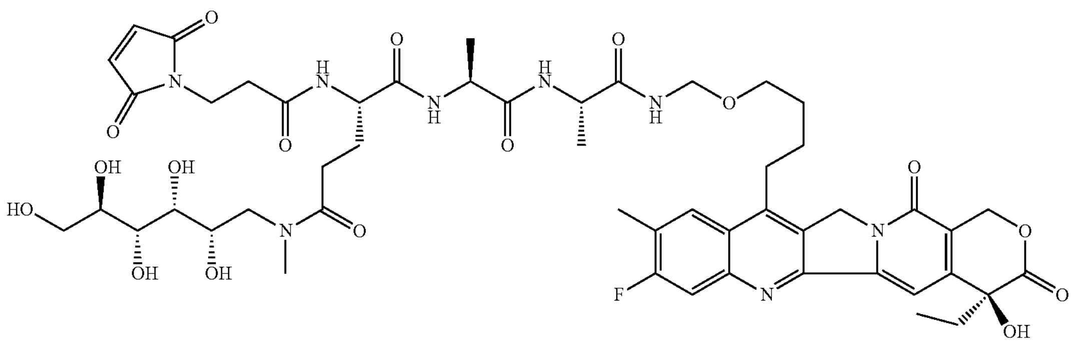 [SMILES: CC[C@@]1(O)C(=O)OCc2c1cc1n(c2=O)Cc2c-1nc1cc(F)c(C)cc1c2CCCCOCNC(=O)[C@H](C)NC(=O)[C@H](C)NC(=O)[C@H](CCC(=O)N(C)C[C@H](O)[C@@H](O)[C@H](O)[C@H](O)CO)NC(=O)CCN1C(=O)C=CC1=O] |
| af | 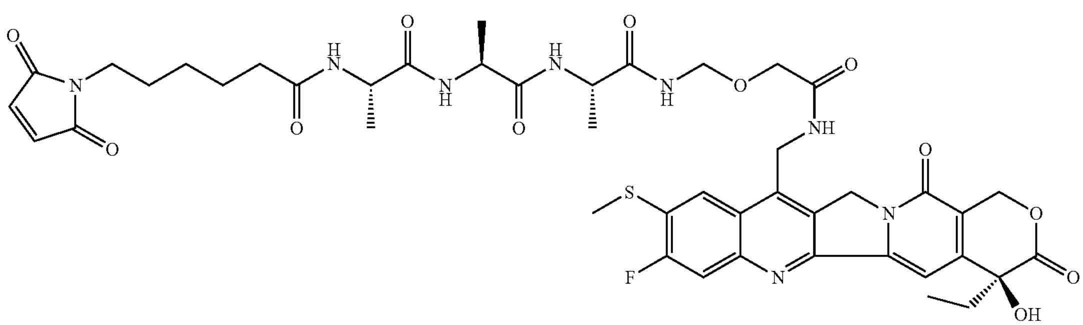 [SMILES: CC[C@@]1(O)C(=O)OCc2c1cc1n(c2=O)Cc2c-1nc1cc(F)c(SC)cc1c2CNC(=O)COCNC(=O)[C@H](C)NC(=O)[C@H](C)NC(=O)[C@H](C)NC(=O)CCCCCN1C(=O)C=CC1=O] |
| 28b | 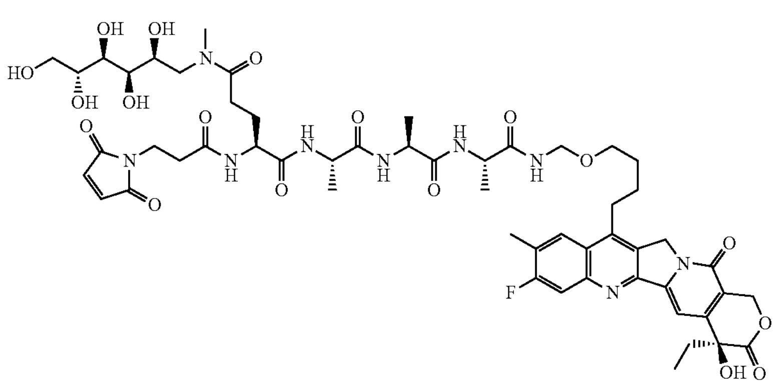 [SMILES: CC[C@@]1(O)C(=O)OCc2c1cc1n(c2=O)Cc2c-1nc1cc(F)c(C)cc1c2CCCCOCNC(=O)[C@H](C)NC(=O)[C@H](C)NC(=O)[C@H](C)NC(=O)[C@H](CCC(=O)N(C)C[C@H](O)[C@@H](O)[C@H](O)[C@H](O)CO)NC(=O)CCN1C(=O)C=CC1=O] |

TABLE 2-continued

| Compound No. | Structure |
|---|---|
| ag | 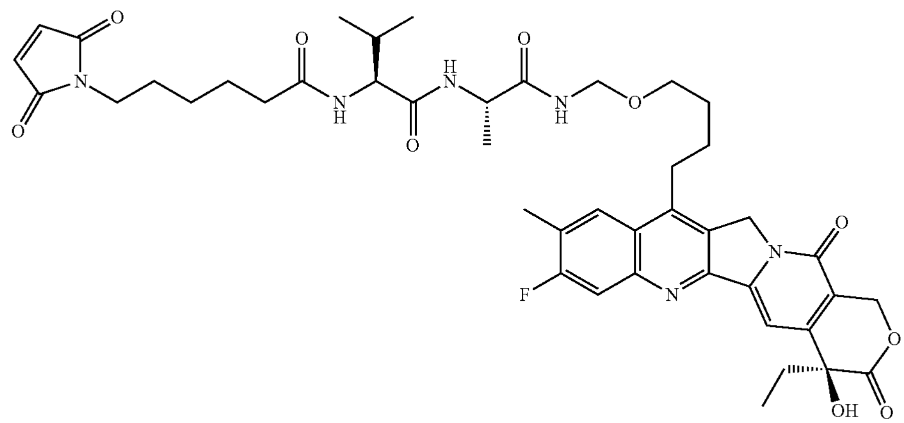 [SMILES: CC[C@@]1(O)C(=O)OCc2c1cc1n(c2=O)Cc2c-1nc1cc(F)c(C)cc1c2CCCCOCNC(=O)[C@H](C)NC(=O)[C@@H](NC(=O)CCCCCN1C(=O)C=CC1=O)C(C)C] |
| ah | 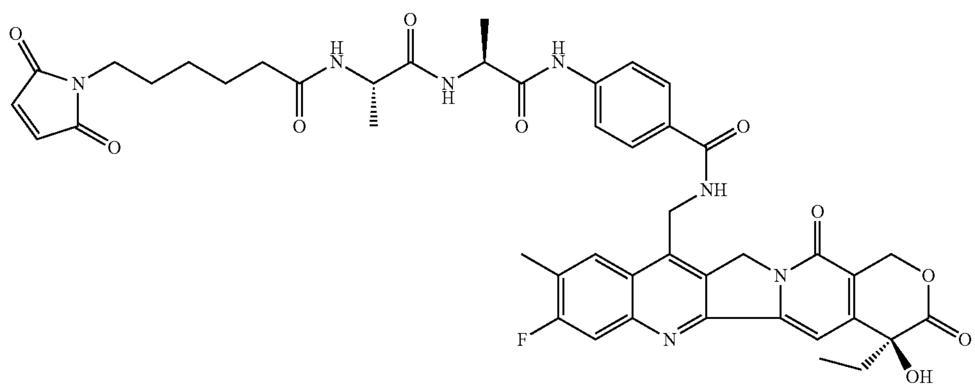 [SMILES: CC[C@@]1(O)C(=O)OCc2c1cc1n(c2=O)Cc2c-1nc1cc(F)c(C)cc1c2CNC(=O)c1ccc(NC(=O)[C@H](C)NC(=O)[C@H](C)NC(=O)CCCCCN2C(=O)C=CC2=O)cc1] |
| ai | 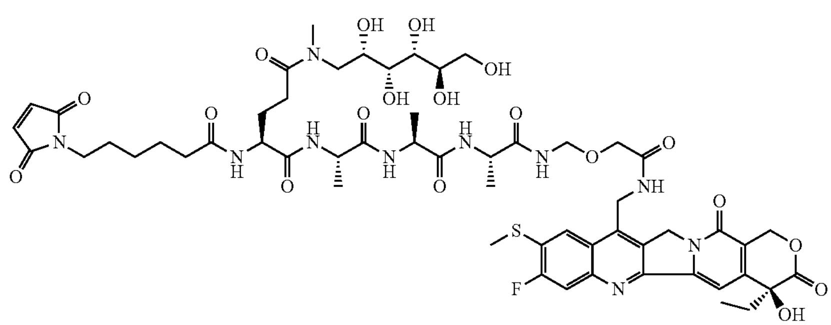 [SMILES: CC[C@@]1(O)C(=O)OCc2c1cc1n(c2=O)Cc2c-1nc1cc(F)c(SC)cc1c2CNC(=O)COCNC(=O)[C@H](C)NC(=O)[C@H](C)NC(=O)[C@H](C)NC(=O)[C@H](CCC(=O)N(C)C[C@H](O)[C@@H](O)[C@H](O)[C@H](O)CO)NC(=O)CCCCCN1C(=O)C=CC1=O] |
| aj | 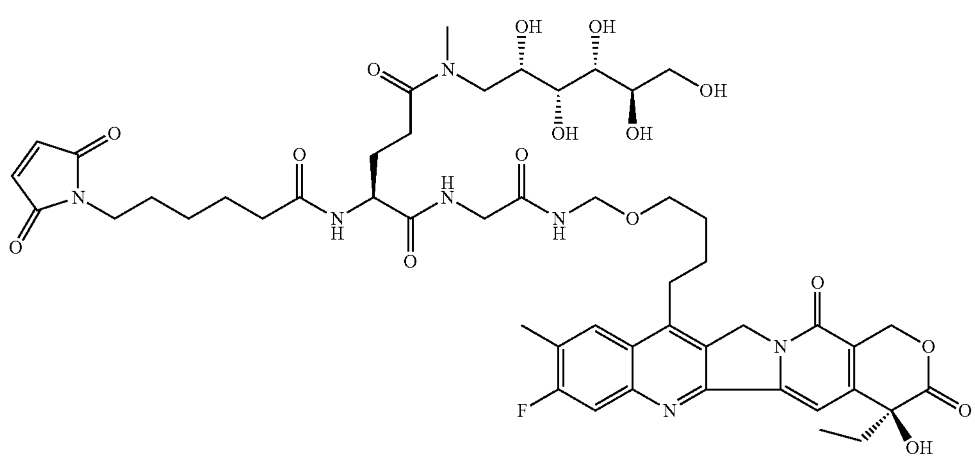 [SMILES: CC[C@@]1(O)C(=O)OCc2c1cc1n(c2=O)Cc2c-1nc1cc(F)c(C)cc1c2CCCCOCNC(=O)CNC(=O)[C@H](CCC(=O)N(C)C[C@H](O)[C@@H](O)[C@H](O)[C@H](O)CO)NC(=O)CCCCCN1C(=O)C=CC1=O] |

TABLE 2-continued
| Compound No. | Structure |
| --- | --- |
| ak | 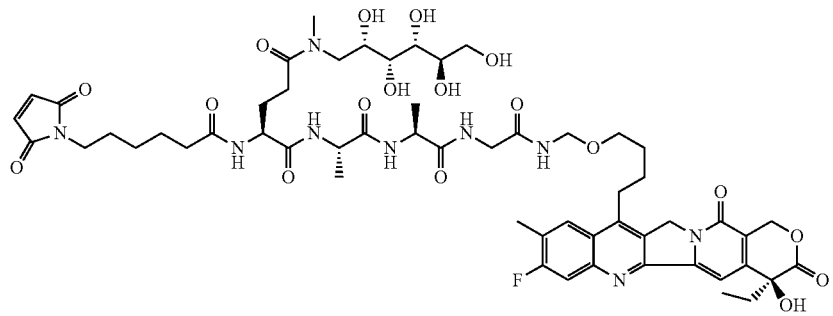 [SMILES: CC[C@@]1(O)C(=O)OCc2c1cc1n(c2=O)Cc2c-1nc1cc(F)c(C)cc1c2CCCCOCNC(=O)CNC(=O)[C@H](C)NC(=O)[C@H](C)NC(=O)[C@H](CCC(=O)N(C)C[C@H](O)[C@@H](O)[C@H](O)[C@H](O)CO)NC(=O)CCCCCN1C(=O)C=CC1=O] |
| al | 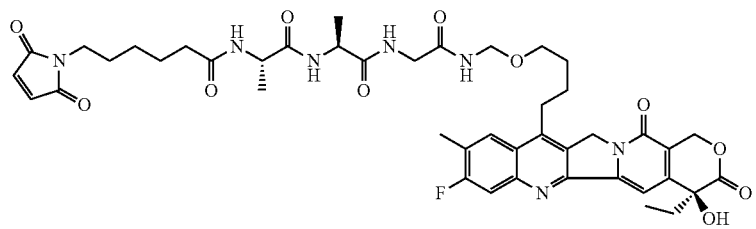 [SMILES: CC[C@@]1(O)C(=O)OCc2c1cc1n(c2=O)Cc2c-1nc1cc(F)c(C)cc1c2CCCCOCNC(=O)CNC(=O)[C@H](C)NC(=O)[C@H](C)NC(=O)CCCCCN1C(=O)C=CC1=O] |
In some embodiments, where the compound comprises a sulfoxide and the sulfoxide is either the R or S configuration. In some embodiments, the compound is any one of the following:
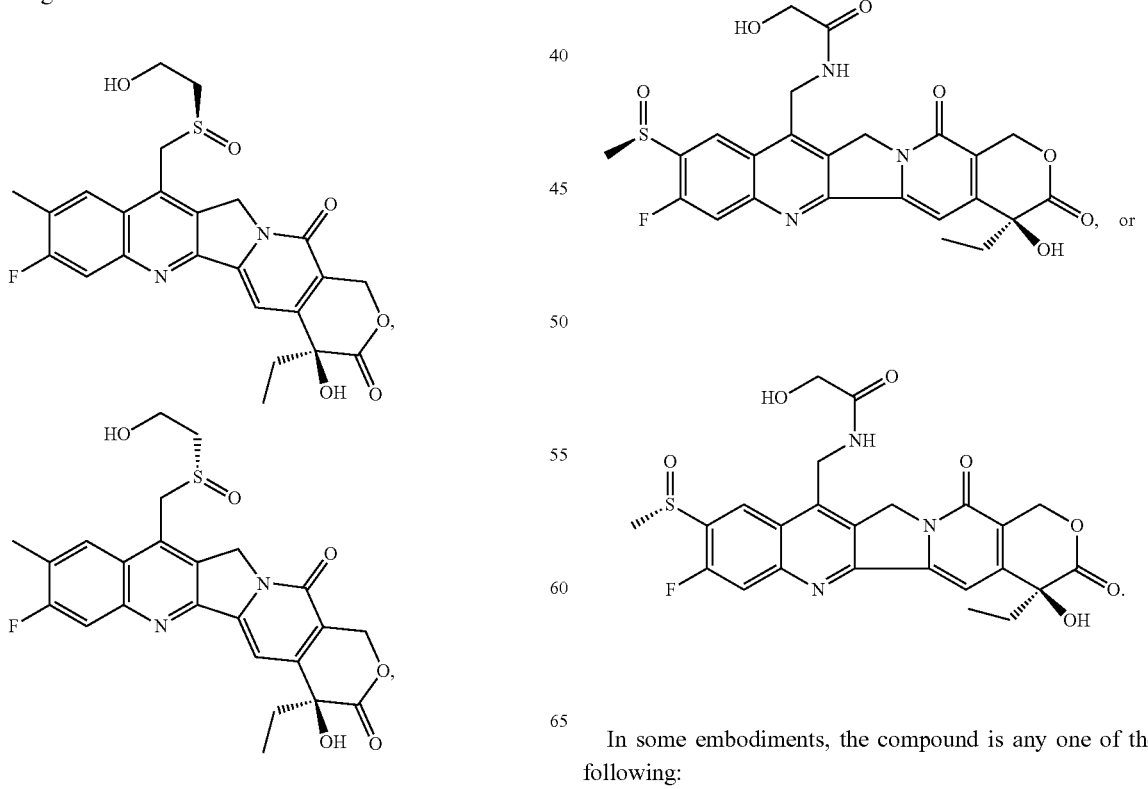
In some embodiments, the compound is any one of the following:

| 95 | 96 |
|---|---|
| 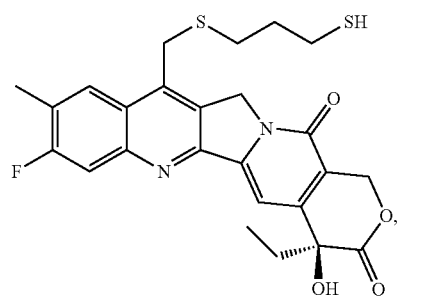 | 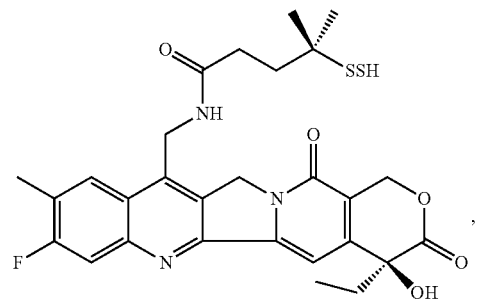 |
| 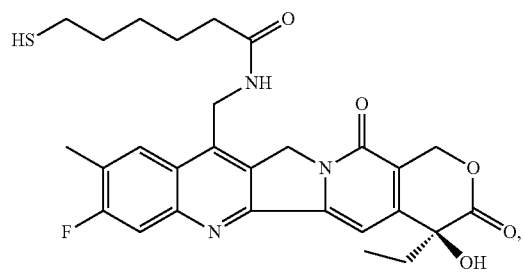 | 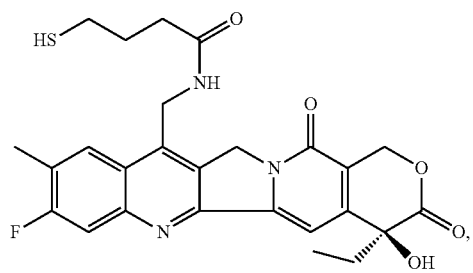 |
| 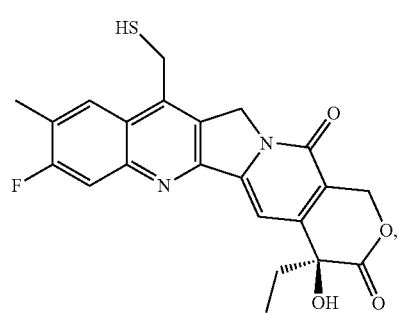 | 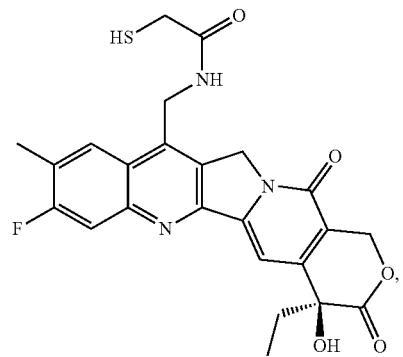 |
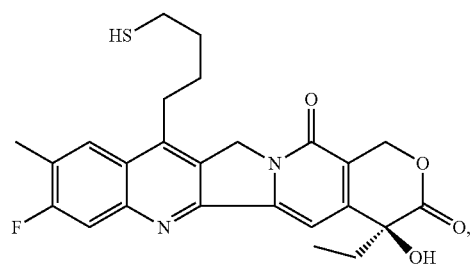
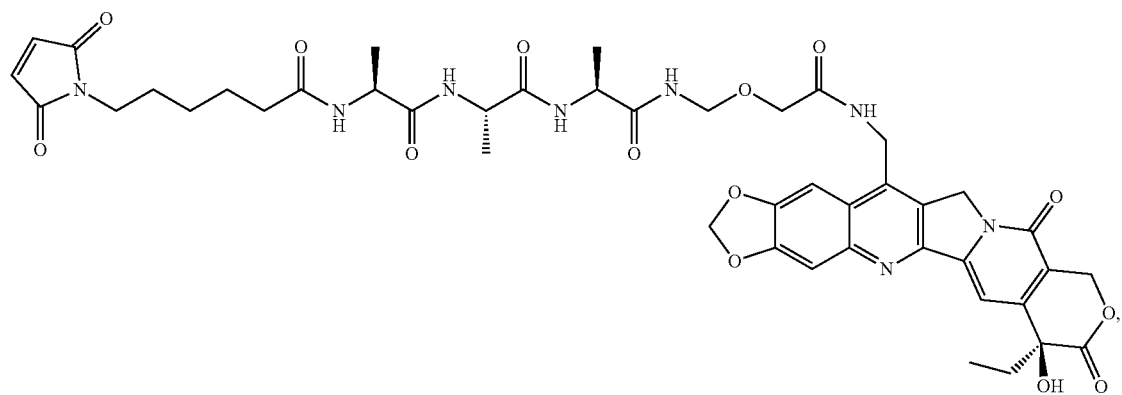

-continued
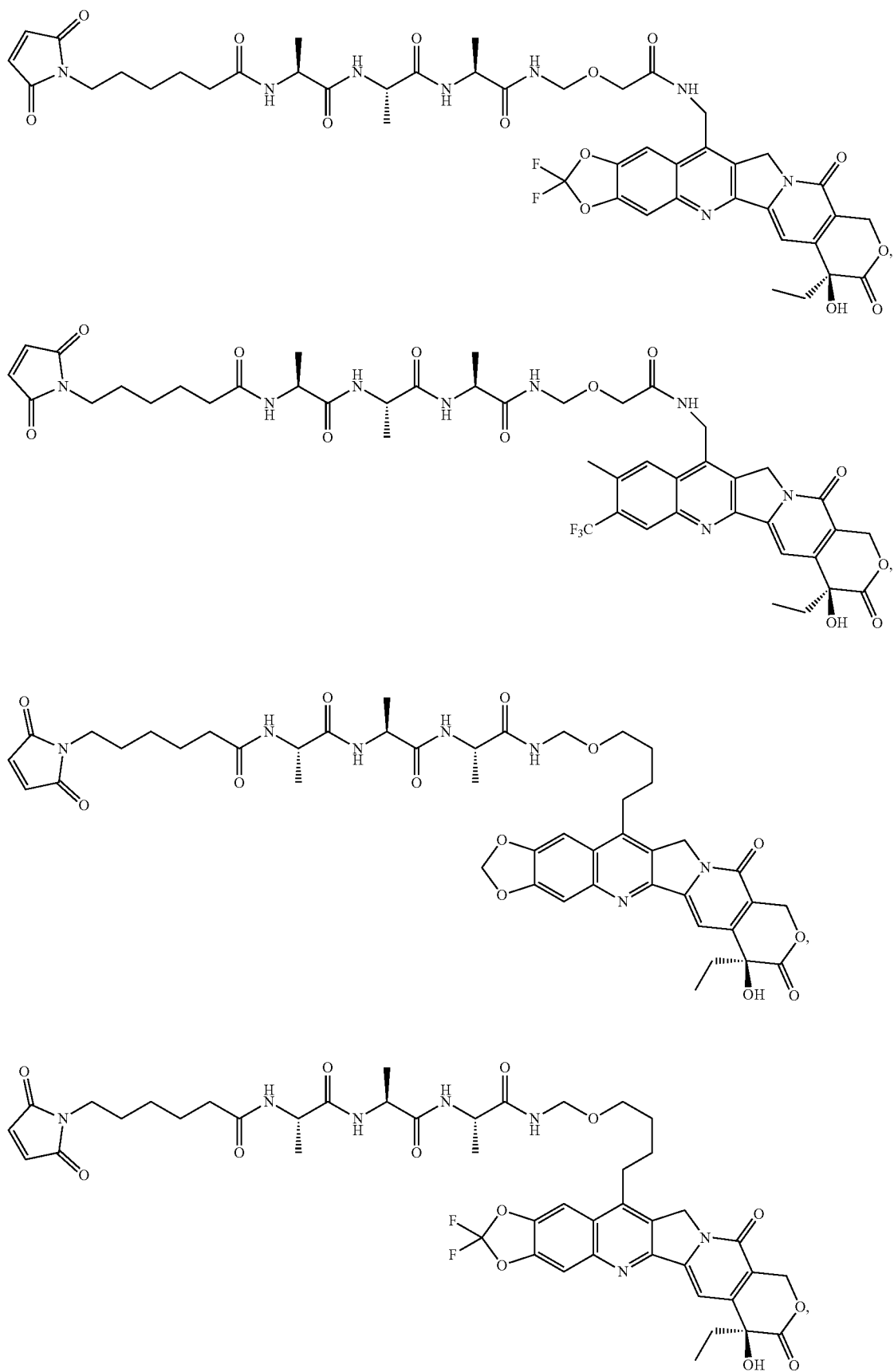

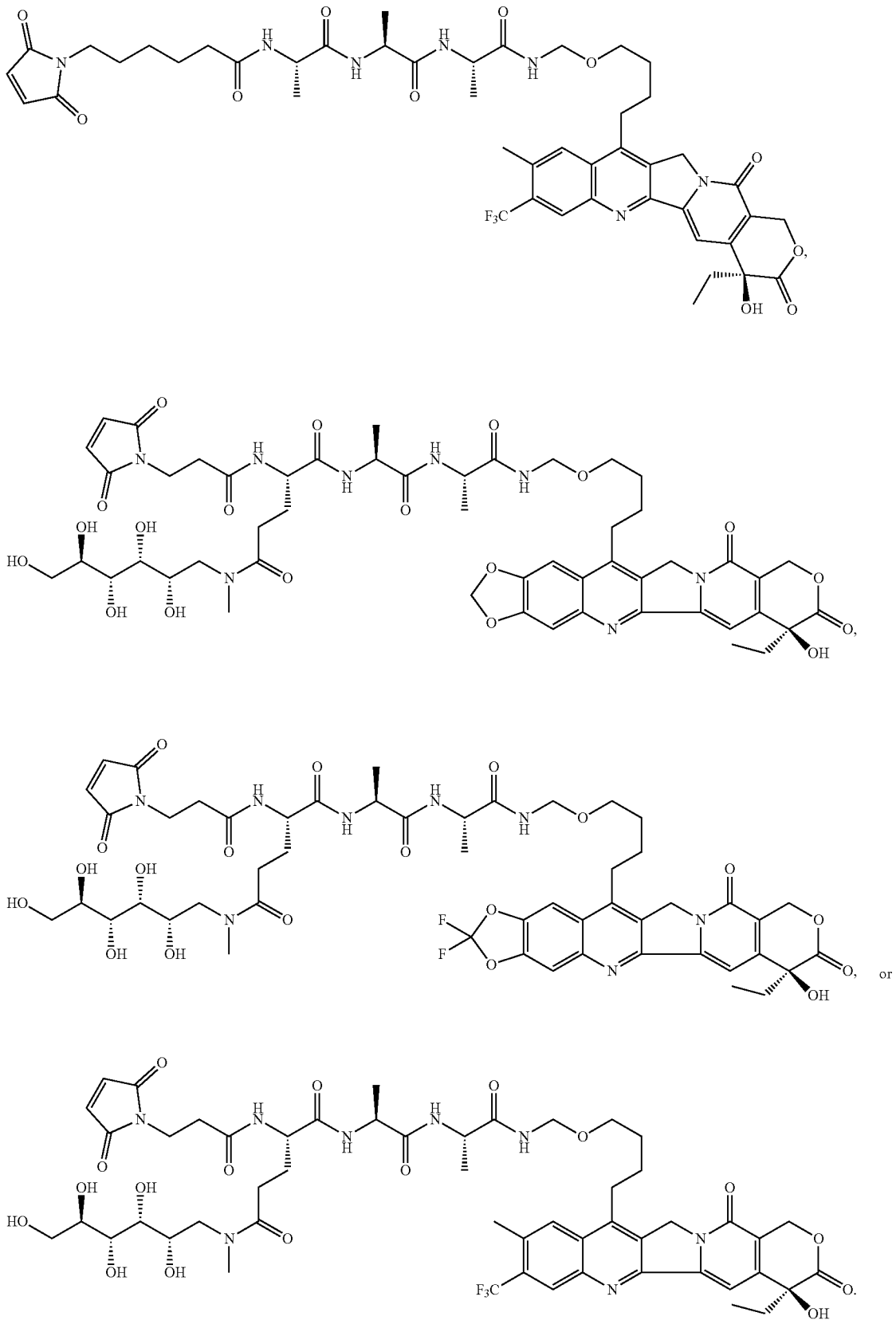

Synthesis of Compounds

The compounds described herein are prepared by the general synthetic routes described in the following schemes.

In some embodiments, the compounds described herein are prepared as outlined in Scheme 1.

Scheme 1. General Synthetic Scheme for Prparting RNH₂ Compounds (A-6)

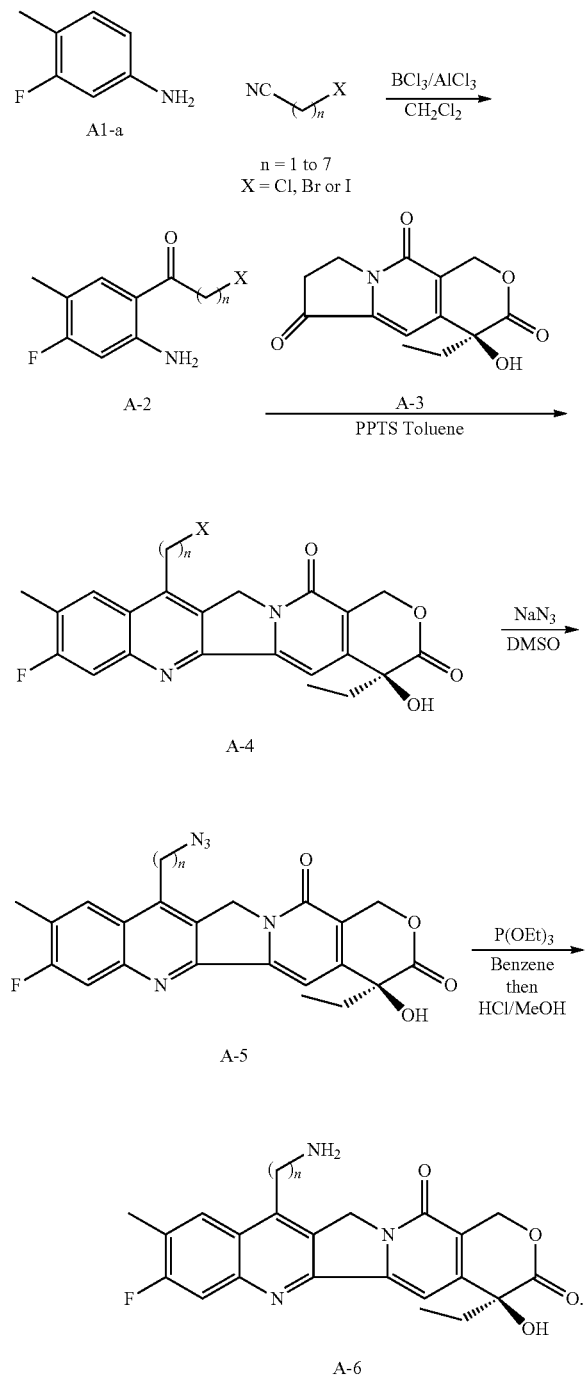

In some embodiments, the compounds described herein are prepared as outlined in Scheme 2.

Scheme 2. General Synthetic Scheme for Preparing ROH Compounds (B-2)

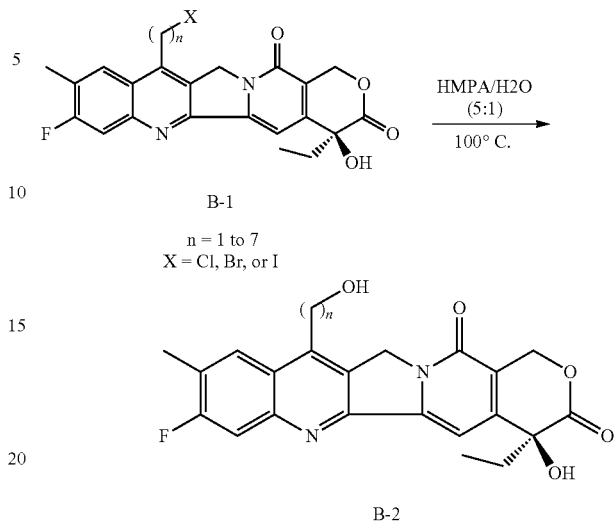

In some embodiments, the compounds described herein are prepared as outlined in Scheme 3.

Scheme 3. General Synthetic Scheme for Preparing RNHR$_{C1}$ Compounds (C-4)

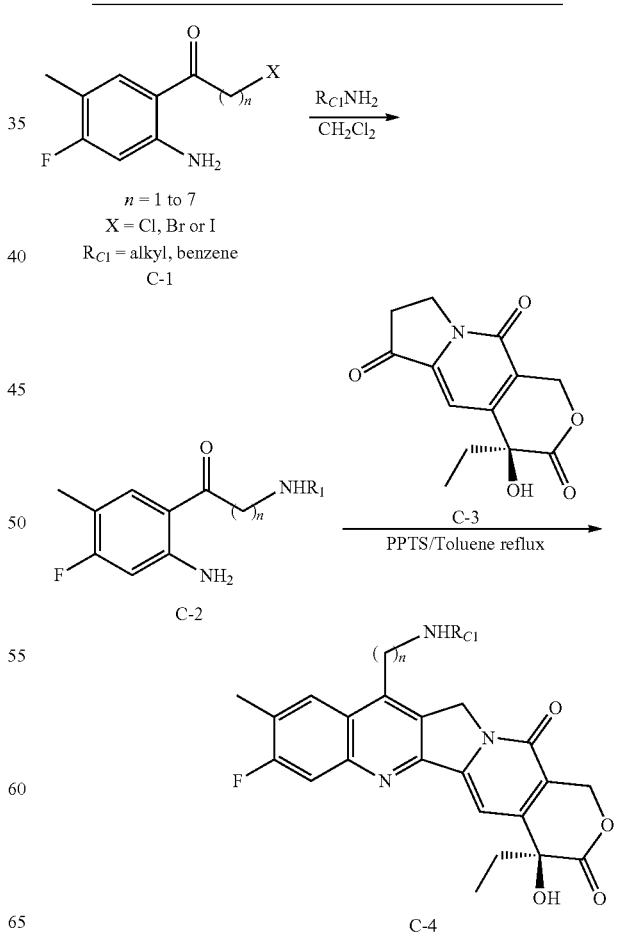

In some embodiments, the compounds described herein are prepared as outlined in Scheme 4.

Scheme 4. General Synthetic Scheme for Preparing RS(CH$_2$)$_n$OH Compounds (D-2)

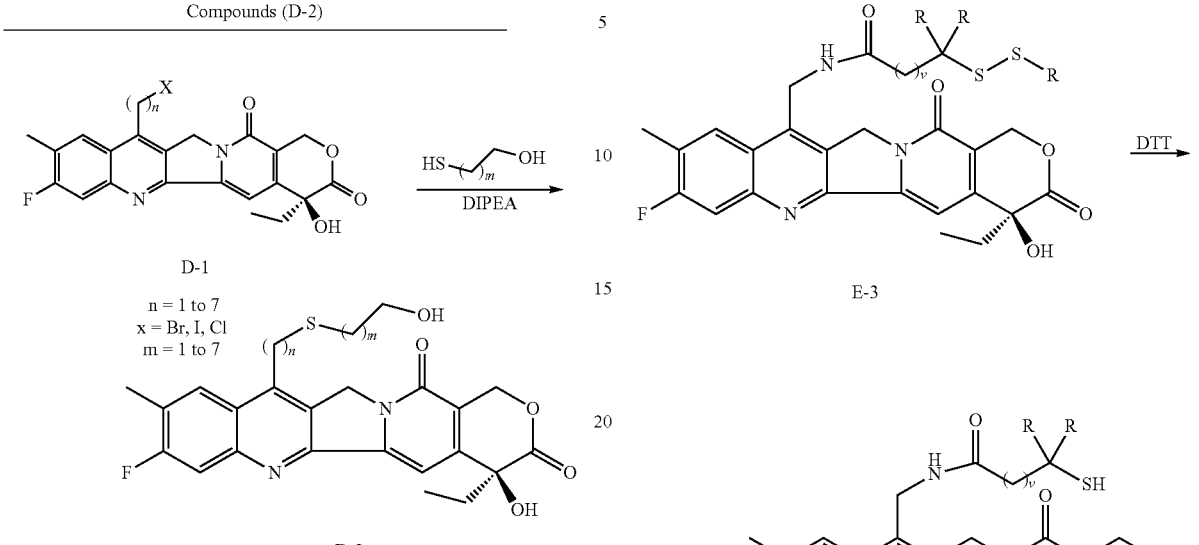

In some embodiments, the compounds described herein are prepared as outlined in Scheme 5.

Scheme 5. General Method for Preparing Thiol-Bearing Camptothecin Derivative (E-4)

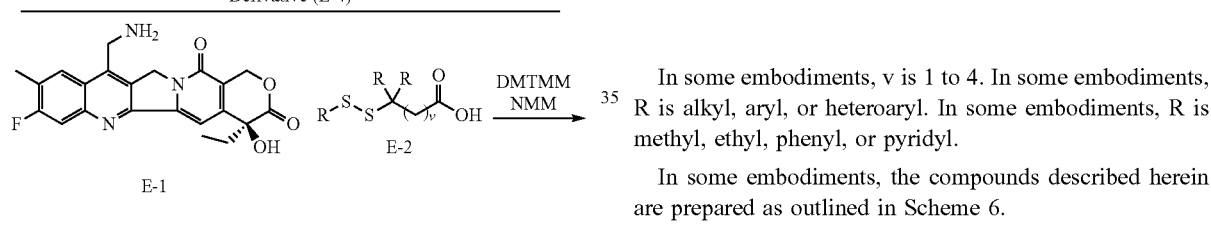

In some embodiments, v is 1 to 4. In some embodiments, R is alkyl, aryl, or heteroaryl. In some embodiments, R is methyl, ethyl, phenyl, or pyridyl.

In some embodiments, the compounds described herein are prepared as outlined in Scheme 6.

Scheme 6. General Method for Preparing Thioaminal-Peptide Linkages That Can Be Further Derivatized to Incorporate Thiols or Maleimides

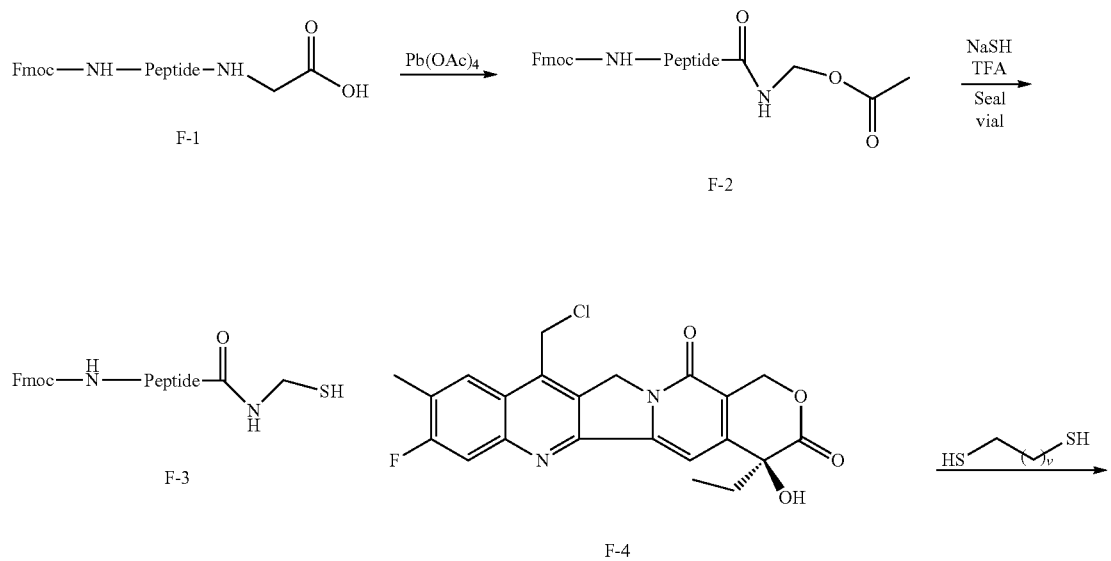

-continued
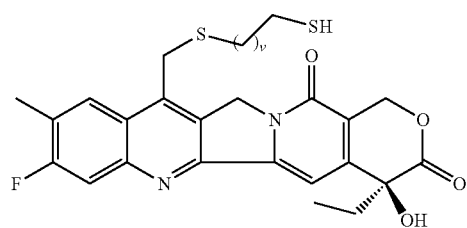
F-5
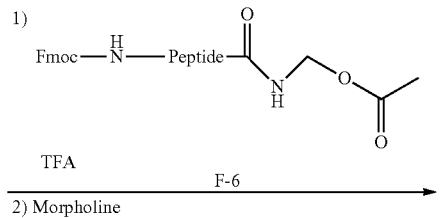
F-6
1)
$$\text{Fmoc}-\overset{H}{N}-\text{Peptide}-\overset{O}{\underset{}{C}}-\overset{H}{N}-\text{CH}_2-O-\overset{O}{\underset{}{C}}-\text{CH}_3$$
$$\xrightarrow[\text{2) Morpholine}]{\text{TFA}}$$
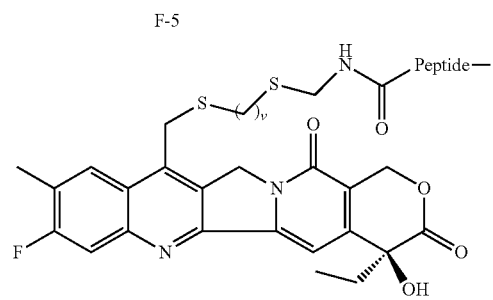
F-7
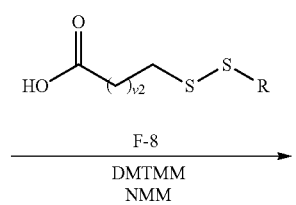
F-8
$$\xrightarrow[\text{NMM}]{\text{DMTMM}}$$
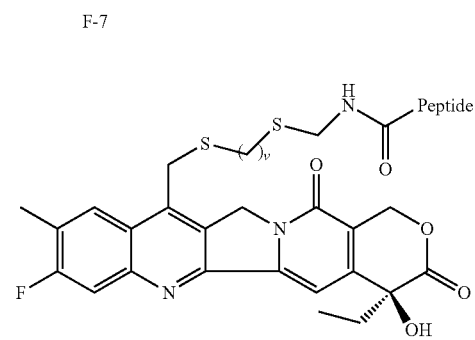
F-9
$$\xrightarrow{\text{DTT}}$$
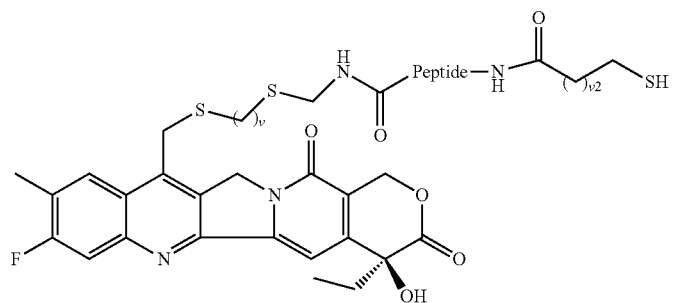
F-10
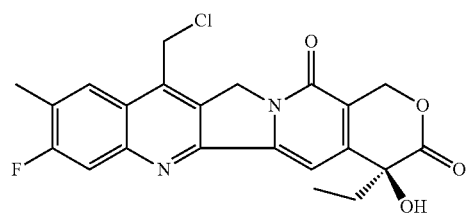
F-11
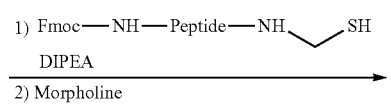
1) Fmoc—NH—Peptide—NH⁀SH
   DIPEA
2) Morpholine
$\longrightarrow$

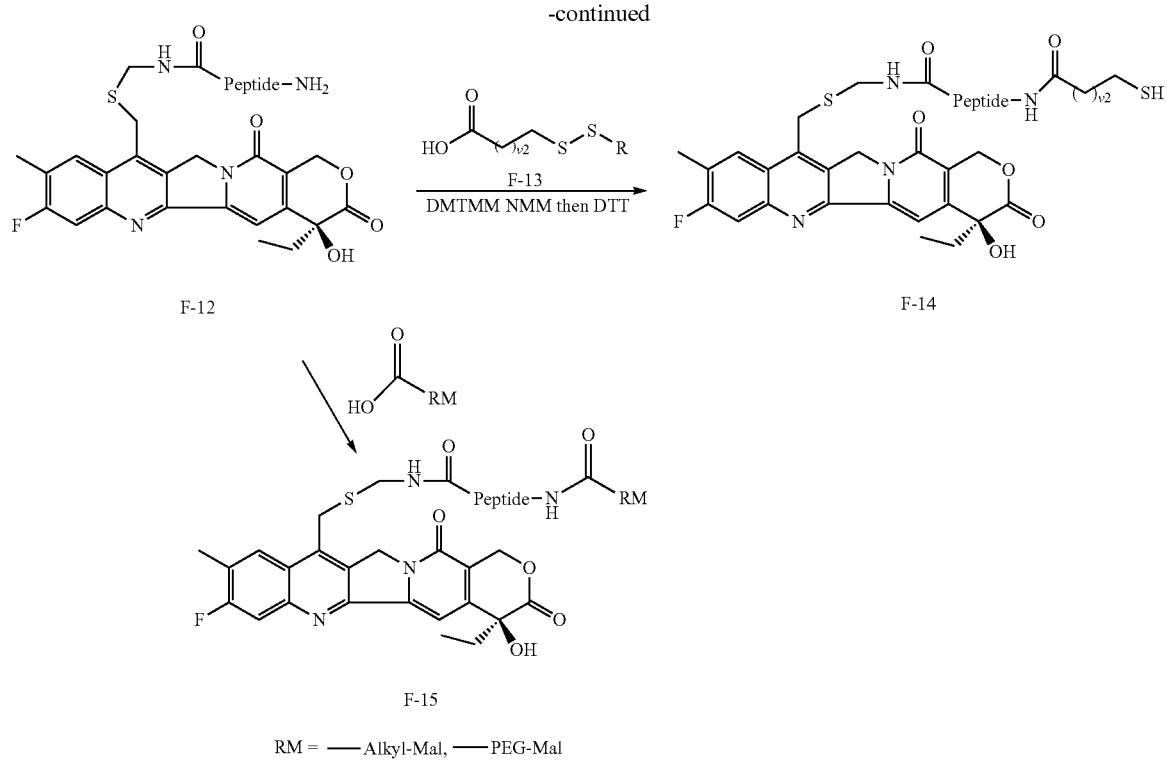
In some embodiments, v is 1 to 4. In some embodiments, v2 is 1 to 4. In some embodiments, R is alkyl, aryl, or heteroaryl. In some embodiments, R is methyl, ethyl, phenyl, or pyridyl.
In some embodiments, the compounds described herein are prepared as outlined in Scheme 7.
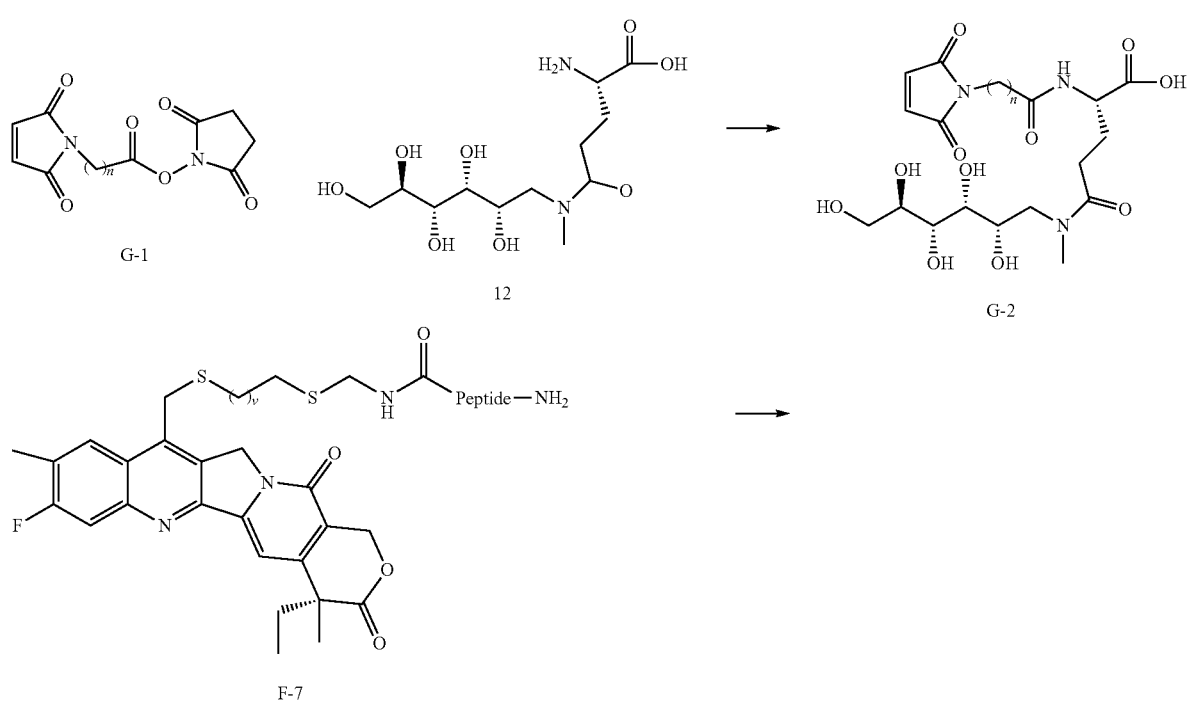

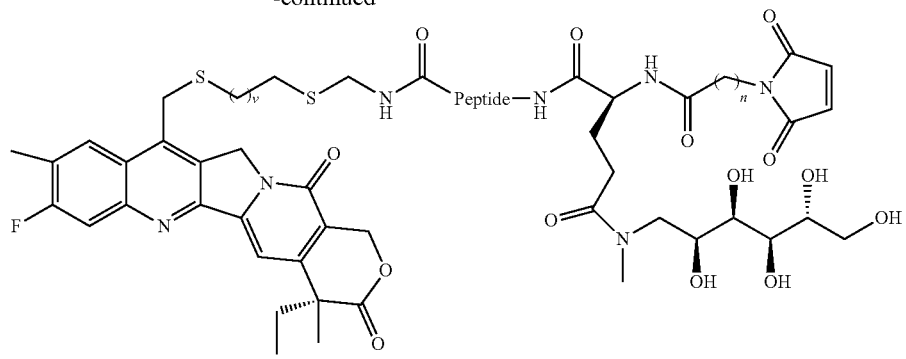

G-3

In some embodiments, n is 1 to 10. In some embodiments, n is 1 to 5. In some embodiments, v is 1 to 10. In some embodiments, v is 1 to 5.

In some embodiments, the compounds described here are prepared as outlined in Scheme 8.

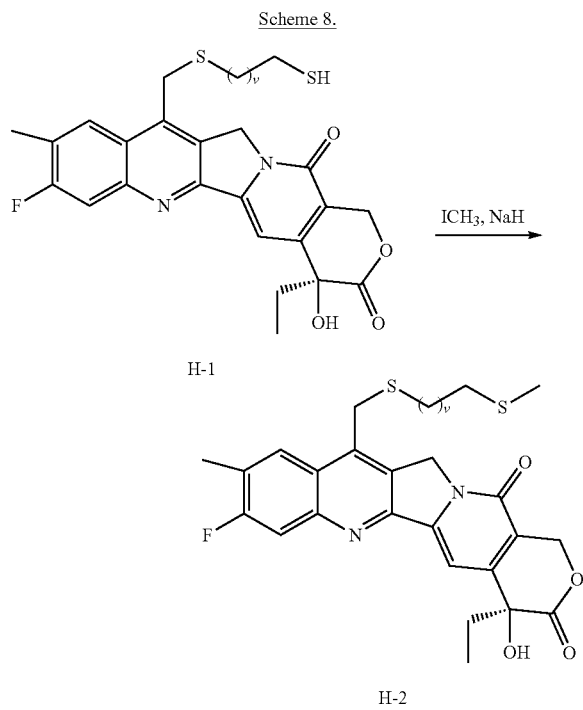

In some embodiments, v is 1 to 10. In some embodiments, v is 1 to 5.

Cell-Binding Agents

Cell-binding agents in the immunoconjugates of the present invention can be of any kind presently known, or that become known, including peptides and non-peptides that binds to a cell or cell component (e.g., receptor, protein, DNA, RNA, etc.). Generally, these can be antibodies (such as polyclonal antibodies and monoclonal antibodies, especially monoclonal antibodies) or fragments thereof, lymphokines, hormones, growth factors, vitamins (such as folate etc., which can bind to a cell surface receptor thereof, e.g., a folate receptor), nutrient-transport molecules (such as transferrin), probodies, nanobodies, or any other cell-binding molecule or substance.

In certain embodiments, the cell-binding agent is an antibody, a single chain antibody, an antibody fragment that specifically binds to the target cell, a monoclonal antibody, a single chain monoclonal antibody, a monoclonal antibody fragment (or "antigen-binding portion" or "antigen-binding fragment") that specifically binds to a target cell, a chimeric antibody, a chimeric antibody fragment (or "antigen-binding portion" or "antigen-binding fragment") that specifically binds to the target cell, a domain antibody (e.g., sdAb), or a domain antibody fragment that specifically binds to the target cell.

In certain embodiments, the cell-binding agent is a humanized antibody, a humanized single chain antibody, or a humanized antibody fragment (or "antigen-binding portion" or "antigen-binding fragment").

In certain embodiments, the cell-binding agent is a resurfaced antibody, a resurfaced single chain antibody, or a resurfaced antibody fragment (or "antigen-binding portion" or "antigen-binding fragment").

In certain embodiments, the cell-binding agent is an antibody or an antigen-binding portion thereof (including antibody derivatives), the CBA may bind to a ligand on the target cell, such as a cell-surface ligand, including cell-surface receptors.

In certain embodiments, the cell-binding agent (CBA) binds to target cells selected from tumor cells, virus infected cells, microorganism infected cells, parasite infected cells, autoimmune cells, activated cells, myeloid cells, activated T-cells, B cells, or melanocytes. In some embodiments, the CBA binds to cells expressing any one or more of 5T4, ADAM-9, ALK, AMHRII, ASCT2, Axl, B7-H3, BCMA, C4.4a, CA6, CA9, CanAg, CD123, CD138, CD142, CD166, CD184, CD19, CD20, CD205, CD22, CD248, CD25, CD3, CD30, CD33, CD352, CD37, CD38, CD40L, CD44v6, CD45, CD46, CD48, CD51, CD56, CD7, CD70, CD71, CD74, CD79b, CDH6, CEACAM5, CEACAM6, cKIT, CLDN18.2, CLDN6, CLL-1, c-MET, Cripto, CSP-1, CXCR5, DLK-1, DLL3, DPEP3, Dysadherin, EFNA4, EGFR, EGFRviii, ENPP3, EpCAM, EphA2, EphA3, ETBR, FGFR2, FGFR3, FLT3, FOLR-alpha, FSH, GCC, GD2, GD3, Globo H, GPC-1, GPC3, gpNMB, HER-2, HER-3, HLA-DR, HSP90, IGF-1R, IL-13R, IL1RAP, IL7R, Interleukin-4 Receptor (IL4R), KAAG-1, LAMP-1, Lewis Y antigen, LGALS3BP, LGR5, LH/hCG, LHRH, LIV-1, LRP-1, LRRC15, Ly6E, MAGE, Mesothelin (MSLN), MET, MHC class I chain-related protein A and B (MICA and MICB), MT1-MMP, MTX3, MTXS, MUC1, MUC16, NaPi2b, Nectin-4, NOTCH3, OAcGD2, OX001L, p-Cadherin, PD-L1, Phosphatidylserine (PS), Polymorphic epithelial mucin (PEM), Prolactin Receptor (PRLR), PSMA, PTK7, RNF43, ROR1, ROR2, SAIL, SLAMF7, SLC44A4, SLITRK6, SSTR2, STEAP-1, STING, STn, TIM-1, TM4SF1, TNF-alpha, TRA, TROP-2, Tumor-associated glycoprotein 72 (TAG-72), tumor-specific epitope of mucin-1 (TA-MUC1), CDS, TIM-3, UPK2, or UPK1b antigen.

In certain embodiments, the cell-binding agent is a cysteine-engineered antibody or antigen-binding fragment thereof that specifically binds to cells expressing any one or more of the 5T4, ADAM-9, ALK, AMHRII, ASCT2, Axl, B7-H3, BCMA, C4.4a, CA6, CA9, CanAg, CD123, CD138, CD142, CD166, CD184, CD19, CD20, CD205, CD22, CD248, CD25, CD3, CD30, CD33, CD352, CD37, CD38, CD40L, CD44v6, CD45, CD46, CD48, CD51, CD56, CD7, CD70, CD71, CD74, CD79b, CDH6, CEACAM5, CEACAM6, cKIT, CLDN18.2, CLDN6, CLL-1, c-MET, Cripto, CSP-1, CXCRS, DLK-1, DLL3, DPEP3, Dysadherin, EFNA4, EGFR, EGFRviii, ENPP3, EpCAM, EphA2, EphA3, ETBR, FGFR2, FGFR3, FLT3, FOLR-alpha, FSH, GCC, GD2, GD3, Globo H, GPC-1, GPC3, gpNMB, HER-2, HER-3, HLA-DR, HSP90, IGF-1R, IL-13R, IL1RAP, IL7R, Interleukin-4 Receptor (IL4R), KAAG-1, LAMP-1, Lewis Y antigen, LGALS3BP, LGRS, LH/hCG, LHRH, LIV-1, LRP-1, LRRC15, Ly6E, MAGE, Mesothelin (MSLN), MET, MHC class I chain-related protein A and B (MICA and MICB), MT1-MMP, MTX3, MTXS, MUC1, MUC16, NaPi2b, Nectin-4, NOTCH3, OAcGD2, OX001L, p-Cadherin, PD-L1, Phosphatidylserine (PS), Polymorphic epithelial mucin (PEM), Prolactin Receptor (PRLR), PSMA, PTK7, RNF43, ROR1, ROR2, SAIL, SLAMF7, SLC44A4, SLITRK6, SSTR2, STEAP-1, STING, STn, TIM-1, TM4SF1, TNF-alpha, TRA, TROP-2, Tumor-associated glycoprotein 72 (TAG-72), tumor-specific epitope of mucin-1 (TA-MUC1), CDS, TIM-3, UPK2, or UPK1b antigen.

In certain embodiments, the CBA is an antibody selected from the group consisting of an anti-CD37 antibody (e.g., as disclosed in U.S. Pat. No. 8,765,917, the contents of which is incorporated herein by reference in its entirety), an anti-CD19 antibody (e.g., the huB4 antibody as disclosed in U.S. Pat. No. 9,555,126, the contents of which are incorporated herein by reference in its entirety), and an anti-EGFR antibody (e.g., the huML66 antibody as disclosed in U.S. Pat. Nos. 9,238,690 8,790,649, and 9,125,896, the contents of which are incorporated herein by reference in their entirety).

In certain embodiments, the CBA is an anti-CD123 antibody or antigen-binding fragment thereof may comprise: a) at least one light chain variable region or fragment thereof comprising three sequential complementarity-determining regions (CDR) $CDR_L1$, $CDR_L2$, and $CDR_L3$, respectively, wherein $CDR_L1$ has the amino acid sequence of RASQDINSYLS (SEQ ID NO:1), $CDR_L2$ has the amino acid sequence of RVNRLVD (SEQ ID NO:2), and, $CDR_L3$ has the amino acid sequence of LQYDAFPYT (SEQ ID NO:3); and b) at least one heavy chain variable region or fragment thereof comprising three sequential complementarity-determining regions (CDR) $CDR_H1$, $CDR_H2$, and $CDR_H3$, respectively, wherein, $CDR_H1$ has the amino acid sequence of SSIMH (SEQ ID NO:4), $CDR_H2$ has the amino acid sequence of YIKPYNDGTKYNEKFKG (SEQ ID NO:5), and, $CDR_H3$ has the amino acid sequence of EGGNDYYDTMDY (SEQ ID NO:6).

In certain embodiments, the anti-CD123 antibody or antigen-binding fragment thereof comprises a heavy chain variable region ($V_H$) having the amino acid sequence of (SEQ ID NO: 7)
QVQLVQSGAEVKKPGASVKVSCKASGYIFT<u>SSIMH</u>WVRQAPGQGLEWIG <u>YIKPYNDGTKYNEKFKG</u>RATLTSDRSTSTAYMELSSLRSEDTAVYYCAR <u>EGGNDYYDTMDY</u>WGQGTLVTVSS, wherein $CDR_H1$, $CDR_H2$, and $CDR_H3$ are double-underlined;
and a light chain variable region ($V_L$) having the amino acid sequence of (SEQ ID NO: 9)
DIQMTQSPSSLSASVGDRVTITC<u>RASQDINSYLS</u>WFQQKPGKAPKTLIY <u>RVNRLVD</u>GVPSRFSGSGSGNDYTLTISSLQPEDFATYYC<u>LQYDAFPYT</u>F

GQGTKVEIKR, wherein $CDR_L1$, $CDR_L2$, and $CDR_L3$ are double underlined.
In certain embodiments, the anti-CD123 antibody has a heavy chain full length sequence of (SEQ ID NO: 8)
QVQLVQSGAEVKKPGASVKVSCKASGYIFT<u>SSIMH</u>WVRQAPGQGLEWIG <u>YIKPYNDGTKYNEKFKG</u>RATLTSDRSTSTAYMELSSLRSEDTAVYYCAR <u>EGGNDYYDTMDY</u>WGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLCLSPG, wherein $CDR_H1$, $CDR_H2$, and $CDR_H3$ are double-underlined;
and a light chain full length sequence of (SEQ ID NO: 10)
DIQMTQSPSSLSASVGDRVTITC<u>RASQDINSYLS</u>WFQQKPGKAPKTLIY <u>RVNRLVD</u>GVPSRFSGSGSGNDYTLTISSLQPEDFATYYC<u>LQYDAFPYT</u>F

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC, wherein $CDR_L1$, $CDR_L2$, and $CDR_L3$ are underlined.
In certain embodiments, an anti-CD123 antibody or antigen-binding fragment thereof is provided as an activatable antibody or activatable antibody-binding antibody fragment as further described below. In certain other embodiments, the anti-CD123 activatable antibody or activatable CD123 antibody-binding antibody fragment can be conjugated to a compound of Formula I.

In certain embodiments, the CBA is an anti-CD33 antibody or an antigen-binding fragment thereof as described in U.S. Pat. Nos. 7,342,110 and 7,557,189, which are incorporated herein by reference.

In certain embodiments, the anti-CD33 antibody or antigen-binding fragment thereof may comprise: a) at least one light chain variable region or fragment thereof comprising three sequential complementarity-determining regions (CDR) $CDR_L1$, $CDR_L2$, and $CDR_L3$, respectively, wherein $CDR_L1$ has the amino acid sequence of KSSQSVFFSSSQK-NYLA (SEQ ID NO:11), $CDR_L2$ has the amino acid sequence of WASTRES (SEQ ID NO:12), and, $CDR_L3$ has the amino acid sequence of HQYLSSRT (SEQ ID NO:13); and b) at least one heavy chain variable region or fragment thereof comprising three sequential complementarity-determining regions (CDR) $CDR_H1$, $CDR_H2$, and $CDR_H3$, respectively, wherein, $CDR_H1$ has the amino acid sequence of SYYIH (SEQ ID NO:14), $CDR_H2$ has the amino acid sequence of VIYPGNDDISYNQKFQG (SEQ ID NO:15), and, $CDR_H3$ has the amino acid sequence of EVRLRYFDV (SEQ ID NO:16).

In certain embodiments, the anti-CD33 antibody or antigen-binding fragment thereof comprises a heavy chain variable region ($V_H$) having the amino sequence of

```
                                          (SEQ ID NO: 17)
QVQLQQPGAEVVKPGASVKMSCKASGYTFTSYYIHWIKQTPGQGLEWVG

VIYPGNDDISYNQKFQGKATLTADKSSTTAYMQLSSLTSEDSAVYYCAR

EVRLRYFDVWGQGTTVTVSS,
``` wherein $CDR_H1$, $CDR_H2$, and $CDR_H3$ are double-underlined; and a light chain variable region ($V_L$) having the amino acid sequence of

```
                                          (SEQ ID NO: 19)
EIVLTQSPGSLAVSPGERVTMSCKSSQSVFFSSSQKNYLAWYQQIPGQS

PRLLIYWASTRESGVPDRFTGSGSGTDFTLTISSVQPEDLAIYYCHQYL

SSRTFGQGTKLEIKR,
``` wherein $CDR_L1$, $CDR_L2$, and $CDR_L3$ are double-underlined.

In certain embodiments, the anti-CD33 antibody has a heavy chain full length sequence of

```
                                          (SEQ ID NO: 18)
QVQLQQPGAEVVKPGASVKMSCKASGYTFTSYYIHWIKQTPGQGLEWVG

VIYPGNDDISYNQKFQGKATLTADKSSTTAYMQLSSLTSEDSAVYYCAR

EVRLRYFDVWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLEP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LSLSPG,
``` wherein $CDR_H1$, $CDR_H2$, and $CDR_H3$ are double-underlined;

and a light chain full length sequence of

```
                                          (SEQ ID NO: 20)
EIVLTQSPGSLAVSPGERVTMSCKSSQSVFFSSSQKNYLAWYQQIPGQS

PRLLIYWASTRESGVPDRFTGSGSGTDFTLTISSVQPEDLAIYYCHQYL

SSRTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC,
``` wherein $CDR_L1$, $CDR_L2$, and $CDR_L3$ are double-underlined.

In certain embodiments, the anti-CD33 antibody is huMy9-6 antibody.

In certain embodiments, an anti-CD33 antibody or antigen-binding fragment thereof is provided as an activatable antibody or activatable antibody-binding antibody fragment as further described below. In certain other embodiments, the anti-CD33 activatable antibody or activatable CD33 antibody-binding antibody fragment can be conjugated to a compound of Formula I.

In certain embodiment, the CBA is an anti-ADAM9 antibody or an antigen-binding fragment thereof as described in WO2018/119196 and U.S. Provisional Application Nos. 62/690,052 and 62/691,342, each of which are incorporated herein by reference.

In certain embodiments, the anti-ADAM9 antibody or antigen-binding fragment thereof is a humanized anti-ADAM9 antibody or antigen-binding fragment thereof that specifically binds to human ADAM9 and cyno ADAM9.

In certain embodiments, the humanized anti-ADAM9 antibody or ADAM9-binding fragment thereof is optimized to have at least a 100-fold enhancement in binding affinity to cyno ADAM9 and retains high affinity binding to human ADAM9 as compared to the chimeric or murine parental antibody.

In certain embodiments, the anti-ADAM9 antibody or antigen-binding fragment thereof (e.g., the humanized anti-ADAM9 antibody or antigen-binding fragment thereof) comprises: a) at least one light chain variable region or fragment thereof comprising three sequential complementarity-determining regions (CDR) $CDR_L1$, $CDR_L2$, and $CDR_L3$, respectively, wherein $CDR_L1$ has the amino acid sequence of KASQSVDYSGDSYMN (SEQ ID NO:21), $CDR_L2$ has the amino acid sequence of AASDLES (SEQ ID NO:22), and, $CDR_L3$ has the amino acid sequence of QQSHEDPFT (SEQ ID NO:23); and b) at least one heavy chain variable region or fragment thereof comprising three sequential complementarity-determining regions (CDR) $CDR_H1$, $CDR_H2$, and $CDR_H3$, respectively, wherein, $CDR_H1$ has the amino acid sequence of SYWMH (SEQ ID NO:24), $CDR_H2$ has the amino acid sequence of EIIP-IFGHTNYNEKFKS (SEQ ID NO:25), and, $CDR_H3$ has the amino acid sequence of GGYYYYPRQGFLDY (SEQ ID NO:26).

In certain embodiments, the anti-ADAMS antibody or antigen-binding fragment thereof (e.g., the humanized anti-ADAMS antibody or antigen-binding fragment thereof) comprises a heavy chain variable region ($V_H$) having the amino sequence of

```
                                                     (SEQ ID NO: 27)
EVQLVESGGGLVKPGGSLRLSCAASGFTFSSYWMHWVRQAPGKGLEWVG

EIIPIFGHTNYNEKFKSRFTISLDNSKNTLYLQMGSLRAEDTAVYYCAR

GGYYYYPRQGFL DYWGQGTTVTVSS
``` wherein CDR$_H$1, CDR$_H$2, and CDR$_H$3 are double-underlined;
and a light chain variable region (V$_L$) having the amino acid sequence of

```
                                                     (SEQ ID NO: 28)
DIVMTQSPDSLAVSLGERATISCKASQSVDYSGDSYMNWYQQKPGQPPKLLIYAAS
DLES GIPARFSGSG SGTDFTLTIS SLEPEDFATYYCQQSHEDPFTFGQGTKLEI K,
``` wherein CDR$_L$1, CDR$_L$2, and CDR$_L$3 are double-underlined.

In certain embodiments, the anti-ADAMS antibody has a heavy chain full length sequence of

```
                                      (SEQ ID NO: 29)
EVQLVESGGG LVKPGGSLRL SCAASGFTFS SYWMHWVRQA

PGKGLEWVGEIIPIFGHTNY NEKFKSRFTI SLDNSKNTLY

LQMGSLRAED TAVYYCARGGYYYYPRQGFL

DYWGQGTTVT VSSASTKGPS VFPLAPSSKS TSGGTAALGC

LVKDYFPEPV TVSWNSGALT SGVHTFPAVL QSSGLYSLSS

VVTVPSSSLG TQTYICNVNH KPSNTKVDKR

VEPKSCDKTH TCPPCPAPEL LGGPSVFLFP

PKPKDTLYIT REPEVTCVVV DVSHEDPEVK FNWYVDGVEV

HNAKTKPREE QYNSTYRVVS VLTVLHQDWL NGKEYKCKVS

NKALPAPIEK TISKAKGQPR EPQVYTLPPS REEMTKNQVS

LTCLVKGFYP SDIAVEWESN GQPENNYKTT PPVLDSDGSF

FLYSKLTVDK SRWQQGNVFS CSVMHEALHN HYTQKSLCLS

PG,
``` wherein CDR$_H$1, CDR$_H$2, and CDR$_H$3 are double-underlined;
and a light chain full length sequence of

```
                                             (SEQ ID NO: 30)
DIVMTQSPDSLAVSLGERATISCKASQSVDYSGDSYMNWYQQKPGQPPKL

LIYAASDLESGIPARFSGSGSGTDFTLTISSLEPEDFATYYCQQSHEDPF

TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC;
``` wherein CDR$_L$1, CDR$_L$2, and CDR$_L$3 are double-underlined.

In certain embodiments, an anti-ADAM9 antibody or antigen-binding fragment thereof is provided as an activatable antibody or activatable antibody-binding antibody fragment as further described below. In certain other embodiments, the anti-ADAM9 activatable antibody or activatable ADAM9 antibody-binding antibody fragment can be conjugated to a compound of Formula I.

In certain embodiments, the CBA is an anti-folate receptor antibody (i.e., FOLR1 or FRα) (e.g., as described in U.S. Pat. Nos. 8,709,432, 8,557,966, and WO2011106528, all of which are incorporated herein by reference).

In certain embodiments, the anti-FRα antibody or antigen-binding fragment thereof may comprise: a) at least one light chain variable region or fragment thereof comprising three sequential complementarity-determining regions (CDR) CDR$_L$1, CDR$_L$2, and CDR$_L$3, respectively, wherein CDR$_L$1 has the amino acid sequence of KASQSVSFAGTSLMEI (SEQ ID NO:31), CDR$_L$2 has the amino acid sequence of RASNLEA (SEQ ID NO:32), and, CDR$_L$3 has the amino acid sequence of QQSREYPYT (SEQ ID NO:33); and b) at least one heavy chain variable region or fragment thereof comprising three sequential complementarity-determining regions (CDR) CDR$_H$1, CDR$_H$2, and CDR$_H$3, respectively, wherein, CDR$_H$1 has the amino acid sequence of GYFMN (SEQ ID NO:34) or GYTFTGYFMN (SEQ ID NO:37), CDR$_H$2 has the amino acid sequence of RIHPYDGDTFYNQKFQG (SEQ ID NO:35) or RIHPYDGDTF (SEQ ID NO:38), and, CDR$_H$3 has the amino acid sequence of YDGSRAMDY (SEQ ID NO:36).

In certain embodiments, the anti-FRα antibody or antigen-binding fragment thereof comprises a) a light chain variable region comprising a CDR$_L$1 having an amino sequence set forth in SEQ ID NO:31, a CDR$_L$2 having an amino sequence set forth in SEQ ID NO:32, and a CDR$_L$3 having an amino sequence set forth in SEQ ID NO:33; and b) a heavy chain variable region comprising a CDR$_H$1 having an amino sequence set forth in SEQ ID NO:34, a CDR$_H$2 having an amino sequence set forth in SEQ ID NO:35, and a CDR$_H$3 having an amino sequence set forth in SEQ ID NO:36. In certain embodiments, the anti-FRα antibody or antigen-binding fragment thereof comprises a) a light chain variable region comprising a CDR$_L$1 having an amino sequence set forth in SEQ ID NO:31, a CDR$_L$2 having an amino sequence set forth in SEQ ID NO:32, and a CDR$_L$3 having an amino sequence set forth in SEQ ID NO:33; and b) a heavy chain variable region comprising a CDR$_H$1 having an amino sequence set forth in SEQ ID NO:37, a CDR$_H$2 having an amino sequence set forth in SEQ ID NO:38, and a CDR$_H$3 having an amino sequence set forth in SEQ ID NO:36.

In certain embodiments, the anti-FRα antibody or antigen-binding fragment thereof comprises a heavy chain variable region (V$_H$) having the amino sequence of

```
                                                     (SEQ ID NO: 39)
QVQLVQSGAEVVKPGASVKISCKASGYTFTGYFMNWVKQSPGQSLEWIGR
IHPYDGDTFYNQKFQGKATLTVDKSSNTAHMELLSLTSEDFAVYYCTRYD
GSRAMDYWGQGTTVTVSS,
``` wherein CDR$_H$1, CDR$_H$2, and CDR$_H$3 are double-underlined; and a light chain variable region (V$_L$) having the amino acid sequence of

```
                                                     (SEQ ID NO: 40)
DIVLTQSPLSLAVSLGQPAIISCKASQSVSFAGTSLMHWYHQKPGQQPRL
LIYRASNLEAGVPDRFSGSGSKTDFTLNISPVEAEDAATYYCQQSREYPY
TFGGGTKLEIKR,
or
```

-continued (SEQ ID NO: 41)
DIVLTQSPLSLAVSLGQPAIISC<u>KASQSVSFAGTSLMH</u>WYHQKPGGQPRL
LIY<u>RASNLEA</u>GVPDRFSGSGSKTDFTLTISPVEAEDAATYYC<u>QQSREYPY
T</u>FGGGTKLEIKR, wherein CDR$_L$1, CDR$_L$2, and CDR$_L$3 are double-underlined.

In certain embodiments, the anti-FRα antibody has a heavy chain full length sequence of (SEQ ID NO: 42)
QVQLVQSGAEVVKPGASVKISCKAS<u>GYTFTGYFMN</u>WVKQSPGQSLEWIG<u>R IHPYDGDTFYNQKFQG</u>KATLTVDKSSNTAHMELLSLTSEDFAVYYCTR<u>YD GSRAMDY</u>WGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLEPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK, wherein CDR$_H$1, CDR$_H$2, and CDR$_H$3 are double-underlined;
and a light chain full length sequence of (SEQ ID NO: 43)
DIVLTQSPLSLAVSLGQPAIISC<u>KASQSVSFAGTSLMH</u>WYHQKPGGQPRL LIY<u>RASNLEA</u>GVPDRFSGSGSKTDFTLNISPVEAEDAATYYC<u>QQSREYPY T</u>FGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC, or (SEQ ID NO: 44)
DIVLTQSPLSLAVSLGQPAIISC<u>KASQSVSFAGTSLMH</u>WYHQKPGGQPRL

LIY<u>RASNLEA</u>GVPDRFSGSGSKTDFTLTISPVEAEDAATYYC<u>QQSREYPY

T</u>FGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC;

wherein CDR$_L$1, CDR$_L$2, and CDR$_L$3 are double-underlined.

In certain embodiments, the anti-FRα antibody is huMov19 or M9346A antibody.

In certain embodiments, an anti-FRα antibody or antigen-binding fragment thereof is provided as an activatable antibody or activatable antibody-binding antibody fragment as further described below. In certain other embodiments, the anti-FRα activatable antibody or activatable FRα antibody-binding antibody fragment can be conjugated to a compound of Formula I.

In certain embodiments, the CBA is an anti-EpCAM antibody or antigen-binding fragment thereof. In certain embodiments, the anti-EpCAM antibody or antigen-binding fragment thereof may comprise: a) at least one light chain variable region or fragment thereof comprising three sequential complementarity-determining regions (CDR) CDR$_L$1, CDR$_L$2, and CDR$_L$3, respectively, wherein CDR$_L$1 has the amino acid sequence of RSSRSLLHSDGFTYLY (SEQ ID NO:45), CDR$_L$2 has the amino acid sequence of QTSNLAS (SEQ ID NO:46), and, CDR$_L$3 has the amino acid sequence of AQNLELPNT (SEQ ID NO:47); and b) at least one heavy chain variable region or fragment thereof comprising three sequential complementarity-determining regions (CDR) CDR$_H$1, CDR$_H$2, and CDR$_H$3, respectively, wherein, CDR$_H$1 has the amino acid sequence of NYYIH (SEQ ID NO:48), CDR$_H$2 has the amino acid sequence of WIYPGNVYIQYNEKFKG (SEQ ID NO:49), and, CDR$_H$3 has the amino acid sequence of DGPWFAY (SEQ ID NO:50).

In certain embodiments, the anti-EpCAM antibody or antigen-binding fragment thereof comprises a heavy chain variable region (V$_H$) having the amino acid sequence of (SEQ ID NO: 52)
QVQLVQSGAEVKKPGASVKVSCKASGYTFT<u>NYYIH</u>WVRQAPGQRLEYIG<u>W IYPGNVYIQYNEKFKG</u>RATLTADKSASTAYMELSSLRSEDTAVYYCAR<u>DG PWFAY</u>WGQGTLVTVSS, wherein CDR$_H$1, CDR$_H$2, and CDR$_H$3 are double-underlined;
and a light chain variable region (V$_L$) having the amino acid sequence of (SEQ ID NO: 51)
DIVLTQTPLSLSVTPGQPASISC<u>RSSRSLLHSDGFTYLY</u>WFLQKPGQSPQ
LLIY<u>QTSNLAS</u>GVPDRFSSSGSGTDFTLKISRVEAEDVGVYYC<u>AQNLELP NT</u>FGQGTKLEIK, wherein CDR$_L$1, CDR$_L$2, and CDR$_L$3 are double-underlined.

In certain embodiments, the anti-EpCAM antibody has a heavy chain full length sequence of (SEQ ID NO: 54)
QVQLVQSGAEVKKPGASVKVSCKASGYTFT<u>NYYIH</u>WVRQAPGQRLEYIG<u>W IYPGNVYIQYNEKFKG</u>RATLTADKSASTAYMELSSLRSEDTAVYYCAR<u>DG PWFAY</u>WGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLEPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLCLSPG, wherein CDR$_H$1, CDR$_H$2, and CDR$_H$3 are double-underlined;
and a light chain full length sequence of (SEQ ID NO: 53)
DIVLTQTPLSLSVTPGQPASISC<u>RSSRSLLHSDGFTYLY</u>WFLQKPGQSPQL LIY<u>QTSNLAS</u>GVPDRFSSSGSGTDFTLKISRVEAEDVGVYYC<u>AQNLELPNT</u>

FGQGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC, wherein CDR$_L$1, CDR$_L$2, and CDR$_L$3 are double-underlined.

In certain embodiments, the CBA is an anti-EpCAM antibody or antigen-binding fragment thereof may comprise: a) at least one light chain variable (V$_L$) region or fragment thereof comprising three sequential complementarity-determining regions (CDR) CDR$_L$1, CDR$_L$2, and CDR$_L$3, respectively, wherein CDR$_L$1 has an amino acid sequence selected from SEQ ID NOs:78, 45, 79, 80 and 82; CDR$_L$2 has the amino acid sequence of SEQ ID NO:46; and a CDR$_L$3 has amino an acid sequence selected from SEQ ID NOs:47, 81, 83, 84, 85, 86, and 87, and b) at least one heavy chain variable (V$_H$) region or fragment thereof comprising three sequential complementarity-determining regions (CDR) CDR$_H$1, CDR$_H$2, and CDR$_H$3, respectively, wherein, wherein CDR$_H$1 has an amino acid sequence selected from SEQ ID NOs: 48, 57, 58, 60, 61, 62, 68, 69, 70, 77 and 88; CDR$_H$2 has an amino acid sequence selected from SEQ ID NOs:49, 56, 59, 63, and 64; and a CDR$_H$3 has an amino acid sequence selected from SEQ ID NOs:55, 65, 66, 67, 71, 72, 73, 74, 75 and 76.

In certain embodiments, an anti-EpCAM antibody or antigen-binding fragment thereof is provided as an activatable antibody or activatable antibody-binding antibody fragment as further described below. In certain other embodiments, the anti-EpCAM activatable antibody or activatable EpCAM antibody-binding antibody fragment can be conjugated to a compound of Formula I.

Variants in the CDRs of the anti-EpCAM antibody or antigen-binding fragment are summarized in the Tables 3-6 below.

TABLE 3

| huEpCAM-23 4.2 (CDRs and variable domains) | | | |
|---|---|---|---|
| huEpCAM23_VLGv4 | RSSRSLLHSDGFTYLY (SEQ ID NO: 45) | QTSNLAS (SEQ ID NO: 46) | AQNLELPNT (SEQ ID NO: 47) |
| huEpCAM23_VHGv2 | NYYIH (SEQ ID NO: 48) | WIYPGNVYIQYNEKFKG (SEQ ID NO: 49) | DGPWFAY (SEQ ID NO: 50) |
| VL huEpCAM23_VLGv4 | DIVLTQTPLSLSVTPGQPASISC<u>RSSRSLLHSDGFTYLY</u>WFLQKPGQSPQLLIY<u>QTSNLAS</u>GVPDRFSSSGSGTDFTLKISRVEAEDVGVYYC<u>AQNLELPNT</u>FGQGTKLEIK (SEQ ID NO: 51) | | |
| VH huEpCAM23_VHGv2 | QVQLVQSGAEVKKPGASVKVSCKASGYTFT<u>NYYIH</u>WVRQAPGQRLEYIG<u>WIYPGNVYIQYNEKFKG</u>RATLTADKSASTAYMELSSLRSEDTAVYYCARD<u>GPWFAY</u>WGQGTLVTVSS (SEQ ID NO: 52) | | |

TABLE 4

| Humanized variants of huEpCAM-23 (full length sequence) | |
|---|---|
| huEpCAM 23_VLGv4 | DIVLTQTPLSLSVTPGQPASISC<u>RSSRSLLHSDGFTYLY</u>WFLQKPGQSPQLLIY<u>QTSNLAS</u>GVPDRFSSSGSGTDFTLKISRVEAEDVGVYYC<u>AQNLELPNT</u>FGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 53) |
| huEpCAM 23_VHGv2-C442 | QVQLVQSGAEVKKPGASVKVSCKASGYTFT<u>NYYIH</u>WVRQAPGQRLEYIG<u>WIYPGNVYIQYNEKFKG</u>RATLTADKSASTAYMELSSLRSEDTAVYYCARD<u>GPWFAY</u>WGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLCLSPG (SEQ ID NO: 54) |

TABLE 5

| EpCAM23 variant heavy chain CDR sequences | | | |
|---|---|---|---|
| | VH-CDR1 | VH-CDR2 | VH-CDR3 |
| Murine and Chimeric | | | |
| muEpcam23 | NYYLEI (SEQ ID NO: 48) | WIYPGNVYIQYNEKFKG (SEQ ID NO: 49) | DGPWFAY (SEQ ID NO: 55) |
| chEpcam23 | NYYLEI (SEQ ID NO: 48) | WIYPGNVYIQYNEKFKG (SEQ ID NO: 49) | DGPWFAY (SEQ ID NO: 55) |

TABLE 5-continued

EpCAM23 variant heavy chain CDR sequences

| | VH-CDR1 | VH-CDR2 | VH-CDR3 |
|---|---|---|---|
| Humanized Variants | | | |
| huEpCAM23_VHGv1 | NYYIH (SEQ ID NO: 48) | WIYPGNVYIQYSQKFQG (SEQ ID NO: 56) | DGPWFAY (SEQ ID NO: 55) |
| huEpCAM23_VHGv2 | NYYIH (SEQ ID NO: 48) | WIYPGNVYIQYNEKFKG (SEQ ID NO: 49) | DGPWFAY (SEQ ID NO: 55) |
| huEpCAM23_VHGv3 | NYYIH (SEQ ID NO: 48) | WIYPGNVYIQYNEKFKG (SEQ ID NO: 49) | DGPWFAY (SEQ ID NO: 55) |
| huEpCAM23_VHGv4 | NYYIH (SEQ ID NO: 48) | WIYPGNVYIQYSQKFQG (SEQ ID NO: 56) | DGPWFAY (SEQ ID NO: 55) |
| Affinity Variants | | | |
| huEpCAM23HCGv2a | NYYIH (SEQ ID NO: 48) | WIYPGNVYIQYNEKFKG (SEQ ID NO: 49) | DGPWFAY (SEQ ID NO: 55) |
| huEpCAM23HCGv2b | SYYIH (SEQ ID NO: 57) | WIYPGNVYIQYNEKFKG (SEQ ID NO: 49) | DGPWFAY (SEQ ID NO: 55) |
| huEpCAM23HCGv2c | NYNHE (SEQ ID NO: 58) | WIYPGNVYIQYNEKFKG (SEQ ID NO: 49) | DGPWFAY (SEQ ID NO: 55) |
| huEpCAM23HCGv2d | NYYIH (SEQ ID NO: 48) | WIYPGDVYIQYNEKFKG (SEQ ID NO: 59) | DGPWFAY (SEQ ID NO: 55) |
| huEpCAM23HCGv2e | NYFIH (SEQ ID NO: 60) | WIYPGNVYIQYNEKFKG (SEQ ID NO: 49) | DGPWFAY (SEQ ID NO: 55) |
| huEpCAM23HCGv2f | NYSIH (SEQ ID NO: 61) | WIYPGNVYIQYNEKFKG (SEQ ID NO: 49) | DGPWFAY (SEQ ID NO: 55) |
| huEpCAM23HCGv2g | NYWEI (SEQ ID NO: 62) | WIYPGNVYIQYNEKFKG (SEQ ID NO: 49) | DGPWFAY (SEQ ID NO: 55) |
| huEpCAM23HCGv2h | NYYIH (SEQ ID NO: 48) | WFYPGNVYIQYNEKFKG (SEQ ID NO: 63) | DGPWFAY (SEQ ID NO: 55) |
| huEpCAM23HCGv2i/2o | NYYIH (SEQ ID NO: 48) | WIYPGNVYIQYNEKFKG (SEQ ID NO: 49) | DGPWFAY (SEQ ID NO: 55) |
| huEpCAM23HCGv2j | NYYIH (SEQ ID NO: 48) | WINPGNVYIQYNEKFKG (SEQ ID NO: 64) | DGPWFAY (SEQ ID NO: 55) |
| huEpCAM23HCGv2k | NYYIH (SEQ ID NO: 48) | WIYPGNVYIQYNEKFKG (SEQ ID NO: 49) | EGPWFAY (SEQ ID NO: 65) |
| huEpCAM23HCGv2l | NYYIH (SEQ ID NO: 48) | WIYPGNVYIQYNEKFKG (SEQ ID NO: 49) | DGPYFAY (SEQ ID NO: 66) |
| huEpCAM23HCGv2m/ huEpCam23 HG2-1565-A Heavy Chain | NYYIH (SEQ ID NO: 48) | WIYPGNVYIQYNEKFKG (SEQ ID NO: 49) | DGAWFAY (SEQ ID NO: 67) |
| huEpCAM23HCGv2n | NYYMEE (SEQ ID NO: 68) | WIYPGNVYIQYNEKFKG (SEQ ID NO: 49) | DGPWFAY (SEQ ID NO: 55) |
| huEpCAM23HCGv2p | NYYIH (SEQ ID NO: 48) | WIYPGNVYIQYNEKFKG (SEQ ID NO: 49) | DGPWFAY (SEQ ID NO: 55) |
| huEpCAM23HCGv2q | NYYIH (SEQ ID NO: 48) | WIYPGNVYIQYNEKFKG (SEQ ID NO: 49) | DGPWFAY (SEQ ID NO: 55) |
| huEpCAM23HCGv2r | NYYIH (SEQ ID NO: 48) | WIYPGNVYIQYNEKFKG (SEQ ID NO: 49) | DGPWFAY (SEQ ID NO: 55) |
| huEpCAM23HCGv2s | NYYIH (SEQ ID NO: 48) | WIYPGNVYIQYNEKFKG (SEQ ID NO: 49) | DGPWFAY (SEQ ID NO: 55) |
| huEpCam23HG2-1361-H Heavy Chain | NYHIH (SEQ ID NO: 69 | WIYPGNVYIQYNEKFKG (SEQ ID NO: 49) | DGPWFAY (SEQ ID NO: 55) |

TABLE 5-continued

EpCAM23 variant heavy chain CDR sequences

| | VH-CDR1 | VH-CDR2 | VH-CDR3 |
|---|---|---|---|
| huEpCam23HG2-1361-D Heavy Chain | NYDIH (SEQ ID NO: 70) | WIYPGNVYIQYNEKFKG (SEQ ID NO: 49) | DGPWFAY (SEQ ID NO: 55) |
| huEpCam23HG2-1565-Y Heavy Chain | NYYIH (SEQ ID NO: 48) | WIYPGNVYIQYNEKFKG (SEQ ID NO: 49) | DGYWFAY (SEQ ID NO: 71) |
| huEpCam23HG2-1565-S Heavy Chain | NYYIH (SEQ ID NO: 48) | WIYPGNVYIQYNEKFKG (SEQ ID NO: 49) | DGSWFAY (SEQ ID NO: 72) |
| huEpCam23HG2-1565-F Heavy Chain | NYYIH (SEQ ID NO: 48) | WIYPGNVYIQYNEKFKG (SEQ ID NO: 49) | DGFWFAY (SEQ ID NO: 73) |
| huEpCam23HG2-1565-G Heavy Chain | NYYIH (SEQ ID NO: 48) | WIYPGNVYIQYNEKFKG (SEQ ID NO: 49) | DGGWFAY (SEQ ID NO: 74) |
| huEpCam23HG2-1565-T Heavy Chain | NYYIH (SEQ ID NO: 48) | WIYPGNVYIQYNEKFKG (SEQ ID NO: 49) | DGTWFAY (SEQ ID NO: 75) |
| huEpCam23HG2-1565-V Heavy Chain | NYYIH (SEQ ID NO: 48) | WIYPGNVYIQYNEKFKG (SEQ ID NO: 49) | DGVWFAY (SEQ ID NO: 76) |
| huEpCam23HG2-1361-I Heavy Chain | NYIIH (SEQ ID NO: 77) | WIYPGNVYIQYNEKFKG (SEQ ID NO: 49) | DGPWFAY (SEQ ID NO: 55) |
| huEpCam23HG2-1361-L Heavy Chain | NYLIH (SEQ ID NO: 88) | WIYPGNVYIQYNEKFKG (SEQ ID NO: 49) | DGPWFAY (SEQ ID NO: 55) |

TABLE 6

EpCAM23 variant light chain CDR sequences

| Antibody | VL-CDR1 | VL-CDR2 | VL-CDR3 |
|---|---|---|---|
| Murine and Chimeric | | | |
| muEpcam23 | RSSKSLLHSDGFTYLY (SEQ ID NO: 78) | QTSNLAS (SEQ ID NO: 46) | AQNLELPNT (SEQ ID NO: 47) |
| chEpcam23 | RSSKSLLHSDGFTYLY (SEQ ID NO: 78) | QTSNLAS (SEQ ID NO: 46) | AQNLELPNT (SEQ ID NO: 47) |
| Humanized Variants | | | |
| huEpCAM23_VLG v1 | RSSRSLLHSDGFTYLY (SEQ ID NO: 45) | QTSNLAS (SEQ ID NO: 46) | AQNLELPNT (SEQ ID NO: 47) |
| huEpCAM23_VLG v2 | RSSKSLLHSDGFTYLY (SEQ ID NO: 78) | QTSNLAS (SEQ ID NO: 46) | AQNLELPNT (SEQ ID NO: 47) |
| huEpCAM23_VLG v3 | RSSKSLLHSDGFTYLY (SEQ ID NO: 78) | QTSNLAS (SEQ ID NO: 46) | AQNLELPNT (SEQ ID NO: 47) |
| huEpCAM23_VLG v4 | RSSRSLLHSDGFTYLY (SEQ ID NO: 45) | QTSNLAS (SEQ ID NO: 46) | AQNLELPNT (SEQ ID NO: 47) |
| Affinity Variants | | | |
| huEpCAM23LCGy4 a | RSSRSLLHSNGFTYLY (SEQ ID NO: 79) | QTSNLAS (SEQ ID NO: 46) | AQNLELPNT (SEQ ID NO: 47) |
| huEpCAM23LCGy4 b | RSSRSLLHSDGITYLY (SEQ ID NO: 80) | QTSNLAS (SEQ ID NO: 46) | AQNLELPNT (SEQ ID NO: 47) |
| huEpCAM23LCGy4 c | RSSRSLLHSDGFTYLY (SEQ ID NO: 45) | QTSNLAS (SEQ ID NO: 46) | AQNLELPWT (SEQ ID NO: 81) |
| huEpCAM23LCGy4 e | RSSRSLLHSDGFTYLS (SEQ ID NO: 82) | QTSNLAS (SEQ ID NO: 46) | AQNLELPNT (SEQ ID NO: 47) |
| huEpCAM23LCGy4 f | RSSRSLLHSDGFTYLY (SEQ ID NO: 45) | QTSNLAS (SEQ ID NO: 46) | AQNLELPNT (SEQ ID NO: 47) |

TABLE 6-continued

EpCAM23 variant light chain CDR sequences

| Antibody | VL-CDR1 | VL-CDR2 | VL-CDR3 |
|---|---|---|---|
| huEpCAM23LCGy4 g | RSSRSLLHSDGFTYLY (SEQ ID NO: 45) | QTSNLAS (SEQ ID NO: 46) | QQNLELPNT (SEQ ID NO: 83) |
| huEpCAM23LCGy4 h | RSSRSLLHSDGFTYLY (SEQ ID NO: 45) | QTSNLAS (SEQ ID NO: 46) | LQNLELPNT (SEQ ID NO: 84) |
| huEpCAM23LCGy4 i | RSSRSLLHSDGFTYLY (SEQ ID NO: 45) | QTSNLAS (SEQ ID NO: 46) | AQYLELPNT (SEQ ID NO: 85) |
| huEpCAM23LCGy4 j | RSSRSLLHSDGFTYLY (SEQ ID NO: 45) | QTSNLAS (SEQ ID NO: 46) | AQGLELPNT (SEQ ID NO: 86) |
| huEpCAM23LCGy4 k | RSSRSLLHSDGFTYLY (SEQ ID NO: 45) | QTSNLAS (SEQ ID NO: 46) | AQSLELPNT (SEQ ID NO: 87) |

In certain embodiments, the antibody described herein is a murine, non-human mammal, chimeric, humanized, or human antibody. For example, the humanized antibody may be a CDR-grafted antibody or resurfaced antibody. In certain embodiments, the antibody is a full-length antibody. In certain embodiments, the antigen-binding fragment thereof is an Fab, Fab', F(ab')$_2$, F$_d$, single chain Fab (scFab), single chain Fv or scFv, disulfide linked F$_v$, V-NAR domain, IgNar, intrabody, IgGACH$_2$, minibody, F(ab')$_3$, tetrabody, triabody, diabody, duobody, single-domain antibody, DVD-Ig, Fcab, mAb$_2$, (scFv)$_2$, or scFv-Fc.

In certain embodiments, the cell-binding agent is an alternative protein scaffold, such as a peptide targeting a somatostatin receptor (see Barbieri F, Bajetto A, Pattarozzi A, Gatti M, Wurth R, Thellung S, et al. Peptide receptor targeting in cancer: the somatostatin paradigm. Int J Pept 2013; 2013:926295), an inhibitor cystine knot (also known as ICK or Knottin; see Knottins: disulfide-bonded therapeutic and diagnostic peptides. Drug Discov Today Technol 2012; 9(1):e1-e70; Moore S J, Cochran J R. Engineering knottins as novel binding agents. Methods Enzymol 2012; 503:223-51), a duobody (see Labrijn A F, Meesters J I, Priem P, de Jong R N, van den Bremer E T, van Kampen M D, et al. Controlled Fab-arm exchange for the generation of stable bispecific IgG1. Nat Protoc 2014; 9(10):2450-63), a hexabody (see de Jong R N, Beurskens F J, Verploegen S, Strumane K, van Kampen M D, Voorhorst M, et al. A Novel Platform for the Potentiation of Therapeutic Antibodies Based on Antigen-Dependent Formation of IgG Hexamers at the Cell Surface. PLoS Biol 2016; 14(1):e1002344); a Single chain Fab (scFab) fragment (see Koerber J T, Hornsby M J, Wells J A. An improved single-chain Fab platform for efficient display and recombinant expression. J Mol Biol 2015; 427(2):576-86; Hust M, Jostock T, Menzel C, Voedisch B, Mohr A, Brenneis M, et al. Single chain Fab (scFab) fragment. BMC Biotechnol 2007; 7:14), a target identified by drug affinity responsive target stability (DARTS) (see Pai M Y, Lomenick B, Hwang H, Schiestl R, McBride W, Loo J A, et al. Drug affinity responsive target stability (DARTS) for small-molecule target identification. Methods in molecular biology 2015; 1263:287-98), a Centyrin (a protein scaffold based on a consensus sequence of fibronectin type III (FN3) repeats; see U.S. Patent Publication 2010/0255056, 2010/0216708 and 2011/0274623 incorporated herein by reference), an Ankyrin Repeat Protein (e.g., a designed ankyrin repeat protein, known as DARPin; see U.S. Patent Publication Nos. 2004/0132028, 2009/0082274, 2011/0118146, and 2011/0224100, incorporated herein by reference, and also see C. Zahnd et al., Cancer Res. (2010) 70:1595-1605; Zahnd et al., Biol. Chem. (2006) 281(46):35167-35175; and Binz, H. K., Amstutz, P. & Pluckthun, A., Nature Biotechnology (2005) 23:1257-1268, incorporated herein by reference), an ankyrin-like repeats protein or synthetic peptide (see e.g., U.S. Patent Publication No. 2007/0238667; U.S. Pat. No. 7,101,675; WO 2007/147213; and WO 2007/062466, incorporated herein by reference), an Adnectin (a fibronectin domain scaffold protein; see US Patent Publication Nos. 2007/0082365; 2008/0139791, incorporated herein by reference), Knottins (small disulfide rich proteins characterized by disulfide through disulfide knot), Bicyclic peptides (also referred to as Bicycles; see Heinis C, Rutherford T, Freund S, Winter G. Phage-encoded combinatorial chemical libraries based on bicyclic peptides. Nat Chem Biol 2009; 5(7):502-7; Teufel D P, Bennett G, Harrison H, van Rietschoten K, Pavan S, Stace C, et al. Stable and Long-Lasting, Novel Bicyclic Peptide Plasma Kallikrein Inhibitors for the Treatment of Diabetic Macular Edema. J Med Chem 2018; 61(7):2823-36), Avibody (including diabodies, triabodies, and tetrabodies; see U.S. Publication Nos. 2008/0152586 and 2012/0171115), dual receptor retargeting (DART) molecules (P. A. Moore et al., Blood, 2011; 117(17):4542-4551; Veri M C, et al., Arthritis Rheum, 2010 Mar. 30; 62(7):1933-43; Johnson S, et al. J Mot Biol, 2010 Apr. 9; 399(3):436-49), and cell penetrating supercharged proteins (Methods in Enzymol. 502, 293-319 (2012).

Activatable CBAs

In additional embodiments, the provided CBA is an activatable antibody or an activatable antigen-binding antibody fragment (collectively as AA). In some embodiments, the activatable antibody or activatable antigen-binding antibody fragment comprises an antibody or antigen-binding antibody fragment (e.g., antibodies or antigen-binding antibody fragments described herein) specifically binds to a ligand on the target cell (or "a target") coupled to a masking moiety (MM), such that coupling of the MM reduces the ability of the antibody or antigen-binding antibody fragment to bind the target. In some embodiments, the MM is coupled via a sequence that includes a substrate for a protease, for example, a protease that is active in diseased tissue and/or a protease that is co-localized with the target at a treatment site in a subject. The activatable antibodies are preferably stable in circulation, activated at intended sites of therapy and/or diagnosis but not in normal, e.g., healthy tissue or other tissue not targeted for treatment and/or diagnosis, and, when activated, exhibit binding to the target that is at least comparable to the corresponding, unmodified antibody. In some embodiments, the AAs are those described in WO 2009/025846, WO 2010/081173, WO 2015/048329, WO 2015/116933 and WO 2016/118629, each of which is incorporated by reference in its entirety.

In some embodiments, the activatable antibody or antibody fragment comprises:
(a) a cleavable moiety (CM) coupled to the antibody or antibody fragment (collectively as "AB"), wherein the CM is a polypeptide that functions as a substrate for a protease; and
(b) a masking moiety (MM) coupled to the antibody or antibody fragment, wherein the MM inhibits the binding of the antibody or antibody fragment to the ligand when the activatable antibody is in an uncleaved state, wherein the activatable antibody in the uncleaved state has the structural arrangement from N-terminus to C-terminus as follows: (MM)-(CM)-(AB) or (AB)-(CM)-(MM).

In some embodiments, the masking moiety (or "mask") is an amino acid sequence that is coupled or otherwise attached to the antibody and is positioned within the activatable antibody construct such that the masking moiety reduces the ability of the antibody to specifically bind the target. Suitable masking moieties are identified using any of a variety of known techniques. For example, peptide masking moieties are identified using the methods described in WO 2009/025846, the contents of which is herein incorporated by reference in its entirety.

The $K_d$ of the AB modified with a MM towards the target can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM or the parental AB towards the target. Conversely, the binding affinity of the AB modified with a MM towards the target can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM or the parental AB towards the target.

The dissociation constant ($K_d$) of the MM towards the AB is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target.

When the AB is modified with a MM and is in the presence of the target, specific binding of the AB to its target can be reduced or inhibited, as compared to the specific binding of the AB not modified with an MM or the specific binding of the parental AB to the target. When compared to the binding of the AB not modified with an MM or the binding of the parental AB to the target, the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, 96, hours, or 5, 10, 15, 30, 45, 60, 90, 120, 150, 180 days, or 1, 2, 3, 4, 5, 6, 7, 8, 9, 10, 11, 12 months or greater when measured in vivo or in a Target Displacement in vitro immunoabsorbant assay, as described WO 2010/081173.

The MM can inhibit the binding of the AB to the target. The MM can bind the antigen binding domain of the AB and inhibit binding of the AB to its target. The MM can sterically inhibit the binding of the AB to the target. The MM can allosterically inhibit the binding of the AB to its target. In these embodiments when the AB is modified or coupled to a MM and in the presence of target, there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, 96, hours, or 5, 10, 15, 30, 45, 60, 90, 120, 150, 180 days, or 1, 2, 3, 4, 5, 6, 7, 8, 9, 10, 11, 12 months or greater when measured in vivo or in a Target Displacement in vitro immunoabsorbant assay, as described WO 2010/081173.

When an AB is coupled to or modified by a MM, the MM can 'mask' or reduce, or inhibit the specific binding of the AB to its target. When an AB is coupled to or modified by a MM, such coupling or modification can effect a structural change which reduces or inhibits the ability of the AB to specifically bind its target.

An AB coupled to or modified with an MM can be represented by the following formulae (in order from an amino (N) terminal region to carboxyl (C) terminal region):

(MM)-(AB)

(AB)-(MM)

(MM)-L-(AB)

(AB)-L-(MM)

where MM is a masking moiety, the Ab is an antibody or target-binding antigen fragment, and L is a linker. In many embodiments, it may be desirable to insert one or more linkers, e.g., flexible linkers, into the composition so as to provide for flexibility.

In certain embodiments, the MM is not a natural binding partner of the Ab. In some embodiments, the MM contains no or substantially no homology to any natural binding partner of the Ab. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the Ab. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the Ab. In some embodiments, the MM is no more than 25% identical to any natural binding partner of the Ab. In some embodiments, the MM is no more than 50% identical to any natural binding partner of the Ab. In some embodiments, the MM is no more than 20% identical to any natural binding partner of the Ab.

In some embodiments, the MM is no more than 10% identical to any natural binding partner of the Ab.

The activatable antibodies provided herein can also include a cleavable moiety (CM). Such AAs exhibit activatable/switchable binding, to the AB's target. AAs generally include an antibody or antibody fragment (AB), modified by or coupled to a masking moiety (MM) and a modifiable or cleavable moiety (CM). In some embodiments, the CM contains an amino acid sequence that serves as a substrate for a protease of interest. In other embodiments, the CM provides a cysteine-cysteine disulfide bond that is cleavable by reduction. In yet other embodiments the CM provides a photolytic substrate that is activatable by photolysis.

In some embodiments, the cleavable moiety (or "substrate") includes an amino acid sequence that is a substrate for a protease, usually an extracellular protease. Suitable substrates are identified using any of a variety of known techniques. For example, peptide substrates are identified using the methods described in U.S. Pat. Nos. 7,666,817 and 8,563,269; and WO 2014/026136, the contents of each of which is herein incorporated by reference in its entirety. (See also, Boulware et al., Biotechnol Bioeng. 106(3):339-346 (2010)). Optionally, the CM comprises a cysteine-cysteine pair capable of forming a disulfide bond, which can be cleaved by action of a reducing agent. The CM is positioned such that when the CM is cleaved by a cleaving agent (e.g., a protease substrate of a CM is cleaved by the protease and/or the cysteine-cysteine disulfide bond is disrupted via reduction by exposure to a reducing agent), in the presence of a target, resulting in a cleaved state, the Ab binds the target, and in an uncleaved state, in the presence of the target, binding of the Ab to the target is inhibited by the MM. It should be noted that the amino acid sequence of the CM may overlap with or be included within the MM, such that all or a portion of the CM facilitates "masking" of the Ab when the activatable antibody is in the uncleaved conformation.

In some embodiments, the CM may be selected based on a protease that is co-localized in tissue with the desired target of the activatable antibody. A variety of different conditions are known in which a target of interest is co-localized with a protease, where the substrate of the protease is known in the art. For example, the target tissue can be a cancerous tissue, particularly cancerous tissue of a solid tumor. There are many reports in the literature of increased levels of proteases having known substrates in a number of cancers, e.g., solid tumors. See, e.g., La Rocca et al, (2004) British J. of Cancer 90(7): 1414-1421.

Wxemplary substrates can include but are not limited to substrates cleavable by one or more of the following enzymes: MMP-I, MMP-2, MMP-3, MMP-8, MMP-9, MMP-14, PLASMIN, PSA, PSMA, CATHEPSIN D, CATHEPSIN K, CATHEPSIN S, ADAM1O, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, AND TACE.

In some embodiments, the CM is a polypeptide of up to 15 amino acids in length.

In some embodiments, the CM is a polypeptide that includes a first cleavable moiety (CM1) that is a substrate for at least one matrix metalloprotease (MMP) and a second cleavable moiety (CM2) that is a substrate for at least one serine protease (SP). In some embodiments, each of the CM1 substrate sequence and the CM2 substrate sequence of the CM1-CM2 substrate is independently a polypeptide of up to 15 amino acids in length.

In some embodiments the CM is a substrate for legumain, plasmin, TMPRSS-3/4, MMP-9, MT1-MMP, cathepsin, caspase, human neutrophil elastase, beta-secretase, uPA, or PSA.

The $K_d$ of the Ab modified with a MM and a CM towards the target can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the Ab not modified with an MM and a CM or the parental Ab towards the target. Conversely, the binding affinity of the Ab modified with a MM and a CM towards the target can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the Ab not modified with an MM and a CM or the parental Ab towards the target.

When the Ab is modified with a MM and a CM and is in the presence of the target but not in the presence of a modifying agent (for example an enzyme, protease, reduction agent, light), specific binding of the Ab to its target can be reduced or inhibited, as compared to the specific binding of the Ab not modified with an MM and a CM or the parental Ab to the target. When compared to the binding of the parental Ab or the binding of an Ab not modified with an MM and a CM to its target, the Ab's ability to bind the target when modified with an MM and a CM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, 96 hours, or 5, 10, 15, 30, 45, 60, 90, 120, 150, 180 days, or 1, 2, 3, 4, 5, 6, 7, 8, 9, 10, 11, 12 months or greater when measured in vivo or in a Target Displacement in vitro immunoabsorbant assay, as described in WO201008117, incorporated herein by reference in its entirety.

As used herein, the term cleaved state refers to the condition of the AA following modification of the CM by a protease and/or reduction of a cysteine-cysteine disulfide, bond of the CM, and/or photoactivation. The term uncleaved state, as used herein, refers to the condition of the AA in the absence of cleavage of the CM by a protease and/or in the absence reduction of a cysteine-cysteine disulfide bond of the CM, and/or in the absence of light. As discussed above, the term AA is used herein to refer to an AA in both its uncleaved (native) state, as well as in its cleaved state. It will be apparent to the ordinarily skilled artisan that in some embodiments a cleaved AA may lack an MM due to cleavage of the CM by protease, resulting in release of at least the MM (e.g., where the MM is not joined to the AA by a covalent bond (e.g., a disulfide bond between cysteine residues).

By activatable or switchable is meant that the AA exhibits a first level of binding to a target when in a inhibited, masked or uncleaved state (i.e., a first conformation), and a second level of binding to the target in the uninhibited, unmasked and/or cleaved state (i.e., a second conformation), where the second level of target binding is greater than the first level of binding. In general, the access of target to the Ab of the AA is greater in the presence of a cleaving agent capable of cleaving the CM than in the absence of such a cleaving agent. Thus, when the AA is in the uncleaved state, the Ab is inhibited from target binding and can be masked from target binding (i.e., the first conformation is such the Ab can not bind the target), and in the cleaved state the AB is not inhibited or is unmasked to target binding.

The CM and AB of the AA may be selected so that the AB represents a binding moiety for a target of interest, and the CM represents a substrate for a protease that is co-localized with the target at a treatment site in a subject. Alternatively or in addition, the CM is a cysteine-cysteine disulfide bond that is cleavable as a result of reduction of this disulfide bond. AAs contain at least one of a protease-cleavable CM or a cysteine-cysteine disulfide bond, and in some embodiments include both kinds of CMs. The AAs can alternatively or further include a photolabile substrate, activatable by a light source. The AAs disclosed herein find particular use where, for example, a protease capable of cleaving a site in the CM is present at relatively higher levels in target-containing tissue of a treatment site (for example diseased tissue; for example for therapeutic treatment or diagnostic treatment) than in tissue of non-treatment sites (for example in healthy tissue). The AAs disclosed herein also find particular use where, for example, a reducing agent capable of reducing a site in the CM is present at relatively higher levels in target-containing tissue of a treatment or diagnostic site than in tissue of non-treatment non-diagnostic sites. The AAs disclosed herein also find particular use where, for example, a light source, for example, by way of laser, capable of photolysing a site in the CM is introduced to a target-containing tissue of a treatment or diagnostic site.

In some embodiments AAs can provide for reduced toxicity and/or adverse side effects that could otherwise result from binding of the Ab at non-treatment sites if the Ab were not masked or otherwise inhibited from binding its target. Where the AA contains a CM that is cleavable by a reducing agent that facilitates reduction of a disulfide bond, the ABs of such AAs may selected to exploit activation of an Ab where a target of interest is present at a desired treatment site characterized by elevated levels of a reducing agent, such that the environment is of a higher reduction potential than, for example, an environment of a non-treatment site.

In general, an AA can be designed by selecting an Ab of interest and constructing the remainder of the AA so that, when conformationally constrained, the MM provides for masking of the Ab or reduction of binding of the Ab to its target. Structural design criteria to be taken into account to provide for this functional feature.

AAs exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an AA, the dynamic range refers to the ratio of (a) a maximum detected level of target protein binding to an AA in the presence of protease capable of cleaving the CM of the AA to (b) a minimum detected level of target protein binding to an AA in the absence of the protease. The dynamic range of an AA can be calculated as the ratio of the equilibrium dissociation constant of an AA cleaving agent (e.g., enzyme) treatment to the equilibrium dissociation constant of the AA cleaving agent treatment. The greater the dynamic range of an AA, the better the switchable phenotype of the AA. AAs having relatively higher dynamic range values (e.g., greater than 1) exhibit more desirable switching phenotypes such that target protein binding by the AA occurs to a greater extent (e.g., predominantly occurs) in the presence of a cleaving agent (e.g., enzyme) capable of cleaving the CM of the AA than in the absence of a cleaving agent.

AAs can be provided in a variety of structural configurations. Exemplary formulae for AAs are provided below. It is specifically contemplated that the N- to C-terminal order of the AB, MM and CM may be reversed within an AA. It is also specifically contemplated that the CM and MM may overlap in amino acid sequence, e.g., such that the CM is contained within the MM.

For example, AAs can be represented by the following formula (in order from an amino (N) terminal region to carboxyl (C) terminal region:

(MM)-(CM)-(AB)

(AB)-(CM)-(MM) where MM is a masking moiety, CM is a cleavable moiety, and AB is an antibody or fragment thereof. It should be noted that although MM and CM are indicated as distinct components in the formula above, in all exemplary embodiments (including formulae) disclosed herein it is contemplated that the amino acid sequences of the MM and the CM could overlap, e.g., such that the CM is completely or partially contained within the MM. In addition, the formulae above provide for additional amino acid sequences that may be positioned N-terminal or C-terminal to the AA elements.

In certain embodiments, it may be desirable to insert one or more linkers, e.g., flexible linkers, into the AA construct so as to provide for flexibility at one or more of the MM-CM junction, the CM-AB junction, or both. For example, the AB, MM, and/or CM may not contain a sufficient number of residues (e.g., Gly, Ser, Asp, Asn, especially Gly and Ser, particularly Gly) to provide the desired flexibility. As such, the switchable phenotype of such AA constructs may benefit from introduction of one or more amino acids to provide for a flexible linker. In addition, as described below, where the AA is provided as a conformationally constrained construct, a flexible linker can be operably inserted to facilitate formation and maintenance of a cyclic structure in the uncleaved AA.

For example, in certain embodiments an AA comprises one of the following formulae (where the formula below represent an amino acid sequence in either N- to C-terminal direction or C- to N-terminal direction):

(MM)-$L_1$-(CM)-(AB)

(MM)-(CM)-$L_1$-(AB)

(MM)-$L_1$-(CM)-$L_2$-(AB)

CyClo[$L_1$-(MM)-$L_2$-(CM)-$L_3$-(AB)]

wherein MM, CM, and AB are as defined above; wherein $L_1$, $L_2$ and $L_3$ are each independently and optionally present or absent, are the same or different flexible linkers that include at least 1 flexible amino acid (e.g., Gly); and wherein CyClo where present, the AA is in the form of a cyclic structure due to the presence of a disulfide bond between a pair of cysteines in the AA. In addition, the formulae above provide for additional amino acid sequences that may be positioned N-terminal or C-terminal to the AA elements. It should be understood that in the formula CyClo[$L_1$-(MM)-$L_2$-(CM)-

L₃-(AB)], the cysteines responsible for the disulfide bond may be positioned in the AA to allow for one or two tails, thereby generating a lasso or omega structure when the AA is in a disulfide-bonded structure (and thus conformationally constrained state). The amino acid sequence of the tail(s) can provide for additional AA features, such as binding to a target receptor to facilitate localization of the AA, increasing serum half-life of the AA, and the like. Targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HSA)).

Linkers suitable for use in the AAs described herein are generally ones that provide flexibility of the modified AB or the AA to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $(GSGGS)_n$ and $(GGGS)_n$, where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 108), Gly-Gly-Ser-Gly-Gly (SEQ ID NO: 109), Gly-Ser-Gly-Ser-Gly (SEQ ID NO: 110), Gly-Ser-Gly-Gly-Gly (SEQ ID NO: 111), Gly-Gly-Gly-Ser-Gly (SEQ ID NO: 112), Gly-Ser-Ser-Ser-Gly (SEQ ID NO: 113), and the like. The ordinarily skilled artisan will recognize that design of an AA can include linkers that are all or partially flexible, such that the linker can include a flexible linker as well as one or more portions that confer less flexible structure to provide for a desired AA structure.

In addition to the elements described above, the modified ABs and AAs can contain additional elements such as, for example, amino acid sequence N- or C-terminal of the AA. For example, AAs can include a targeting moiety to facilitate delivery to a cell or tissue of interest. Moreover, the AA can be provided in the context of a scaffold protein to facilitate display of the AA on a cell surface.

In some embodiments, the activatable antibody, also includes a signal peptide. In some embodiments, the signal peptide is conjugated to the activatable antibody, via a spacer. In some embodiments, the spacer is conjugated to the activatable antibody, in the absence of a signal peptide. In some embodiments, the spacer is joined directly to the MM of the activatable antibody. In some embodiments, the spacer is joined directly to the MM of the activatable antibody, in the structural arrangement from N-terminus to C-terminus of spacer-MM-CM-AB.

Suitable spacers and spacer technology is known in the art and can routinely be used to incorporate spacers in some embodiments of the provided activatable antibodies. See, for example, WO 2016/179285 (e.g., at pages 52-53), the contents of which is herein incorporated by reference in its entirety.

In some embodiments, the activatable antibody is exposed to and cleaved by a protease such that, in the activated or cleaved state, the activated antibody includes a light chain sequence that includes at least a portion of LP2 and/or CM sequence after the protease has cleaved the CM.

The CM is specifically cleaved by at least one protease at a rate of about $0.001\text{-}1500\times10^4 M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4\ M^{-1}S^1$. In some embodiments, the CM is specifically cleaved at a rate of about 100,000 $M^{-1}S^{-1}$. In some embodiments, the CM is specifically cleaved at a rate from about $1\times10^2$ to about $1\times10^6\ M^{-1}\ S^{-1}$ (i.e., from about $1\times10^2$ to about $1\times10^6\ M^{-1}S^{-1}$). For specific cleavage by an enzyme, contact between the enzyme and CM is made. When the activatable antibody, comprising an Ab (e.g., an antibody or EpCAM-binding antibody fragment) coupled to a MM and a CM is in the presence of the target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but unable to cleave because of other cellular factors or protein modification of the enzyme.

Production of Cell-Binding Agent-Drug Conjugates

In order to link the any one of the cytotoxic compounds or derivative thereof described herein to the cell-binding agent, the cytotoxic compound can comprise a linking moiety with a reactive group bonded thereto. These compounds can be directly linked to the cell-binding agent. Representative processes for linking the cytotoxic compounds having a reactive group bonded thereof with the cell-binding agent to produce the cell-binding agent-cytotoxic agent conjugates are described in the Examples.

In some embodiments, a bifunctional crosslinking reagent can be first reacted with the cytotoxic compound to provide the compound bearing a linking moiety with one reactive group bonded thereto (i.e., drug-linker compound), which can then react with a cell binding agent. Alternatively, one end of the bifunctional crosslinking reagent can first react with the cell binding agent to provide the cell binding agent bearing a linking moiety with one reactive group bonded thereto, which can then react with a cytotoxic compound. The linking moiety can contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 2005/0169933, or charged linkers or hydrophilic linkers and are described in US 2009/0274713, US 2010/01293140 and WO 2009/134976, each of which is expressly incorporated herein by reference, each of which is expressly incorporated herein by reference.

In some embodiments, a solution of a cell-binding agent (e.g., an antibody) in aqueous buffer may be incubated with a molar excess of a bifunctional crosslinking agent, such as N-succinimidyl-4-(2-pyridyldithio)pentanoate (SPP), N-succinimidyl-4-(2-pyridyldithio)butanoate (SPDB), N-succinimidyl-4-(2-pyridyldithio)$_2$-sulfo butanoate (sulfo-SPDB) to introduce dithiopyridyl groups. The modified cell-binding agent (e.g., modified antibody) is then reacted with the thiol-containing cytotoxic compound described herein, to produce a disulfide-linked cell-binding agent-cytotoxic agent conjugate of the present invention.

In another embodiment, the thiol-containing cytotoxic compound described herein, can react with a bifunctional crosslinking agent such as N-succinimidyl-4-(2-pyridyldithio)pentanoate (SPP), N-succinimidyl-4-(2-pyridyldithio) butanoate (SPDB), N-succinimidyl-4-(2-pyridyldithio)$_2$-sulfo butanoate (sulfo-SPDB) to form a cytotoxic agent-linker compound, which can then react with a cell-biding agent to produce a disulfide-linked cell-binding agent-cytotoxic agent conjugate of the present invention. The cytotoxic agent-linker compound can be prepared in situ without purification before reacting with the cell-binding agent. Alternatively, the cytotoxic agent-linker compound can be purified prior to reacting with the cell-binding agent.

The cell binding agent-cytotoxic agent conjugate may be purified using any purification methods known in the art, such as those described in U.S. Pat. No. 7,811,572 and US Publication No. 2006/0182750, both of which are incorporated herein by reference. For example, the cell-binding agent-cytotoxic agent conjugate can be purified using tangential flow filtration, adsorptive chromatography, adsorptive filtration, selective precipitation, non-absorptive filtration or combination thereof. Preferably, tangential flow filtration (TFF, also known as cross flow filtration, ultrafiltration and diafiltration) and/or adsorptive chromatography resins are used for the purification of the conjugates.

The number of cytotoxic molecules bound per antibody molecule can be determined spectrophotometrically by measuring the ratio of the absorbance at 280 nm and 330 nm. In some embodiments, an average of 1-10 cytotoxic compounds/antibody molecule(s) can be linked by the methods described herein. In some embodiments, the average number of linked cytotoxic compounds per antibody molecule (DAR) is 2-12. In some embodiments, the DAR value is 2-10. In some embodiments, the DAR value is 2-8. In some embodiments, the DAR value is 2.5-4.0. In some embodiments, the DAR value is 4-8. In some embodiments, the DAR value is 5-8. In some embodiments, the DAR value is 6-8. In some embodiments, the DAR value is 6.5-8. In some embodiments, the DAR value is 7-8. In some embodiments, the DAR value is 7.1-8. In some embodiments, the DAR value is 7.2-8. In some embodiments, the DAR value is 7.3-8. In some embodiments, the DAR value is 7.4-8. In some embodiments, the DAR value is 7.5-8. In some embodiments, the DAR value is 7.6-8. In some embodiments, the DAR value is 7.7-8. In some embodiments, the DAR value is 7.8-8. In some embodiments, the DAR value is 7.9-8. In some embodiment, a composition (e.g., pharmaceutical composition) comprising the conjugates of the invention has a DAR value between 2 and 12, between 2 and 10, more specifically between 6 and 8. In some embodiments, the average number of linked cytotoxic compounds per antibody molecule (DAR) is 7-8, and more specifically 8.

In some embodiments, when the antibody is linked to the cytotoxic agent through a cysteine thiol group, the conjugate has 1 cytotoxic compounds per antibody molecule. In some embodiments, the conjugate has 1 or 2 cytotoxic compounds per antibody molecule. In some embodiments, the conjugate has 2 cytotoxic compounds per antibody molecule. In some embodiments, the average number of linked cytotoxic compounds per antibody molecule (DAR) is 1.5 to 2.5, more specifically 1.8-2.2. In some embodiments, a composition (e.g., pharmaceutical composition) comprising the conjugates of the invention has a DAR value between 1.0 and 2.5, between 1.5 and 2.5, more specifically between 1.8 and 2.2 or between 1.9 and 2.1.

Representative processes for preparing the cell-binding agent-drug conjugates of the present invention are described in U.S. Pat. No. 8,765,740 and U.S. Application Publication No. 2012/0238731. The entire teachings of these references are incorporated herein by reference.

Compositions

The present invention includes a composition (e.g., a pharmaceutical composition) comprising any one of the compounds described herein, derivatives thereof, or conjugates thereof, (and/or solvates, hydrates and/or salts thereof) and a carrier (a pharmaceutically acceptable carrier).

The pharmaceutical compositions described herein can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration. In some particular embodiments, the administration is intravenous. The pharmaceutical compositions described herein can also be used in vitro or in ex vivo.

Suitable pharmaceutically acceptable carriers, diluents, and excipients are well known and can be determined by those of ordinary skill in the art as the clinical situation warrants. Examples of suitable carriers, diluents and/or excipients include: (1) Dulbecco's phosphate buffered saline, pH about 7.4, containing or not containing about 1 mg/mL to 25 mg/mL human serum albumin, (2) 0.9% saline (0.9% w/v NaCl), and (3) 5% (w/v) dextrose;

and may also contain an antioxidant such as tryptamine and a stabilizing agent such as Tween 20.

Methods of Use

The present compositions are useful for inhibiting abnormal cell growth or treating a proliferative disorder in a mammal (e.g., human).

The present invention includes a method of inhibiting abnormal cell growth or treating a proliferative disorder, an autoimmune disorder, destructive bone disorder, infectious disease, viral disease, fibrotic disease, neurodegenerative disorder, pancreatitis or kidney disease in a mammal (e.g., human) comprising administering to said mammal a therapeutically effective amount of cytotoxic compounds described herein, derivatives thereof, or conjugates thereof, (and/or solvates and salts thereof) or a composition thereof.

In certain embodiments, the proliferative disorder in a mammal is cancer, including hematologic cancer, leukemia, or lymphoma. In certain embodiments, the proliferative disorder is a cancer of a lymphatic organ, or a hematological malignancy. In some embodiments, the cancer is a lymphoma or a leukemia.

For example, the cancer may be selected from the group consisting of: acute myeloid leukemia (AML, including CD33-low AML, P-glycoprotein positive AML, relapsed AML, or refractory AML), chronic myelogenous leukemia (CML), including blastic crisis of CML and Abelson oncogene associated with CML (Bcr-ABL translocation), myelodysplastic syndrome (MDS), acute lymphoblastic leukemia (ALL), including, but not limited to, acute B lymphoblastic leukemia or B-cell acute lymphoblastic leukemia (B-ALL), chronic lymphocytic leukemia (CLL), including Richter's syndrome or Richter's transformation of CLL, hairy cell leukemia (HCL), acute promyelocytic leukemia (APL), B-cell chronic lymphoproliferative disease (B-CLPD), atypical chronic lymphocytic leukemia (preferably with a marked CD11c expression), diffuse large B-cell lymphoma (DLBCL), blastic plasmacytoid dendritic cell neoplasm (BPDCN), non-Hodgkin lymphomas (NHL), including mantel cell leukemia (MCL), and small lymphocytic lymphoma (SLL), Hodgkin's lymphoma, systemic mastocytosis, and Burkitt's lymphoma.

In some embodiments, the cancer is endometrial cancer, lung cancer, colorectal cancer, bladder cancer, gastric cancer, pancreatic cancer, renal cell carcinoma, prostate cancer, esophageal cancer, breast cancer (e.g., triple negative breast cancer (TNBC)), head and neck cancer, uterine cancer, ovarian cancer, liver cancer, cervical cancer, thyroid cancer, testicular cancer, myeloid cancer, melanoma, and lymphoid cancer. In some embodiments, the lung cancer is non-small cell lung cancer or small-cell lung cancer. In further embodiments, compounds of the present invention may be useful in the treatment of non-small-cell lung cancer (squamous cell, nonsquamous cell, adenocarcinoma, or large-cell undifferentiated carcinoma), colorectal cancer (adenocarcinoma, gastrointestinal carcinoid tumors, gastrointestinal stromal tumors, primary colorectal lymphoma, leiomyosarcoma, or squamous cell carcinoma) or breast cancer (e.g., triple negative breast cancer (TNBC)).

The present invention, thus generally described, will be understood more readily by reference to the following examples, which are provided by way of illustration and are not intended to be limiting of the present invention.

Examples

The following abbreviations are used for the following terms:
DAR Drug to antibody ratio;
DIPEA Diisopropylethylamine;
DMF Dimethylformamide;
DMSO Dimethylsulfoxide;
DMTMM (4-(4,6-dimethoxy-1,3,5-triazin-2-yl)-4-methyl-morpholinium chloride;
EDTA Ethylenediaminetetraacetic acid;
EPPS 3-[4-(2-Hydroxyethyl)-1-piperazinyl]propanesulfonic acid;
Fmoc 9-Fluoroenylmethoxycarbonyl;
HMPA Hexamethylphosphoramide;
i.v. Intravenous;
NMM N-methylmorpholine;
PPTS Pyridinium p-toluenesulfonate;
SEC Size exclusion chromatography;
SEM Standard error of the mean;
TCEP 3,3',3"-phosphinetriyltripropanoic acid hydrochloride;
TEA Triethylamine; and
TFA Trifluoroacetic acid.

Figure 2:
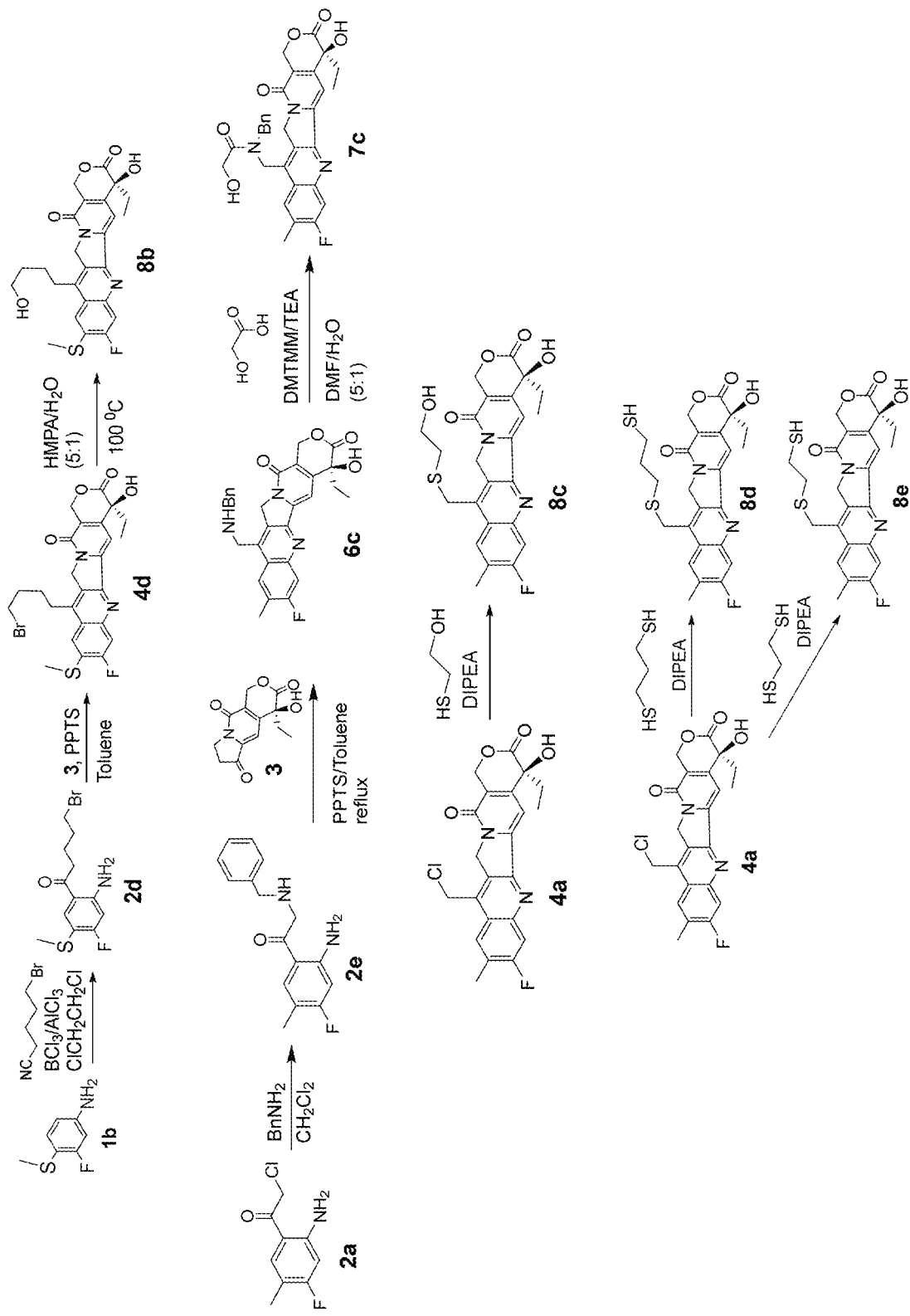
FIG. 2 depicts the second part of the synthesis of camptothecin building blocks.
Figure 3:
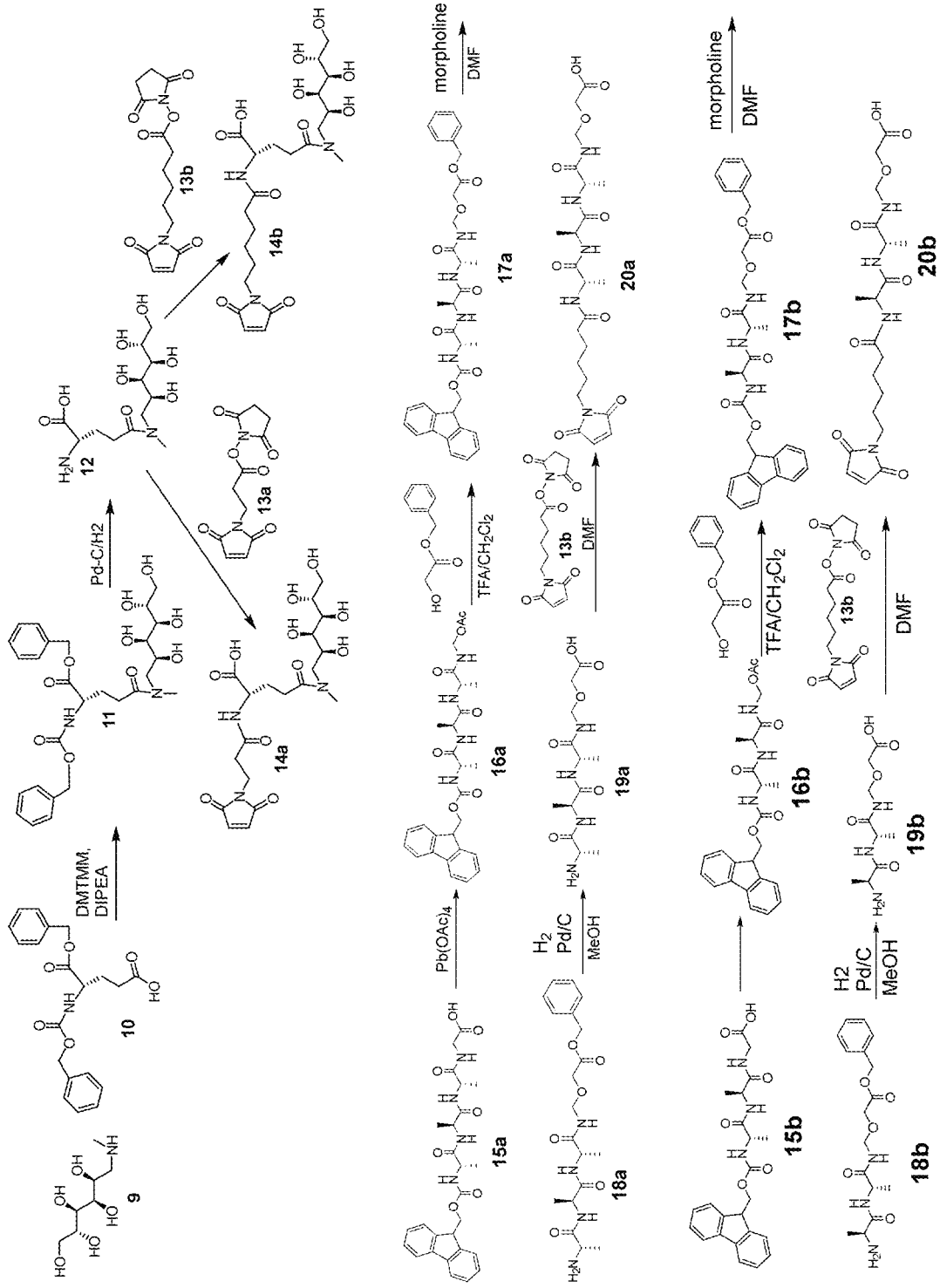
FIG. 3 depicts the first part of the synthesis of the side chains.
Figure 4:
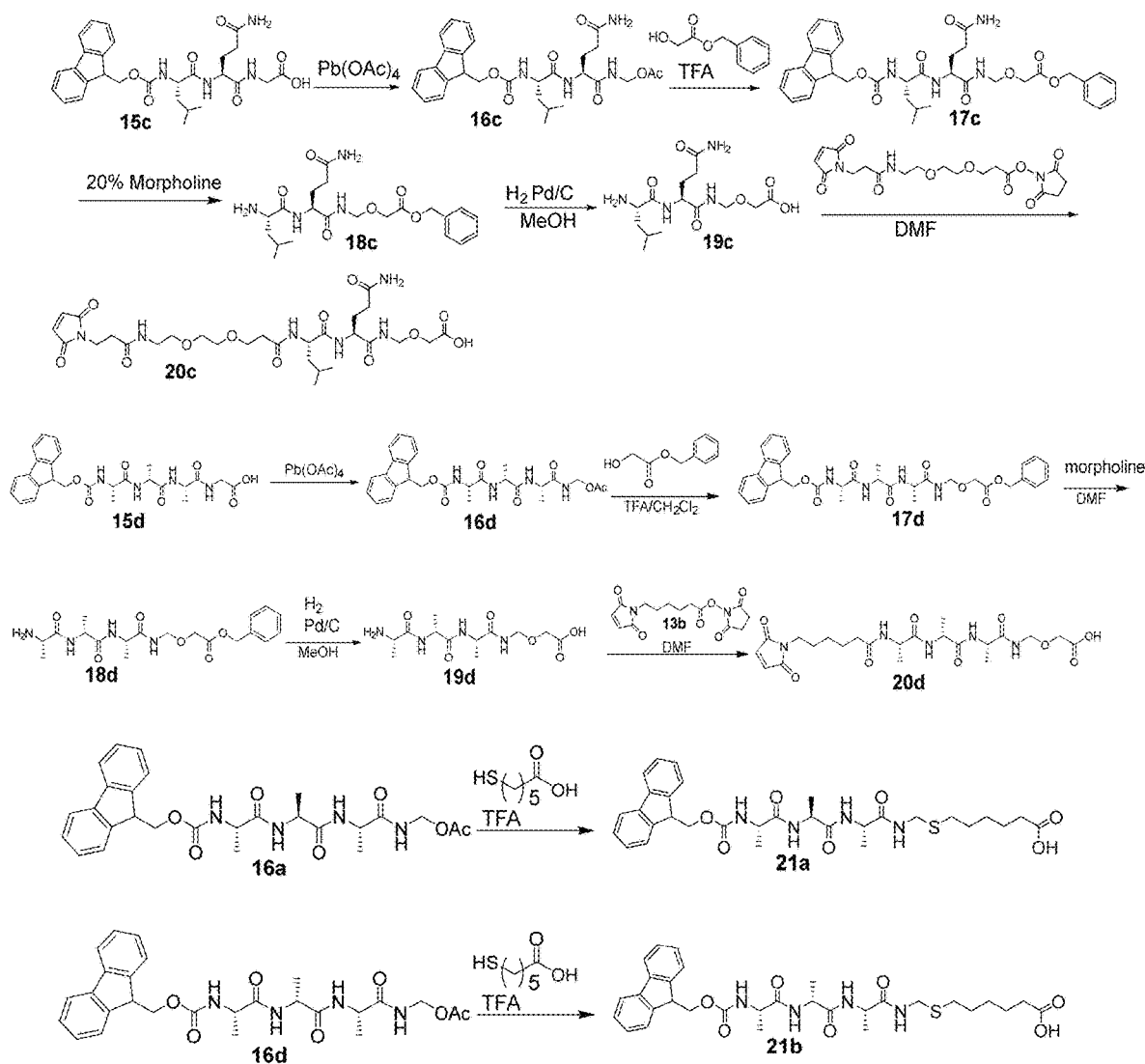
FIG. 4 depicts the second part of the synthesis of the side chains.
Figure 5:
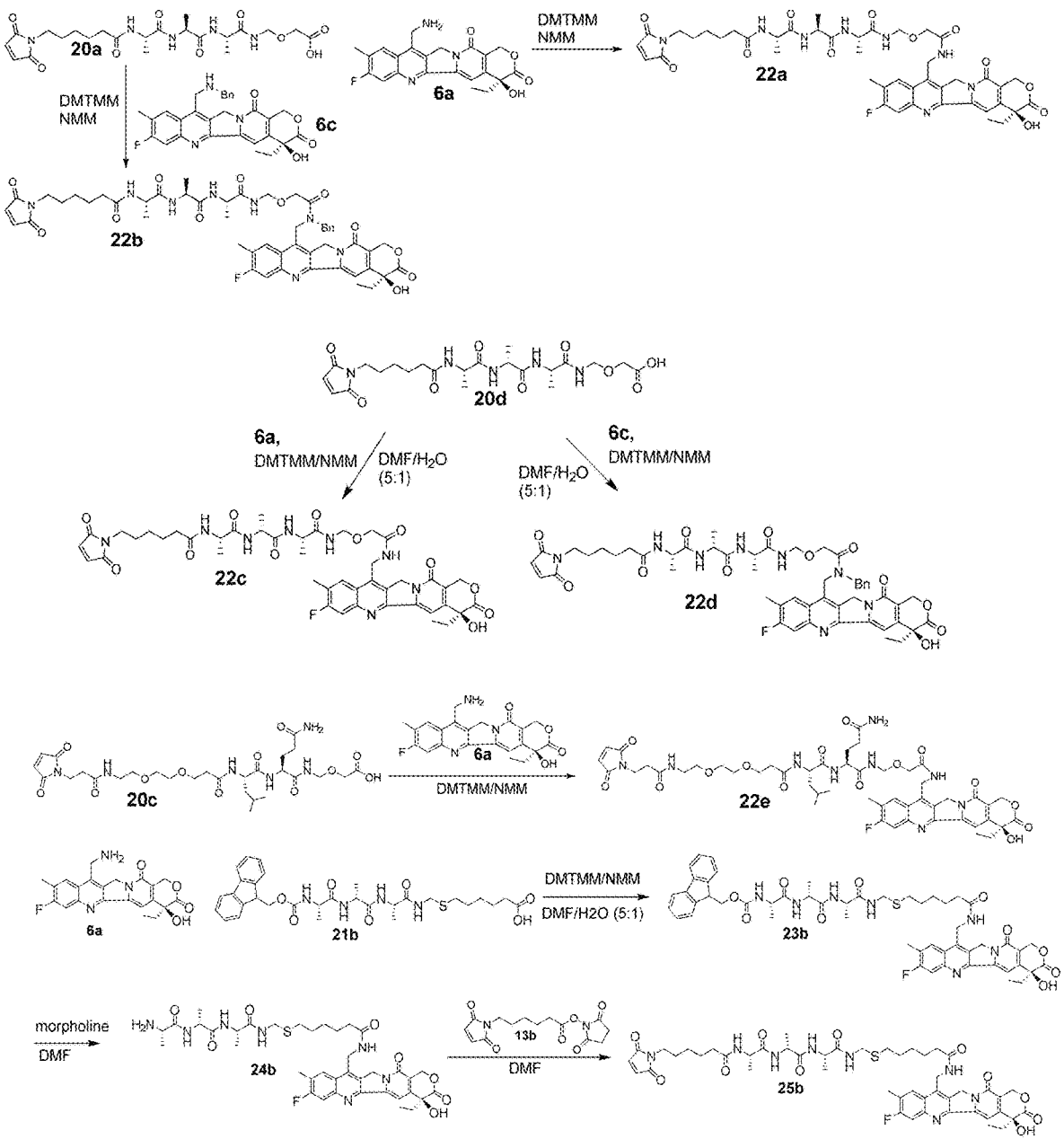
FIG. 5 depicts the first part of coupling the camptothecin building blocks to the side chains.
Figure 6:
FIG. 6 depicts the second part of coupling the camptothecin building blocks to the side chains.
Figure 7:
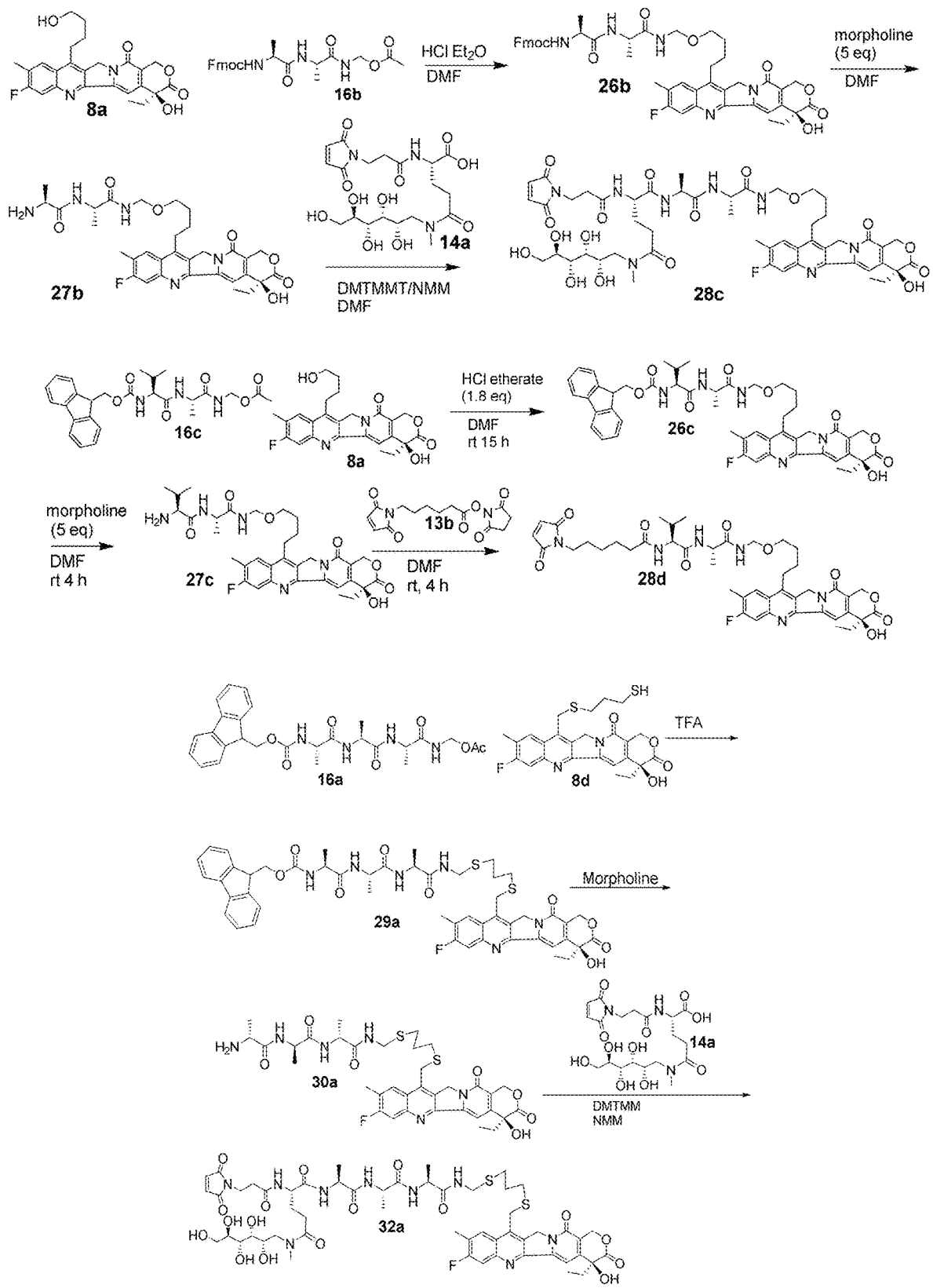
FIG. 7 depicts the third part of coupling the camptothecin building blocks to of the side chains.
Figure 8:
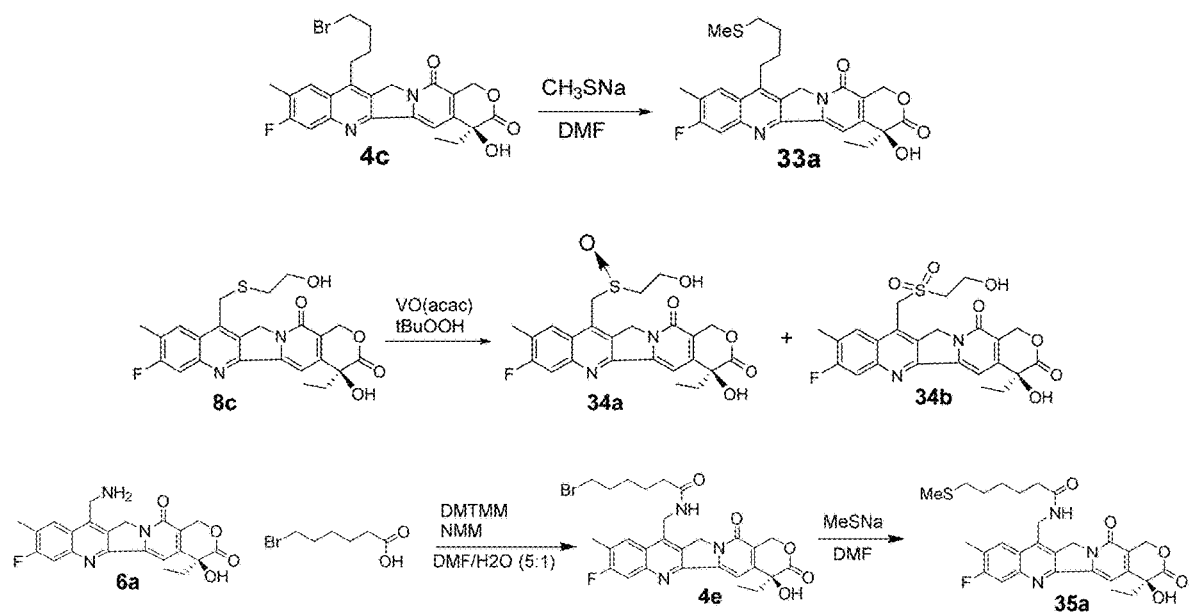
FIG. 8 depicts the synthesis of additional camptothecin metabolites.
Figure 9:
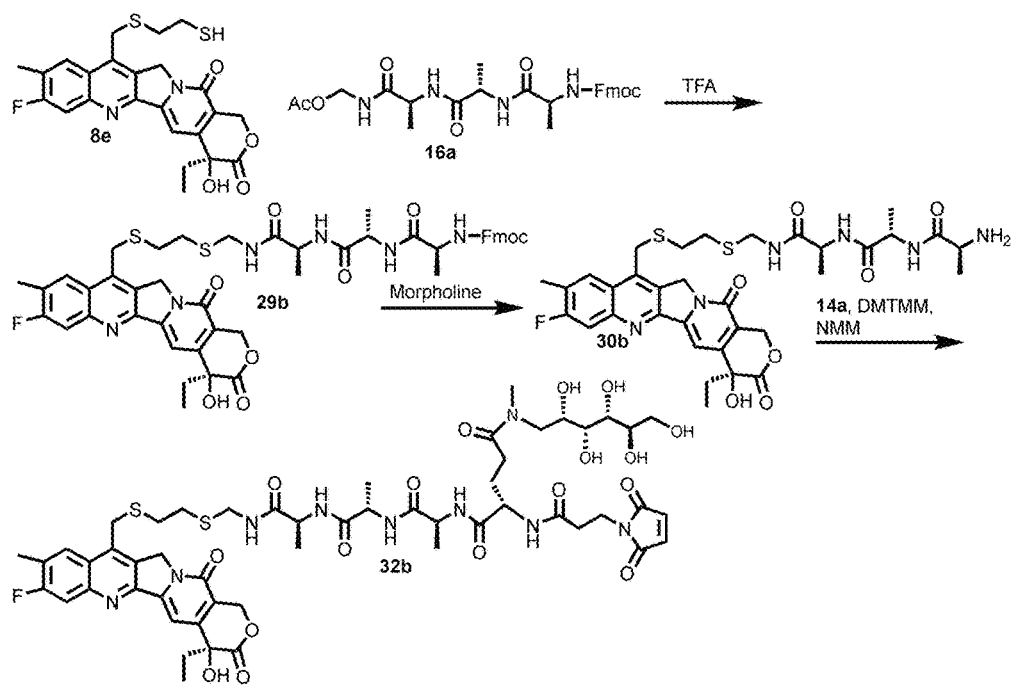
FIG. 9 depicts the coupling of camptothecin building blocks to side chains.
Figure 10:
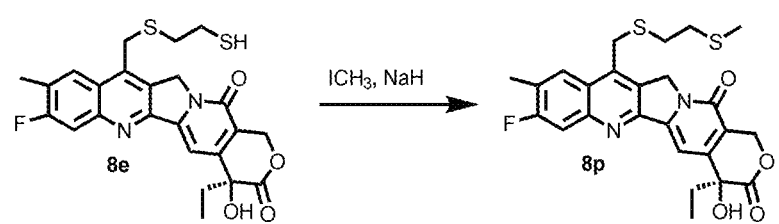
FIG. 10 depicts the synthesis of additional camptothecin compounds.

FIG. 1 and FIG. 2 depict the synthesis of camptothecin building blocks. FIG. 3, FIG. 4, and FIG. 5 depict the synthesis of the side chains. FIG. 6 and FIG. 7 depict the coupling of the camptothecin building blocks to the side chains. FIG. 8 depicts the synthesis of additional camptothecin metabolites. FIG. 9 depicts the coupling of camptothecin building blocks to side chains. FIG. 10 depicts the synthesis of additional camptothecin compounds.

Figure 11:
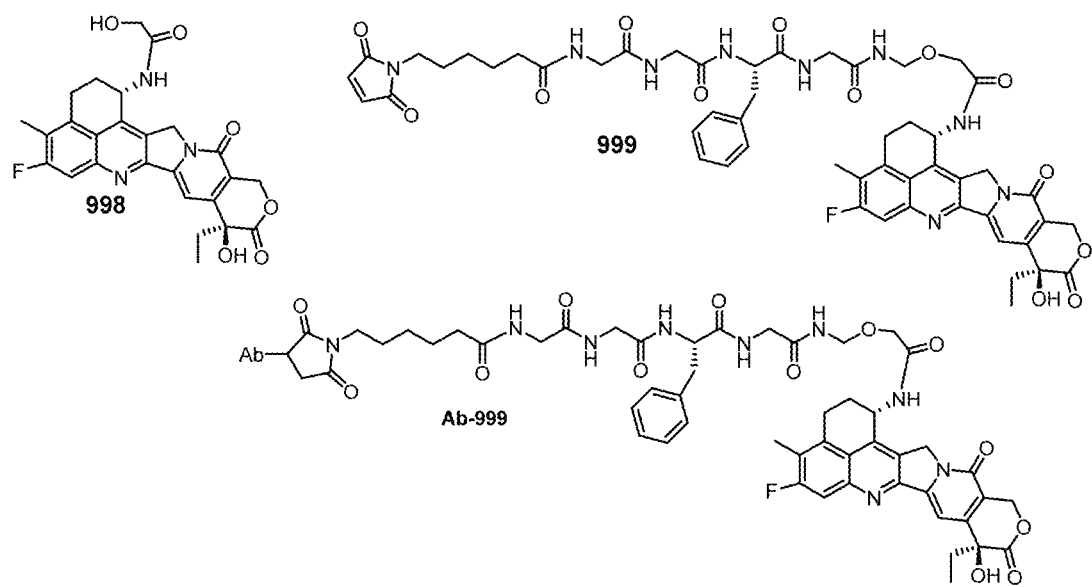
FIG. 11 depicts compounds used for comparison, which include a generic Ab-999 structure of an ADC bearing the 999 moiety linked through reduced inter-chain disulfides of an antibody.

FIG. 11 depicts compounds used for comparison, which include a generic Ab-999 structure of an ADC bearing the 999 moiety linked through reduced inter-chain disulfides of an antibody. Compounds 998 and 999 were prepared as described in US patent 2016/0297890 A1 and references therein.

Example 1. Synthesis of Compounds 2a-2e

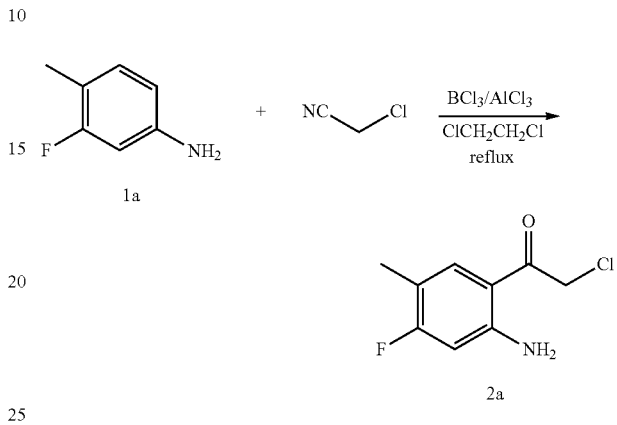

2a: To flask containing anhydrous 1,2-dichloroethane (80 mL) was added 1 M boron trichloride in dichloromethane (16 mL, 16 mmol) then cooled to 0° C. with an ice water bath. 1a (2.5 g, 20 mmol) was added in portions then stirred at 0° C. for 10 min, then chloroacetonitrile (2.7 mL, 23.5 mmol) was added followed by the addition of aluminum chloride (3.5 g, 26 mmol). The ice bath was removed and the reaction solution was gradually warmed to room temperature. After stirring at room temperature for 10 min, the reaction mixture was heated at reflux for 39 h. The reaction solution was cooled to room temperature and cold water (40 mL) was added slowly followed by the addition of 5% HCl water solution. After 30 min, it was diluted with dichloromethane (80 mL). The organic layer was washed with water and brine, dried over anhydrous sodium sulfate and filtered. The filtrate was stripped under reduced pressure and the residue was purified by reverse phase HPLC (200 g C18 column, 80 mL/min, $CH_3CN/H_2O$, 25% $CH_3CN$ for 5 min then to 95% $CH_3CN$ in 22 min then 95% $CH_3CN$ for 5 min) to give compound 2a as an off-white solid (1.52 g, yield 38%). MS (ESI): $(M+H)^+$ calcd. 202.0, found 202.2.

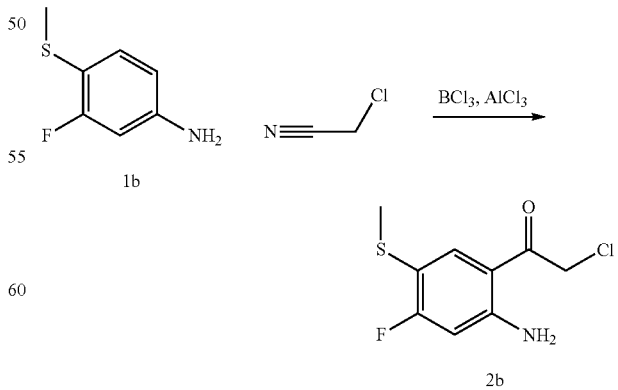

2b: $AlCl_3$ (1.0 g, 7.7 mmol) and toluene (3.4 mL) were added to a 100 mL flask equipped with magnetic stirring. A solution of 1b (1.0 g, 6.4 mmol) in toluene (3.85 mL) was added to the flask under a nitrogen atmosphere followed by 1 M BCl$_3$ in toluene (3.85 mL, 7.6 mmol). 2-chloroacetonitrile (1.7 mL, 26.6 mmol) was added dropwise over approximately 2 min then the flask was fit with a reflux condenser and heated in a 114° C. oil bath for 3 h. The heating bath was removed and after 4 min a thermometer was placed in the flask. After cooling to 50° C. the reaction mixture was poured into deionized water (50 mL) then extracted with ethyl acetate (2×60 mL). The organic layer was separated, dried over anhydrous Na$_2$SO$_4$ then solvent was removed by rotary evaporation under vacuum. The residue was taken up in a minimum volume of ethyl acetate then purified on an 80 g silica column eluting with 92:8 hexanes:ethyl acetate. Fractions containing pure desired product were combined and solvent was removed by rotary evaporation under vacuum to give 0.69 g of desired product 2b (46% yield) as a yellow solid. MS (M+H)+ 233.8; $^1$H NMR (400 MHz, Chloroform-d) δ 7.79 (d, J=7.9 Hz, 1H), 6.40 (d, J=11.0 Hz, 1H), 4.62 (s, 3H), 2.39 (s, 3H), 1.54 (s, 4H).

2c: To flask containing anhydrous 1,2-dichloroethane (50 mL) was added 1 M boron trichloride in dichloromethane (9.95 mL, 9.95 mmol) then cooled to 0° C. with an ice water bath. 1a (1.56 g, 12.4 mmol) was added in portions then stirred at 0° C. for 10 minutes, 5-bromovaleronitrile (1.72 mL, 14.9 mmol) was added followed by the addition of aluminum chloride (2.16 g, 16.2 mmol). The ice bath was removed and the reaction solution was gradually warmed to room temperature. After stirring at room temperature for 10 minutes, the reaction mixture was heated at reflux for 39.5 hours. The reaction solution was cooled to room temperature and cold water (25 mL) was added slowly followed by the addition of 5% HCl water solution. After 30 minutes, it was diluted with dichloromethane (50 mL). The organic layer was washed with water and brine, dried over anhydrous sodium sulfate and filtered. The filtrate was stripped under reduced pressure and the residue was purified by reverse phase HPLC (100 g C18 column, CH$_3$CN/H$_2$O, 25% CH$_3$CN for 5 minutes then to 95% CH$_3$CN in 15 minutes then 95% CH$_3$CN for 5 minutes) to give compound 2c as an off-white solid (1.42 g, yield 40%). MS (ESI): m/z 289.2 (M+H)$^+$.

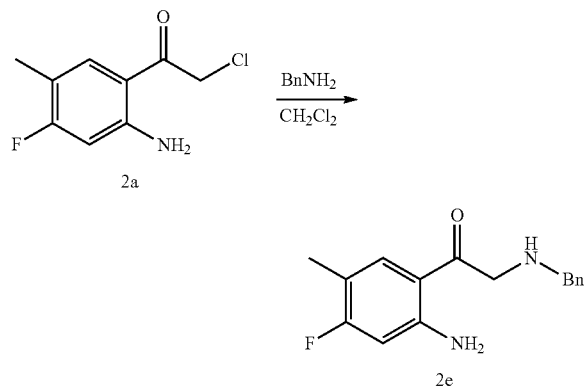

2e: To a solution of compound 2a (155 mg, 0.77 mmol) in anhydrous dichloromethane (1.5 mL) was added benzylamine (0.68 mL, 6.2 mmol) and the reaction mixture was stirred at room temperature for 6 hours. The reaction solution was stripped under reduced pressure and the residue was purified by silica gel chromatography (12 g silica column, CH$_2$Cl$_2$/MeOH, 0 to 10% MeOH in 16 minutes) to give 156 mg of 2e (74% yield). MS (ESI): m/z 273.4 (M+H)$^+$.

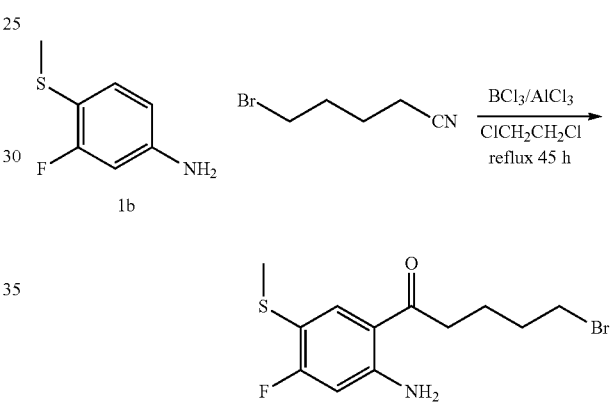

2d: To a dried flask contained anhydrous 1,2-dichloroethane (40 mL) was added boron trichloride (4.73 mL, 4.73 mmol, 1 M in CH$_2$Cl$_2$) and cooled to 0° C. with an ice water bath. Compound 1b (0.93 g, 5.92 mmol) was added in portions and after stirring at 0° C. for 10 minutes, 5-bromovaleronitrile (0.819 mL, 7.1 mmol) was added followed by the addition of aluminum chloride (1.025 g, 7.69 mmol). The ice bath was removed and the reaction solution was gradually warmed to room temperature. After stirred at room temperature for 10 minutes, the reaction mixture was heated at reflux for 45 hours. The reaction solution was cooled to room temperature and cold water (25 mL) was added slowly followed by 5 mL 5% HCl water solution. After 30 minutes, it was diluted with dichloromethane (50 mL). The organic layer was washed with water and brine, dried over anhydrous sodium sulfate and filtered. The filtrate was stripped under reduced pressure and the residue was purified by reverse phase HPLC (100 g C18 column, CH$_3$CN/H$_2$O, 25% CH$_3$CN for 3 minutes then to 95% CH$_3$CN in 15 minutes then 95% CH$_3$CN for 5 minutes) to give compound 2d as an off-white solid (0.776 g, yield 41%). MS (ESI): m/z 321.0 (M+H)$^+$.

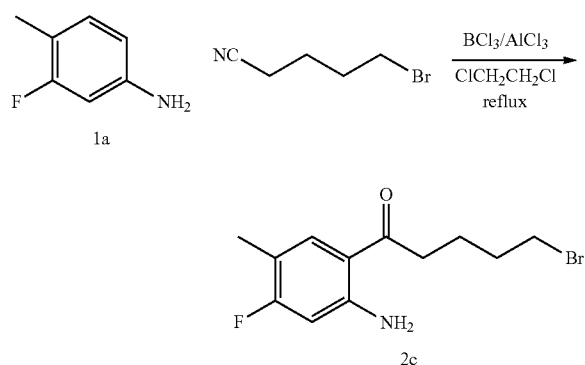

Example 2. General Procedure for Compounds 4a-4d

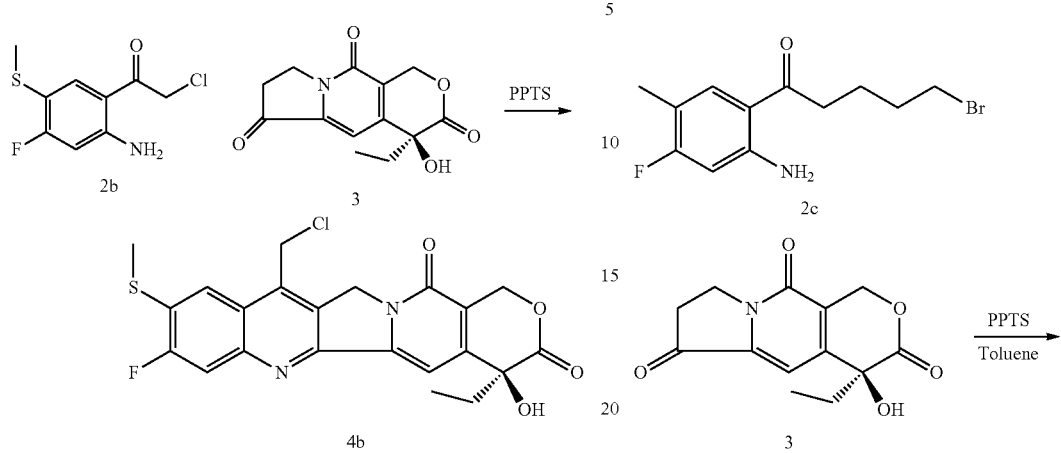

4b: Compound 3 (777 mg, 2.95 mmol), 2b (690 mg, 2.95 mmol) and PPTS (37 mg, 0.15 mmol) were suspended in a 50 mL flask equipped with a reflux condenser containing anhydrous toluene (10 mL). The reaction was heated to reflux with magnetic stirring under an argon atmosphere overnight then allowed to cool to room temperature. The mixture was vacuum filtered and the solids were washed with toluene (5 mL) to give 1.08 g desired product 4b as a brown solid (79% yield). MS (M+H)+ 461, MS (M−H) 459.

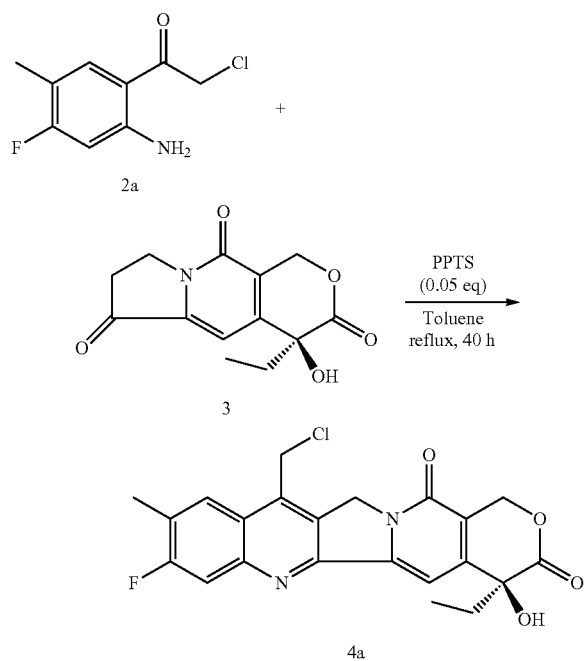

4a: Prepared by the general procedure, a solution of compound 2a (3.15 g, 15.64 mmol) and compound 3 (3.92 g, 14.89 mmol) in toluene (200 mL) with PPTS (187 mg, 0.75 mmol) was refluxed for 40 hours to give 4a (4.74 g) in 74% yield. MS (ESI): m/z 429.2. 431.0 (M+H)+. ¹H NMR (400 MHz, DMSO-d6) δ 8.37 (d, J=8.3, 1.2 Hz, 1H), 8.10-7.90 (m, 1H), 7.33 (d, J=2.1 Hz, 1H), 6.55 (d, J=4.8 Hz, 1H), 5.85-5.20 (m, 6H), 2.61-2.45 (m, 3H), 1.98-1.76 (m, 2H), 0.89 (t, J=7.3 Hz, 3H). HRMS (M+H)+ calcd. 429.1017, found 429.1023.

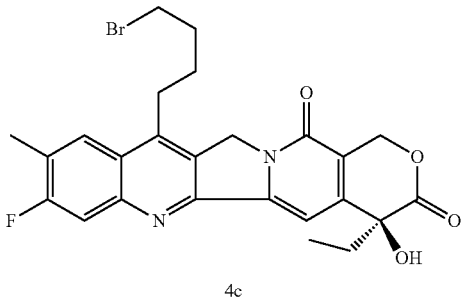

4c: Following the general procedure, a solution of compound 2c (1.695 g, 5.88 mmol) and compound 3 (1.548 g, 5.88 mmol) in toluene (50 mL) with PPTS (0.074 g, 0.294 mmol) was refluxed for 21.5 hours. Solvent was evaporated and residue was taken up in a minimum volume of 10% methanol in CH₂Cl₂ then purified by silica gel chromatography (40 g silica column, CH₂Cl₂/MeOH, 0 to 10% MeOH over 20 min) to give 4c (2.56 g) in 84% yield after silica gel chromatography (40 g silica column, CH₂Cl₂/MeOH, 0 to 10% MeOH in 20 minutes). MS (ESI): m/z 515.2 and 517.1 (M+H)+, 513.1 and 515.1 (M−H)⁻. ¹H NMR (400 MHz, DMSO-d6) δ 8.39-8.17 (m, 1H), 7.89 (d, J=10.9 Hz, 1H), 7.31 (s, 1H), 6.52 (d, J=6.2 Hz, 1H), 5.44 (s, 2H), 5.31 (s, 2H), 3.65 (t, J=6.7 Hz, 2H), 3.28-3.09 (m, 2H), 2.51 (t, J=1.8 Hz, 3H), 2.15-1.95 (m, 2H), 1.95-1.71 (m, 4H), 0.88 (t, J=7.4 Hz, 3H). HRMS (M+H)+ calcd. 515.0981, found 515.0992.

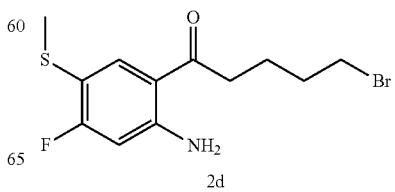

-continued

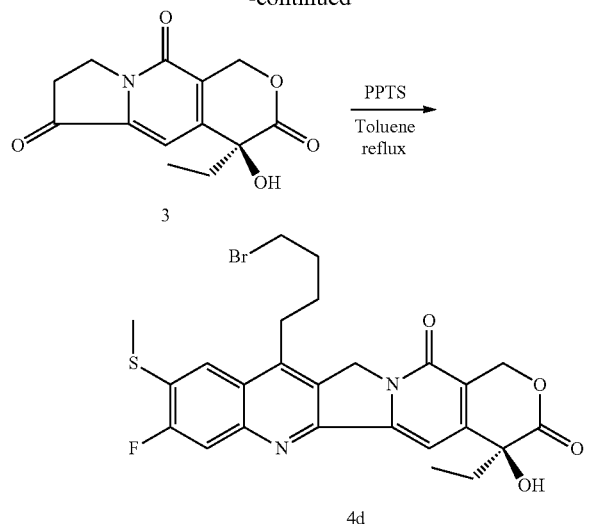

4d: Following the general procedure, a solution of compound 2d (776 mg, 2.42 mmol) and compound 3 (670 mg, 2.54 mmol) in toluene (20 mL) with PPTS (30 mg, 0.12 mmol) was refluxed for 24 hours to give 4d (1.02 g) in 77% yield after silica gel chromatography (40 g silica column, $CH_2Cl_2$/MeOH, 0 to 10% MeOH in 23 minutes). MS (ESI): m/z 547.0 and 548.9 $(M+H)^+$, 544.8 and 546.8 $(M-H)^-$.

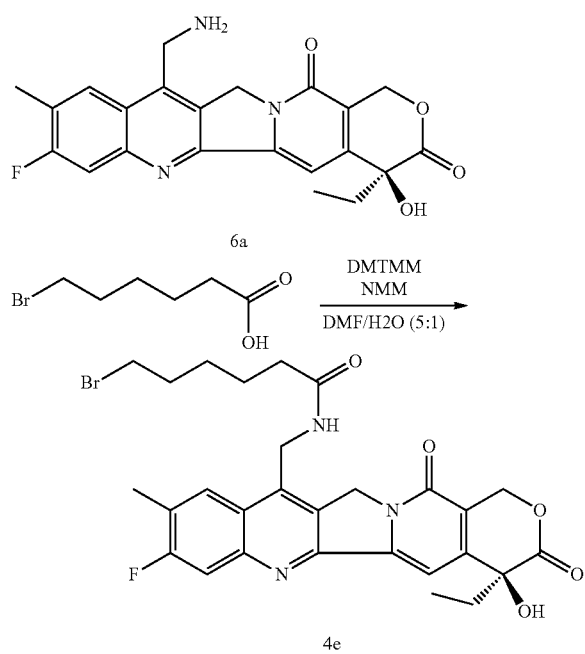

4e: To a solution of 6a (10 mg, 0.024 mmol) in DMF (0.5 mL) was added NMM (3 μL, 0.027 mmol) and 6-bromohexalic acid (7.2 mg, 0.037 mmol) and the solution is cooled to 0° C. with an ice bath and DMTMM (13.5 mg, 0.049 mmol) in deionized water was added. The ice bath was removed and the reaction mixture was stirred at room temperature for 3 hours. The reaction solution was stripped under reduced pressure and the residue was purified by silica gel chromatography (4 g column, $CH_2Cl_2$/MeOH, 0 to 10% MeOH in 15 minutes) to give 15 mg of 4e (yield 98%). MS (ESI): m/z 586.1 $(M+H)^+$, 588.0 $(M+H)^+$.

Example 3. Synthesis of Compounds 8a-8e and 8p

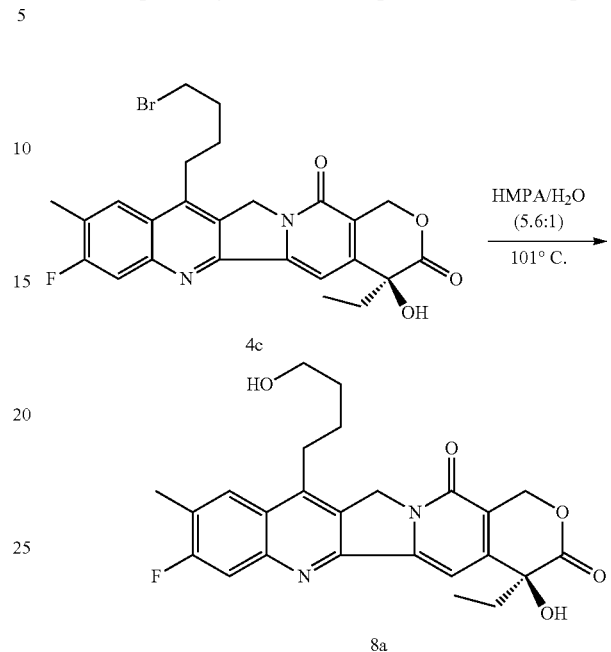

8a: A solution of compound 4c (860 mg, 1.67 mmol) in HMPA (5 mL) and deionized water (0.9 mL) was heated at 101° C. for 18 hours. The reaction mixture was cooled to room temperature and the solution was loaded on a C18 cartridge and purified by reverse phase HPLC (30 g C18 column, $CH_3CN$/$H_2O$, 25% $CH_3CN$ for 3 minutes then to 95% $CH_3CN$ in 15 minutes then 95% $CH_3CN$ for 5 minutes) to give 8a as a solid which was contaminated with impurities. It was further purified by silica gel chromatography ($CH_2Cl_2$/MeOH, 0 to 20% MeOH) to give 392 mg of 8a as an off-white solid (51% yield). MS (ESI): m/z 453.2 $(M+H)^+$, 451.1 $(M-H)^-$. $^1$H NMR (400 MHz, Methanol-d4) δ 8.00 (dd, J=8.2, 1.1 Hz, 1H), 7.52-7.33 (m, 2H), 5.53 (d, J=16.1 Hz, 1H), 5.33 (d, J=16.1 Hz, 1H), 5.18-4.96 (m, 2H), 3.66 (q, J=7.2, 6.7 Hz, 2H), 3.24-3.06 (m, 2H), 2.45 (dd, J=20.1, 2.7 Hz, 3H), 1.94 (tdd, J=7.1, 6.0, 2.0 Hz, 2H), 1.88-1.66 (m, 4H), 1.00 (td, J=7.4, 2.5 Hz, 3H). $^{13}$C NMR (101 MHz, Methanol-d4) δ 173.32, 163.68, 161.19, 157.56, 151.44, 151.09, 148.68, 148.56, 146.06, 144.46, 128.10, 127.89, 127.22, 125.66, 125.60, 124.26, 118.92, 111.91, 111.69, 97.96, 72.74, 65.28, 60.97, 49.40, 32.15, 30.80, 29.00, 25.96, 14.09, 14.06, 6.75; HRMS $(M+H)^+$ calcd. 453.1826, found 453.1832.

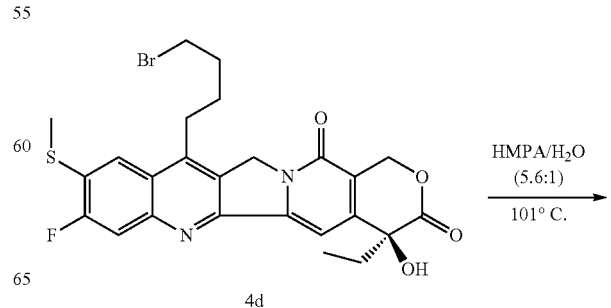

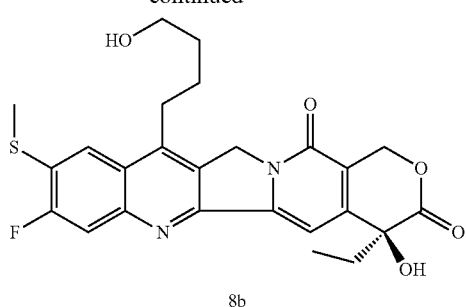

8b

8b: Prepared from 4d using the 8a procedure. Yield (48% yield). MS (ESI): m/z (M+H)+ 485.7.

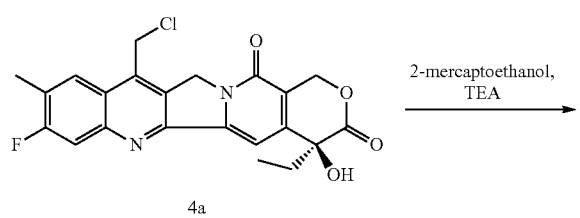

4a

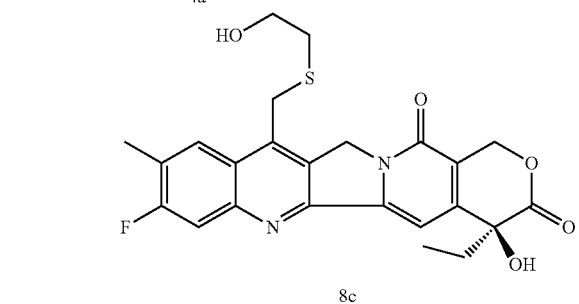

8c

8c: Compound 4a (100 mg, 0.23 mmol) was dissolved in anhydrous DMF (2 mL) to which was added 2-mercaptoethanol (0.2 mL, 2.8 mmol) followed by TEA (0.13 mL, 0.94 mmol) and magnetically stirred for 20 min. The reaction mix was injected onto 250 g medium pressure C18 column that was pre-equilibrated with 95:5 deionized water containing 0.2% formic acid: acetonitrile. The column was eluted at 50 mL/min with 95:5 deionized water containing 0.2% formic acid: acetonitrile for 5 min then with a linear gradient of 5% acetonitrile at 5 min to 95% acetonitrile at 35 min. Fractions containing desired product were combined, frozen and lyophilized to give 85 mg of 8c (78% yield). MS (ESI): m/z 471.4 (M+H)+. $^1$H NMR (400 MHz, DMSO-d6) δ 8.25 (d, J=8.2 Hz, 1H), 7.78 (d, J=10.8 Hz, 1H), 7.27 (s, 1H), 6.52 (s, 1H), 5.42 (s, 2H), 5.22 (s, 2H), 4.87 (t, J=5.4 Hz, 1H), 4.47-4.28 (m, 2H), 3.56 (q, J=6.3 Hz, 2H), 3.33 (s, 2H), 2.62 (t, J=6.6 Hz, 2H), 2.48-2.44 (m, 3H), 1.87 (hept, J=7.1, Hz, 2H), 0.88 (t, J=7.3 Hz, 3H). $^{13}$C NMR (101 MHz, DMSO-d6) δ 172.44, 163.07, 160.58, 156.69, 152.16, 149.97, 148.66, 148.53, 145.48, 140.06, 128.18, 128.16, 127.28, 127.07, 126.61, 126.54, 123.59, 119.09, 112.56, 112.35, 96.77, 72.36, 65.26, 60.83, 49.69, 34.38, 30.31, 28.78, 15.24, 15.20, 7.75. HRMS (M+H)+ calcd. 471.1390, found 471.1393.

8d: Prepared similarly to 8c by the reaction of 1,3-propanedithiol with 4a (60% yield). MS (ESI): m/z 501.7 (M+H)+.

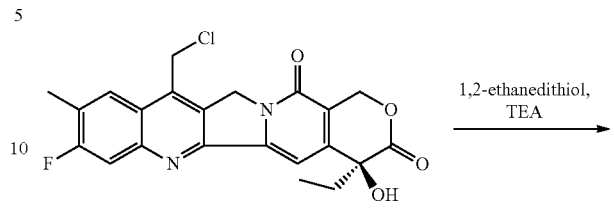

4a

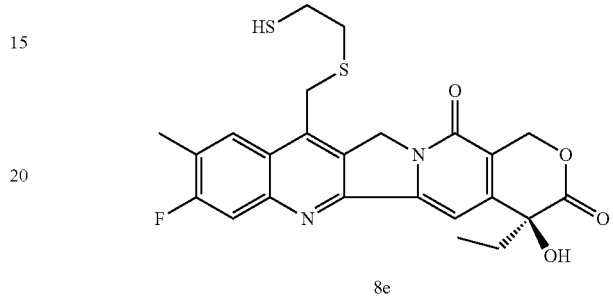

8e

8e: Prepared similarly to 8c by the reaction of 1,2-ethanedithiol with 4a (47% yield). MS (ESI): (M+H)+ calcd. 487.1, found 487.3.

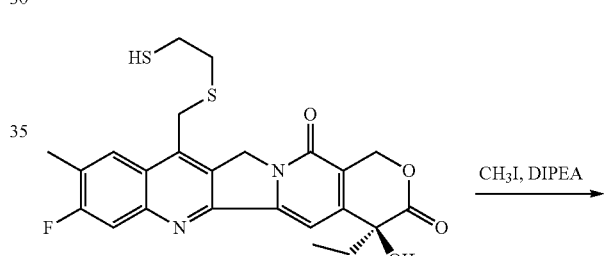

8e

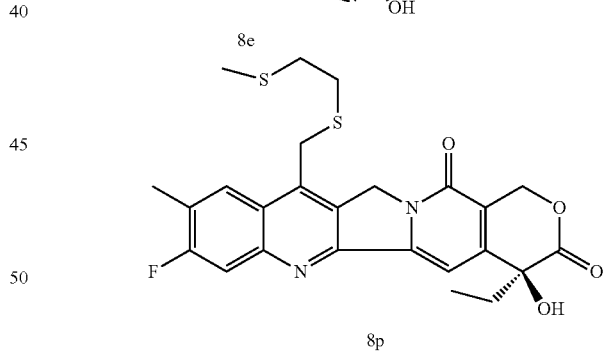

8p

8p: Compound 8e (28 mg, 0.057 mmol) was dissolved in anhydrous THF (1 mL) to which was added 60% NaH emulsion in mineral oil (5 mg, 2.1 mmol) with magnetic stirring. After 2 min, iodomethane (200.32 mmol) was added. After 20 min solvent was evaporated under vacuum and residue was taken up in anhydrous DMF (1 mL) then purified by medium pressure C18 chromatography. Column 100 g C18, 50 mL/min, 0.2% formic acid in deionized water with 5% acetonitrile from 0-5 min then a linear gradient of 5%-95% from 5 min 28 min. fractions containing desired product were combined, frozen and lyophilized to give 15 mg of 8p as a yellow solid (54% yield). $^1$H NMR (400 MHz, DMSO-d6) δ 8.40-8.27 (m, 1H), 7.89 (d, J=10.8 Hz, 1H), 7.31 (s, 1H), 6.52 (s, 1H), 5.43 (s, 2H), 5.39 (s, 1H), 5.32 (s, 1H), 4.57-4.39 (m, 2H), 2.84-2.69 (m, 3H), 2.44 (m, 1H), 2.07 (m, 1H), 2.02 (s, 3H), 1.87 (m, 2H), 1.23 (s, 1H), 0.87 (t, J=7.3 Hz, 3H). HRMS (M+H)$^+$ calcd. 501.1318; found 501.1322.

Example 4. Synthesis of Compound 5a

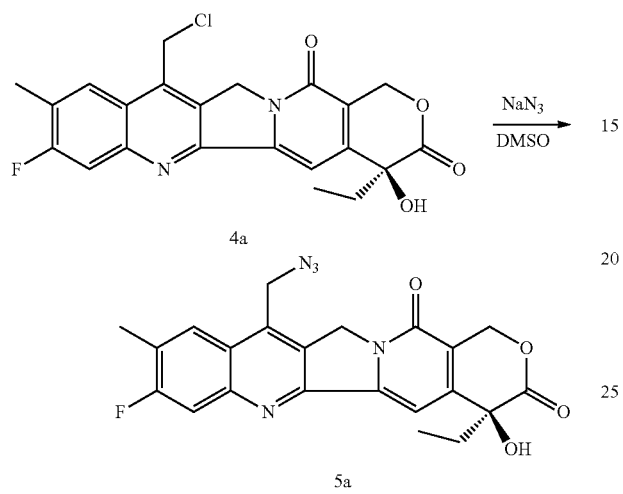

5a: A solution of 4a (2 g, 4.66 mmol) and sodium azide (0.455 g, 7.0 mmol) in 25 mL anhydrous DMSO was stirred at room temperature for 6 h followed by dilution with deionized water (200 mL). The product precipitated and was collected by vacuum filtration then dried under vacuum to give 2.03 g of 5a in (100% yield). MS (ESI): (M+H)$^+$ calcd. 435.1, found 436.2, MS (ESI): (M−H)$^-$ calcd. 433.1, found 434.2.

Example 5. Synthesis of Compound 6a

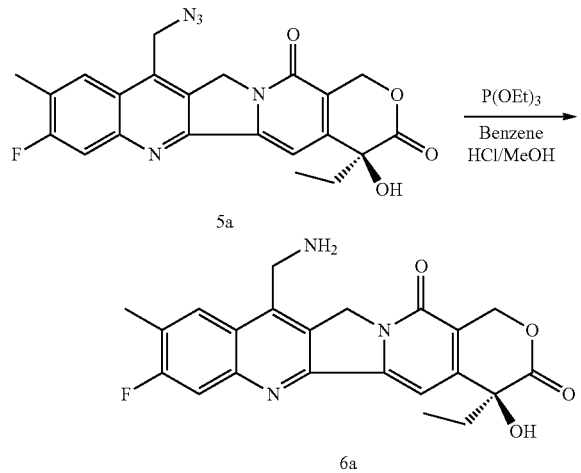

6a: To a solution of 5a (2.03 g, 4.66 mmol) in anhydrous benzene (60 mL) was added triethyl phosphite (1.94 g, 11.66 mmol) and the solution was flushed with argon then heated at reflux for 4 hours. The reaction was cooled to room temperature and 3 M methanolic HCl (30 mL) was added and heated at reflux (80° C. bath) for 38 h. The reaction was allowed to cool to room temperature then vacuum filtered to give 6a (1.016 g) as off-white solid. The filtrate was concentrated and the residue was purified by silica gel chromatography (12 g silica column, CH$_2$Cl$_2$/MeOH, 0 to 20% MeOH in 16 minutes) to give an additional 6a (0.079 g). 1.09 g of combined 6a was obtained (57% yield). $^1$H NMR (400 MHz, DMSO-d6) δ 8.62 (s, 3H), 8.43 (d, J=8.0 Hz, 1H), 7.99 (d, J=10.7 Hz, 1H), 7.35 (s, 1H), 5.59 (s, 2H), 5.45 (s, 2H), 4.70 (d, J=6.0 Hz, 2H), 2.55 (s, 3H), 1.88 (hept, J=7.1 Hz, 2H), 0.88 (t, J=7.3 Hz, 3H). MS (ESI): m/z calcd. 410.2, found 410.4 (M+H)$^+$; 408.1 (M−H)$^-$.

Example 6. Synthesis of Compound 7a

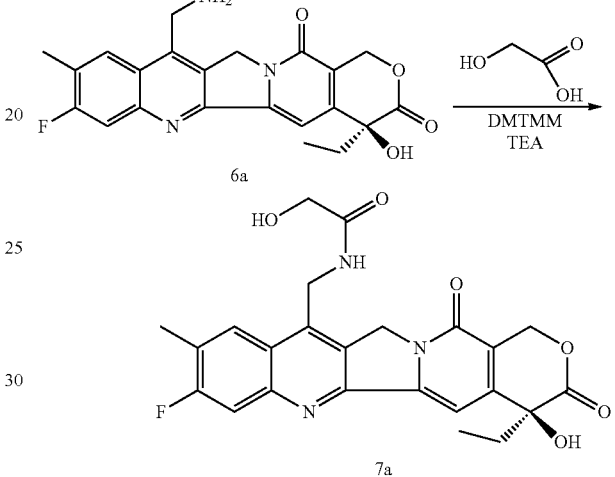

7a: To a solution of 6a (7.5 mg, 0.018 mmol) in DMF (0.5 mL) was added triethylamine (2.6 μL, 0.018 mml) and glycolic acid (1.5 mg, 0.020 mmol). The solution was cooled to 0° C. with an ice bath and DMTMM (10.1 mg, 0.037 mmol) in deionized water (0.1 mL) was added. The ice bath was removed and the reaction mixture was stirred at room temperature for 2 hours. The reaction solution was stripped under reduced pressure and the residue was purified by silica gel chromatography (4 g silica column, CH$_2$Cl$_2$/MeOH, 0 to 20% MeOH in 15 minutes) to give the desired product 7a (8 mg, yield 93%). MS (ESI): m/z 468.2 (M+H)$^+$, 466.1 (M−H)$^-$. $^1$HNMR (400 MHz, DMSO-d6) δ 0.88 (t, J=7.3 Hz, 3H), 1.79-1.98 (m, 3H), 2.55 (s, OH), 3.84 (d, J=5.6 Hz, 3H), 4.85 (d, J=6.0 Hz, 2H), 5.44 (s, 3H), 5.51 (s, 2H), 5.58 (t, J=5.7 Hz, 1H), 6.53 (s, 1H), 7.32 (s, 1H), 7.90 (d, J=10.8 Hz, 1H), 8.48 (d, J=1.2, 8.3 Hz, 1H), 8.76 (t, J=6.0 Hz, 1H). $^{13}$C NMR (101 MHz, DMSO-d6) δ 172.95, 172.89, 157.23, 152.85, 150.44, 149.07, 145.85, 140.12, 129.27, 127.97, 124.28, 119.63, 97.23, 72.83, 65.74, 61.91, 54.06, 50.54, 49.58, 44.06, 37.34, 30.72, 15.74, 8.22. HRMS (M+H)$^+$ calcd. 468.1571, found 468.1593.

Example 7. Synthesis of Compound 6c

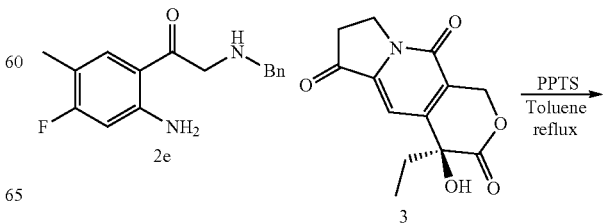

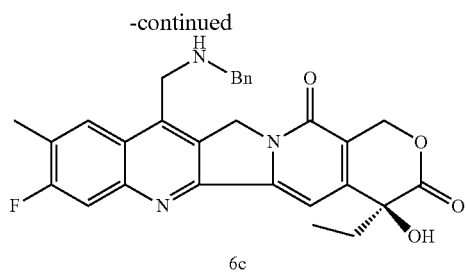

6c

6c: A stirring solution of compound 2e (129 mg, 0.47 mmol), compound 3 (125 mg, 0.47 mmol) and PPTS (131 mg, 0.52 mmol) in anhydrous toluene (10 mL) was briefly placed under vacuum then heated at reflux for 20 hours. The reaction solution was cooled to room temperature and stripped and the residue was purified by silica gel chromatography (12 g column, $CH_2Cl_2$/MeOH, 0 to 20% MeOH in 16 minutes) to give 196 mg impure product as black solid. It was further purified by reverse phase HPLC (30 g C18 column, $CH_3CN/H_2O$, 20% to 60% $CH_3CN$ in 15 minutes then 95% $CH_3CN$ for 5 minutes) to give 6c (31 mg, yield 13%). MS (ESI): m/z 500.4 (M+H)$^+$, 498.3 (M−H)$^-$.

Example 8. Synthesis of Compound 7c

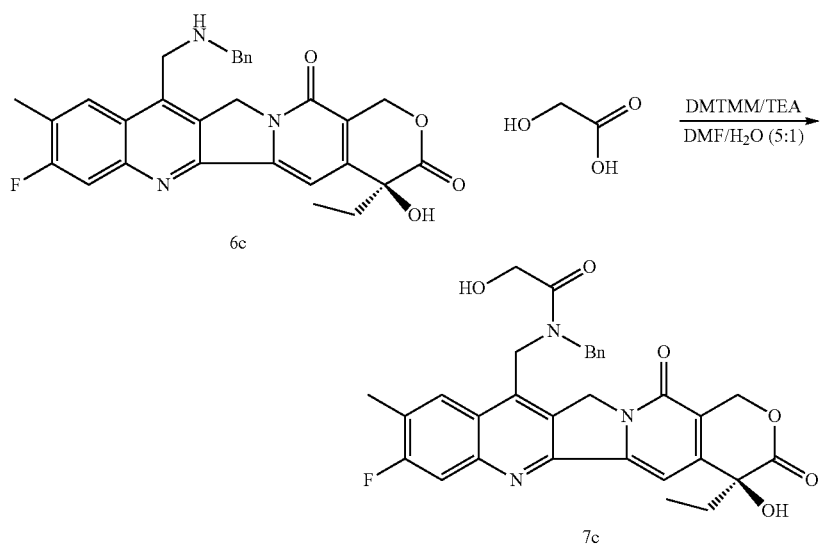

7c: To the solution of 6c (8.5 mg, 0.017 mmol) in DMF (0.5 mL) was added triethylamine (2.4μL, 0.017 mml) and glycolic acid (1.9 mg, 0.026 mmol). The solution was cooled to 0° C. with an ice bath and DMTMM (9.4 mg, 0.034 mmol) in deionized water (0.1 mL) was added. The ice bath was removed and the reaction mixture was stirred at room temperature for 3 hours. The reaction solution was stripped under reduced pressure (35° C. bath) and the residue was purified by semi-prep HPLC (C18 column, $CH_3CN/H_2O$, 25% to 65% $CH_3CN$ in 23 minutes) to give 2.5 mg of 7c (26% yield). MS (ESI): m/z 558.5 (M+H)$^+$, 556.3 (M−H)$^-$.

Example 9. Synthesis of Side Chains

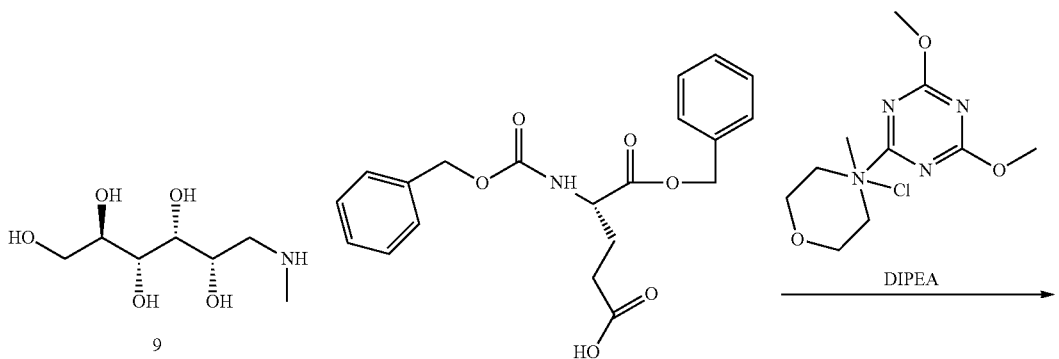

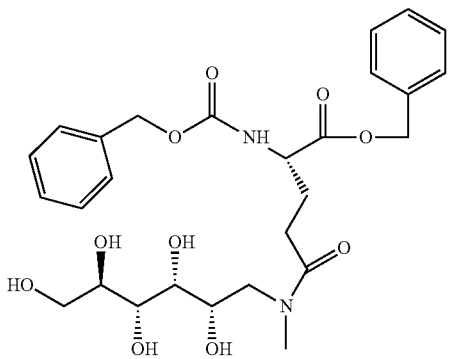

11: N-Methyl-D-Glucamine 9 (3.94 g, 20.19 mmol) and Z-L-Glu-OBn 10 (5 g, 13.46 mmol) were weighed into a 200 mL flask to which DMF (50 mL) was added and magnetically stirred. Then DIPEA (2.351 ml, 13.46 mmol) was added followed by as a suspension of DMTMM (5.22 g, 18.85 mmol) in DMF (30 mL) and deionized water (10 mL). After 2 h ⅓$^{rd}$ of the reaction was loaded on a 450 g C18 cartridge that was pre-equilibrated with 95:5 deionized water: acetonitrile. The column was eluted at 100 mL/min with 95:5 Deionized water: acetonitrile for 5 min then with a linear gradient of 5% acetonitrile to 95% acetonitrile over 38 min. Chromatography was repeated two more times and fractions containing pure desired product were pooled. Solvent was removed by rotary evaporation under vacuum. Methanol (100 mL) was added and evaporated 2 times to give 5 g of desired product 11 as a thick colorless oil (68% yield). MS (ESI): MS (M+H)$^+$ calcd. 549.2, found 549.3, MS (ESI): (M−H)$^-$ calcd 547.2, found 547.2.

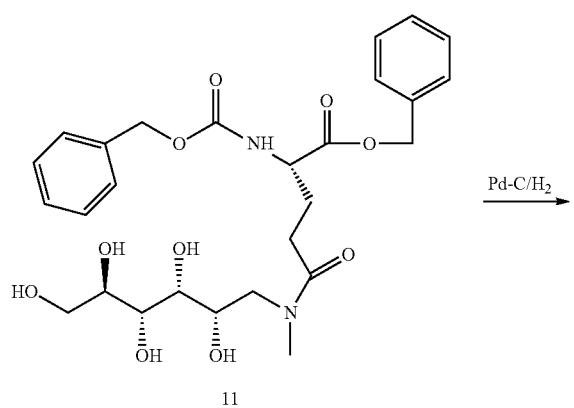

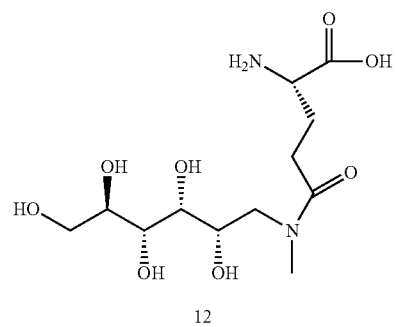

12: Compound 11 (5 g, 9.1 mmol) was suspended in 95:5 methanol:deionized water (100 mL) in a 250 mL PARR shaker flask to which was added 10% Pd—C (0.13 g, 1.222 mmol) and hydrogenated at 30 PSI H2 for 45 min, adding H2 periodically to reestablish pressure. The solution was vacuum filtered through celite filter aid. The clear colorless filtrate was concentrated under by rotary evaporation under vacuum then left under vacuum over night to give 2.8 g of desired product 12 as a white solid (94% yield). $^1$H NMR (400 MHz, DMSO-d6) δ 4.09-3.98 (m, 1H), 3.84 (dt, J=6.1, 3.1 Hz, 1H), 3.79 (d, J=6.0 Hz, 1H), 3.75 (ddd, J=7.5, 4.2, 2.3 Hz, 1H), 3.72-3.59 (m, 3H), 3.56-3.51 (m, 1H), 3.48 (dd, J=15.0, 3.6 Hz, 1H), 3.13 (s, 2H), 2.97 (s, 1H), 2.78-2.49 (m, 2H), 2.22-2.06 (m, 2H). MS (ESI): MS (M−H)$^-$ calcd. 323.1, found 323.4.

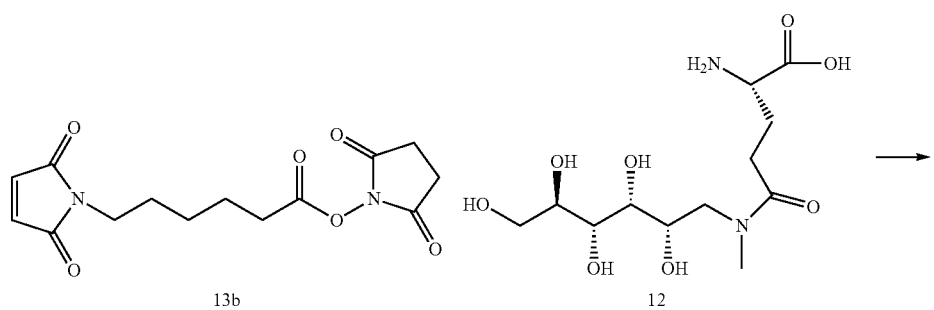

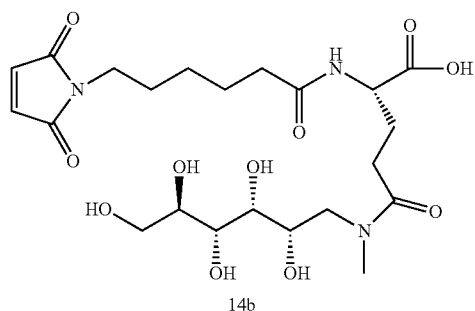

14b

14b: Compound 13b (1.4, 4.5 mmol) was added to a magnetically stirred solution of 12 (1.4 g, 4.3 mmol) in DMF (10 mL) and DIPEA (1.1 mL, 6.3 mmol). After stirring for 15 min the reaction was injected onto a medium pressure 350 g C18 column that was pre-equilibrated with 98:2 deionized water containing 0.1% formic acid: acetonitrile. The column was eluted at 100 mL/min at 2% acetonitrile for 5 min then with a linear gradient of 2% acetonitrile at 5 min to 60% acetonitrile at 35 min detecting at 214 and 306 nm. Fractions containing pure product were combined, frozen and lyophilized to give 1.3 g of desired product 14b as a white solid (58% yield). MS (M+H)+ 518.5, $^1$H NMR (400 MHz, DMSO-d6) δ 8.03 (dd, J=15.3, 7.7 Hz, 1H), 6.99 (s, 3H), 4.79 (d, J=65.9 Hz, 1H), 4.33 (d, J=30.0 Hz, 1H), 4.22-4.07 (m, 1H), 3.75 (p, J=4.2 Hz, 1H), 3.57 (ddt, J=11.4, 6.7, 3.6 Hz, 1H), 3.52-3.39 (m, 2H), 3.39-3.30 (m, 3H), 3.30-3.19 (m, 1H), 2.97 (s, 2H), 2.80 (s, 2H), 2.45-2.21 (m, 1H), 2.08 (h, J=3.4 Hz, 2H), 2.01-1.85 (m, 1H), 1.76 (qd, J=8.5, 3.9 Hz, 1H), 1.59-1.39 (m, 3H), 1.30-1.08 (m, 2H).

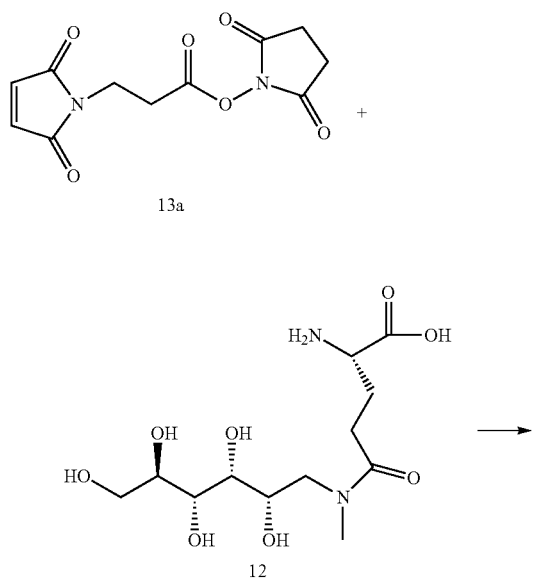

-continued

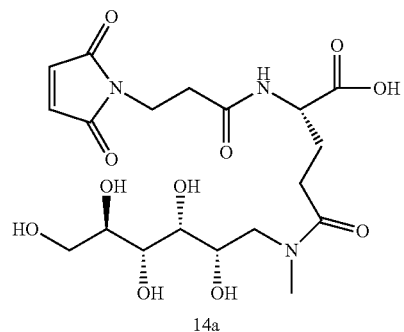

14a

14a: Compound 13a (1.4, 5.3 mmol) was added to a magnetically stirred solution of 12 (1.8 g, 5.5 mmol) in DMF (10 mL) and DIPEA (1.1 mL, mmol). After stirring for 15 min the reaction was injected onto a medium pressure 350 g C18 column that was pre-equilibrated with 98:2 deionized water containing 0.1% formic acid: acetonitrile. The column was eluted at 100 mL/min at 2% acetonitrile for 5 min then with a linear gradient of 2% acetonitrile at 5 min to 60% acetonitrile at 35 min detecting at 214 and 306 nm. Fractions containing pure product were combined, frozen and lyophilized to give 1.4 g of 14a as a white solid (55% yield). $^1$H NMR (400 MHz, DMSO-d6) δ 8.33 (dd, J=9.2, 7.7 Hz, 1H), 7.08 (d, J=1.1 Hz, 2H), 4.24 (qd, J=8.8, 4.8 Hz, 1H), 3.86 (dt, J=8.2, 4.0 Hz, 1H), 3.76-3.63 (m, 4H), 3.62-3.43 (m, 4H), 3.41-3.29 (m, 1H), 3.08 (s, 2H), 2.91 (s, 2H), 2.61 (q, J=1.8 Hz, 1H), 2.40 (dd, J=10.0, 6.4 Hz, 1H), 2.02 (tdd, J=12.6, 10.3, 9.1, 5.8 Hz, 1H), 1.93-1.76 (m, 1H). MS (ESI): MS (M+H)$^+$ calcd. 476.2, found 476.4.

Fmoc protected peptides 15a, 15b, 15c and 15d were prepared by solid phase synthesis using standard procedures.

Example 10. Method for Converting
Fmoc-Peptide-Gly-OH to
Fmoc-Peptide-NHCH₂OAc (Compounds 16a-16d)

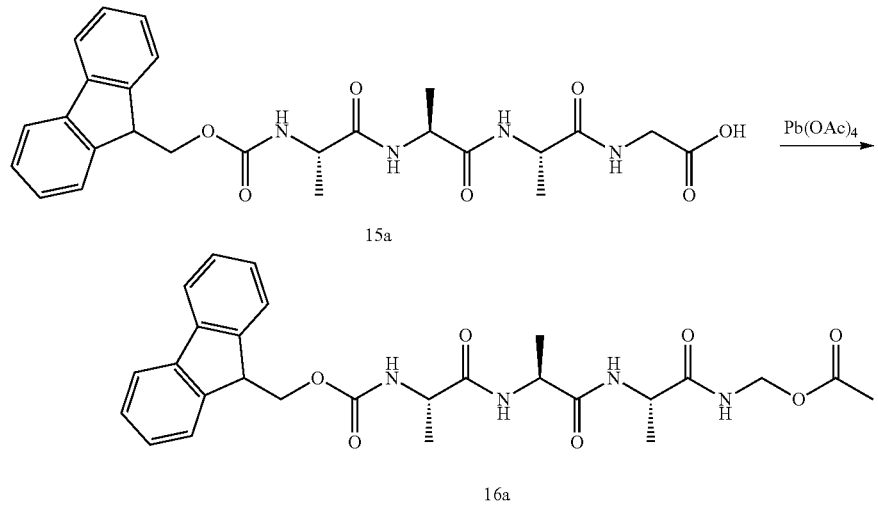

16a: Compound 15a (2.5 g, 4.9 mmol) was dissolved in anhydrous DMF (40 mL) and magnetically stirred in a 100 mL flask as copper (II) acetate (0.334 g, 1.84 mmol), acetic acid (0.64 mL, 11.1 mmol), and lead tetraacetate (2.5 g, 5.6 mmol) were added. The flask was heated in a 60° C. oil bath for 15 min. The oil bath was removed and the reaction was allowed to cool to room temperature. Approximately ½ of the mixture was purified on a 350 g medium pressure C18 column that was equilibrated with 90:10 deionized water containing 0.3% formic acid:acetonitrile. The column was eluted at 100 mL/min with 10% acetonitrile for 5 min then with a linear gradient of 10% acetonitrile from 5 min to 95% acetonitrile at 38 min. This procedure was repeated for the other 1/2 of reaction mixture and fractions containing desired product 16a were combined, frozen and lyophilized to give 1.2 g of white semi-solid (62% yield). ¹H NMR (400 MHz, DMSO-d6) δ 8.86 (t, J=6.9 Hz, 1H), 7.97 (dd, J=16.1, 7.4 Hz, 2H), 7.89 (dt, J=7.6, 0.9 Hz, 2H), 7.72 (t, J=7.1 Hz, 2H), 7.53 (d, J=7.5 Hz, 1H), 7.42 (td, J=7.5, 1.2 Hz, 2H), 7.33 (td, J=7.5, 1.2 Hz, 2H), 5.13-5.01 (m, 2H), 4.30-4.17 (m, 4H), 4.06 (t, J=7.3 Hz, 1H), 3.32 (s, 1H), 1.99 (s, 3H), 1.27-1.13 (m, 9H). MS (ESI): MS (M+Na)⁺ calcd. 547.2, found 547.5.

16b was prepared from Fmoc-Ala-Ala-Gly-OH 15b in 55% yield. MS (M+Na)+476.7.

16c was prepared from Fmoc-Leu-Gln-Gly-OH 15c in 46% yield. MS (M+Na)+575.6.

16d was prepared from Fmoc-Ala-D-Ala-Ala-Gly-OH (Ala-D-Ala-Ala-Gly is SEQ ID NO: 114) 15d in 52% yield. MS (M+Na)+547.3.

Example 11. Method for Reacting
Benzyl-2-Hydroxyacetate with
Fmoc-Peptide-NHCH₂OAc (Compounds 17a-17d)

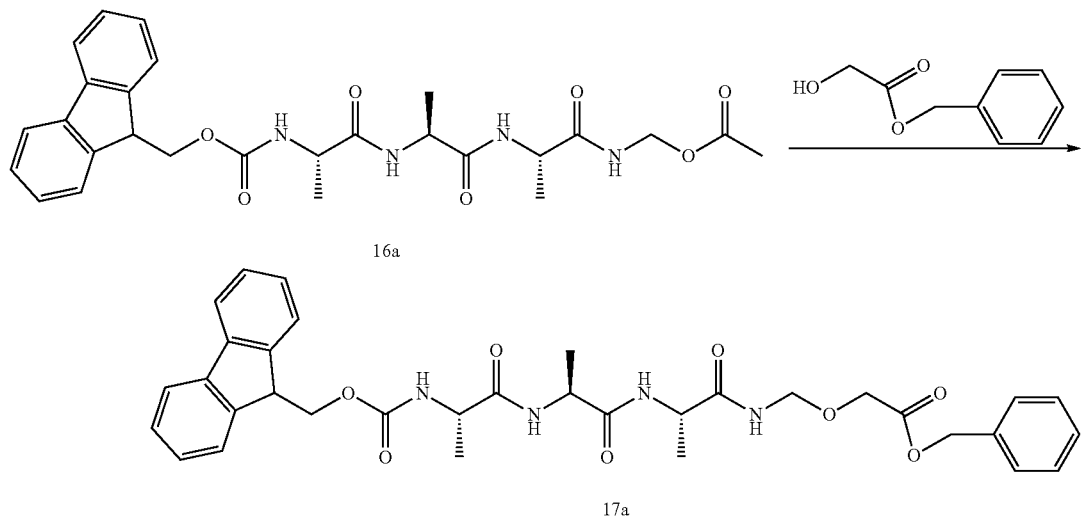

17a: Compound 16a (142 mg, 0.27 mmol) and benzyl-2-hydroxyacetate (226 mg, 1.36 mmol) were suspended in a solution of 20% TFA in dichloromethane (7 mL) and magnetically stirred at room temperature for 30 min. Solvent was rotary evaporated under vacuum and the residue was taken up in a minimum volume of DMF then purified on a 200 g C18 medium pressure column that was pre-equilibrated with 90:10 deionized water containing 0.1% formic acid: acetonitrile. The column was then eluted at 60 mL/min with 10% acetonitrile for 5 min followed by a linear gradient of 10% acetonitrile from 5 min to 95% acetonitrile at 38 min. Fractions containing desired product were combined, frozen and lyophilized to give 102 mg of white solid 17a (59% yield). MS (ESI): MS (M+Na) calcd. 653.3, found 653.5.

17b was prepared from 16b in 61% yield. MS (M+Na)+ 582.7.

17c was prepared from 16c in 52% yield. MS (M+H)+ 659.5.

17d was prepared from 16d in 56% yield. MS (M+Na)+ 653.4.

Example 12. Conversion of Fmoc-Peptide-NHCH$_2$OCH$_2$COOBn to H-Peptide-NHCH$_2$OCH$_2$COOBn (Compounds 18a-18d)

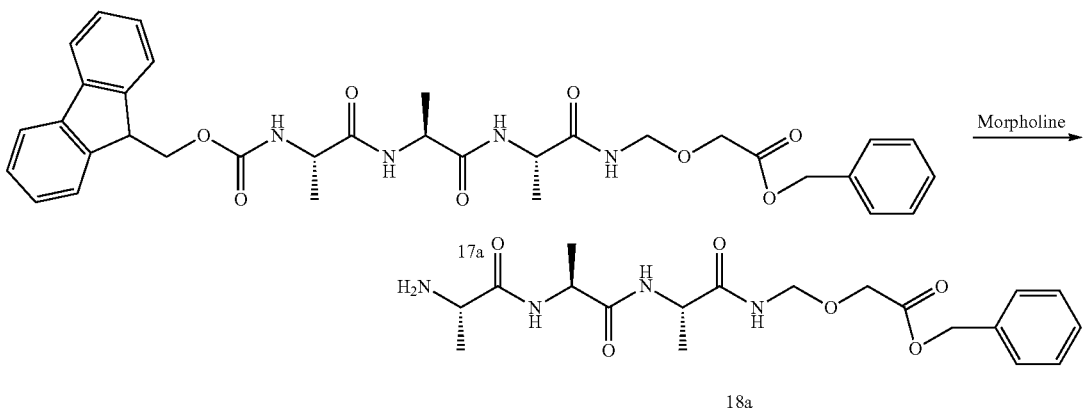

18a: Compound 17a (100 mg, 0.16 mmol) was dissolved in DMF (4 mL) to which morpholine (0.6 mL, 6.9 mmol) was added and magnetically stirred. After 1 h the reaction mixture was purified on a 200 g C18 medium pressure column that was pre-equilibrated with 95:5 deionized water containing 0.1% formic acid: acetonitrile. The column was then eluted at 60 mL/min with 5% acetonitrile for 5 min followed by a linear gradient of 5% acetonitrile from 5 min to 70% acetonitrile at 38 min. Fractions containing desired product were combined, frozen and lyophilized to give 50 mg of white solid 18a (76% yield). MS (ESI): MS (M+H)$^+$ calcd. 409.2, found 409.6.

18b was prepared from 17b in 80% yield. MS (M+H)+ 338.3.

18c was prepared from 17c in 61% yield. MS (M+H)+ 437.6.

18d was prepared from 17d in 61% yield. MS (M+H)+ 409.6.

Example 13. Conversion of H-Peptide-NHCH$_2$OCH$_2$COOBn to H-Peptide-NHCH$_2$OCH$_2$COOH (Compounds 19a-19d)

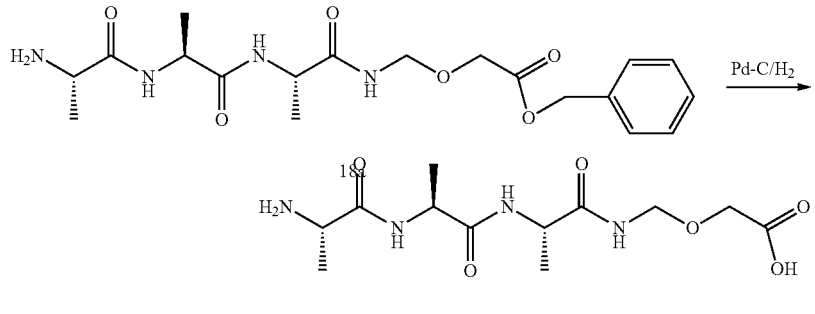

19a: In a 100 mL PARR shaker flask, H-Ala-Ala-Ala-NHCH$_2$OCH$_2$COOBn 18a (50 mg, 0.12 mmol) was dissolved in 5:95 deionized water: methanol (50 mL) to which was added 10% palladium on carbon (0.1 g) and reaction was hydrogenated in a PARR shaker at 30 PSI H2 for 1 h. The solution was vacuum filtered through celite filter aid and solvent was removed from the filtrate by rotary evaporation under vacuum to give 35 mg of desired product 19a as a thick oil (91% yield). MS (ESI): MS (M+H)$^+$ calcd. 319.2, found 319.3.

19b was prepared from 18b in 92% yield. MS (M+H)+ 248.3.

19c was prepared from 18c in 83% yield. MS (M+H)+ 347.4.

19d was prepared from 18d in 81% yield. MS (M+H)+ 319.5.

Example 14. Method for Preparing Mal-(CH$_2$)$_5$—CO-Peptide NHCH$_2$OCH$_2$COOH Compounds (Compounds 20a-20d)

20a: Mal-(CH$_2$)$_5$—COONHS 13b (46 mg, 0.15 mmol) was dissolved in anhydrous DMF (2 mL) to which was added DIPEA (0.1 mL, 0.31 mmol) and H-Ala-Ala-Ala-NHCH$_2$OCH$_2$COOH 19a (30 mg, 0.093 mmol). The reaction was magnetically stirred for 15 min then purified on a 50 g C18 medium pressure column that was pre-equilibrated with 95:5 deionized water containing 0.1% formic acid: acetonitrile. The column was then eluted at 40 mL/min with 5% acetonitrile for 5 min followed by a linear gradient of 5% acetonitrile from 5 min to 90% acetonitrile at 38 min. Fractions containing desired product were combined, frozen and lyophilized to give 30 mg of white solid 20a (63% yield). MS (ESI): MS (M–H)$^-$ calcd. 510.2, found 510.1. $^1$H NMR (400 MHz, DMSO-d6) δ 12.16 (s, 1H), 8.64-8.48 (m, 1H), 7.97 (dd, J=7.3, 3.2 Hz, 2H), 7.89 (d, J=7.5 Hz, 1H), 7.00 (s, 2H), 4.3-4.7 (m, 4H), 4.21 (dt, J=10.3, 7.2 Hz, 4H), 3.55 (t, J=6.4 Hz, 2H), 3.37 (t, J=7.1 Hz, 2H), 2.41 (t, J=6.4 Hz, 2H), 2.08 (t, J=7.4 Hz, 2H), 1.47 (p, J=7.2 Hz, 4H), 1.27-1.10 (m, 6H).

20b was prepared from 19b in 83% yield. MS (M+H)+ 441.4.

20c was prepared from 19c in 83% yield. MS (M–H)- 655.4.

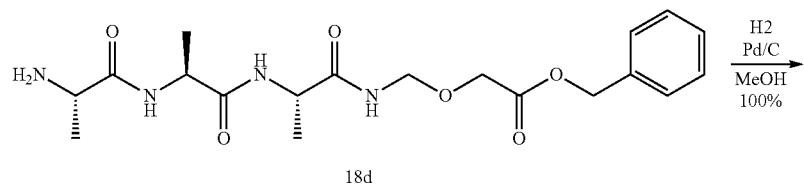

18d

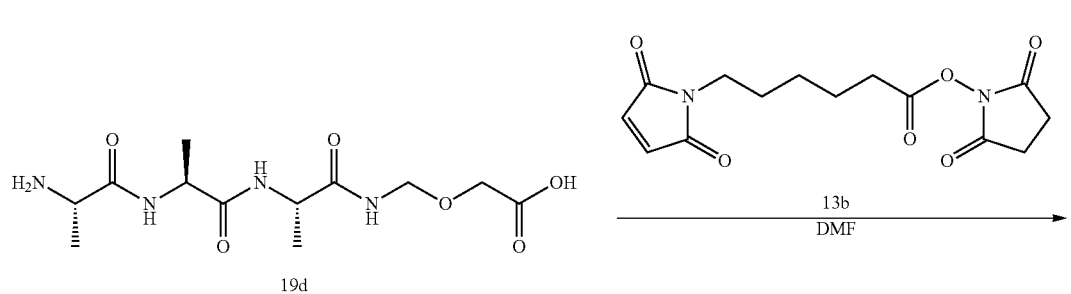

19d

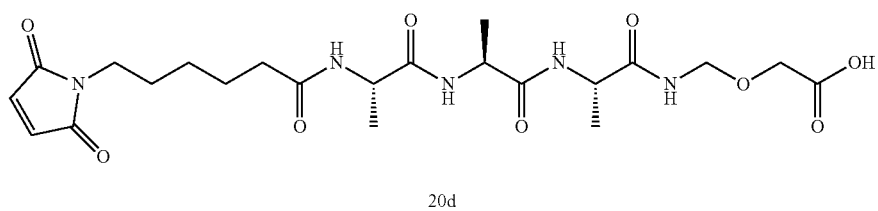

20d

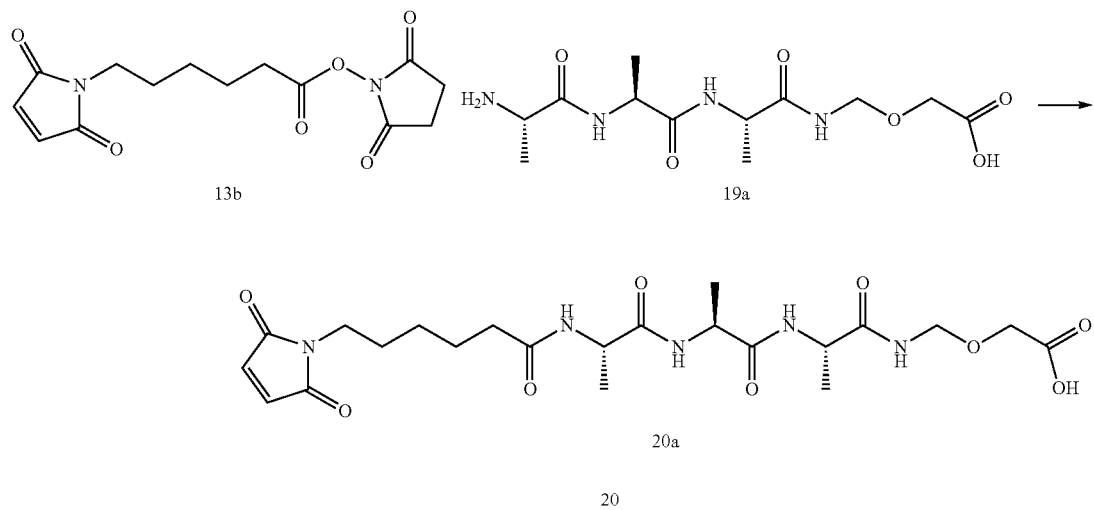

20d: To a solution of compound 18d (99.7 mg, 0.24 mmol) in methanol (3 mL) was added Pd (10% on carbon, 26 mg, 0.024 mmol) and the reaction flask was purged with hydrogen. It was hydrogenated with a hydrogen balloon at room temperature for 3 hours and then filtered. The filtrate was stripped to give compound 19d as a white solid (78 mg, yield 100%). 41.9 mg (0.13 mmol) was taken and dissolved in anhydrous DMF (0.5 mL) and 6-maleimidohexanoic acid N-hydroxysuccinimide ester 13b (40.6 mg, 0.13 mmol) was added. The obtained colorless clear solution was stirred at room temperature for 24 hours. It was stripped under reduced pressure and the residue was purified by reverse phase HPLC (C18 column and eluted with $CH_3CN/H_2O$, 10 to 50% $CH_3CN$ in 15 minutes then then 95% $CH_3CN$ for 5 minutes) to give compound 20d (30.8 mg, yield 45%). MS (ESI): m/z 512.4 $(M+H)^+$, 510.4 $(M-H)^-$.

Example 15. Synthesis of Compounds 21a and 21b

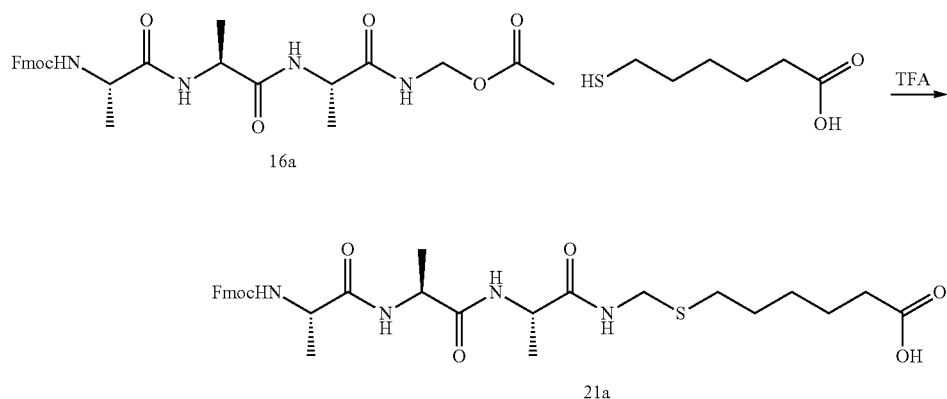

21a: Compound 16a (300 mg, 0.57 mmol) and 6-mercapto hexanoic acid (254 mg, 1.7 mmol) were suspended in a solution of 20% TFA in dichloromethane (10 mL) and magnetically stirred at room temperature for 30 min. Solvent was rotary evaporated under vacuum and the residue was taken up in a minimum volume of DMF then purified on a 200 g C18 medium pressure column that was pre-equilibrated with 95:5 deionized water containing 0.1% formic acid: acetonitrile. The column was then eluted at 60 mL/min with 10% acetonitrile for 5 min followed by a linear gradient of 5% acetonitrile from 5 min to 95% acetonitrile at 38 min. Fractions containing desired product were combined, frozen and lyophilized to give 202 mg of white solid 21a (58% yield). MS (M+Na)+613.9.

21b was prepared similarly to 21a from 16d and 6-mercaptohexanoic acid in 60% yield. MS (M+H)+ 613.7.

Example 16. Synthesis of Compound 22a

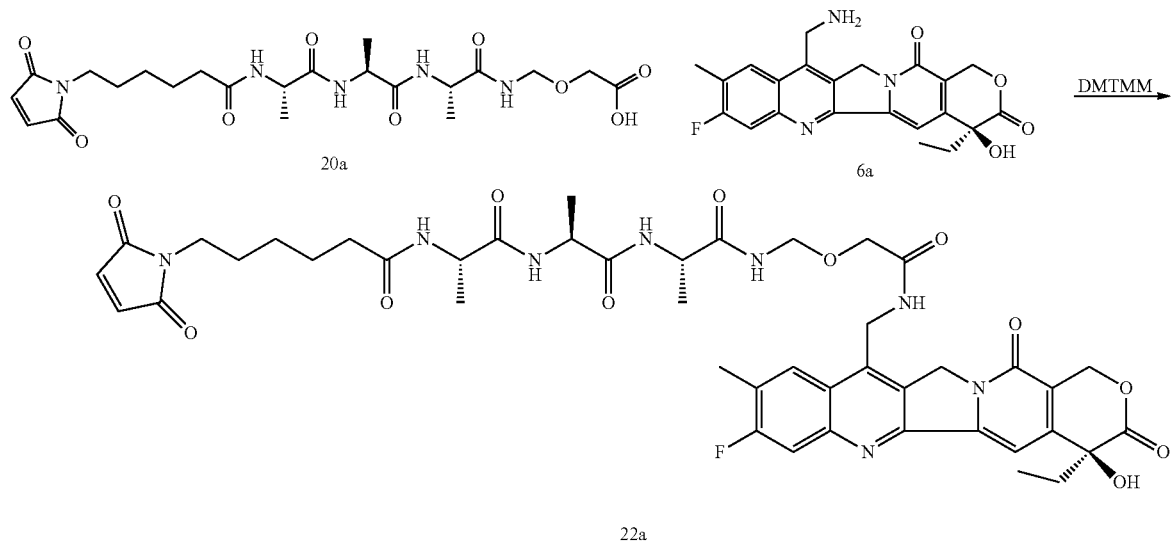

22a: Compound 6a (20 mg, 0.049 mmol) and DMTMM (18 mg, 0.065 mmol) in 85:15 DMF:deionized water (0.8 mL) were magnetically stirred as 20a (35 mg, 0.068 mmol) and TEA (0.04 mL, 0.28 mmol) were sequentially added. After 1 h the reaction mixture was loaded onto a 50 g medium pressure silica column that was equilibrated with dichloromethane and run at 30 mL/min with dichloromethane using a linear gradient of 0% to 100% of 20% methanol in dichloromethane over 40 min. Fractions containing pure product were combined and solvent was removed by rotary evaporation under vacuum to give 16 mg of a brown solid 22a (36% yield). MS (M+Na)+925.6. $^1$H NMR (400 MHz, DMSO-d6) δ 0.88 (t, J=7.3 Hz, 3H), 1.11-1.23 (m, 15H), 1.46 (p, J=7.3 Hz, 5H), 1.79-1.95 (m, 2H), 2.07 (t, J=7.4 Hz, 2H), 3.04-3.16 (m, 2H), 3.88 (s, 2H), 4.18 (dd, J=7.1, 11.0 Hz, 2H), 4.50-4.65 (m, 2H), 4.86 (d, J=5.9 Hz, 2H), 5.44 (s, 2H), 5.49 (s, 2H), 6.53 (s, 1H), 7.00 (s, 2H), 7.32 (s, 1H), 7.91 (d, J=10.0 Hz, 1H), 7.97 (d, J=7.0 Hz, 2H), 8.43 (d, J=8.3 Hz, 1H), 8.65 (t, J=6.6 Hz, 1H), 8.73 (t, J=5.9 Hz, 1H). $^{13}$C NMR (101 MHz, DMSO-d6) δ 180.20, 173.96, 172.96, 172.89, 172.56, 172.36, 171.54, 170.03, 163.99, 157.27, 156.21, 152.90, 150.48, 145.85, 139.87, 134.92, 129.28, 128.06, 124.24, 119.65, 97.28, 72.84, 70.18, 67.29, 65.74, 50.53, 48.81, 48.68, 48.60, 46.26, 41.01, 37.44, 35.26, 30.71, 28.24, 26.23, 25.09, 18.33, 18.24, 18.18, 15.77, 15.74, 9.12, 8.21. HRMS (M+H)$^+$ calcd. 903.3688, found 903.3676.

Example 17. Synthesis of Compound 22c

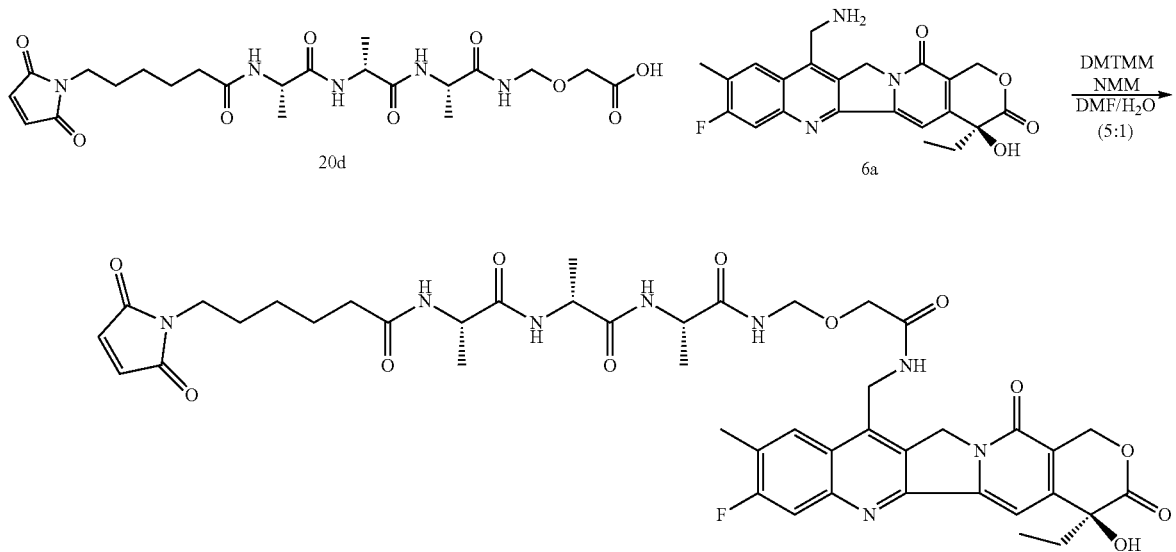

22c: To the solution of 6a (8 mg, 0.02 mmol) in DMF (0.5 mL) was added NMM (2.2 µL, 0.02 mmol) and compound 20d (10 mg, 0.02 mmol). The solution was cooled to 0° C. with an ice bath and DMTMM (10.8 mg, 0.04 mmol) in deionized water (0.1 mL) was added. The ice bath was removed and the reaction mixture was stirred at room temperature for 3 hours. The reaction solution was stripped under reduced pressure (35° C. bath) and the residue was purified by reverse phase HPLC (30 g C18 column, CH$_3$CN/H$_2$O, 25% CH$_3$CN for 3 minutes then to 95% CH$_3$CN in 12 minutes then at 95% CH$_3$CN for 5 minutes). The product fractions were combined and lyophilized to give a white solid. It was further purified by silica gel chromatography (4 g silica column, CH$_2$Cl$_2$/MeOH, 0 to 20% MeOH in 15 minutes) to give the desired product 22c (9.8 mg, yield 55%). MS (ESI): m/z 903.9 (M+H)$^+$, 901.9 (M−H)$^−$, 947.9 (M+HCOOH−H)$^−$.

Example 18. Synthesis of Compound 22b

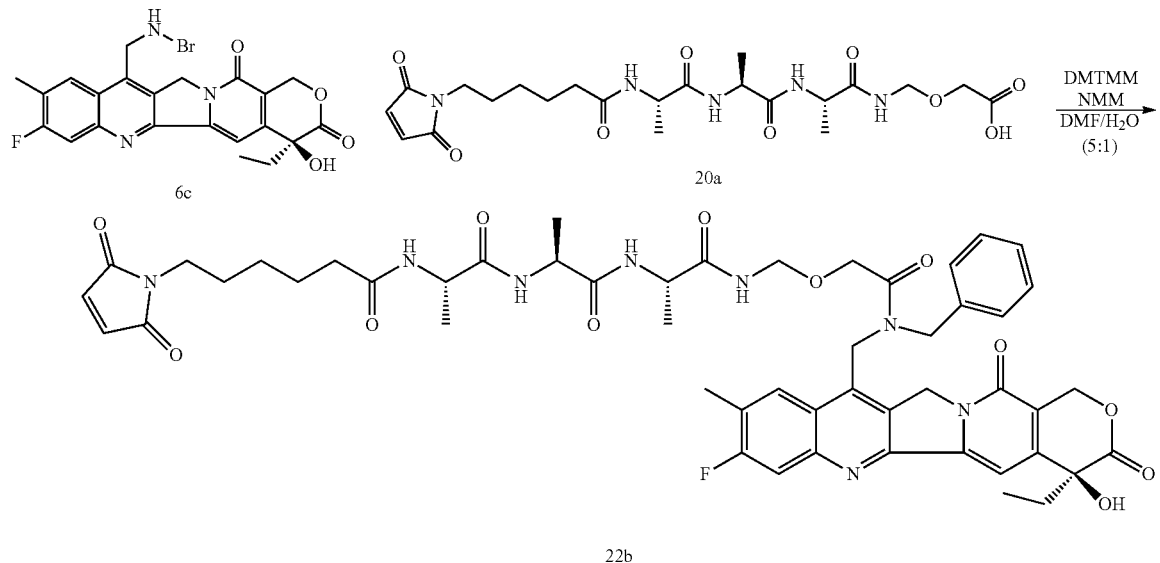

22b: To the solution of 6c (10.7 mg, 0.022 mmol) in DMF (0.5 mL) was added NMM (2.4 µL, 0.022 mmol) and compound 20a (11 mg, 0.022 mmol). The solution was cooled to 0° C. with an ice bath and DMTMM (11.9 mg, 0.043 mmol) in deionized water (0.1 mL) was added. The ice bath was removed and the reaction mixture was stirred at room temperature for 3 hours. The reaction solution was stripped under reduced pressure (35° C. bath) and the residue was purified by reverse phase HPLC (30 g C18 column, CH$_3$CN/H$_2$O, 25% CH$_3$CN for 3 minutes then to 95% CH$_3$CN in 12 minutes then at 95% CH$_3$CN for 5 minutes) to give the desired product 22b (4 mg, yield 18%). MS (ESI): m/z 1015.9 (M+Na), 991.9 (M−H)$^−$, 1037.9 (M+HCOOH−H)$^−$.

Example 19. Synthesis of Compound 22d

22d: Prepared similarly to 22c by the reaction of 6c with 20d (22% yield). MS (ESI): m/z 1015.8 (M+Na)$^+$ Example 20. Synthesis of Compound 22e

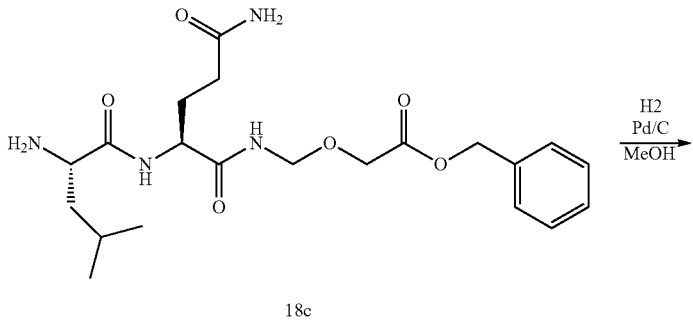

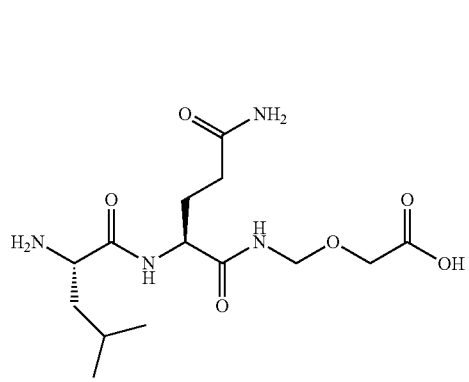

19c

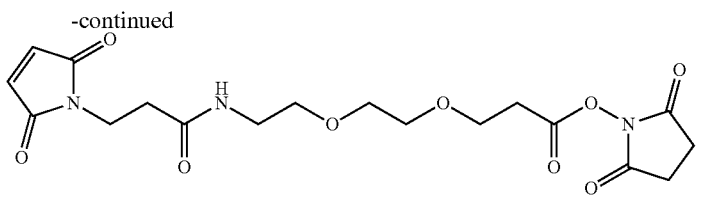

13d
6a, DMTMM in
DMF/H₂O

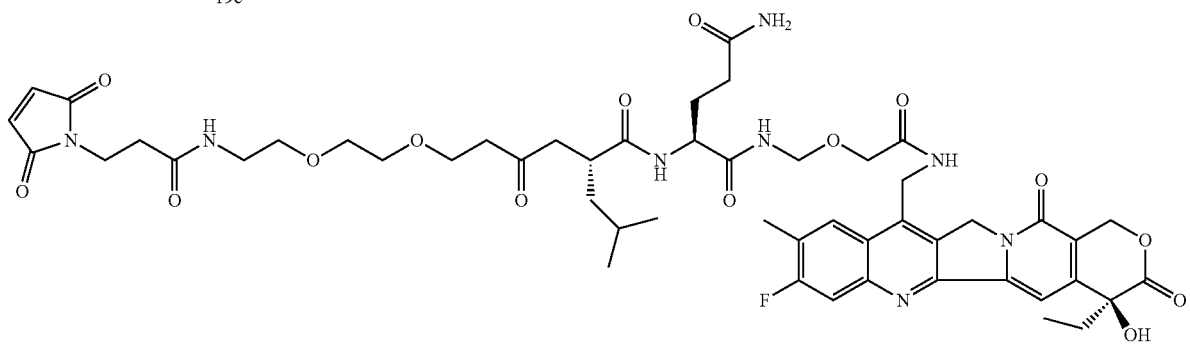

22e

22e: The solution of compound 18c (15.2 mg, 0.035 mmol) in methanol (2 mL) was added Pd (10% on carbon, 3.7 mg, 0.0035 mmol) and the reaction flask was purged with hydrogen. It was hydrogenated with a hydrogen balloon at room temperature for 3 hours and then filtered. The filtrate was stripped to give compound 19c as a colorless foam. It was dissolved in anhydrous DMF (0.3 mL) and 13d (15.9 mg, 0.03 mmol) was added. The obtained colorless clear solution was stirred at room temperature for 15 hours. It was diluted with DMF (0.2 mL) followed by addition of 6a (15.3 mg, 0.037 mmol) and NMM (4.1 μL, 0.037 mmol). DMTMM (20.7 mg, 0.075 mmol) in deionized water (0.1 mL) was then added and the reaction solution was stirred at room temperature for 1.5 hours. The reaction mixture was stripped under reduced pressure and the residue was purified by silica gel chromatography (CH₂Cl₂/MeOH, 0 to 20% MeOH) to give desired 22e (10 mg, yield 26%). MS (ESI): m/z 1049.1 (M+H)⁺, 1093.2 (M+HCOOH−H)⁻.

Example 21. Synthesis of Compound 23a

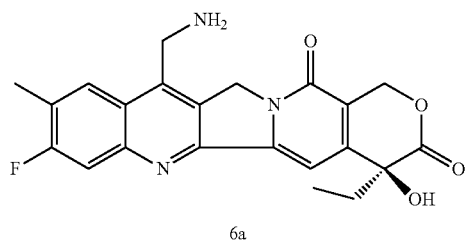

6a

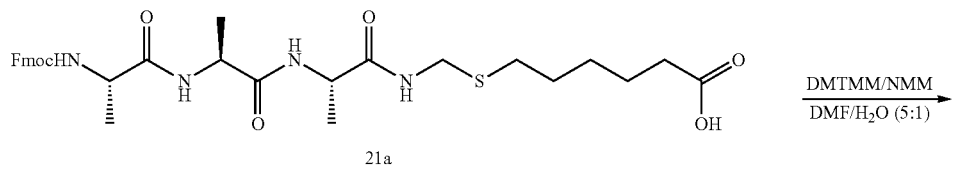

21a

-continued

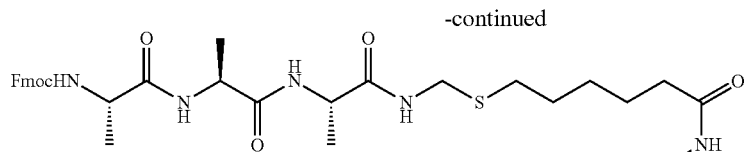

23a

23a: To the solution of 6a (32 mg, 0.078 mmol) in DMF (0.8 mL) was added NMM (8.6 μL, 0.078 mmol) and the Fmoc protected L-Ala-L-Ala-L-Ala tripeptide linker 21a (53 mg, 0.078 mmol) followed by the addition of DMTMM (43 mg, 0.156 mmol) in deionized water (0.16 mL). The reaction mixture was stirred at room temperature for 2 hours. The reaction solution was stripped under reduced pressure and the residue was purified by silica gel chromatography (4 g column, $CH_2Cl_2$/MeOH, 0 to 20% MeOH in 15 minutes) to give the desired compound 23a (78 mg, yield 99%). MS (ESI): m/z 1004.5 $(M+H)^+$, 1026.6 (M+Na), 1048.4 $(M+HCOOH-H)^-$.

Example 22. Synthesis of Compound 24a

24a: To the solution of compound 23a (78 mg, 0.078 mmol) in anhydrous DMF (1 mL) was added morpholine (0.24 mL, 2.7 mmol) and the reaction mixture was stirred at room temperature for 2 hours. The reaction solution was stripped under reduced pressure and the residue was purified by silica gel chromatography (4 g silica column, eluted with $CH_2Cl_2$/MeOH, 0 to 20% MeOH in 9 minutes then 20% MeOH for 11 minutes) to give the desired compound 24a (39.6 mg, yield 65%). MS (ESI): m/z 782.4 $(M+H)^+$, 780.0 $(M-H)^-$.

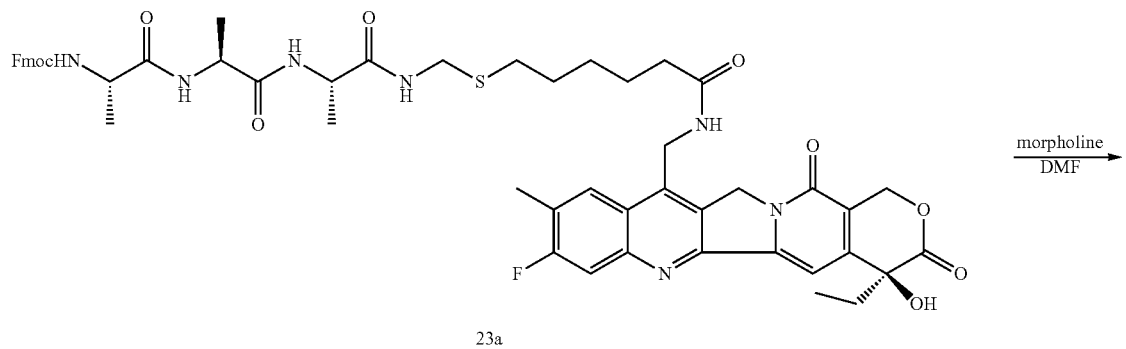

23a

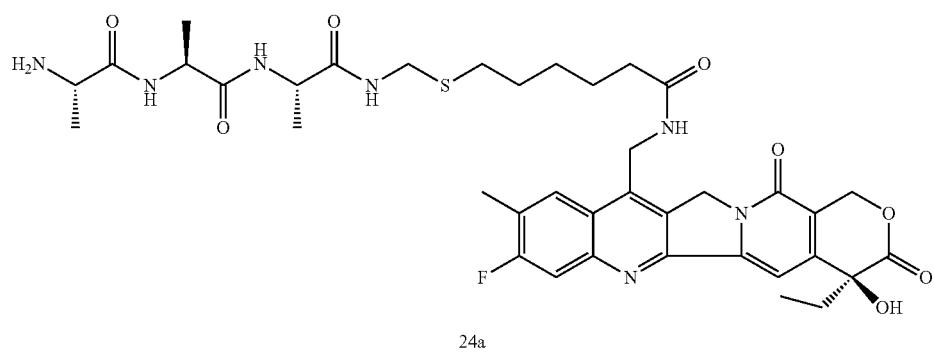

24a

Example 23. Synthesis of Compound 25a

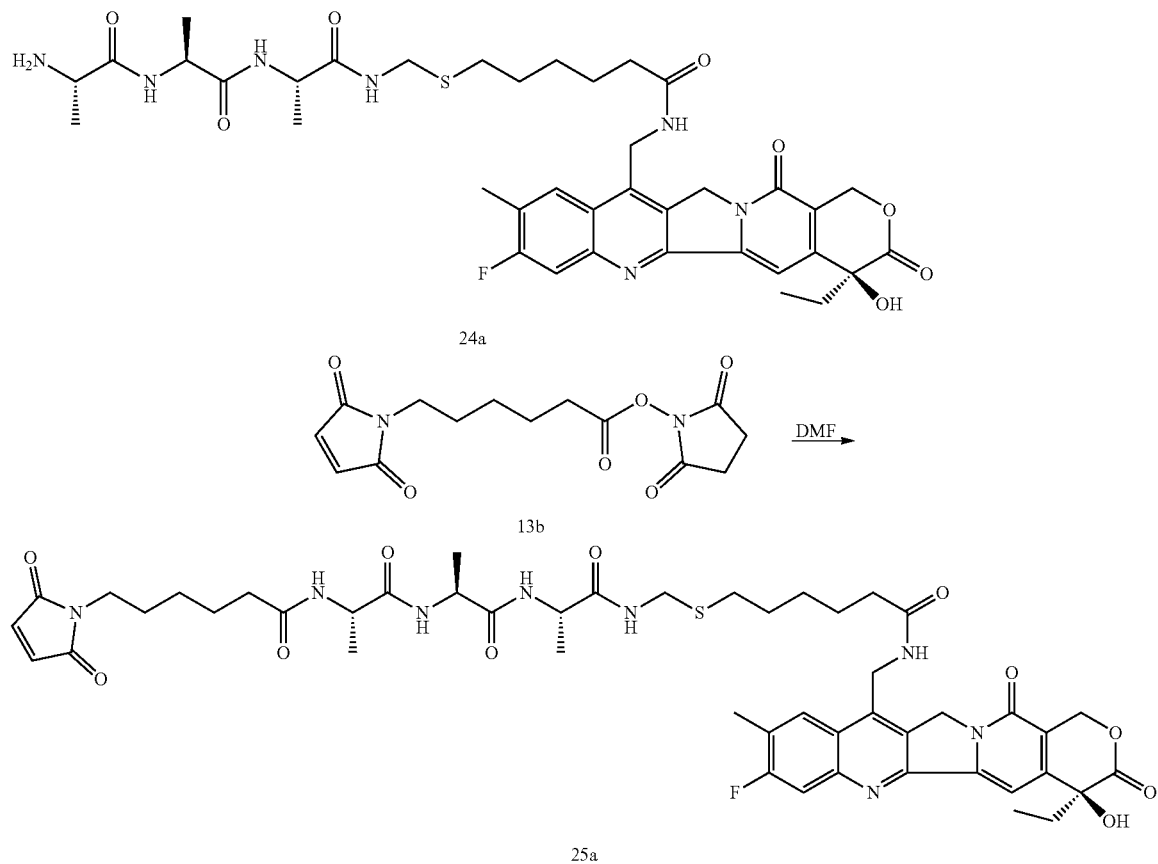

25a: To the solution of the compound 24a (20 mg, 0.026 mmol) in anhydrous DMF (0.3 mL) was added 13b (9.6 mg, 0.031 mmol) and the reaction mixture was stirred at room temperature for 4 hours. The reaction solution was diluted with DMSO and purified by reverse phase semi-prep HPLC (C18 column, eluted with $CH_3CN/H_2O$, 25% to 55% $CH_3CN$ in 23 minutes then 95% $CH_3CN$ for 7 minutes). The fractions containing 25a were combined and lyophilized to give 25a as a white solid. It was further purified by silica gel chromatography (4 g silica column, $CH_2Cl_2$/MeOH, 0 to 20% MeOH in 15 minutes) to give the desired 25a (7.7 mg, yield 30%). MS (ESI): m/z 975.8 (M+H)$^+$, 997.8 (M+Na), 773.7 (M-H)$^-$, 1019.7 (M+HCOOH-H)$^-$.

Example 24. Synthesis of Compound 23b

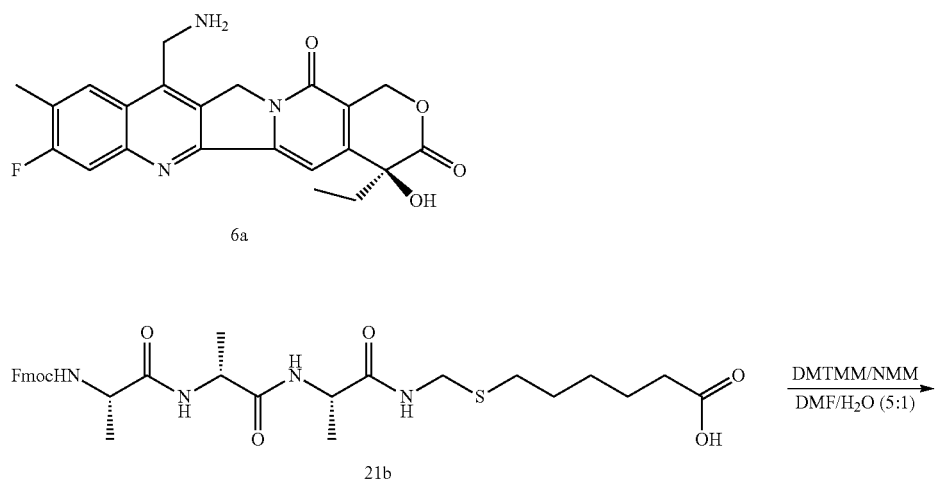

-continued

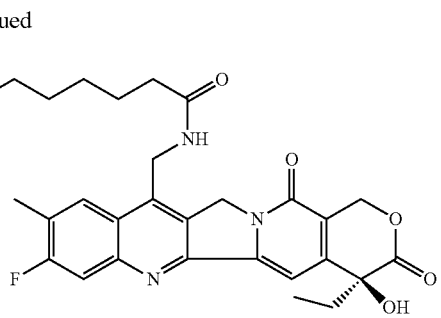

23b

23b: To a solution of 6a (31 mg, 0.076 mmol) in DMF (0.8 mL) was added NMM (8.3 μL, 0.076 mml) and 21b (46.4 mg, 0.076 mmol). The solution was cooled to 0° C. with an ice bath and DMTMM (48 mg, 0.16 mmol)) in deionized water (0.16 mL) was added. The ice bath was removed and the reaction mixture was stirred at room temperature for 2.5 hours.

The reaction solution was stripped under reduced pressure and the residue was purified by silica gel chromatography (4 g silica column, $CH_2Cl_2$/MeOH, 0 to 20% MeOH in 15 minutes) to give the desired product compound 23b (31 mg, yield 40%). MS (ESI): m/z 1004.6 $(M+H)^+$, 1048.7 $(M+HCOOH-H)^-$.

Example 25. Synthesis of Compound 24b

24b: To a solution of 23b (31 mg, 0.031 mmol) in anhydrous DMF (0.4 mL) was added morpholine (95 μL, 1.08 mmol) and the reaction mixture was stirred at room temperature for 2.5 hours. The reaction solution was stripped under reduced pressure and the residue was purified by silica gel chromatography (4 g silica column, eluted with $CH_2Cl_2$/MeOH, 0 to 20% MeOH in 15 minutes then 20% MeOH for 5 minutes) to give product compound 24b (18 mg, yield 75%). MS (ESI): m/z 782.5 $(M+H)^+$, 780.2 $(M-H)^-$, 826.4 $(M+HCOOH-H)^-$.

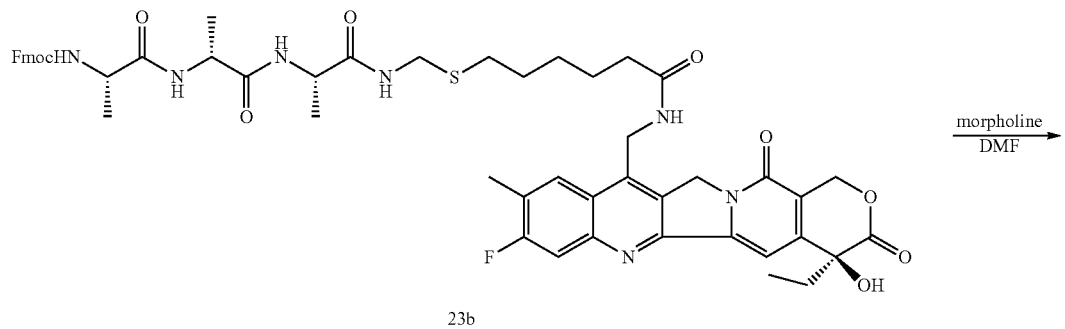

23b

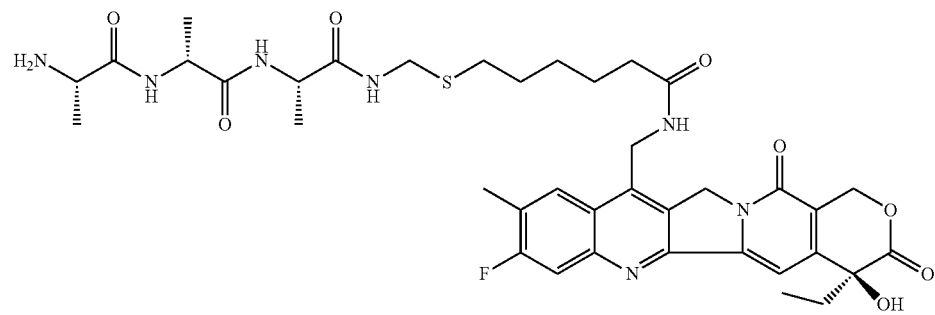

24b

Example 26. Synthesis of Compound 25b

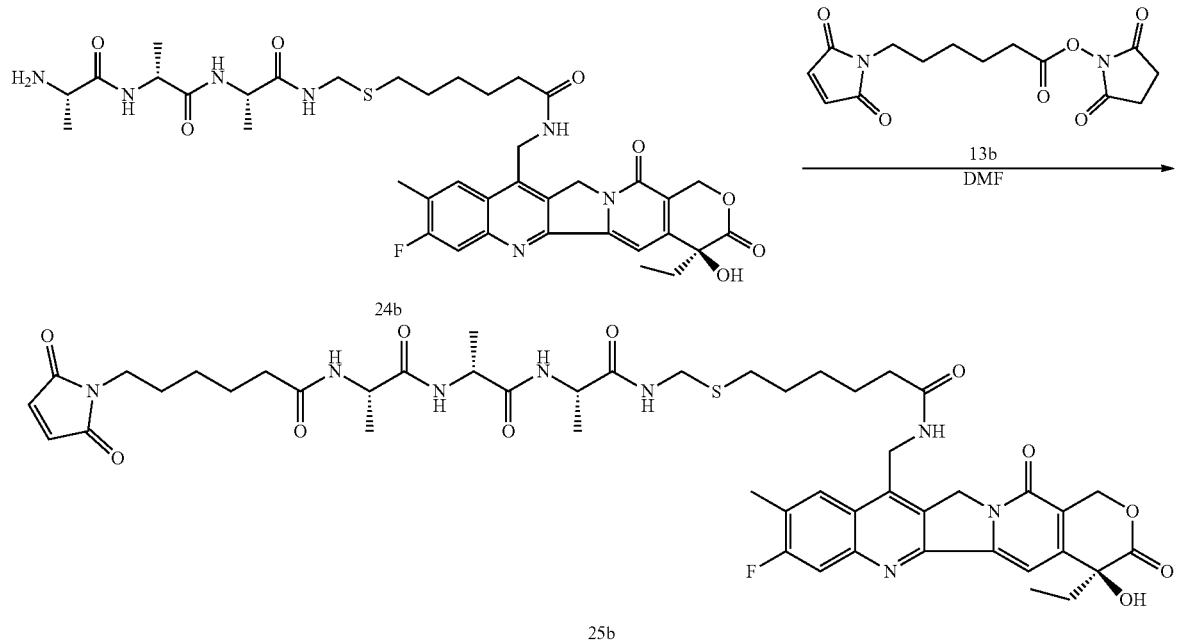

25b: To a solution of 24b (12.3 mg, 0.016 mmol) in anhydrous DMF (0.3 mL) was added 5-maleimidohexanoic acid N-hydroxysuccinimide ester 13b (7.3 mg, 0.024 mmol) and the reaction mixture was stirred at room temperature for 4 hours. The reaction solution was stripped under reduced pressure and the residue was purified by silica gel chromatography (4 g column, $CH_2Cl_2$/MeOH, 0 to 20% MeOH in 15 minutes) to give 3.2 mg 25b and another 6.5 mg impure product. The impure product was further purified by semi-prep reverse phase HPLC (C18 column, eluted with $CH_3CN/H_2O$, 25% to 55% $CH_3CN$ in 23 minutes then 95% $CH_3CN$ for 7 minutes to give 2.8 mg 25b. In total 6 mg of 25b was isolated (39% yield). MS (ESI): m/z 975.6 (M+H)$^+$, 997.6 (M+Na), 973.7 (M−H)$^−$, 1019.6 (M+HCOOH−H)$^−$.

Example 27. Synthesis of Compound 26a

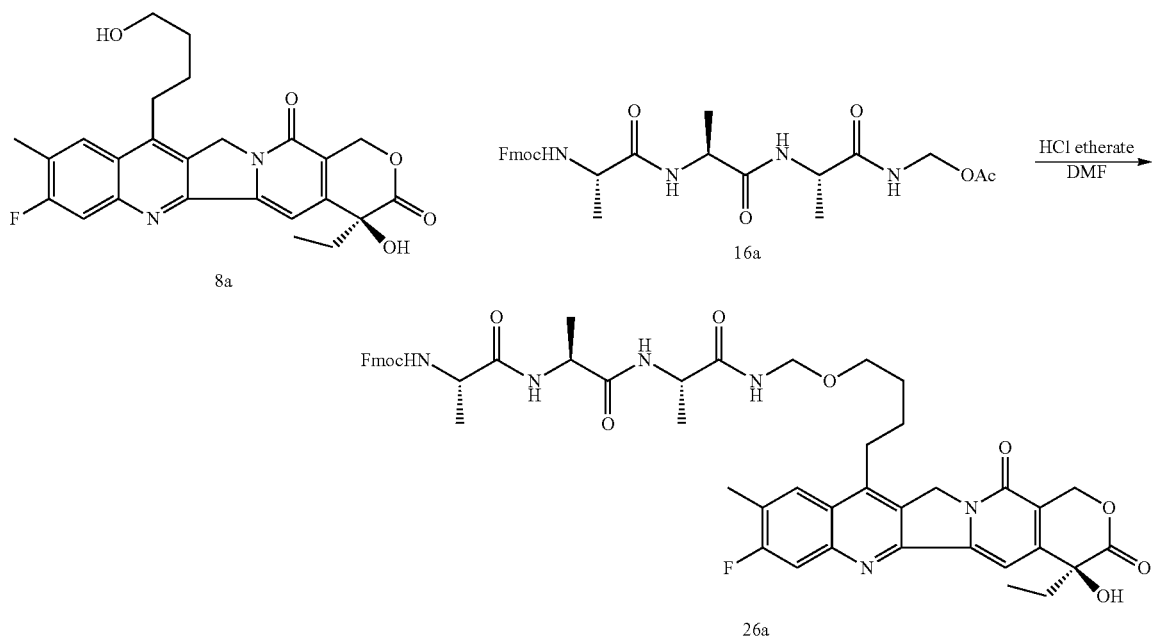

26a: To a stirring solution of 8a (58 mg, 0.106 mmol) and compound 16a (55.8 mg, 0.106 mmol) in anhydrous DMF (1.5 mL) was added HCl etherate (2 M HCl diethyl ether solution, 64 μL, 0.128 mmol). After stirred 22 hours at room temperature, the reaction solution was stripped under reduced pressure (35° C. heating bath). The residue was purified by reverse phase HPLC (30 g C18 column, CH$_3$CN/H$_2$O, 25% CH$_3$CN for 3 minutes then to 90% CH$_3$CN in 12 minutes then 90% CH$_3$CN for 3 minutes) to give compound 26a as a white solid (47 mg, yield 48%). MS (ESI): m/z cald. 917.4, found 917.6 (M+H)$^+$, 961.5 (M+HCOOH−H)$^−$. Unreacted 8a was also recovered (12 mg).

Example 28. Synthesis of Compound 27a

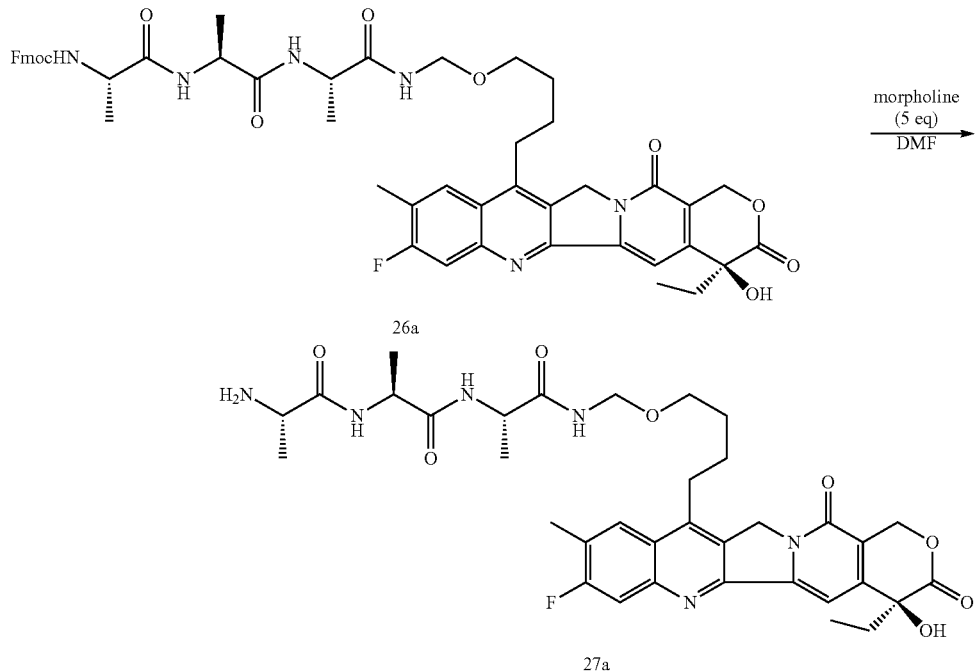

27a: To a stirring solution of compound 26a (57 mg, 0.062 mmol) in anhydrous DMF (0.8 mL) was added morpholine (27 μL, 0.31 mmol). After stirred at room temperature for 6 hours, the reaction solution was stripped under reduced pressure. The residue was purified by reverse phase HPLC (30 g C18 column and eluted with CH$_3$CN/H$_2$O, 20% CH$_3$CN for 3 minutes then to 90% CH$_3$CN in 15 minutes then 90% CH$_3$CN for 3 minutes) to give compound 27a as an off-white solid (35.9 mg, yield 83%). MS (ESI): m/z 695.5 (M+H)$^+$, 739.3 (M+HCOOH−H)$^−$.

Example 29. Synthesis of Compound 28a

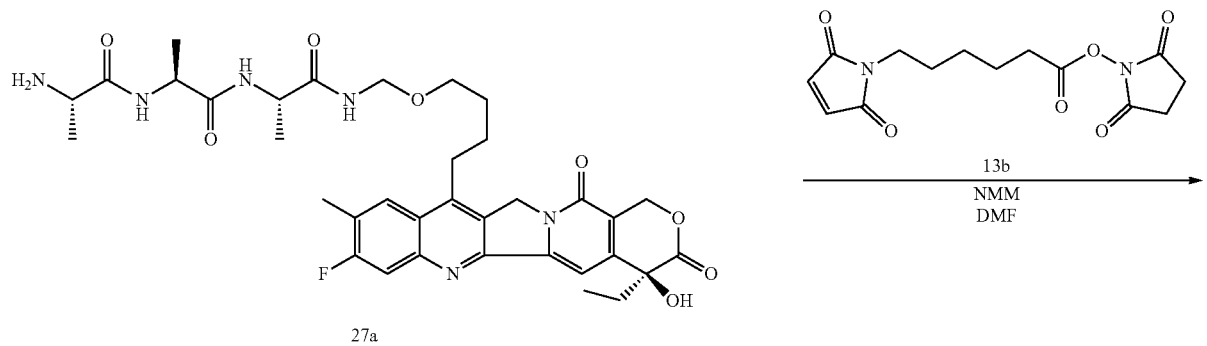

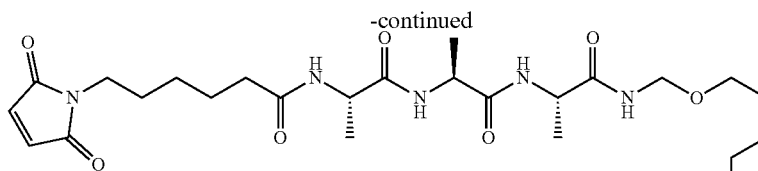
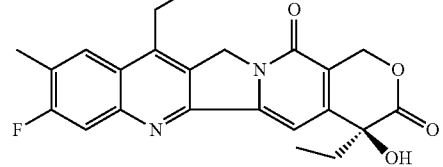

28a

28a: To a solution of compound 27a (18 mg, 0.026 mmol) in anhydrous DMF (0.3 mL) was added 5-maleimidohexanoic acid N-hydroxysuccinimide ester 13b (12 mg, 0.039 mmol) and NMM (3.1 μL, 0.028 mmol). After stirred at room temperature for 4 hours the reaction solution was stripped under reduced pressure. The residue was purified by reverse phase HPLC (30 g C18 column, eluted with $CH_3CN$/$H_2O$, 18 minutes run, 20% $CH_3CN$ for 3 minutes, then 20% to 90% $CH_3CN$ in 12 minutes then 90% $CH_3CN$ for 3 minutes) to give product 28a as a white solid (11.9 mg, yield 51%). MS (ESI): m/z 888.5 $(M+H)^+$, 932.5 $(M+HCOOH-H)^-$. $^1$HNMR (400 MHz, DMSO-$d_6$) δ 8.45 (t, J=6.7 Hz, 1H), 8.11 (d, J=8.2 Hz, 1H), 7.90 (t, J=7.5 Hz, 2H), 7.78 (dd, J=15.2, 9.1 Hz, 2H), 7.22 (s, 1H), 6.92 (s, 2H), 6.45 (s, 1H), 5.36 (s, 2H), 5.17 (s, 2H), 4.54-4.38 (m, 2H), 4.15-4.09 (m, 2H), 3.38-3.33 (m, 1H), 3.32-3.21 (m, 1H), 3.15-3.06 (m, 1H), 2.50-2.42 (m, 3H), 1.99 (t, J=7.4 Hz, 2H), 1.79 (h, J=7.0 Hz, 2H), 1.67-1.55 (m, 6H), 1.38 (p, J=7.4 Hz, 5H), 1.15-1.04 (m, 12H), 0.81 (t, J=7.4 Hz, 3H). $^{13}$C NMR (101 MHz, DMSO-$d_6$) δ 174.54, 173.86, 171.34, 171.26, 170.84, 170.79, 170.47, 170.15, 161.42, 158.95, 155.71, 155.16, 150.43, 148.38, 146.97, 146.80, 144.22, 142.23, 129.03, 126.25, 125.69, 125.48, 124.98, 124.50, 122.77, 122.48, 117.29, 111.01, 110.78, 95.09, 70.75, 70.67, 67.55, 65.17, 63.64, 48.03, 46.55, 33.20, 28.68, 27.46, 26.96, 25.04, 24.55, 24.05, 23.06, 22.84, 16.39, 16.14, 13.54, 6.13, 5.98; HRMS $(M+H)^+$ calcd. 888.3943, found 888.3966.

Example 30. Synthesis of Compound 26b

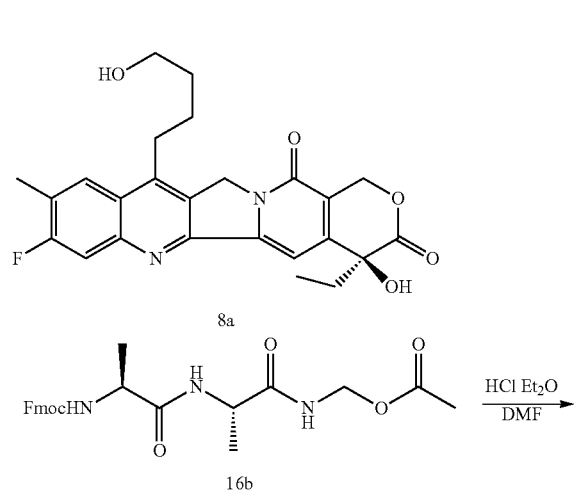

26b: To a stirring solution of 8a (73 mg, 0.14 mmol) and compound 16b (64 mg, 0.14 mmol) in anhydrous DMF (1.2 mL) was added HCl etherate (2 M HCl diethyl ether solution, 0.14 mL, 0.28 mmol). After stirring 6 h at room temperature, the reaction solution was stripped under reduced pressure (35° C. heating bath). The residue was purified by reverse phase HPLC (30 g C18 column, $CH_3CN$/$H_2O$, 25% $CH_3CN$ for 3 minutes then to 90% $CH_3CN$ in 12 min then 90% $CH_3CN$ for 3 min) to give compound 26b as an off-white solid (60 mg, yield 50%). MS (ESI): m/z 846.4 $(M+H)^+$, 890.3 $(M+HCOOH-H)^-$.

Example 31. Synthesis of Compound 26c

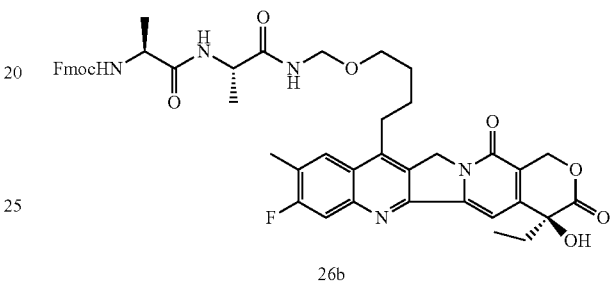
16c

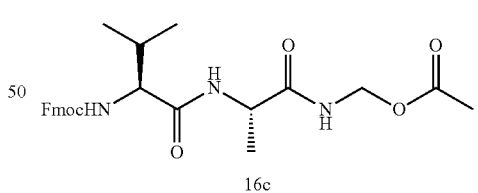
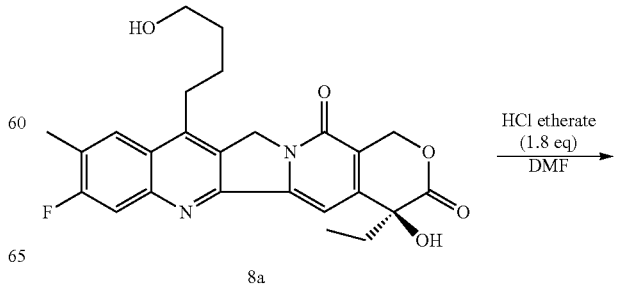

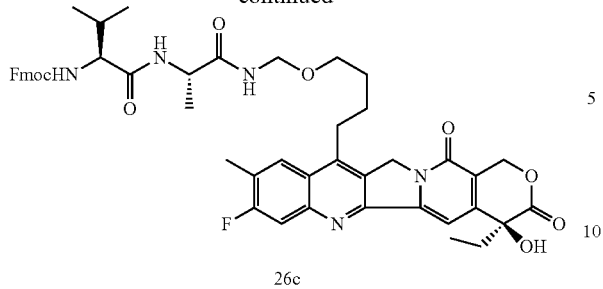

26c

26c: To a stirring solution of 8a (36 mg, 0.08 mmol) and 16c (40.2 mg, 0.084 mmol) in anhydrous DMF (0.6 mL) was added HCl etherate (2 M HCl diethyl ether solution, 72 μL, 0.43 mmol). After stirred 15 h at room temperature, the reaction solution was stripped under reduced pressure (35° C. heating bath). The residue was purified by reverse phase HPLC (30 g C18 column, CH$_3$CN/H$_2$O, 25% CH$_3$CN for 3 minutes then to 95% CH$_3$CN in 12 min then 95% CH$_3$CN for 3 min) to give compound 26c as a white solid (41.9 mg, yield 60%). MS (ESI): m/z 874.4 (M+H)$^+$, 918.5 (M+HCOOH−H)$^−$. Unreacted 8a was also recovered (12 mg).

Example 32. Synthesis of Compound 27b

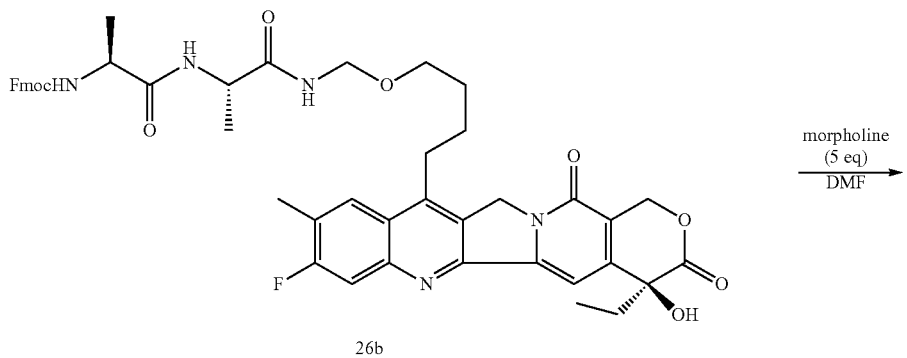

26b

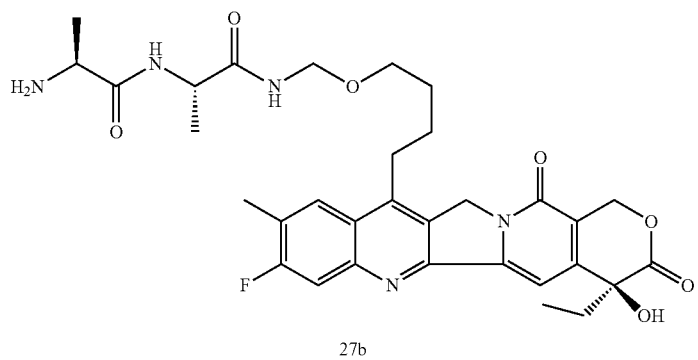

27b

27b: To a stirring solution of compound 26b (60 mg, 0.071 mmol) in anhydrous DMF (0.4 mL) was added morpholine (310.36 mmol). After stirred at room temperature for 3.5 hours, the reaction solution was stripped under reduced pressure. The residue was purified by reverse phase HPLC (15.5 g C18 column and eluted with CH$_3$CN/H$_2$O, 10% CH$_3$CN for 3 minutes then to 90% CH$_3$CN in 9 minutes then 90% CH$_3$CN for 3 minutes) to give compound 27b as an off-white solid (36.7 mg, yield 83%). MS (ESI): m/z 624.5 (M+H)$^+$, 668.3 (M+HCOOH−H)$^−$.

Example 33. Synthesis of Compound 27c

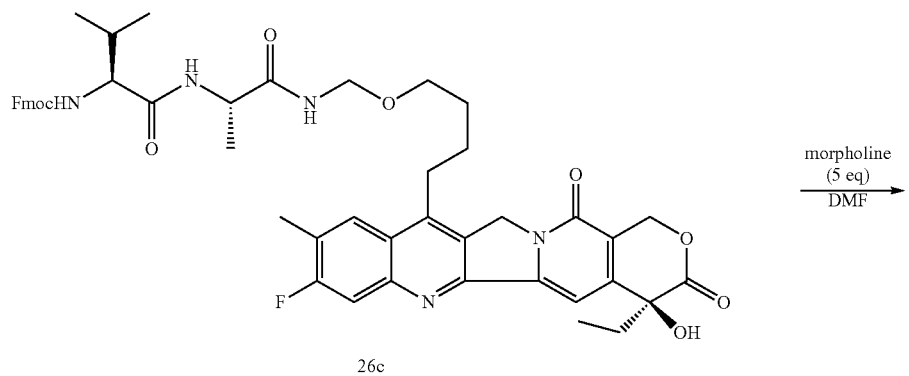

26c

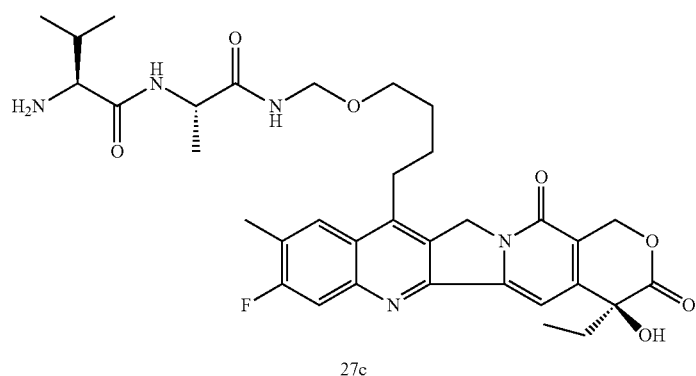

27c

27c: To a stirring solution of compound 26c (41.9 mg, 0.048 mmol) in anhydrous DMF (0.4 mL) was added morpholine (210.24 mmol). After stirring at room temperature for 5 h, the reaction solution was stripped under reduced pressure. The residue was purified by reverse phase HPLC (30 g C18 column and eluted with $CH_3CN/H_2O$, 20% $CH_3CN$ for 3 min then to 90% $CH_3CN$ in 12 min then 90% $CH_3CN$ for 5 min) to give compound 27c as a white solid (25.5 mg, yield 82%). MS (ESI): m/z 652.5 $(M+H)^+$, 650.2 $(M-H)^-$. 696.2 $(M+HCOOH-H)^-$.

Example 34. Synthesis of Compound 28b

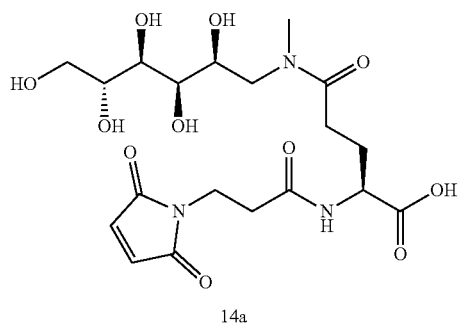

14a

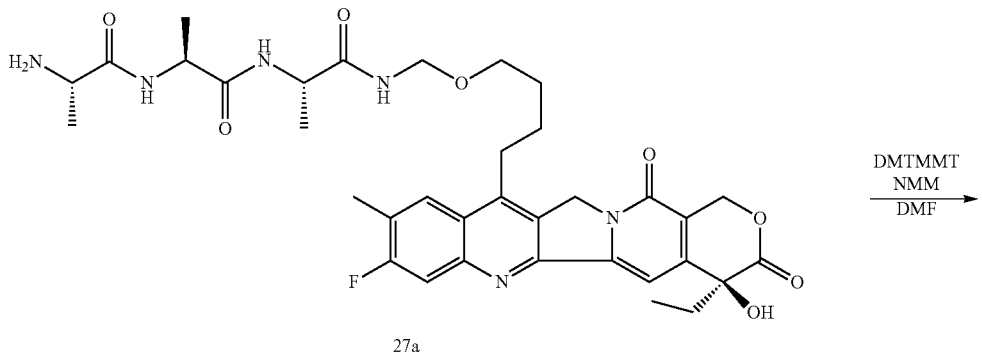

27a

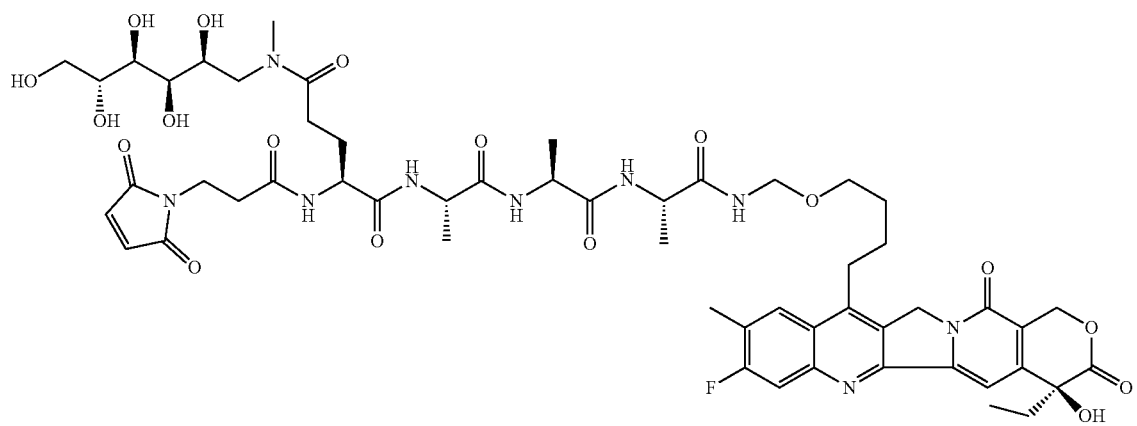

28b

28b: To a stirring solution of the compound 27a (18 mg, 0.026 mmol) and 14a (18.5 mg, 0.039 mmol) in anhydrous DMF (0.2 mL) was added DMTMM (17 mg, 0.052 mmol) and NMM (2.9 μL, 0.026 mmol) at room temperature. After stirred at room temperature for 19 h, the reaction solution was stripped under reduced pressure (bath temperature 35° C.) and the residue was purified by reverse phase HPLC (30 g C18 column, CH$_3$CN/H$_2$O, 20% CH$_3$CN for 3 minutes then to 90% CH$_3$CN in 12 min then 90% CH$_3$CN for 3 min). The fractions that contained product were combined and lyophilized to give 28b as a white solid (2.3 mg, 7% yield). MS (ESI): m/z 1152.5 (M+H)$^+$, 1150.0 (M−H)$^−$, 1196.5 (M+HCOOH−H)$^−$.

Example 35. Synthesis of Compound 28c

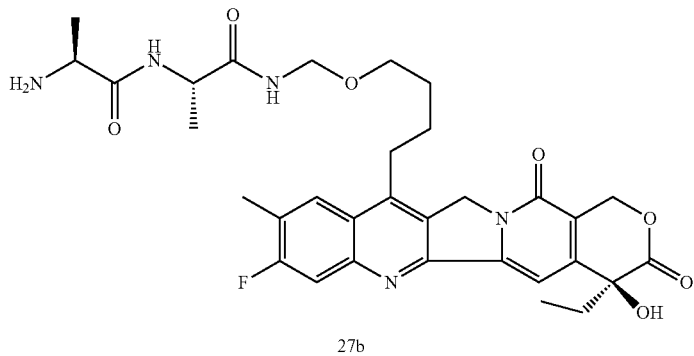

27b

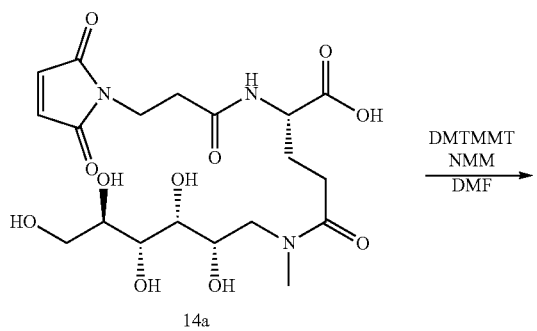

14a

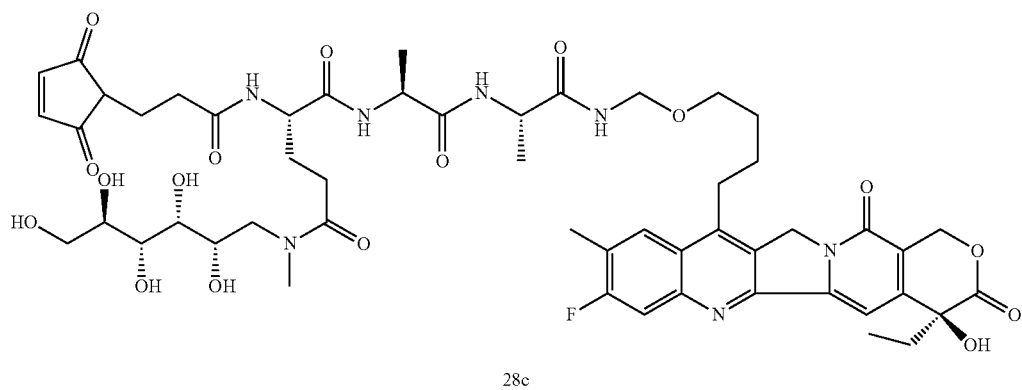

28c

28c: To a stirring solution of 27b (36.7 mg, 0.059 mmol) and 14a (42 mg, 0.088 mmol) in anhydrous DMF (0.6 mL) was added DMTMM (39 mg, 0.12 mmol) and NMM (3.2 μL, 0.029 mmol) at room temperature. After stirring at room temperature for 5 h, the reaction solution was directly loaded on a C18 cartridge and purified by reverse phase HPLC (30 g C18 column, $CH_3CN/H_2O$, 20% $CH_3CN$ for 3 minutes then to 90% $CH_3CN$ in 12 min then 90% $CH_3CN$ for 3 min). The fractions that contained product were combined and lyophilized to give 28c as a white solid (9.9 mg, yield 15%). MS (ESI): m/z 1081.5 $(M+H)^+$, 1079.2 $(M-H)^-$, 1025.5 $(M+HCOOH-H)^-$.

Example 36. Synthesis of Compound 28d

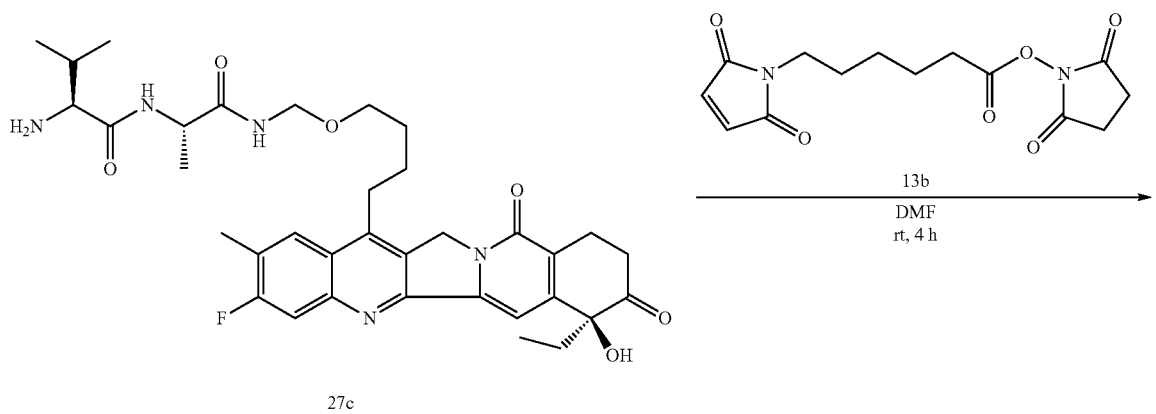

27c

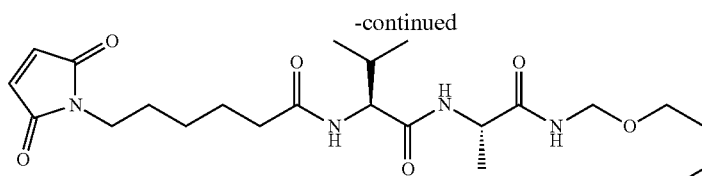

28d

28d: To the solution of 27c (10.5 mg, 0.016 mmol) in anhydrous DMF (0.2 mL) was added 5-maleimidohexanoic acid N-hydroxysuccinimide ester 13b (6 mg, 0.019 mmol) and NMM (2.1 μL, 0.019 mmol). After stirring at room temperature for 4 h the reaction solution was stripped under reduced pressure. The residue was purified by reverse phase HPLC (30 g C18 column, eluted with CH₃CN/H₂O, 18 minutes run, 20% CH₃CN for 3 minutes, then 20% to 90% CH₃CN in 12 minutes then 90% CH₃CN for 3 minutes) to give product 28d as a white solid (8.7 mg, yield 63%). MS (ESI): m/z 845.4 (M+H)⁺, 989.4 (M+HCOOH−H)⁻.

Example 37. Synthesis of Compound 29a

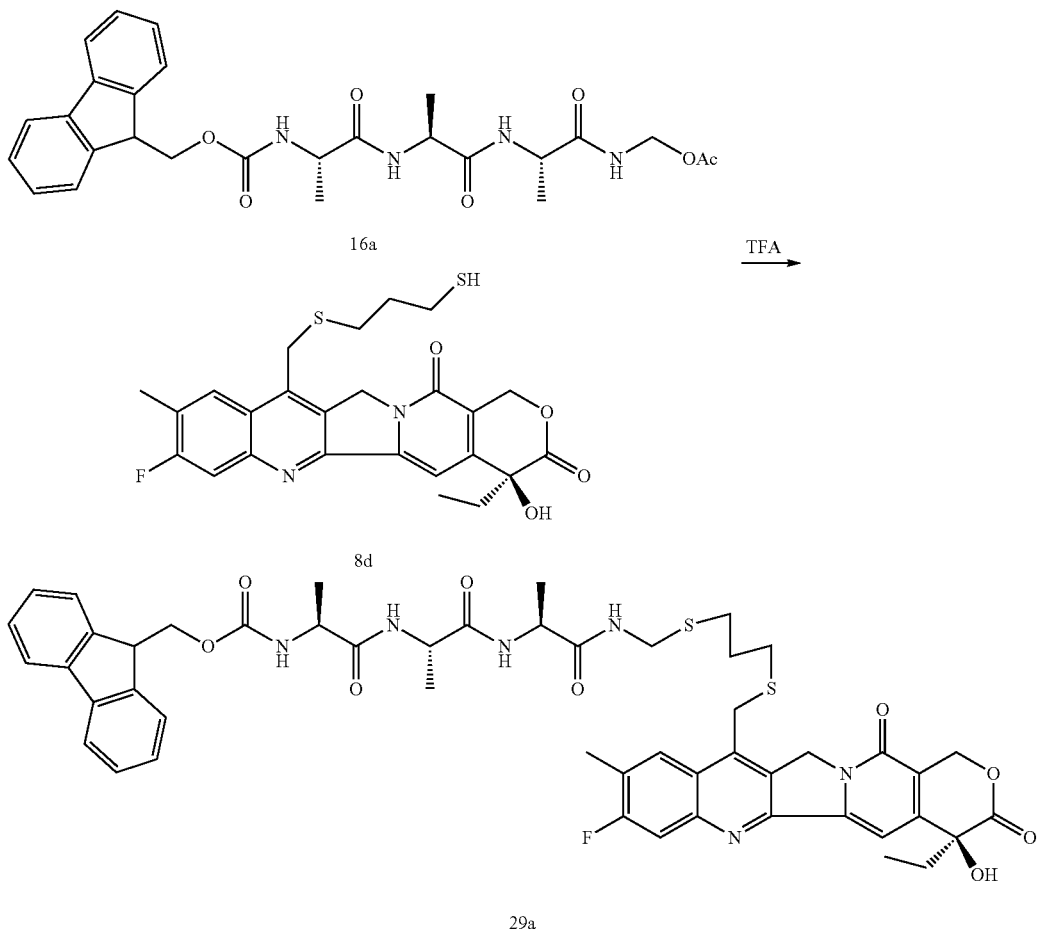

29a: Compound 16a (30 mg, 0.057 mmol) and 8d (50 mg, 0.1 mmol) were suspended in a solution of 20% TFA in dichloromethane (10 mL) and magnetically stirred at room temperature for 30 min. Solvent was rotary evaporated under vacuum and the residue was taken up in a minimum volume of DMF then purified on a 100 g C18 medium pressure column that was pre-equilibrated with 90:10 deionized water containing 0.1% formic acid: acetonitrile. The column was then eluted at 30 mL/min with 10% acetonitrile for 5 min followed by a linear gradient of 10% acetonitrile from 5 min to 95% acetonitrile at 38 min. Fractions containing desired product were combined, frozen and lyophilized to give 31 mg of white solid 29a (56% yield). MS (M+Na)+987.5.

Example 38. Synthesis of Compound 30a

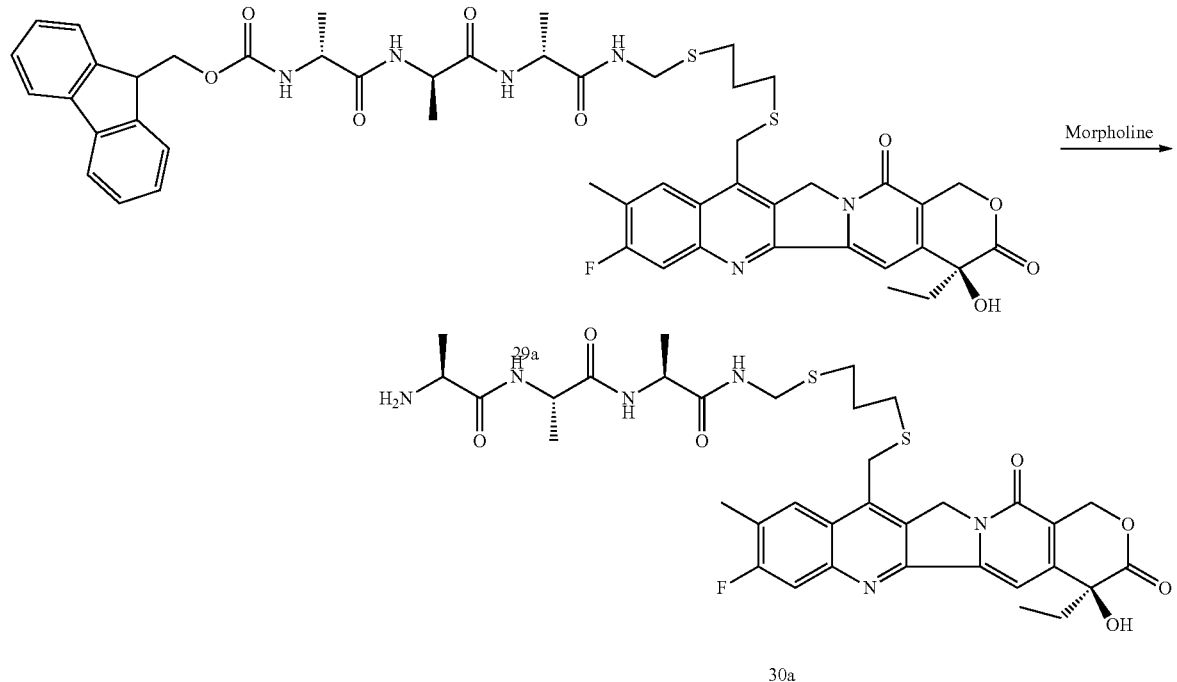

30a: Compound 29a (28 mg, 0.029 mmol) was dissolved in anhydrous DMF (0.8 mL) and magnetically stirred as morpholine (0.2 mL) was added. After 1 h the reaction mixture was directly loaded on a 100 g C18 cartridge 25:75 $CH_3CN/H_2O$, run at 50 mL/min 25% $CH_3CN$ for 3 minutes then with a linear gradient to 90% $CH_3CN$ from 3-23 min. Fractions containing desired product were combined, frozen and lyophilized to give 18 mg (83% yield) of 30a as a yellow solid. MS (M+H)+ 743.5.

Example 39. Synthesis of Compound 32a

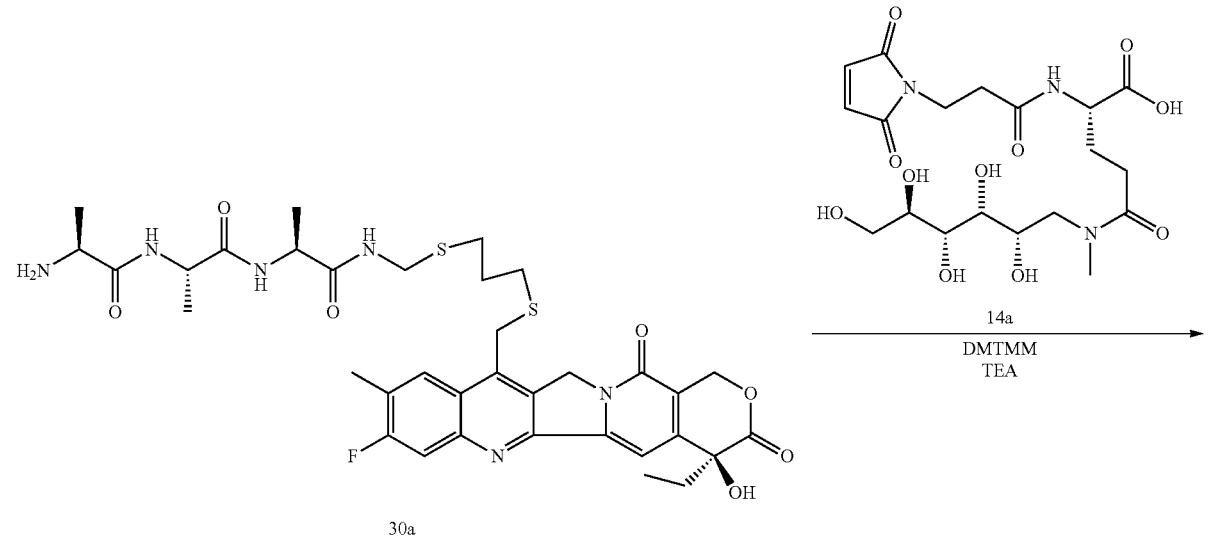

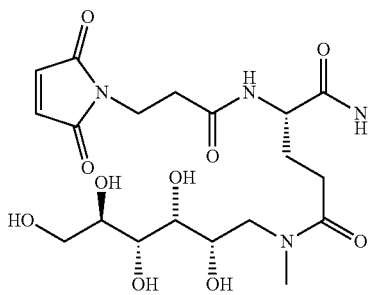

32a

32a: Compound 30a (16 mg, 0.02 mmol) was dissolved in 84:16 DMF:deionized water (0.5 mL) to which DMTMM (15 mg, 0.054 mmol), TEA (0.02 mL, 0.14 mmol) and 14a (20 mg, 0.042 mmol) were quickly added and magnetically stirred. After 35 min the reaction mixture was loaded on a 100 g silica cartridge preequilibrated with dichloromethane then run at 35 mL/min with a linear gradient from 0% to 100% over 30 min of 40:60 methanol:dichloromethane. Fractions containing desired product were combined and solvent was evaporated under vacuum to give 7 mg (29% yield) of 32a as a thick oil. MS (M+Na)+1223.0.

Example 40. Synthesis of Compound 33a

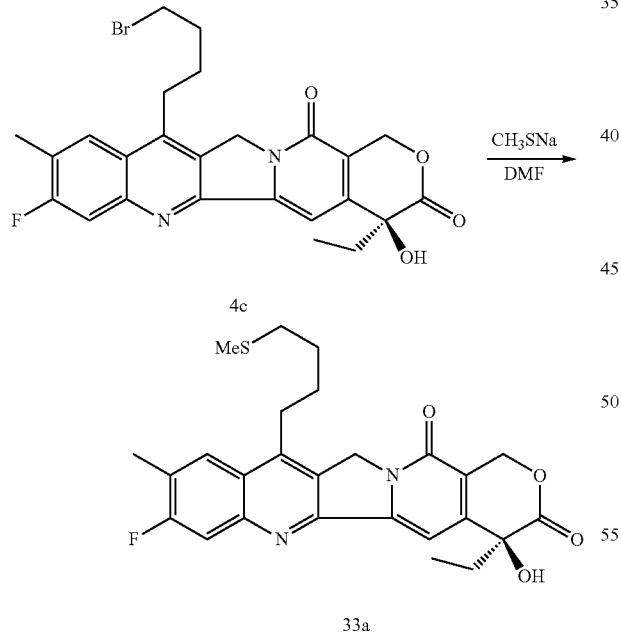

33a: To a solution of 4c (11 mg, 0.021 mmol) in anhydrous DMF (0.2 mL) was added sodium thiomethoxide (3.6 mg, 0.052 mmol) and the reaction mixture was stirred at room temperature for 18 hours. The reaction solution was directly loaded on a 30 g C18 cartridge 25:75 $CH_3CN/H_2O$, run at 20 mL/min 25% $CH_3CN$ for 3 minutes then with a linear gradient to 90% $CH_3CN$ from 3-12 min. Fractions containing desired product were combined and evaporated under vacuum to give compound 33a as a white solid (3.1 mg, yield 30%). MS (ESI): m/z 483.4 (M+H)$^+$, 481.3 (M−H)$^−$.

Example 41. Synthesis of Compound 34a and Compound 34b

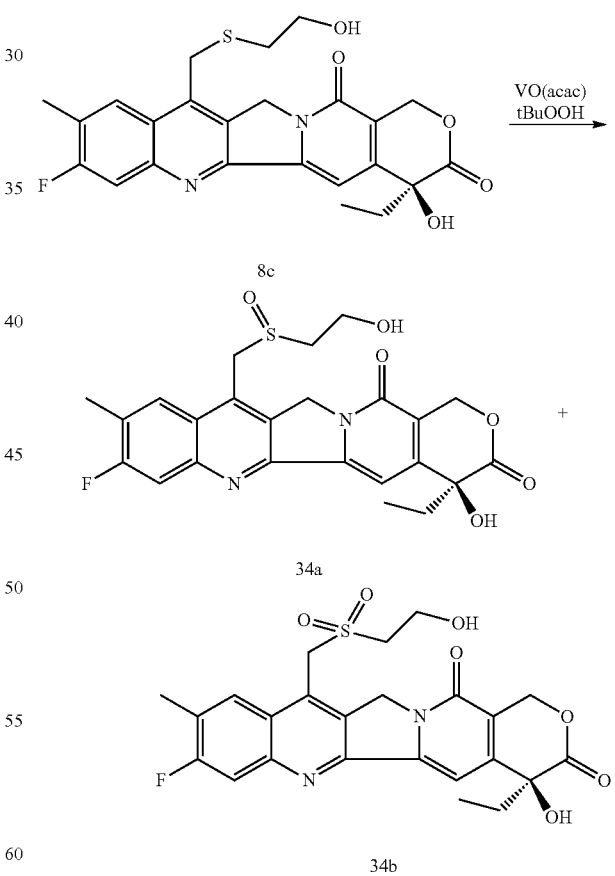

34a and 34b: Compound 8c (30 mg, 0.064 mmol) was magnetically stirred in DMF (1 mL) to which vanadium acetylacetonate (3 mg, 0.008 mmol) and a solution of 5 M tert-butyl hydroperoxide in decane (0.05 mL, 0.25 mmol) were added. After 5 min the solution was directly loaded on a 30 g C18 cartridge 25:75 CH$_3$CN/H$_2$O, run at 20 mL/min 25% CH$_3$CN for 3 minutes then with a linear gradient to 90% CH$_3$CN from 3-12 min. Fractions containing pure 34a were combined separately from fractions containing pure 34b and both were separately frozen and lyophilized to give 6 mg 34a (19% yield) and 15 mg 34b (47% yield) both as yellow solids. 34a MS (M+H)+ 487.4, 34b MS (M+H)+ 503.6.

Example 42. Synthesis of Compound 35a

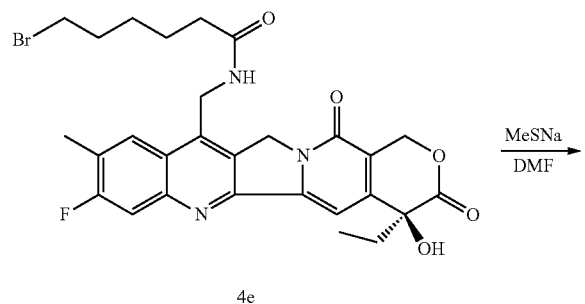

4e

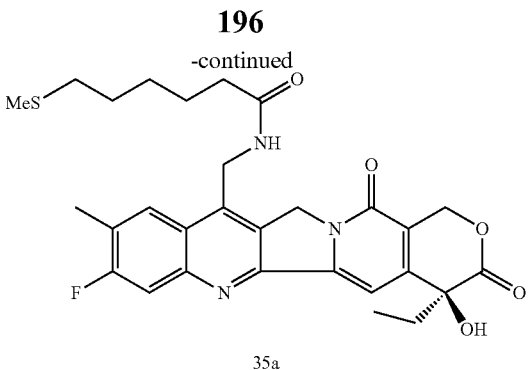

35a

35a: To a solution of compound 4e (17 mg, 0.025 mmol) in anhydrous DMF (0.3 mL) was added sodium thiomethoxide (7 mg, 0.1 mmol) and the reaction mixture was stirred at room temperature for 24 hours. The reaction solution was diluted with DMSO and injected on the semi-prep HPLC for purification (C18 column, CH$_3$CN/H$_2$O, 25% to 65% CH$_3$CN in 23 minutes) to give the desire product 35a (2.7 mg, yield 19%). MS (ESI): m/z 554.4 (M+H)$^+$, 552.5 (M−H)$^−$.

Example 43. Synthesis of Compound 29b

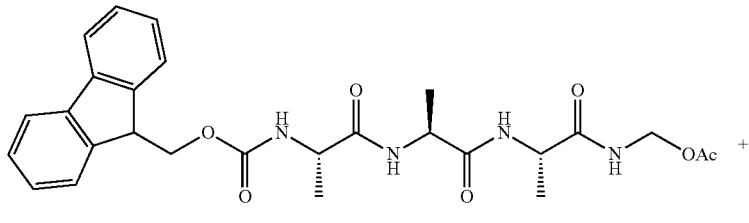

16a

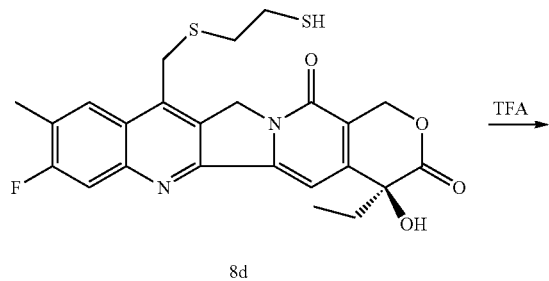

8d

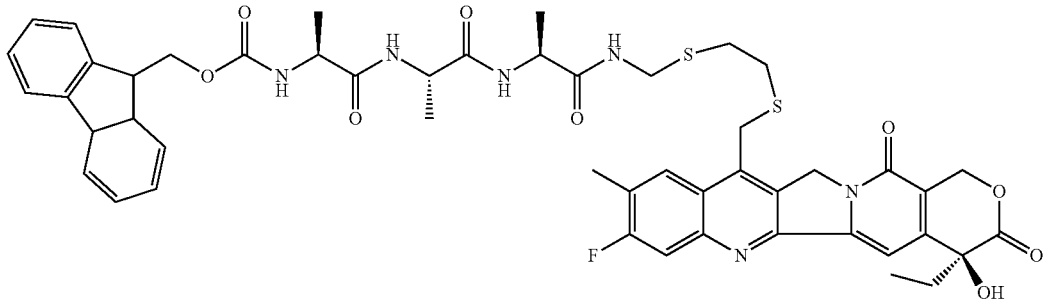

29b

29b: Compound 16a (30 mg, 0.057 mmol) and 8e (50 mg, 0.1 mmol) were suspended in a solution of 20% TFA in dichloromethane (10 mL) and magnetically stirred at room temperature for 30 min. Solvent was rotary evaporated under vacuum and the residue was taken up in a minimum volume of DMF then purified on a 100 g C18 medium pressure column that was pre-equilibrated with 90:10 deionized water containing 0.1% formic acid: acetonitrile. The column was then eluted at 30 mL/min with 10% acetonitrile for 5 min followed by a linear gradient of 10% acetonitrile from 5 min to 95% acetonitrile at 38 min. Fractions containing desired product were combined, frozen and lyophilized to give 31 mg of white solid 29b (56% yield). MS (ESI): MS (M+Na) calcd. 973.3, found 973.7.

Example 44. Synthesis of Compound 30b

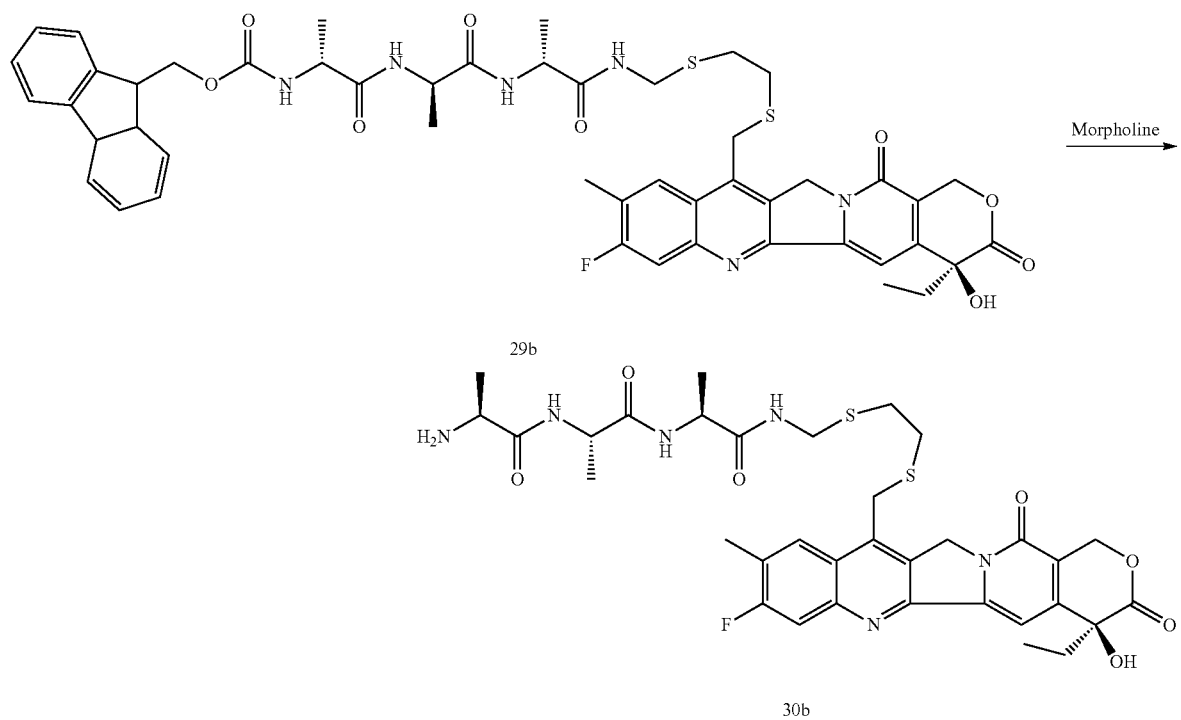

30b: Compound 29b (28 mg, 0.029 mmol) was dissolved in anhydrous DMF (0.8 mL) and magnetically stirred as morpholine (0.2 mL, 2.32 mmol) was added. After 1 h the reaction mixture was directly loaded on a 100 g C18 cartridge 25:75 $CH_3CN/H_2O$, run at 50 mL/min 25% $CH_3CN$ for 3 min then with a linear gradient to 90% $CH_3CN$ from 3-23 min. Fractions containing desired product were combined, frozen and lyophilized to give 18 mg (83% yield) of 30b as a yellow solid. $^1$H NMR (400 MHz, DMSO-d6) δ 8.52 (t, J=6.3 Hz, 1H), 8.31 (d, J=8.3 Hz, 1H), 8.11 (d, J=7.4 Hz, 2H), 7.87 (t, J=9.1 Hz, 2H), 7.69 (d, J=7.5 Hz, 1H), 7.37 (t, J=7.4 Hz, 1H), 7.31 (t, J=3.7 Hz, 2H), 5.43 (s, 2H), 5.31 (s, 2H), 4.47 (d, J=2.6 Hz, 2H), 4.32-4.09 (m, 4H), 3.69 (t, J=4.6 Hz, 2H), 3.36 (q, J=6.9 Hz, 1H), 2.84 (s, 4H), 2.61-2.54 (m, 3H), 2.46-2.42 (m, 4H), 1.94-1.75 (m, 2H), 1.17 (dd, J=7.2, 3.4 Hz, 6H), 1.12 (d, J=6.8 Hz, 3H), 0.87 (t, J=7.3 Hz, 3H). MS (ESI): MS (M+H)$^+$ calcd. 729.3, found 729.4.

Example 45. Synthesis of Compound 32b

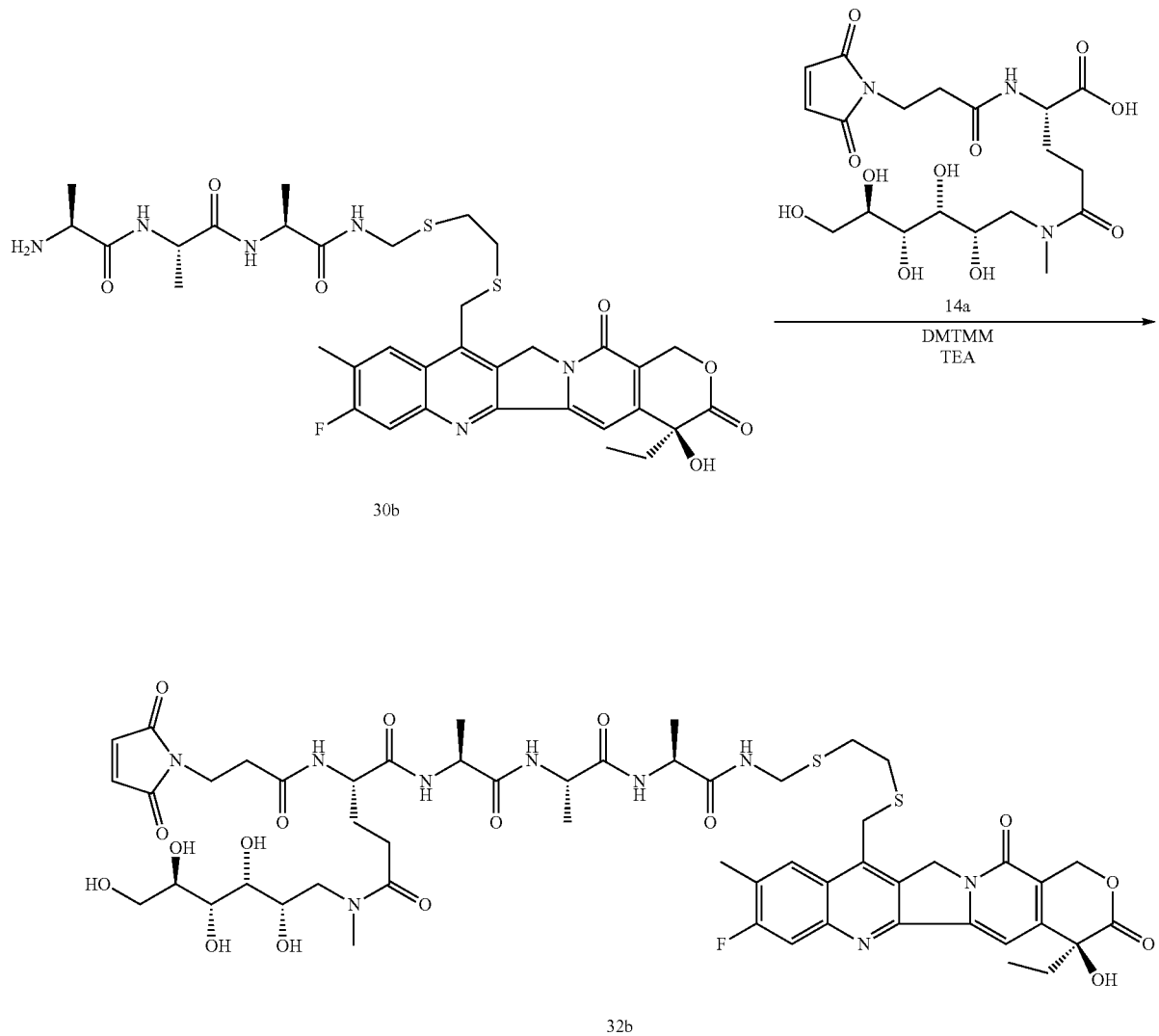

32b: Compound 30b (16 mg, 0.02 mmol) was dissolved in 84:16 DMF:deionized water (0.5 mL) to which DMTMM (15 mg, 0.054 mmol), TEA (0.02 mL, 0.14 mmol) and 14a (20 mg, 0.042 mmol) were quickly added and magnetically stirred. After 35 min the reaction mixture was loaded on a 100 g silica cartridge preequilibrated with dichloromethane then run at 35 mL/min with a linear gradient over 30 min from 0% to 100% of 40:60 methanol:dichloromethane. Fractions containing desired product were combined and solvent was evaporated under vacuum to give 7 mg of 32b (29% yield) as a thick oil. $^1$H NMR (400 MHz, DMSO-d6) δ 7.86-7.83 (m, 1H), 7.71 (s, 1H), 7.69 (d, J=1.1 Hz, 1H), 7.66 (d, J=8.2 Hz, 1H), 7.51-7.47 (m, 2H), 7.28 (t, J=1.0 Hz, 1H), 6.61 (s, 2H), 5.59-5.53 (m, 1H), 5.40 (dd, J=3.3, 1.1 Hz, 2H), 5.29-5.26 (m, 2H), 4.72 (s, 2H), 4.52-4.46 (m, 1H), 4.38 (s, 1H), 4.35 (dd, J=3.5, 1.8 Hz, 2H), 4.28-4.22 (m, 2H), 4.21-4.13 (m, 2H), 3.74 (t, J=6.5 Hz, 2H), 3.70 (ddd, J=11.9, 5.7, 4.8 Hz, 1H), 3.60-3.51 (m, 2H), 3.44 (dd, J=11.9, 4.9 Hz, 1H), 3.3 (broad s, 8H), 3.20 (dd, J=4.7, 3.7 Hz, 2H), 2.91 (s, 3H), 2.89 (s, 3H), 2.56 (td, J=6.4, 1.7 Hz, 2H), 2.31 (s, 3H), 2.37-2.21 (m, 2H), 2.07-1.82 (m, 3H), 1.72 (dq, J=13.7, 8.1 Hz, 1H), 1.53 (d, J=5.5 Hz, 6H), 1.45 (d, J=5.9 Hz, 3H), 0.86 (t, J=8.0 Hz, 3H). $^{13}$C NMR (101 MHz, DMSO-d6) δ 174.75, 174.58, 172.85, 172.75, 172.45, 171.62, 171.37, 169.30, 163.44, 160.52, 157.18, 149.96, 148.73, 147.39, 147.32, 142.26, 132.98, 131.74, 127.54, 127.38, 127.24. 126.88, 124.90, 124.84, 124.34, 122.88, 118.32, 116.83, 116.67, 97.97, 74.87, 73.80, 72.41, 72.34, 69.44, 65.10, 62.94, 53.02, 50.02, 49.92, 49.62, 48.46, 45.53, 42.38, 40.85, 35.32, 35.13, 34.00, 32.31, 32.24, 30.20, 26.63, 20.49, 17.81, 17.71, 17.61, 7.68. HRMS (M+H)$^+$ calcd. 1186.4237, found 1186.4220.

Example 46. General Method for the Preparation of Conjugates

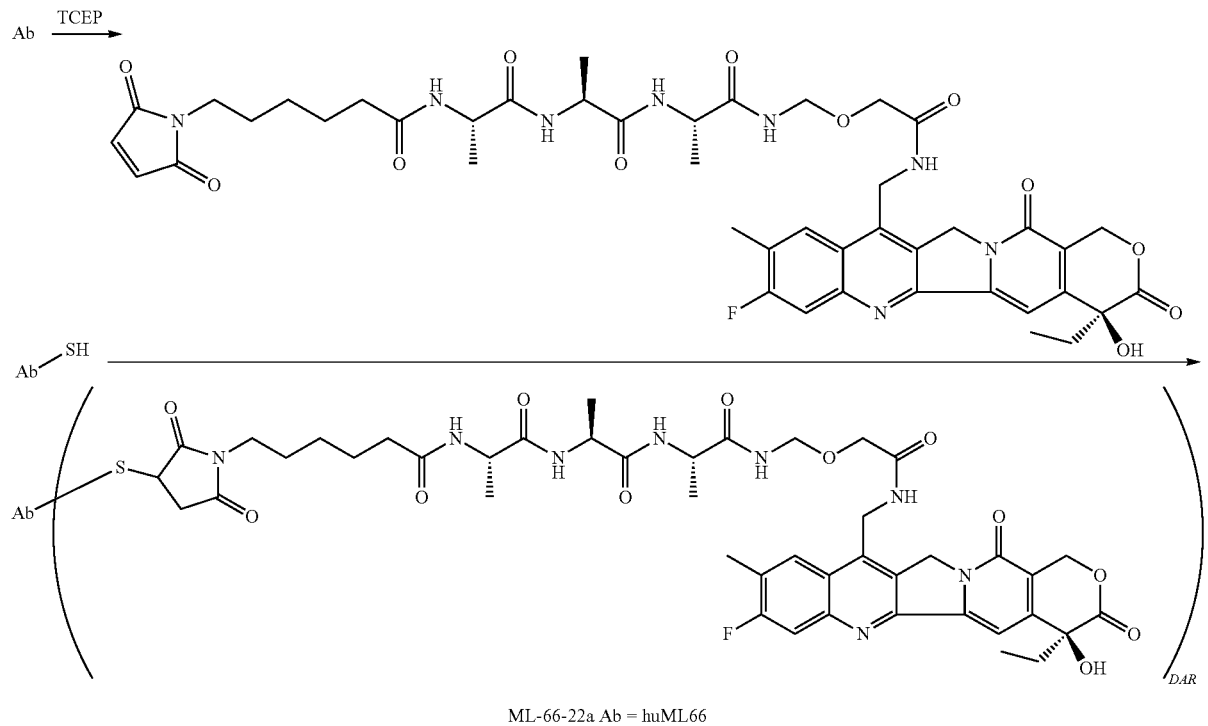

ML-66-22a Ab = huML66

Humanized IgG1 antibodies such as anti-epidermal growth factor (ML66), anti-folate receptor α (FRα) and the chimeric antibody that binds to Kunitz soybean trypsin inhibitor (KTI) were generated. Conjugation of antibodies to maleimide-bearing payloads were performed as described for the preparation of ML66-22a. The resulting conjugates will be designated herein as target binder-payload, for example ML66 conjugated to 22a is ML66-22a Example 47. Synthesis of ML66-22a ML66-22a: ML66 at 5 mg/ml was treated with 7.0 equivalents of TCEP in 50 mM EPPS pH7.4, 5 mM EDTA at 37° C. for 1-1.5 hrs. The mixture was then cooled to room temperature. The conjugation reaction between antibody and the payload was performed at 2 mg/ml by adding 15-20 equivalents of 22a dissolved in DMSO in buffer (50 mM EPPS, pH7.4) containing 20% DMSO, and spinning on a tube rotator for 1.5-2.5 hrs at room temperature. The reaction mixture was immediately purified into formulation buffer (10 mM acetate, 9% sucrose, 0.01% Tween-20, pH 5.0) using NAP desalting columns (Illustra Sephadex G-25, GE Healthcare). The resulting conjugate had a drug to antibody ratio (DAR) of 7.5, and was 99% monomeric measured by size exclusion chromatography.

Biophysical evaluations for inter-chain high DAR conjugate, including determination of conjugate concentration, yield, DAR (drug to antibody ratio), free drug, percent monomer and DAR distribution, were carried out. The conjugate concentration was determined to have a final protein concentration of 4.5 mg/ml (via UV-Vis using extinction coefficient E280=205520 $M^{-1}$ $cm^{-1}$), DAR 7.5 (via UV-Vis using extinction coefficients E280=10764 $M^{-1}$ $cm^{-1}$, ε370=20982 $M^{-1}$ $cm^{-1}$ for 22a), 99% monomer (via size exclusion UPLC protein BEH SEC column), <1% free drug (via HiSEP HPLC column), and mostly homogenous 8 drug linked per antibody (via Q-ToF Mass Spectrometry, and Butyl-NPR HIC chromatography). The yield for this specific inter-chain conjugation ML66-22a was 75%.

UPLC protein BEH SEC Method: The monomer percentage analysis was carried out on a Waters Acquity UPLC H-class system equipped with an Acquity UPLC protein BEH SEC column (200 Å, 1.7 um, 4.6 mm×150 mm, part #186005225). The mobile phase was 400 mM sodium perchloride, 50 mM sodium phosphate, 5% IPA, pH7.0, flow rate 0.30 mL/min, run time 20 min.

HiSep HPLC Method: The free drug percentage analysis was performed on Agilent HPLC system equipped with a Supelco analytical HiSep column (25 cm×4.6 mm, Sum, Cat #58919). The mobile phase consisted of 0.1 M ammonium, pH 7.0 (solvent A) and acetonitrile (solvent B). The method was run at 0.70 mL/min with solvent A, using a linear gradient starting from 25% solvent B to 40% solvent B from 0-25 min.

Example 48. In Vitro Cytotoxicity Assay

Cytotoxic potencies were assessed in flat-bottomed 96 well plates (Costar) using a water-soluble tetrazonium salt (WST-8) based cell viability assay (Dojindo, Molecular Technologies, Inc.) as previously described (Kovtun Y V, et al. Antibody-maytansinoid conjugates designed to bypass multidrug resistance. Cancer Res 2010; 70(6):2528-37). Briefly, human tumor cells (1,000-5,000 cells/well, depending on the cell line), in the appropriate culture medium were incubated, with conjugates in the presence or absence of an excess of the corresponding unconjugated antibodies, or with the metabolites for 5 days, at 37° C., 6% CO2. Cell viability was determined from background-corrected WST-8 absorbance.

Figure 12:
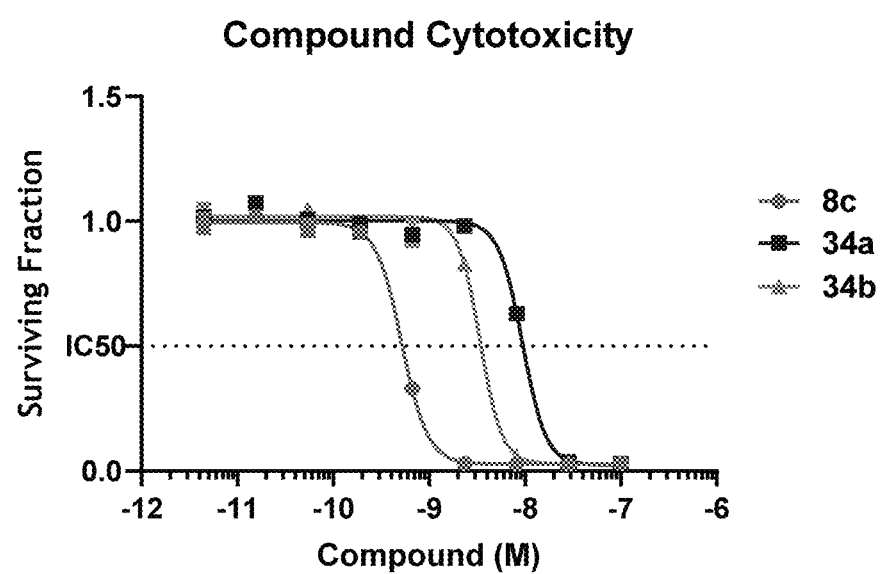
FIG. 12 depicts the cytotoxicity of the sulfide-bearing compound 8c and its sulfoxide 34a and sulfone 34b.

The results of this study are summarized in the following tables. FIG. 12 depicts the cytotoxicity of the sulfide-bearing compound 8c and its sulfoxide 34a and sulfone 34b.

TABLE 7A

In vitro cytotoxicities ($IC_{50}$ values) of non-conjugated compounds

| Compound | Cell Lines (Compound concentrations Molar) | | | | | |
|---|---|---|---|---|---|---|
| | Namalwa | KB | N-Luc | SUDHL-1 | HSC-2 | MDA-MB-468 |
| 998 | 3.E−10 | | 4.E−10 | 2.E−10 | 1.E−09 | 9.E−10 |
| 4a | 3.E−09 | | | | 4.E−09 | |
| 4b | 1.E−09 | | | | 3.E−09 | |
| 7a | 9.E−10 | | 1.E−09 | 5.E−10 | 4.E−09 | 3.E−09 |
| 7b | | | 2.E−09 | | 7.E−09 | |
| 7c | | | 7.E−10 | 2.E−10 | 1.E−09 | 1.E−09 |
| 8a | 2.E−10 | 6.E−10 | 9.E−10 | | 6.E−10 | 2.E−09 |
| 33a | 7.E−10 | | | | 2.E−09 | |
| 34a | | 7.E−09 | | | 9.E−09 | 7.E−09 |
| 34b | | 2.E−09 | | | 3.E−09 | 3.E−09 |
| 35a | | | | 6.E−10 | 7.E−09 | |

TABLE 7B

In vitro cytotoxicities ($IC_{50}$ values) of non-conjugated compounds

| Compound | Cell Lines (Compound concentrations Molar) | |
|---|---|---|
| | N-Luc | HSC-2 |
| 998 | 6E−10 | 1E−09 |
| 7a | 9E−10 | 2E−9 |
| 8a | 2E−10 | 5E−10 |
| 8c | 2E−10 | 4E−10 |
| 8p | 2E−10 | 6E−10 |

N-Luc indicates Namalwa cells that were stably transfected with the Luciferase gene Example 49. Bystander Cell Killing Assay Cell Titer Glo and One Glo reagents were purchased from Promega. The ability of ADCs to induce bystander killing was determined by one of two assays. Both assays were performed in U-bottomed 96-well plates (Costar) to keep mixed antigen negative (Ag−) and antigen positive (Ag+) cells in close proximity to each other.

Namalwa-Luciferase (N-Luc) Ag− cells (1000 cells per well) in the appropriate culture media were incubated in wells of a U-bottomed 96 well plate with the designated number of MDA-MB-468 Ag+cells and ADC (1.1 nM) for 5 days, at 37° C., 6% $CO_2$. The concentration of conjugate used in the assay was high enough to kill all Ag+ cells but not able to kill Ag− cells unless Ag+cells were also present. On day 5, cell viability was determined by Cell Titer Glo assay according to the manufacturer's protocol; luminescence signals were read using a Victor3 plate reader. The table below shows the in vitro cytotoxicities as obtained in the previous Example and the bystander killing of the compounds described herein.

TABLE 8

In vitro cytotoxicities and bystander killing of ADCs

| ADC | DAR | Cell Lines (ADC Concentrations) | | | Bystander |
|---|---|---|---|---|---|
| | | HSC-2 | N-Luc | MDA-MB-468 | MDA + N-Luc |
| ML66-999 | 7.5 | 7.0E−11 | 1E−7 | 7E−10 | 2E−9 |
| ML66-22a | 7.5 | 7.0E−11 | 1E−7 | 4E−10 | 4E−9 |
| ML66-22c | 7.8 | | 1.0E−7 | 2.0E−9 | 6.0E−8 |
| ML66-22d | 7.1 | | 2.0E−7 | 4.0E−8 | 9.0E−9 |
| ML66-22e | 6.9 | | 3.0E−7 | 4.0E−10 | 2.0E−9 |
| ML66-25a | 6.9 | 1.0E−8 | | | |
| ML66-25b | 7.3 | >4E−7 | | | |
| ML66-28a | 6.6 | | 5E−7 | 7E−10 | 5E−10 |
| ML66-28c | 5.9 | | 7.0E−8 | | |
| ML66-28b | 6.9 | | 2.0E−8 | 7.0E−10 | 5.0E−10 |
| ML66-28d | 6.6 | | >2E−7 | 7.0E−10 | 4.0E−10 |
| ML66-32a | 6.5 | | 3.0E−8 | 3E−9 | 2.0E−9 |
| ML66-32b | | | 6E−7 | 1E−9 | 6E−10 |

N-Luc indicates Namalwa cells that were stably transfected with the Luciferase gene Example 50. Method for Determining In Vivo Efficacy in Xenograft Models Female CB.17 SCID mice at 6 weeks of age were received from Charles River Laboratories. All in vivo procedures were performed in strict accordance with the NIH Guide for the Care and Use of Laboratory Animals. The in vivo efficacy of ADCs were evaluated in the given tumor xenograft models. Female SCID mice were inoculated subcutaneously in the right flank with the desired cell type in 1:1 ratio of serum-free medium. The animals were then randomly distributed into groups of 6 or 8 mice per group. Control mice were treated with phosphate-buffered saline, vehicle. The required concentrations of ADCs were made by diluting stock samples with vehicle. Xenografts were grown to approximately 100 $mm^3$, then mice were administered ADC or vehicle by tail vein intravenous (i.v.) injection (200 µL/mouse). All dosing was based on the weight of the antibody component of the conjugate. Tumor sizes were measured twice weekly in three dimensions using a caliper with tumor volumes expressed in $mm^3$ calculated using the formula V=½(length×width×height). Body weight was also measured twice per week. Data from these studies was interpreted using standardized methods as previously described (Bissery M C et al. Experimental antitumor activity of taxotere (RP 56976, NSC 628503), a taxol analogue. Cancer Res 1991; 51(18):4845-52).

Example 51. Mouse Tolerability to ML66-999, ML66-22a and ML-28a ADCs

Figure 19:
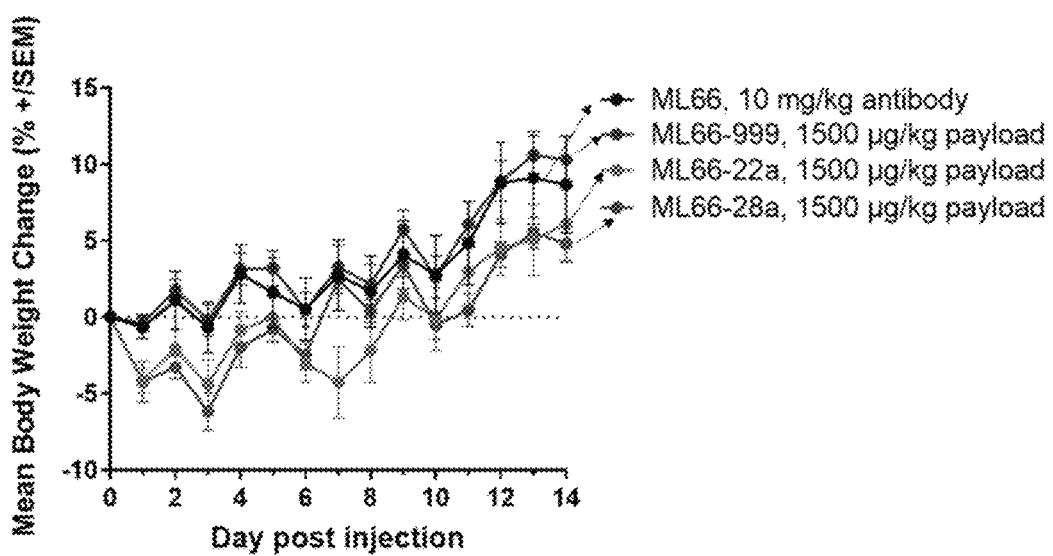
FIG. 19 depicts the mouse tolerability to ML66-999, ML66-22a and ML66-28a ADCs.

The tolerability of ADCs was evaluated in female CD-1 mice by performing daily body weight measurements and clinical observations for 2 weeks following injection of the ADCs. A 10 mg/kg pre-dose of naked ML66 antibody was intravenously administered to thirty-two 7-week-old female CD-1 mice because this was shown to alleviate the acute infusion reaction caused by ML66 alone at doses of greater than 20 mg/kg. One mouse died following this injection of naked antibody. Two hours later, three groups of seven to eight mice each were dosed with an intravenous bolus injection of 1500 µg/kg payload of ML66-999 (58 mg/kg antibody), ML66-22a (59 mg/kg antibody), or ML66-28a (69 mg/kg antibody). The maximum tolerated dose (MTD) was defined as the highest dose at which no animals died or were required to be euthanized due to >20% body weight loss or signs of distress or morbidity (hunching, lack of movement, inability to eat or drink, or signs of pain/distress). Based on these criteria, all three ADCs were well tolerated at a 1500 μg/kg payload dose. FIG. 19 depicts the mouse tolerability to ML66-999, ML66-22a and ML66-28a ADCs.

Example 52. Method for Determination of ADC Pharmacokinetic (PK) Parameters in Mice Three groups of eleven 7-week-old female CD-1 mice were each dosed with a single intravenous bolus injection of 10 mg/kg naked antibody or ADC. Terminal blood samples were collected from 3 mice at 2 minutes, 3 mice at 24 hours, and 5 mice at 72 hours after injections for each ADC. The blood was processed to serum and the ADCs were purified using affinity capture with anti-human Fc beads. The samples were analyzed by anti-human Fc ELISA to determine the concentration of the antibody component (irrespective of payload loading). Samples were also analyzed by size exclusion chromatography (SEC) and mass spectrometry (MS). Partial loss of linker-payload from the captured ADC at all time points were measured by intact MS method. The ADC concentration was calculated based on the total antibody concentration and the drug-to-antibody ratio (DAR).

Figure 13:
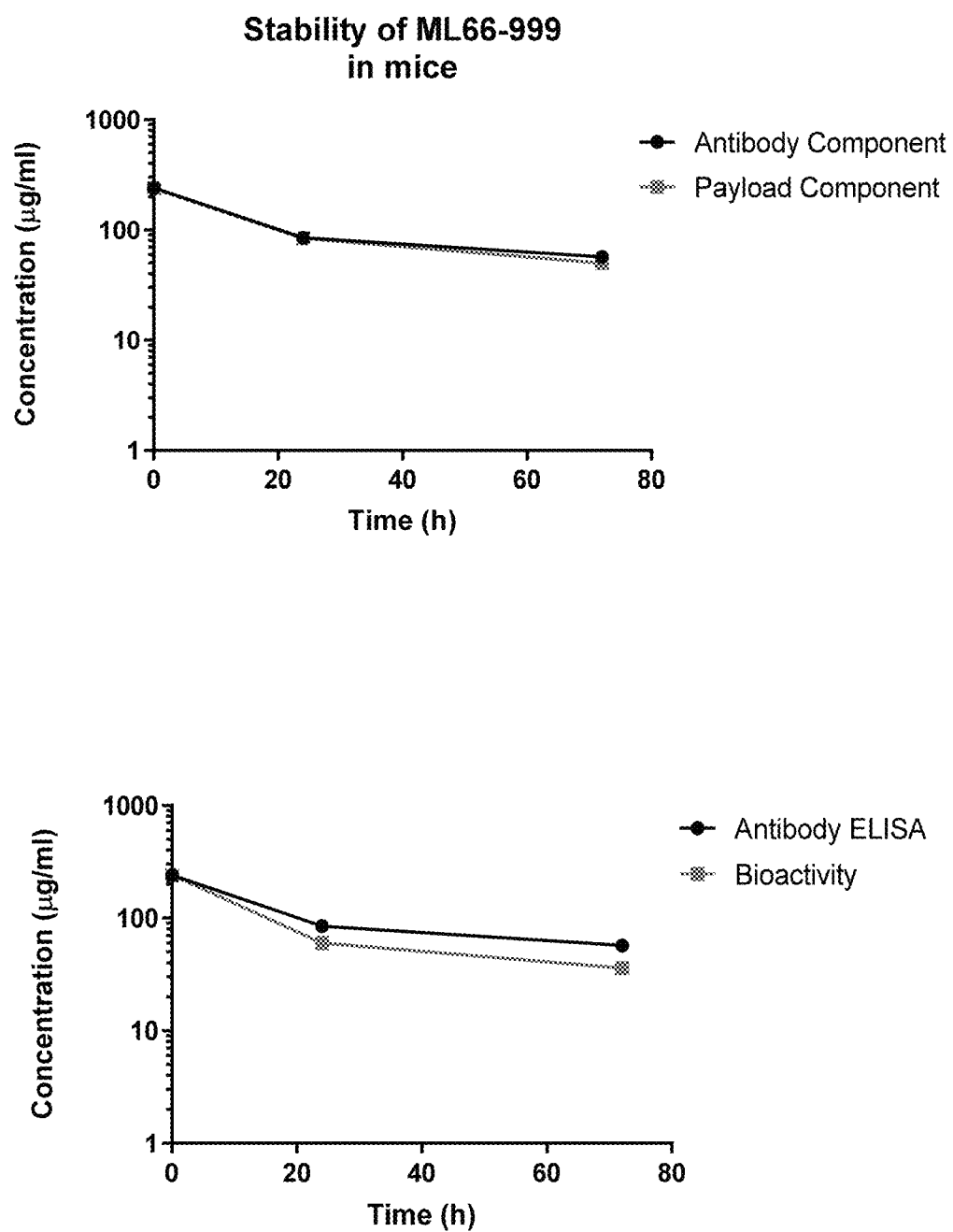
FIG. 13 depicts the pharmacokinetics of ML66-999 in mice. Top panel depicts plots of concentration (µg/mL) vs time of the mAb component (average), and payload component, at 2 min, 1 day and 3 day time points post administration in mice. Bottom panel depicts plots of concentration (µg/mL) vs time of the mAb component (average), and retained Bioactivity (pooled samples), of ADCs at 2 min, 1 day and 3 day time points post administration in mice.
Figure 14:
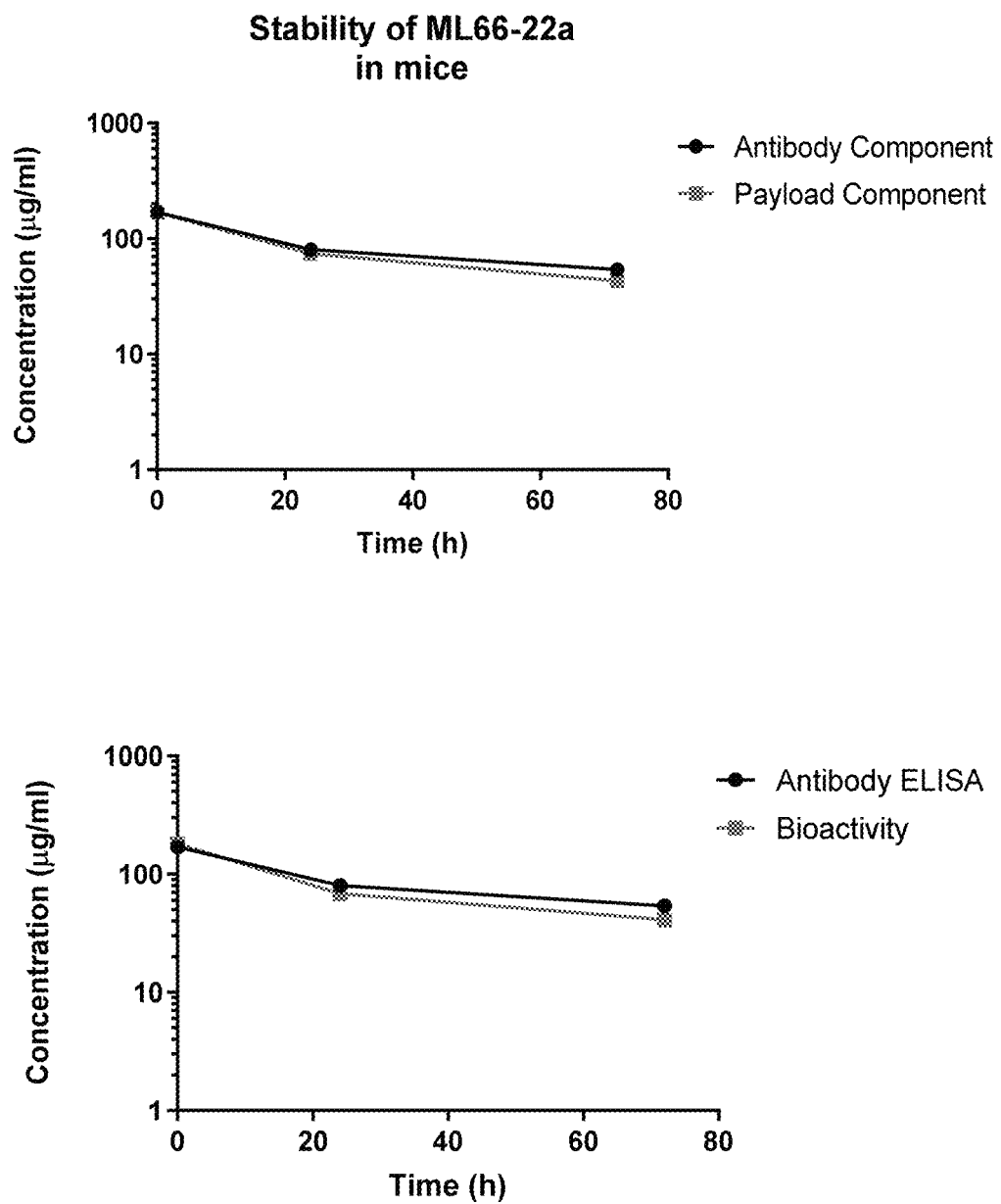
FIG. 14 depicts the pharmacokinetics of ML66-22a in mice. Top panel depicts plots of concentration (µg/mL) vs time of the mAb component (average), and payload component, at 2 min, 1 day and 3 day time points post administration in mice. Bottom panel depicts plots of concentration (µg/mL) vs time of the mAb component (average), and retained Bioactivity (pooled samples), of ADCs at 2 min, 1 day and 3 day time points post administration in mice.
Figure 15:
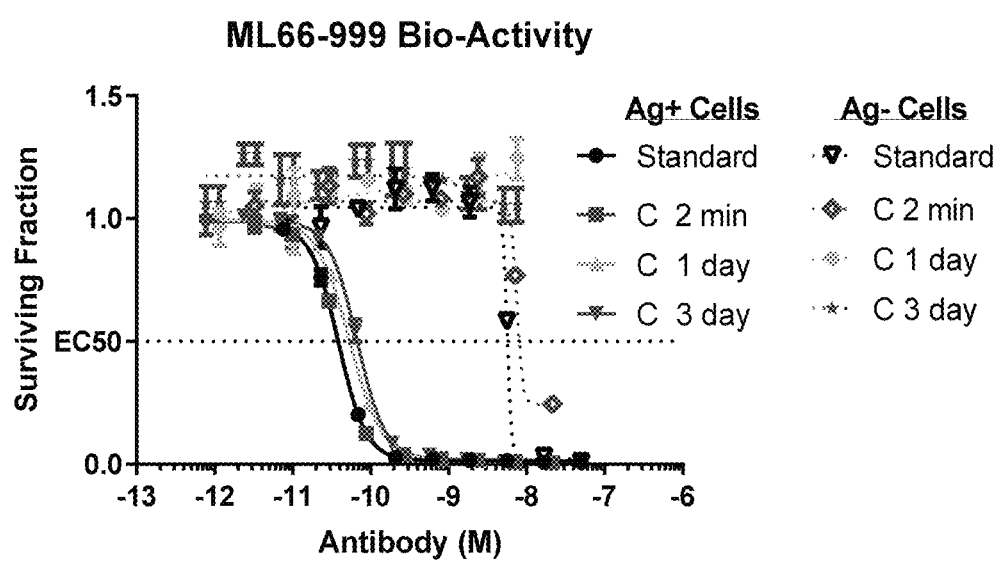
FIG. 15 depicts the in vitro cytotoxicities of ADCs against Ag+ and Ag− cells. ADC standard in formulation (Standard) or blood serum (pooled) containing ADC taken at 2 min, 1 day or 3 days post administration into mice for ML66-999.
Figure 16:
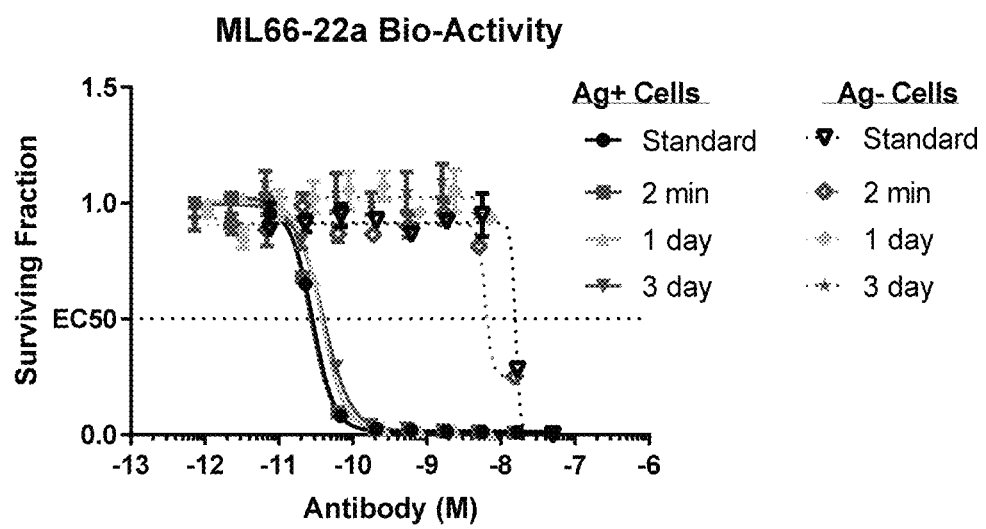

FIG. 13 and Table 9 show the pharmacokinetics of ML66-999 in mice. FIG. 14 and Table 10 show the pharmacokinetics of ML66-999 in mice. Table 11 summarizes the binding of ADCs or naked antibody to the corresponding antigen expressing cell lines. FIGS. 15 and 16 show the in vitro cytotoxicities of ML66-999 and ML66-22a against Ag+ and Ag-cells. Fractional retained bioactivity of the ADC in the plasma samples over time was determined in cytotoxicity assays with Ag+ or Ag− cells. The ADCs retained most of their activity against Ag+ cells at each of the time points, while remaining over 200-fold less active against Ag− cells, indicating that the cytotoxicities, were due to intact ADC, with little or no contribution from any released payload.

TABLE 9

| ML-66-999 | Total Ab Conc. (μg/mL) by ELISA | ADC Conc. (μg/mL) by Mass Spec | DAR by Mass Spec |
|---|---|---|---|
| ADC standard | NA | NA | 7.68 |
| 0.033 h (2 min) | 240 | 238 | 7.62 |
| 24 h | 85 | 84 | 7.62 |
| 72 h | 57 | 50 | 6.72 |

TABLE 10

| ML-66-22a | Total Ab Conc. (μg/mL) by ELISA | ADC Conc. (μg/mL) by Mass Spec | DAR by Mass Spec |
|---|---|---|---|
| ADC standard | NA | NA | 6.98 |
| 0.033 h (2 min) | 169 | 168 | 6.92 |
| 24 h | 80 | 74 | 6.50 |
| 72 h | 54 | 43 | 5.60 |

TABLE 11

Binding of ADCs or naked antibody to the corresponding antigen expressing cell lines

| Designation | DAR | Cell Line (Binding EC50, M) | |
|---|---|---|---|
| | | NCI-H2110 | PC-9 |
| Naked ML66 | | 2E−9 | |
| ML66-999 | 7.4 | 3E−9 | |
| ML66-22a | 7.5 | 3E−9 | |
| ML66-22c | 7.8 | 7E−10 | |
| ML66-22d | 7.1 | 2E−9 | |
| ML66-22e | 6.9 | 2E−9 | |
| ML66-25a | 6.9 | 5E−9 | |
| ML66-25b | 7.2 | 3E−9 | |
| ML66-28a | 6.6 | 1E−9 | |
| ML66-28b | 6.9 | | 1E−9 |
| ML66-28c | 5.9 | | 2E−9 |
| ML66-28d | 6.6 | | 1E−9 |
| ML66-32a | 7.5 | 1E−09 | |

Example 53. Anti-Tumor Activity of Anti-EGFR Antibody Drug Conjugates in Nude Mice Bearing HSC-2 Human Head and Neck Squamous Cell Carcinoma Xenografts The anti-tumor activity of 1, 3, and 10 mg/kg of ML66-999 and ML66-22a were evaluated in female Nude mice bearing HSC-2 cells, a human head and neck squamous cell carcinoma xenograft model.

Mice were inoculated with $1 \times 10^7$ HSC-2 cells in 0.1 ml 50% Matrigel/50% serum free medium by subcutaneous injection in the area on the right hind flank. Female athymic Foxn1$^{nu}$ mice (6 weeks of age) were obtained. Upon receipt, the animals were observed for 9 days prior to study initiation. Animals showed no sign of disease or illness upon arrival, or prior to treatment.

Forty-eight mice were randomized into 8 groups (6 mice per group) by tumor volume. The tumor volumes ranged from 68.48 to 118.26 (93.42±11.25, Mean±SD) mm$^3$. The mice were measured, randomized, and dosed based on the tumor volume on day 4 post implantation (11/12/18). Body weights of the mice ranged from 19.46 to 25.77 (22.98±1.50, Mean±SD) grams. Mice in each group were identified by punch method. Administration of the test agents and vehicle were carried out intravenously by using a 1.0 ml syringe fitted with a 27 gauge, ½ inch needle. Antibody drug conjugate test agents were dosed qdx1 at 1, 3, or 10 mg/kg, where 75 μg/kg or 250 μg/kg based on payload correlates to approximately 3 or 10 mg/kg based on antibody concentration. The groups included: a control group dosed with vehicle (PBS, 200 μL), a control group dosed with the non-targeting KTI-999 at 10 mg/kg, ML66-999 dosed at 1, 3, and 10 mg/kg based on antibody concentration, and ML66-22a dosed at 1, 3, and 10 mg/kg based on antibody concentration.

Tumor size was measured two times per week in three dimensions using a caliper. The tumor volume was expressed in mm$^3$ using the formula Volume=Length×Width×Height×½. A mouse was considered to have a partial regression (PR) when tumor volume was reduced by 50% or greater and a complete tumor regression (CR) was when no palpable tumor could be detected. Tumor volume was determined by StudyLog software.

Tumor growth inhibition (% T/C) is the ratio of the median tumor volume (TV) of the treatment group (T) to the median TV of the control group (C) at a predetermined time (e.g. the time when the median TV for control tumors reach a maximum tumor volume ~1000 mm³, which is when the mice are euthanized). % T/C was calculated on day 22 post inoculation, when the median TV of the control group reached 1038 mm³. According to NCI standards, a T/C≤42% is the minimum level of anti-tumor activity and a T/C<10% is considered a high anti-tumor activity level.

Body weight (BW) of all the mice was measured two times per week as a rough index of drug toxicity and was determined by StudyLog software. Body weights of mice were expressed as percent change in body weight from the pre-treatment body weight as follows: % BW change= [(BWpost/BWpre)−1]×100, where BWpost is weight after treatment and BWpre is the starting body weight prior to treatment. Percent body weight loss (BWL) was expressed as the mean change in body weight post treatment. Animals were euthanized if the tumor volume became larger than 1000 mm³, the tumors became necrotic, the mice lost >20% of their initial body weight, or the mice become moribund at any time during the study.

Figure 17:
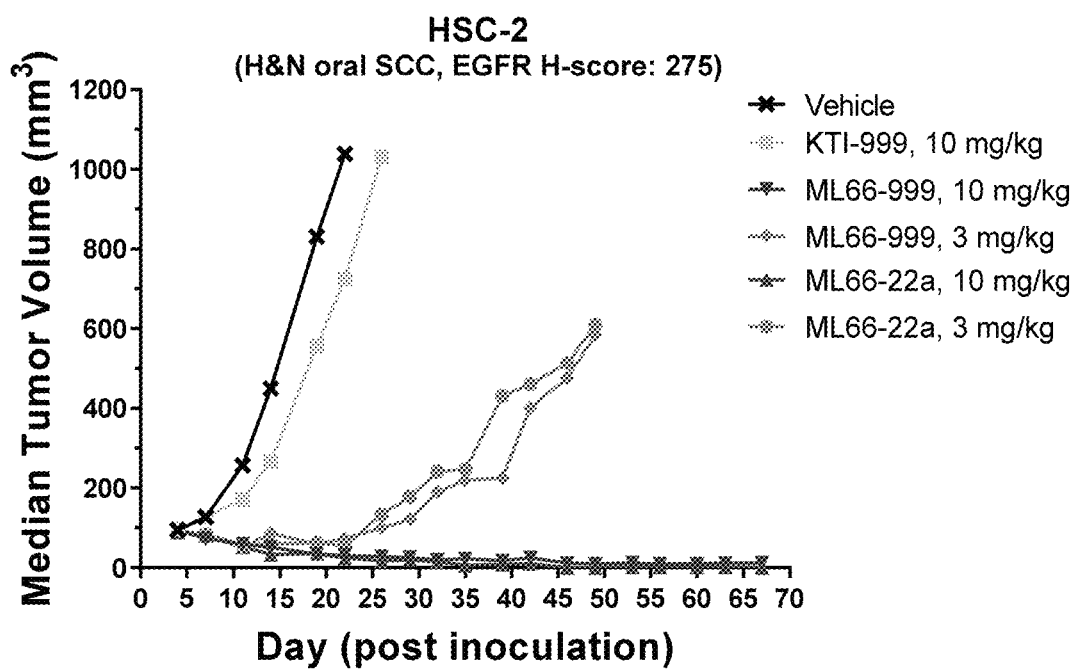
FIG. 17 depicts the efficacy of ADCs in a HSC-2 xenograft model. Dosing is based on payload (75 µg/kg and 250 µg/kg are 3 mg/kg and 10 mg/kg based on antibody).

FIG. 17 and Table 12 depict the efficacy of ADCs in a HSC-2 xenograft models. The ML66-999 and ML66-22a conjugates had similar anti-tumor activity. ML66-KTI dosed at 10 mg/kg had a T/C value of 70% (inactive), with no tumor regressions. This demonstrated that the activity of the ML66 conjugates is EGFR-targeted since the control ADC was inactive. ML66-999 dosed at 1 mg/kg had a T/C value of 49% (inactive), with no tumor regressions. ML66-999 dosed at 3 mg/kg had a T/C value of 7% (highly active), with 4 partial tumor regressions out of 6 mice and 1 complete regression. ML66-999 dosed at 10 mg/kg had a T/C value of 3% (highly active), with 6 partial tumor regressions out of 6 mice and 2 complete regressions. ML66-22a dosed at 1 mg/kg had a T/C value of 39% (active), with 1 partial tumor regressions out of 6 mice and no complete regressions. ML66-22a dosed at 3 mg/kg had a T/C value of 5% (highly active), with 3 partial tumor regressions out of 6 mice and 1 complete regression. ML66-22a dosed at 10 mg/kg had a T/C value of 2% (highly active), with 6 partial tumor regressions out of 6 mice and 5 complete regressions. No significant body weight loss was observed at any of the indicated doses for any of the conjugates indicating that the conjugates were well tolerated. The results from this study suggest that both the ML66-999 and ML66-22a conjugates demonstrated dose dependent anti-tumor activity and were efficacious in the HSC-2 head and neck squamous cell carcinoma tumor xenograft model.

TABLE 12

| ADC (DAR) | ADC Dose | | HSC-2 | | |
|---|---|---|---|---|---|
| | μg/kg payload | mg/kg Ab | T/C (Day 22) | PR | CR |
| KTI-999 (7.6) | 259 | 10 | 70% | 0/6 | 0/6 |
| ML66-999 (7.5) | 254 | 10 | 3% | 6/6 | 2/6 |
| ML66-999 (7.5) | 76 | 3 | 7% | 4/6 | 1/6 |
| ML66-999(7.5) | | 1 | 49% | 0/6 | 0/6 |
| ML66-22a (7.5) | 258 | 10 | 2% | 6/6 | 5/6 |
| ML-66-22a (7.5) | 77 | 3 | 5% | 3/6 | 1/6 |
| ML66-22a (7.5) | | 1 | 39% | 1/6 | 0/6 |

Example 54. Anti-Tumor Activity of Conjugates in Nude Mice Bearing Non-Small Cell Lung Cancer (NSCLC) Xenografts The anti-tumor activity of the conjugates in Nude Mice Bearing Non-Small Cell Lung Cancer (NSCLC) Xenografts was determined in a manner similar to that for HSC-2 cells as described in Example 53.

Female athymic Nude mice (Foxn1$^{nu}$) at 6 weeks of age were received from Charles River Laboratories. All in vivo procedures were performed in strict accordance with the NIH Guide for the Care and Use of Laboratory Animals. The anti-tumor activity of the ADCs was evaluated in non-small cell lung cancer (NSCLC) squamous H1703 tumor xenograft models. Female Nude mice were inoculated subcutaneously in the right flank with the desired cell type in 1:1 ratio of serum-free medium:Matrigel (5×10⁶ cells/mouse). Tumor volumes (TV) were measured twice weekly in three dimensions using a caliper with tumor volumes expressed in mm³ calculated using the formula TV=½(length×width×height). Xenografts were grown to 100 mm³ and mice were randomly distributed into groups of 6 mice per group based on their TV on day 16 (with a 116.0+/−18.5 mm³ [mean+/−SD] TV) post cell inoculation. Stock ADCs were diluted with conjugate dilution buffer and mice were dosed by individual body weights. Mice received a single intravenous (IV) bolus injection of vehicle (phosphate-buffered saline (PBS) at 200 μL/mouse) or ADC at 75 μg/kg or 250 μg/kg based on payload (approximately 3 or 10 mg/kg based on antibody concentration) at a dose volume of 5 mL/kg. Tumor growth inhibition (T/C) is the ratio of the median tumor volume (TV) of the treatment group (T) to the median TV of the control group (C) at a predetermined time (e.g. the time when the median TV for control tumors reach a maximum tumor volume ~1000 mm³, which is when the mice are euthanized). According to NCI standards, a T/C<42% is the minimum level of anti-tumor activity and a T/C<10% is considered a high anti-tumor activity level. A mouse was considered to have a partial regression (PR) when TV was reduced by 50% or greater and a complete regression (CR) when no palpable tumor could be detected. T/C, PR, and CR for both efficacy studies are listed in the table below. Body weights were also measured twice per week as a rough index of drug toxicity.

Figure 20:
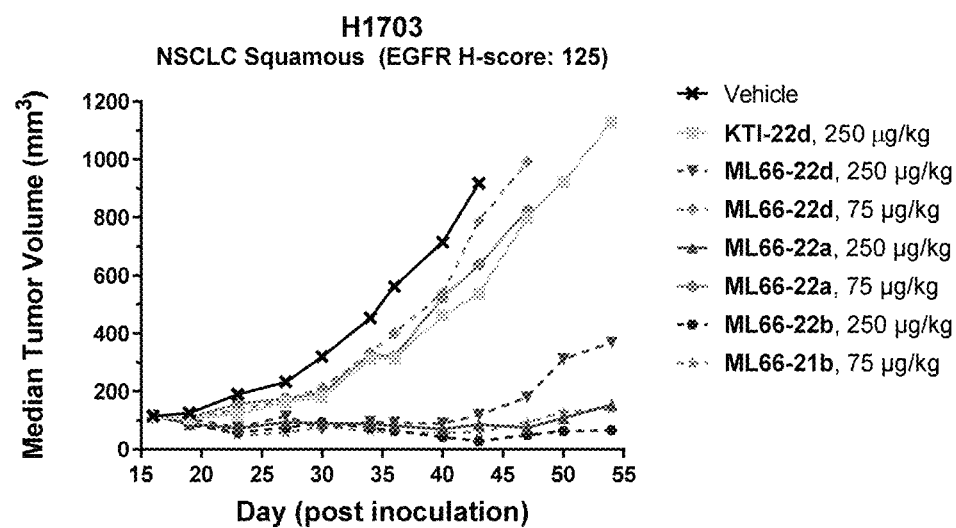
FIG. 20 depicts the anti-tumor activity of ADCs in a H1703 mouse xenograft model. Dosing is based on payload (75 µg/kg and 250 µg/kg are 3 mg/kg and 10 mg/kg based on antibody).

FIG. 20 and Table 14 depict the efficacy of ADCs in H1703 xenografts models. The results suggest that both the ML66-999 and ML66-22a conjugates demonstrated dose dependent anti-tumor activity and were efficacious in the H1703 tumor xenograft model.

TABLE 14

H1703 efficacy study results

| ADC (DAR) | ADC Dose | | H1703 | | |
|---|---|---|---|---|---|
| | μg/kg payload | mg/kg Ab | T/C (Day 43) | PR | CR |
| KTI-999 (7.6) | 250 | 9.9 | 58 | 0/6 | 0/6 |
| ML66-999 (7.6) | 250 | 9.7 | 13 | 3/6 | 1/6 |
| ML66-999 (7.6) | 75 | 2.9 | 86 | 0/6 | 0/6 |
| ML66-22a (7.5) | 250 | 9.8 | 9 | 3/6 | 0/6 |
| ML66-22a (7.5) | 75 | 2.9 | 69 | 0/6 | 0/6 |
| ML66-22b (6.4) | 250 | 11.4 | 3 | 6/6 | 0/6 |
| ML66-22b (6.4) | 75 | 3.4 | 7 | 4/6 | 2/6 |

Example 55. Anti-Tumor Activity of Anti-EGFR Antibody Drug Conjugates in Nude Mice Bearing FaDu Human Head and Neck Squamous Cell Carcinoma Xenografts The anti-tumor activity of 1, 3, and 10 mg/kg of ML66-999 and ML66-22a were evaluated in female Nude mice bearing FaDu cells, a human head and neck squamous cell carcinoma xenograft model.

Mice were inoculated with 1×10⁷ FaDu cells in 0.1 ml 50% Matrigel/50% serum free medium by subcutaneous injection in the area on the right hind flank. Female athymic Foxn1$^{nu}$ mice (6 weeks of age) were obtained. Upon receipt, the animals were observed for 7 days prior to study initiation. Animals showed no sign of disease or illness upon arrival, or prior to treatment.

Sixty-four mice were randomized into 8 groups (8 mice per group) by tumor volume. The tumor volumes ranged from 74.07 to 128.73 (104.66±15.70, Mean±SD) mm³. The mice were measured, randomized, and dosed based on the tumor volume on day 6 post implantation (11/19/18). Body weights of the mice ranged from 20.48 to 25.77 (23.55±1.25, Mean±SD) grams. Mice in each group were identified by punch method. Administration of the test agents and vehicle were carried out intravenously by using a 1.0 ml syringe fitted with a 27 gauge, ½ inch needle. Antibody drug conjugate test agents were dosed qdx1 at 1, 3, or 10 mg/kg. The groups included: a control group dosed with vehicle (PBS, 200 µL), a control group dosed with the non-targeting KTI-999 at 10 mg/kg, ML66-999 dosed at 1, 3, and 10 mg/kg, and ML66-22a dosed at 1, 3, and 10 mg/kg.

Tumor size was measured two times per week in three dimensions using a caliper. The tumor volume was expressed in mm³ using the formula Volume=Length x Width x Height×½. A mouse was considered to have a partial regression (PR) when tumor volume was reduced by 50% or greater and a complete tumor regression (CR) was when no palpable tumor could be detected. Tumor volume was determined by StudyLog software.

Tumor growth inhibition (% T/C) is the ratio of the median tumor volume (TV) of the treatment group (T) to the median TV of the control group (C) at a predetermined time (e.g. the time when the median TV for control tumors reach a maximum tumor volume 1000 mm³, which is when the mice are euthanized). % T/C was calculated on day 21 post inoculation, when the median TV of the control group reached 749 mm³. According to NCI standards, a T/C≤42% is the minimum level of anti-tumor activity and a T/C<10% is considered a high anti-tumor activity level.

Body weight (BW) of all the mice was measured two times per week as a rough index of drug toxicity and was determined by StudyLog software. Body weights of mice were expressed as percent change in body weight from the pre-treatment body weight as follows: % BW change= [(BWpost/BWpre)−1]×100, where BWpost is weight after treatment and BWpre is the starting body weight prior to treatment. Percent body weight loss (BWL) was expressed as the mean change in body weight post treatment. Animals were euthanized if the tumor volume became larger than 1000 mm³, the tumors became necrotic, the mice lost >20% of their initial body weight, or the mice become moribund at any time during the study.

Figure 18:
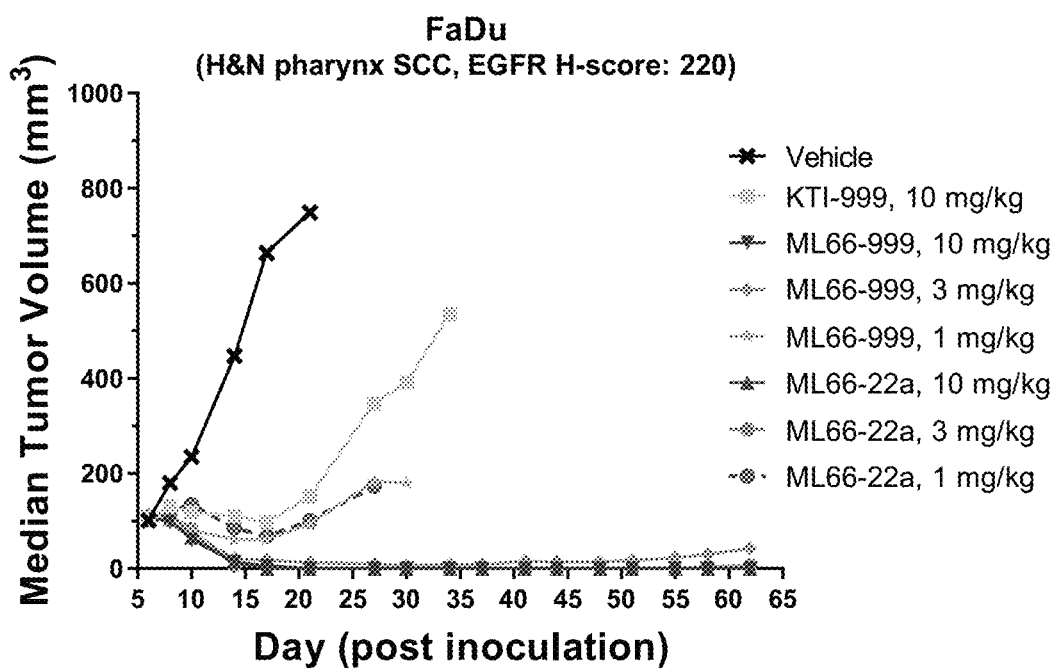
FIG. 18 depicts the efficacy of ADCs in a FaDu xenograft models. Dosing is based on payload (75 µg/kg and 250 µg/kg are 3 mg/kg and 10 mg/kg based on antibody).

FIG. 18 and Table 13 depict the efficacy of ADCs in a FaDu xenograft models. The ML66-999 and ML66-22a conjugates had similar anti-tumor activity. ML66-KTI dosed at 10 mg/kg had a T/C value of 20% (active), with 2 partial tumor regressions out of 8 mice and 2 complete regressions. This demonstrated that some of the anti-tumor activity in this model is non-targeted. ML66-999 dosed at 1 mg/kg had a T/C value of 12% (active), with 4 partial tumor regressions out of 8 mice and 2 complete regressions. ML66-999 dosed at 3 mg/kg had a T/C value of 2% (highly active), with 8 partial tumor regressions out of 8 mice and 4 complete regressions. ML66-999 dosed at 10 mg/kg had a T/C value of 0% (highly active), with 8 partial tumor regressions out of 8 mice and 8 complete regressions. ML66-22a dosed at 1 mg/kg had a T/C value of 13% (active), with 4 partial tumor regressions out of 8 mice and 3 complete regressions. ML66-22a dosed at 3 mg/kg had a T/C value of 0% (highly active), with 8 partial tumor regressions out of 8 mice and 8 complete regressions. ML66-22a dosed at 10 mg/kg had a T/C value of 0% (highly active), with 8 partial tumor regressions out of 8 mice and 8 complete regressions. No significant body weight loss was observed at any of the indicated doses for any of the conjugates indicating that the conjugates were well tolerated. The results from this study suggest that both the ML66-999 and ML66-22a conjugates demonstrated dose dependent anti-tumor activity and were efficacious in the FaDu head and neck squamous cell carcinoma tumor xenograft model.

TABLE 13

| ADC, dose (mg/kg) | T/C Day 21 | PR | CR |
| --- | --- | --- | --- |
| KTI-999 (10) | 20% | 2/8 | 2/8 |
| ML66-999 (10) | 0% | 8/8 | 8/8 |
| ML66-999 (3) | 2% | 8/8 | 4/8 |
| ML66-999 (1) | 12% | 4/8 | 2/8 |
| ML66-22a (10) | 0% | 8/8 | 8/8 |
| ML66-22a (3) | 0% | 8/8 | 8/8 |
| ML66-22a (1) | 13% | 4/8 | 3/8 |

Example 56. Mouse Tolerability of Ab$_F$-999 and Ab$_F$-22a ADCs

Figure 21:
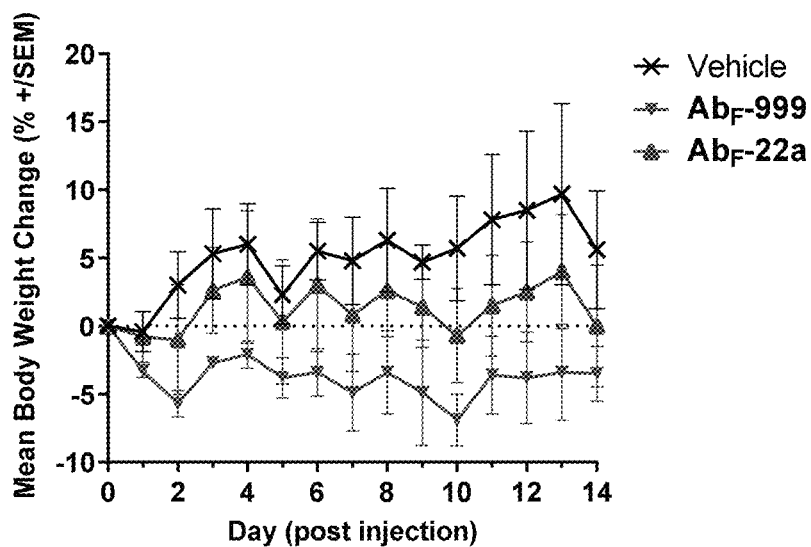
FIG. 21 depicts the mouse tolerability of non-cross-reactive ADCs at 5000 µg/kg payload dose (~200 mg/kg based on the Ab component). $Ab_F$=humanized anti-folate receptor antibody.

The tolerability of non-cross-reactive ADCs was evaluated in female CD-1 mice by performing daily body weight measurements and clinical observations for 2 weeks following injection of the ADCs. Three groups of three mice each were dosed with an IV bolus injection of 5000 µg/kg based on payload of Ab$_F$-22a (184 mg/kg based on antibody) or Ab$_F$-999 (198 mg/kg antibody). The maximum tolerated dose (MTD) was defined as the highest dose at which no animals died or were required to be euthanized due to >20% body weight loss or signs of distress or morbidity (hunching, lack of movement, inability to eat or drink, or signs of pain/distress). GraphPad was used for statistical analyses of the body weights in each group (two-way ANOVA with a Tukey's multiple comparisons test showed that the Ab$_F$-999 group was significantly different from both the vehicle and Ab$_F$-22a groups, p<0.05). FIG. 21 depicts these results.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Embodiments of the Disclosure

1. A compound of Formula I, or a pharmaceutically acceptable salt, thereof:

Z-L$^1$-D    (Formula I)

wherein:
D is represented by the following structural formula:

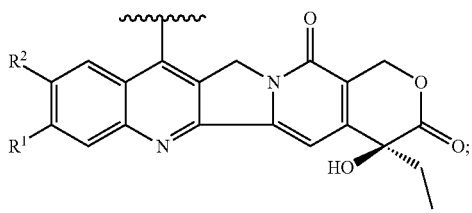

$R^1$ is —F, —CH$_3$, or —CF$_3$;
$R^2$ is —H, —F, —OR$^3$, —SR$^3$, —S(O)R$^4$, —S(O)$_2$R$^4$, C$_1$-C$_6$ alkyl, or C$_1$-C$_6$ fluoroalkyl; or $R^1$ and $R^2$ taken together with the carbon atoms to which they are attached form a methylenedioxy or a difluoromethylenedioxy ring;
$R^3$ is H or C$_1$-C$_6$ alkyl;
$R^4$ is C$_1$-C$_6$ alkyl;
$L^1$ is absent, —(C$_1$-C$_6$ alkylene)-, —(C$_1$-C$_6$ alkylene)-X$^1$—(C$_1$-C$_6$ alkylene)-, —X$^{1'}$—(C$_1$-C$_6$ alkylene)-*, or —(C$_1$-C$_6$ alkylene)-X$^1$-L$^2$-*; where * is the site covalently attached to Z;

X$^1$ is —O—, —S—, —S(O)—, —S(O)$_2$—, —C(=O)—, —NR$^5$—, —NR$^5$C(=O)—, or —C(=O)NR$^5$—;
X$^{1'}$ is —O—, —S—, —S(O)—, or —S(O)$_2$—;
L$^2$ is phenylene;
each R$^5$ is independently —H, C$_1$-C$_6$ alkyl, C$_1$-C$_6$ fluoroalkyl, C$_3$-C$_6$ cycloalkyl, aryl, heteroaryl, or benzyl;
Z is —H or —X$^2$;
X$^2$ is —OR$^6$, —SR$^6$, —S(O)R$^6$, —S(O)$_2$R$^6$, —SSR$^6$, or —N(R$^6$)$_2$;
each R$^6$ is independently —H, C$_1$-C$_6$ alkyl, C$_1$-C$_6$ fluoroalkyl, C$_3$-C$_6$ cycloalkyl, aryl, heteroaryl, or benzyl;
L$^1$ and L$^2$ are each independently optionally substituted with 1-4 substituents selected from halogen, —CN, —OR', —SR', —N(R$^7$)$_2$, C$_1$-C$_6$ alkyl, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, or heteroaryl; and
each R$^7$ is independently H, C$_1$-C$_6$ alkyl, C$_1$-C$_6$ fluoroalkyl, C$_3$-C$_6$ cycloalkyl, aryl, heteroaryl, or benzyl;
with the proviso that if R$^1$ is F, then L$^1$ is —(C$_1$-C$_6$ alkylene)-, —(C$_1$-C$_6$ alkylene)-X$^1$—(C$_1$-C$_6$ alkylene)-, —X$^{1'}$—(C$_1$-C$_6$ alkylene)-*, or —(C$_1$-C$_6$ alkylene)-X$^1$-L$^2$-*; where * is the site covalently attached to Z; and Z is —X$^2$; and
with the proviso that if R$^1$ is F and R$^2$ is OMe, then L$^1$-Z cannot be NH$_2$.

2. A compound of Formula I, or a pharmaceutically acceptable salt, thereof:

Z-L$^1$-D    (Formula I)

wherein:
D is represented by the following structural formula:

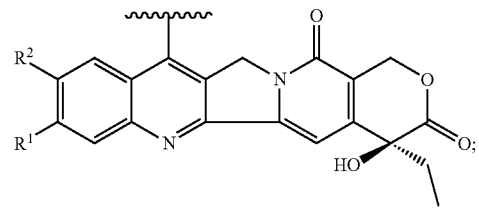

R$^1$ is —F, —CH$_3$, or 3;
R$^2$ is —H, —F, —OR$^3$, —SR$^3$, —S(O)R$^4$, —S(O)$_2$R$^4$, C$_1$-C$_6$ alkyl, or C$_1$-C$_6$ fluoroalkyl; or R$^1$ and R$^2$ taken together with the carbon atoms to which they are attached form a methylenedioxy or a difluoromethylenedioxy ring;
R$^3$ is H or C$_1$-C$_6$ alkyl;
R$^4$ is C$_1$-C$_6$ alkyl;
L$^1$ is absent, —(C$_1$-C$_6$ alkylene)-, —(C$_1$-C$_6$ alkylene)-X$^1$—(C$_1$-C$_6$ alkylene)-, —X$^{1'}$—(C$_1$-C$_6$ alkylene)-*, or —(C$_1$-C$_6$ alkylene)-X$^1$-L$^2$-*; where * is the site covalently attached to Z;
X$^1$ is —O—, —S—, —S(O)—, —S(O)$_2$—, —C(=O)—, —NR$^5$—, —NR$^5$C(=O)—, or —C(=O)NR$^5$—;
X$^{1'}$ is —O—, —S—, —S(O)—, or —S(O)$_2$—;
L$^2$ is phenylene;
each R$^5$ is independently —H, C$_1$-C$_6$ alkyl, C$_1$-C$_6$ fluoroalkyl, C$_3$-C$_6$ cycloalkyl, aryl, heteroaryl, or benzyl;
Z is —H or —X$^2$;
X$^2$ is —OR$^6$, —SR$^6$, —S(O)R$^6$, —S(O)$_2$R$^6$, —SSR$^6$, or —N(R$^6$)$_2$;
each R$^6$ is independently —H, C$_1$-C$_6$ alkyl, C$_1$-C$_6$ fluoroalkyl, C$_3$-C$_6$ cycloalkyl, aryl, heteroaryl, or benzyl;
L$^1$ and L$^2$ are each independently optionally substituted with 1-4 substituents selected from halogen, —CN, —SR⁷, —N(R⁷)₂, $C_1$-$C_6$ alkyl, $C_1$-$C_6$ fluoroalkyl, $C_1$-$C_6$ heteroalkyl, $C_3$-$C_6$ cycloalkyl, $C_2$-$C_{10}$ heterocycloalkyl, aryl, or heteroaryl; and each R⁷ is independently H, $C_1$-$C_6$ alkyl, $C_1$-$C_6$ fluoroalkyl, $C_3$-$C_6$ cycloalkyl, aryl, heteroaryl, or benzyl;

with the proviso that if R¹ is F, then L¹ is —($C_1$-$C_6$ alkylene)-, alkylene)-X¹—($C_1$-$C_6$ alkylene)-, alkylene)-*, or —($C_1$-$C_6$ alkylene)-X¹-L²-*; where * is the site covalently attached to Z; and Z is —X²;

with the proviso that if R¹ is F and R² is OMe, then cannot be NH₂; and with the proviso that if R¹ is F and R² is Me, then cannot be CH₂OH.

3. The compound of embodiment 1 or embodiment 2, wherein R¹ is —H or —F.

4. The compound of any one of embodiments 1-3, wherein R¹ is —F.

5. The compound of any one of embodiments 1-4, R² is —H, —F, —OCF₃, —CF₃, —OMe, —OEt, —SMe, —S(O)Me, —S(O)₂Me, —SEt, —S(O)Et, —S(O₂)Et, methyl, or ethyl.

6. The compound of any one of embodiments 1-5, wherein R² is —F.

7. The compound of any one of embodiments 1-5, wherein R² is —OMe, —SMe, —S(O)Me, or methyl.

8. The compound of any one of embodiments 1-5, wherein R² is methyl. 9. The compound of embodiment 1 or embodiment 2, wherein R¹ is —F and R² is —F.

10. The compound of embodiment 1 or embodiment 2, wherein R¹ is methyl and R² is —F.

11. The compound of embodiment 1 or embodiment 2, wherein R¹ is —F and R² is -methyl.

12. The compound of any one of embodiments 1-11, wherein -L¹-Z is —H.

13. The compound of any one of embodiments 1-11, wherein -12-Z is —($C_1$-$C_6$ alkylene)-H, or —($C_1$-$C_6$ alkylene)-X².

14. The compound of embodiment 13, wherein -L¹-Z is methyl, ethyl, propyl, or butyl.

15. The compound of any one of embodiments 1-11, wherein -12-Z is —($C_1$-$C_4$ alkylene)-OR⁶, —($C_1$-$C_4$ alkylene)-SR⁶, or —($C_1$-$C_4$ alkylene)-N(R⁶)₂.

16. The compound of embodiment 15, wherein -12-Z is —CH₂OH, —(CH₂)₂OH, —(CH₂)₃OH, —(CH₂)₄OH, —CH₂OMe, —(CH₂)₂OMe, —(CH₂)₃OMe, —(CH₂)₄OMe, —CH₂SH, —(CH₂)₂SH, —(CH₂)₃SH, —(CH₂)₄SH, —CH₂SMe, —(CH₂)₂SMe, —(CH₂)₃SMe, —(CH₂)₄SMe, —CH₂NH₂, —(CH₂)₂NH₂, —(CH₂)₃NH₂, —(CH₂)₄NH₂, 17. The compound of embodiments any one of 1-11, wherein -12-Z is —($C_1$-$C_5$ alkylene)-NR⁵C(=O)—($C_1$-$C_5$ alkylene)-OR⁶, —($C_1$-$C_5$ alkylene)-NR⁵C(=O)—($C_1$-$C_5$ alkylene)-SR⁶, —($C_1$-$C_5$ alkylene)-S—($C_1$-$C_5$ alkylene)-SR⁶, or —($C_1$-$C_5$ alkylene)-S—($C_1$-$C_5$ alkylene)-SSR⁶.

18. The compound of embodiment 17, wherein -12-Z is —CH₂NHC(=O)CH₂OH, —CH₂NHC(=O)(CH₂)₂OH, —CH₂NHC(=O)(CH₂)₃OH, —CH₂NHC(=O)(CH₂)₄OH, —CH₂NHC(=O)(CH₂)₅₀H, —CH₂NHC(=O)CH₂OMe, —CH₂NHC(=O)(CH₂)₂OMe, —CH₂NHC(=O)(CH₂)₃OMe, —CH₂NHC(=O)(CH₂)₄OMe, —CH₂NHC(=O)(CH₂)₅OMe, —CH₂NHC(=O)CH₂SH, —CH₂NHC(=O)(CH₂)₂SH, —CH₂NHC(=O)(CH₂)₃SH, —CH₂NHC(=O)(CH₂)₄SH, —CH₂NHC(=O)(CH₂)₅SH, CH₂SMe, —CH₂NHC(=O)(CH₂)₂SMe, —CH₂NHC(=O)(CH₂)₃SMe, —CH₂NHC(=O)(CH₂)₄SMe, —CH₂NHC(=O)(CH₂)₅SMe, —CH₂SCH₂OH, —CH₂S(CH₂)₂OH, —CH₂S(CH₂)₃OH, —CH₂S(CH₂)₄OH, —CH₂S(CH₂)₅OH, —CH₂SCH₂OMe, —CH₂S(CH₂)₂OMe, —CH₂S(CH₂)₃OMe, —CH₂S(CH₂)₄OMe, —CH₂S(CH₂)₅OMe, —CH₂SCH₂SH, —CH₂S(CH₂)₂SH, —CH₂S(CH₂)₃SH, —CH₂S(CH₂)₄SH, —CH₂S(CH₂)₅SH, —CH₂SCH₂SMe, —CH₂S(CH₂)₂SMe, —CH₂S(CH₂)₃SMe, —CH₂S(CH₂)₄SMe, or —CH₂S(CH₂)₅SMe.

19. The compound of embodiment 17 or embodiment 18, wherein each R⁵ is independently —H, methyl, or benzyl.

20. The compound of any one of embodiments 15-18, wherein each R⁶ is independently —H, methyl, or benzyl.

21. The compound of any one of embodiments 1-11, wherein -12-Z is —X¹'—($C_1$-$C_4$ alkylene)-X².

22. The compound of embodiment 21, wherein -12-Z is —OCH₂OH, —O(CH₂)₂OH, —O(CH₂)₃OH, —O(CH₂)₄OH, —SCH₂OH, —S(CH₂)₂OH, —S(CH₂)₃OH, —S(CH₂)₄OH, —S(O)CH₂OH, —S(O)(CH₂)₂OH, —S(O)(CH₂)₃OH, —S(O)(CH₂)₄OH, —S(O)₂CH₂OH, —S(O)₂(CH₂)₂OH, —S(O)₂(CH₂)₃OH, —S(O)₂(CH₂)₄OH, —OCH₂SMe, —O(CH₂)₂SMe, —O(CH₂)₃SMe, —O(CH₂)₄SMe, —SCH₂SMe, —S(CH₂)₂SMe, —S(CH₂)₃SMe, —S(CH₂)₄SMe, —S(O)CH₂SMe, —S(O)(CH₂)₂SMe, —S(O)(CH₂)₃SMe, —S(O)(CH₂)₄SMe, —S(O)₂CH₂SMe, —S(O)₂(CH₂)₂SMe, —S(O)₂(CH₂)₃SMe, or —S(O)₂(CH₂)₄SMe.

23. The compound of any one of embodiments 1-11, wherein -12-Z is —($C_1$-$C_6$ alkylene)-X¹-L²-X².

24. The compound of embodiment 23, wherein -12-Z is

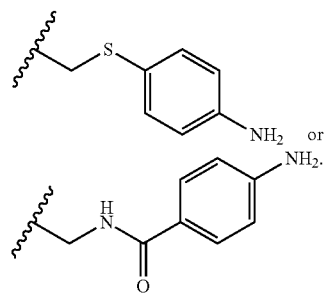

25. The compound of embodiment 1, wherein the compound is any one of the compounds selected from the following:

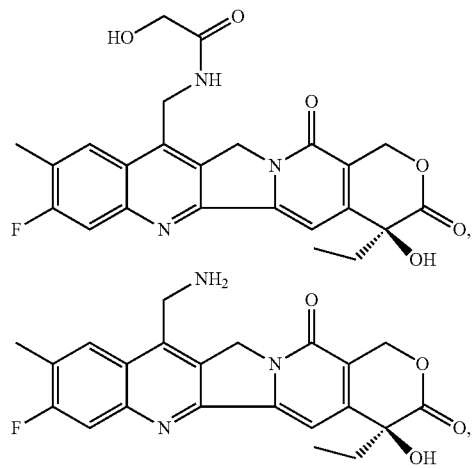

215
-continued

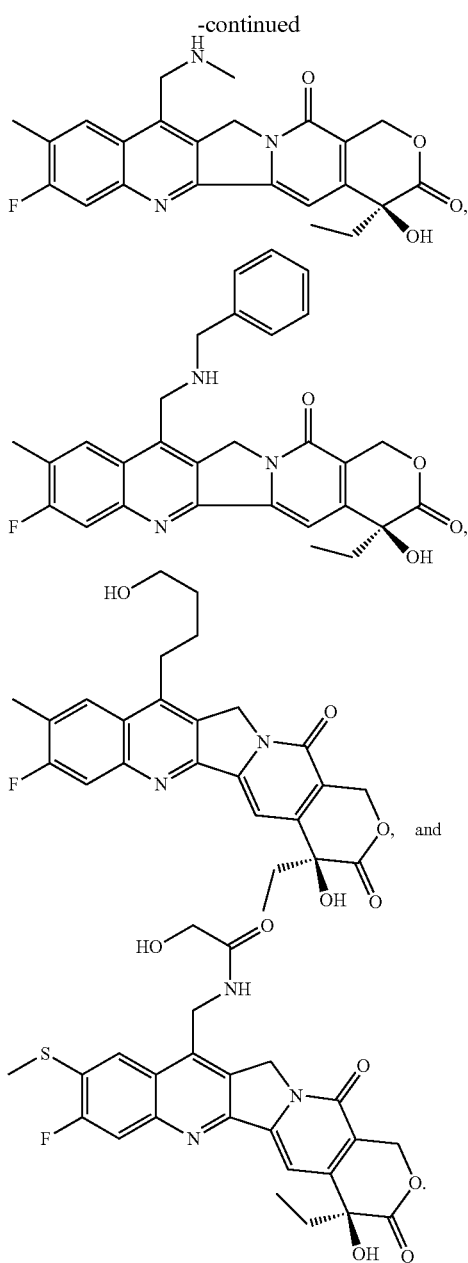

26. The compound of embodiment 1, wherein the compound is any one of the compounds selected from Table 1B.
27. A compound of Formula II, or a pharmaceutically acceptable salt thereof:

E-A-Z'-L¹-D　　(Formula II)

wherein:
D is represented by the following structural formula

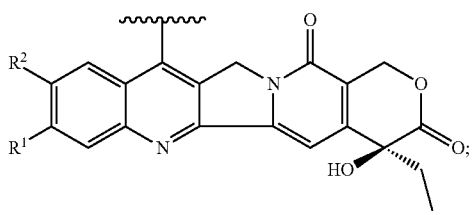

216

$R^1$ is —H, —F, —CH$_3$, or —CF$_3$;

$R^2$ is —H, —F, —OR$^3$, —SR$^3$, —S(O)R$^4$, —S(O)$_2$R$^4$, C$_1$-C$_6$ alkyl, or C$_1$-C$_6$ fluoroalkyl; or R$^1$ and R$^2$ taken together with the carbon atoms to which they are attached form a methylenedioxy or a difluoromethylenedioxy ring; with the proviso that both R$^1$ and R$^2$ cannot be —H;

$R^3$ is H or C$_1$-C$_6$ alkyl;

$R^4$ is C$_1$-C$_6$ alkyl;

$L^1$ is absent, —(C$_1$-C$_6$ alkylene)-, —(C$_1$-C$_6$ alkylene)-X$^1$—(C$_1$-C$_6$ alkylene)-, X$^{1\prime}$—(C$_1$-C$_6$ alkylene)-* or —(C$_1$-C$_6$ alkylene)-X$^1$-L$^2$-*; where * is the site covalently attached to Z';

$X^1$ is —O—, —S—, —S(O)—, —S(O)$_2$—, —C(=O)—, —NR$^5$C(=O)—, or —C(=O)NR$^5$—;

$X^{1\prime}$ is —O—, —S—, —S(O)—, or —S(O)$_2$—;

$L^2$ is phenylene;

each R$^5$ is independently —H, C$_1$-C$_6$ alkyl, C$_1$-C$_6$ fluoroalkyl, C$_3$-C$_6$ cycloalkyl, aryl, heteroaryl, or benzyl;

Z' is —O—CH$_2$—NR$^8$—*, —S—CH$_2$—NR$^8$—*, —NR$^8$—*; where * is the site covalently attached to A;

each R$^8$ is independently —H, C$_1$-C$_6$ alkyl, C$_1$-C$_6$ fluoroalkyl, C$_3$-C$_6$ cycloalkyl, aryl, heteroaryl, or benzyl;

L$^1$ and L$^2$ are each independently optionally substituted with 1-4 substituents selected from halogen, —CN, —OR$^7$, —SR$^7$, —N(R$^7$)$_2$, C$_1$-C$_6$ alkyl, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, or heteroaryl; and each R$^7$ is independently H, C$_1$-C$_6$ alkyl, C$_1$-C$_6$ fluoroalkyl, C$_3$-C$_6$ cycloalkyl, aryl, heteroaryl, or benzyl;

A is a peptide comprising 2 to 10 amino acids; wherein A is optionally substituted with one or more polyol; and E is —C(=O)-L$^3$-X$^3$;

L$^3$ is —(C$_1$-C$_{10}$ alkylene)- or —Y$^1$—(C$_1$-C$_{10}$ alkylene)-X$^4$—Y$^2$—(C$_1$-C$_{10}$ alkylene)-*; where * is the site covalently attached to X$^3$;

Y$^1$ is absent, —(CR$^a$R$^b$O)$_n$—, or —(CR$^a$R$^b$CR$^{a\prime}$R$^{b\prime}$O)$_m$—;

X$^4$ is —NR$^9$C(=O)— or —C(=O)NR$^9$—;

Y$^2$ is absent, —(CR$^c$R$^d$O)$_o$—, or —(CR$^c$R$^d$CR$^{c\prime}$R$^{d\prime}$O)$_p$—;

n, m, o, and p are each independently 1-10;

each R$^a$, R$^b$, R$^{a\prime}$, R$^{b\prime}$, R$^c$, R$^d$, R$^{c\prime}$, and R$^{d\prime}$ are independently —H, C$_1$-C$_6$ alkyl, C$_1$-C$_6$ fluoroalkyl, C$_3$-C$_6$ cycloalkyl, aryl, heteroaryl, or benzyl;

wherein L$^3$ is optionally substituted with 0-4 substituents selected from halogen, —CN, —OR$^{11}$, —SR$^{11}$, —N(R$^{11}$)$_2$, C$_1$-C$_6$ alkyl, C$_1$-C$_6$ fluoroalkyl, C$_1$-C$_6$ heteroalkyl, C$_3$-C$_6$ cycloalkyl, C$_2$-C$_{10}$ heterocycloalkyl, aryl, heteroaryl, and polyol;

each R" is independently H, C$_1$-C$_6$ alkyl, C$_1$-C$_6$ fluoroalkyl, C$_3$-C$_6$ cycloalkyl, aryl, heteroaryl, or benzyl;

$X^3$ is

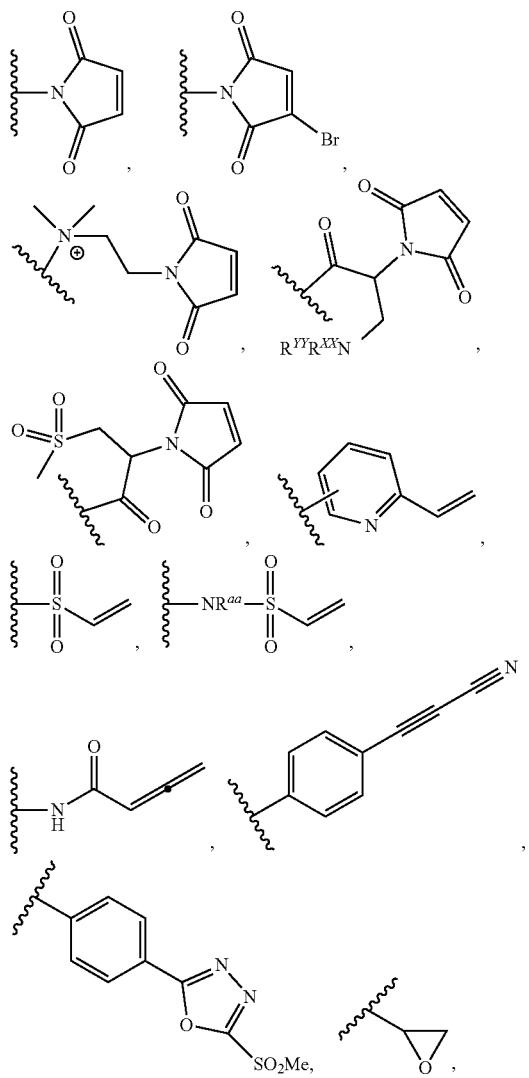

—C(=O)—CR$^{bb}$R$^{cc}$—W', —NR''—C(=O)—CR$^{bb}$R$^{cc}$—W', or —SR$^m$;

each W' is independently —H, —N(R$^{gg}$)$_2$, $C_1$-$C_{10}$ alkyl, $C_1$-$C_{10}$ alkenyl, $C_1$-$C_{10}$ alkynyl, $C_3$-$C_6$ cycloalkyl, aryl, heteroaryl, or —(CH$_2$CH$_2$O)$_q$—R$^{ff}$;

q is 1 to 24;

each R$^{aa}$, R$^{bb}$, R$^{cc}$, R$^{ee}$, and R$^{ff}$ are independently —H or optionally substituted $C_1$-$C_6$ alkyl;

each R$^{YY}$ and R$^o$ are independently —H or $C_1$-$C_6$ alkyl;

R$^{gg}$ are each independently —H or $C_1$-$C_6$ alkyl; and

R$^9$ and R$^{10}$ are each independently —H, $C_1$-$C_6$ alkyl, $C_1$-$C_6$ fluoroalkyl, $C_3$-$C_6$ cycloalkyl, aryl, heteroaryl, or benzyl.

28. The compound of embodiment 27, wherein R$^1$ is —H or —F.

29. The compound of embodiment 27 or embodiment 28, wherein R$^1$ is —F.

30. The compound of any one of embodiments 27-29, R$^2$ is H, —F, —OCF$_3$, —CF$_3$, —OMe, -OEt, —SMe, —S(O)Me, —S(O)$_2$Me, —SEt, —S(O)Et, —S(O$_2$)Et, methyl, or ethyl.

31. The compound of any one of embodiments 27-30, wherein R$^2$ is —F.

32. The compound of any one of embodiments 27-30, wherein R$^2$ is —OMe, —SMe, —S(O)Me, or methyl.

33. The compound of any one of embodiments 27-30, wherein R$^2$ is methyl.

34. The compound of embodiment 27, wherein R$^1$ is —F and R$^2$ is —F.

35. The compound of embodiment 27, wherein R$^1$ is methyl and R$^2$ is —F.

36. The compound of embodiment 27, wherein R$^1$ is —F and R$^2$ is -methyl.

37. The compound of any one of embodiments 27-36, wherein -L$^1$-Z'—* is —(C$_1$-C$_4$ alkylene)-O—CH$_2$—NR$^8$—*, —(C$_1$-C$_4$ alkylene)-S—CH$_2$—NR$^8$—*, or —(C$_1$-C$_4$ alkylene)-NR$^8$—*, where * is the site covalently attached to A.

38. The compound of embodiment 37, wherein -L$^1$-Z'—* is —CH$_2$O—CH$_2$NH—*, —(CH$_2$)$_{20}$—CH$_2$NH—*, —(CH$_2$)$_3$O—CH$_2$NH—*, —(CH$_2$)$_4$O—CH$_2$NH—*, —CH$_2$S—CH$_2$NH—*, —(CH$_2$)$_2$S—CH$_2$NH—*, —(CH$_2$)$_3$S—CH$_2$NH—*, —(CH$_2$)$_4$S—CH$_2$NH—*, —CH$_2$NH—*, —(CH$_2$)$_2$NH—*, —(CH$_2$)$_3$NH—*, or —(CH$_2$)$_4$NH—.

39. The compound of any one of embodiments 27-36, wherein -L$^1$-Z'—* is —(C$_1$-C$_5$ alkylene)-NR$^5$C(=O)—(C$_1$-C$_5$ alkylene)-O—CH$_2$—NR$^8$—*, —(C$_1$-C$_5$ alkylene)-NR$^5$C(=O)—(C$_1$-C$_5$ alkylene)-S—CH$_2$—NR$^8$—*, —(C$_1$-C$_5$ alkylene)-S—(C$_1$-C$_5$ alkylene)-S—CH$_2$—NR$^8$—*, or —(C$_1$-C$_5$ alkylene)-S—(C$_1$-C$_5$ alkylene)-SS—CH$_2$—NR$^8$—*, where * is the site covalently attached to A.

40. The compound of embodiment 39, wherein -L$^1$-Z'—* is —CH$_2$NHC(=O)CH$_2$O—CH$_2$—NH—*, —CH$_2$NHC(=O)(CH$_2$)$_2$O—CH$_2$—NH—*, —CH$_2$NHC(=O)(CH$_2$)$_3$O—CH$_2$—NH—*, —CH$_2$NHC(=O)(CH$_2$)$_4$O—CH$_2$—NH—*, —CH$_2$NHC(=O)(CH$_2$)$_5$O—CH$_2$—NH—*, —CH$_2$NHC(=O)CH$_2$S—CH$_2$—NH—*, —CH$_2$NHC(=O)(CH$_2$)$_2$S—CH$_2$—NH—*, —CH$_2$NHC(=O)(CH$_2$)$_3$S—CH$_2$—NH—*, —CH$_2$NHC(=O)(CH$_2$)$_4$S—CH$_2$—NH—*, —CH$_2$NHC(=O)(CH$_2$)$_5$S—CH$_2$—NH—*, —CH$_2$SCH$_2$O—CH$_2$—NH—*, —CH$_2$S(CH$_2$)$_2$O—CH$_2$—NH—*, —CH$_2$S(CH$_2$)$_3$O—CH$_2$—NH—*, —CH$_2$S(CH$_2$)$_4$O—CH$_2$—NH—*, —CH$_2$S(CH$_2$)$_5$O—CH$_2$—NH—*, —CH$_2$SCH$_2$S—CH$_2$—NH—*, —CH$_2$S(CH$_2$)$_2$S—CH$_2$—NH—*, —CH$_2$S(CH$_2$)$_3$S—CH$_2$—NH—*, —CH$_2$S(CH$_2$)$_4$S—CH$_2$—NH—*, or —CH$_2$S(CH$_2$)$_5$S—CH$_2$—NH—*.

41. The compound of embodiment 39 or embodiment 40, wherein each R$^5$ is independently —H, methyl, or benzyl.

42. The compound of any one of embodiments 37-41, wherein each R$^8$ is independently —H, methyl, or benzyl.

43. The compound of any one of embodiments 27-36, wherein -L$^1$-Z'—* is —X$^{1'}$—(C$_1$-C$_4$ alkylene)-O—CH$_2$—NR$^8$—*, alkylene)-S—CH$_2$—NR$^8$—*, or —X$^y$—(C$_1$-C$_4$ alkylene)-NR$^8$—*, where * is the site covalently attached to A.

44. The compound of embodiment 43, wherein -L$^1$-Z'—* is —OCH$_2$O—CH$_2$—NH—*, —O(CH$_2$)$_{20}$—CH$_2$—NH—*, —O(CH$_2$)$_3$O—CH$_2$—NH—*, —O(CH$_2$)$_4$O—CH$_2$—NH—*, —SCH$_2$O—CH$_2$—NH—*, —S(CH$_2$)$_2$O—CH$_2$—NH—*, —S(CH$_2$)$_3$O—CH$_2$—NH—*, —S(CH$_2$)$_4$O—CH$_2$—NH—*, —S(O)CH$_2$O—CH$_2$—NH—*, —S(O)(CH$_2$)$_2$O—CH$_2$—NH—*, —S(O)(CH$_2$)$_3$O—CH$_2$—NH—*, —S(O)(CH$_2$)$_4$O—CH$_2$—NH—*, —S(O)$_2$CH$_2$O—CH$_2$—NH—*, —S(O)$_2$(CH$_2$)$_2$O—CH$_2$—NH—*, —S(O)$_2$(CH$_2$)$_3$O—CH$_2$—NH—*, —S(O)$_2$(CH$_2$)$_4$O—CH$_2$—NH—*, —OCH$_2$S—

CH₂—NH—*, —O(CH₂)₂S—CH₂—NH—*, —O(CH₂)₃S—CH₂—NH—*, —O(CH₂)₄S—CH₂—NH—*, —SCH₂S—CH₂—NH—*, —S(CH₂)₂S—CH₂—NH—*, —S(CH₂)₃S—CH₂—NH—*, —S(CH₂)₄S—CH₂—NH—*, —S(O)CH₂S—CH₂—NH—*, —S(O)(CH₂)₂S—CH₂—NH—*, —S(O)(CH₂)₃S—CH₂—NH—*, —S(O)(CH₂)₄S—CH₂—NH—*, —S(O)₂CH₂S—CH₂—NH—*, —S(O)₂(CH₂)₂S—CH₂—NH—*, —S(O)₂(CH₂)₃S—CH₂—NH—*, —S(O)₂(CH₂)₄S—CH₂—NH—*, —OCH₂—NH—*, —O(CH₂)₂—NH—*, —O(CH₂)₃—NH—*, —O(CH₂)₄S—NH—*, —SCH₂—NH—*, —S(CH₂)₂—NH—*, —S(CH₂)₃—NH—*, —S(CH₂)₄—NH—*, —S(O)CH₂—NH—*, —S(O)(CH₂)₂—NH—*, —S(O)(CH₂)₃—NH—*, —S(O)(CH₂)₄—NH—*, —S(O)₂CH₂—NH—*, —S(O)₂(CH₂)₂—NH—*, —S(O)₂(CH₂)₃—NH—*, or —S(O)₂(CH₂)₄—NH—*.

45. The compound of any one of embodiments 27-36, wherein -L¹-Z'—* is —(C₁-C₆ alkylene)-X¹-L²-Z'—*, where * is the site covalently attached to A.

46. The compound of embodiment 45, wherein -L¹-Z'—* is

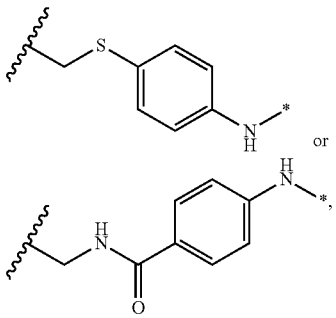

where * is the site covalently attached to A.

47. The compound of any one of embodiments 27-46, wherein A is a peptide comprising 2 to 8 amino acids.
48. The compound of any one of embodiments 27-47, wherein A is a peptide comprising 2 to 4 amino acids.
49. The compound of any one of embodiments 27-48, wherein at least one amino acid in said peptide is a L amino acid.
50. The compound of any one of embodiments 27-49, wherein each amino acid in said peptide is a L amino acid.
51. The compound of any one of embodiments 27-48, wherein at least one amino acid in said peptide is a D amino acid.
52. The compound of any one of embodiments 27-46, wherein A is -(AA¹)-(AA²)$_{a1}$-*, where * is the site covalently attached to E; AA' and AA² are each independently an amino acid residue; and a1 is an integer from 1-9.
53. The compound of embodiment 52, wherein -AA1-(AA2)a1-* is -Gly-Gly-Gly-*, -Ala-Val-*, -Val-Ala-*, -Val-Cit-*, -Val-Lys-*, -Lys-Val-*, -Phe-Lys-*, -Lys-Phe-*, -Lys-Lys-*, -Ala-Lys-*, -Lys-Ala-*, -Phe-Cit-*, -Cit-Phe-*, -Leu-Cit-*, -Cit-Leu-*, -Ile -Cit-*, -Phe-Ala-*, -Ala-Phe-*, -Phe-N9-tosyl-Arg-*, —N9-tosyl-Arg-Phe-*, -Phe-N9-nitro-Arg-*, —N9-nitro-Arg-Phe *, -Phe-Phe-Lys-*, -Lys-Phe-Phe-*, -Gly-Phe-Lys-*, Lys-Phe-Gly-*, -Leu-Ala-Leu-*, -Ile-Ala-Leu-*, -Leu-Ala-Ile-*, -Val-Ala-Val-*, -Ala-Leu-Ala-Leu-(SEQ ID NO: 89)*, -Leu-Ala-Leu-Ala-(SEQ ID NO: 90)*, -β-Ala-Leu-Ala-Leu-(SEQ ID NO: 91)*, -Gly-Phe-Leu-Gly- (SEQ ID NO: 92)*, -Gly-Leu-Phe-Gly- (SEQ ID NO: 93)*, -Val-Arg-*, -Arg-Val-*, -Arg-Arg-*, -Ala-Ala-*, -Ala-Met-*, -Met-Ala-*, -Thr-Thr-*, -Thr-Met-*, -Met-Thr-*, -Leu-Ala-*, -Ala-Leu-*, -Cit-Val-*, -Gln-Val-*, -Val-Gln-*, —Ser-Val-*, -Val-Ser-*, —Ser-Ala-*, —Ser-Gly-*, -Ala-Ser-*, -Gly-Ser-*, -Leu-Gln-*, -Gln-Leu-*, -Phe-Arg-*, -Arg-Phe-*, -Tyr-Arg-*, -Arg-Tyr-*, -Phe-Gln-*, -Gln-Phe-*, -Val-Thr-*, -Thr-Val-*, -Met-Tyr-*, and -Tyr-Met-*.

54. The compound of embodiment 52, wherein -AA¹-(AA²)$_{a1}$-* is -Val-D-Lys-*, -Val-D-Arg-*, -L-Val-Cit-*, -L-Val-Lys-*, -L-Val-Arg-*, -L-Val-D-Cit-*, -L-Phe-Phe-Lys-*, -L-Val-D-Lys-*, -L-Val-D-Arg-*, -L-Arg-D-Arg-*, -L-Ala-Ala-*, -L-Ala-D-Ala-*, -Ala-D-Ala-*, -Val-D-Cit-*, -L-Ala-L-Ala-*, -L-Ala-L-Val-*, -L-Gln-L-Val-*, -L-Gln-L-Leu-*, or -L-Ser-L-Val-*.

55. The compound of embodiment 52, wherein -AA¹-(AA²)$_{a1}$-* is:
-Ala-Ala-*,
-Ala-Val-*,
-Val-Ala-*
-Gln-Leu-*,
-Leu-Gln-*
-Ala-Ala-Ala-*,
-Ala-Ala-Ala-Ala- (SEQ ID NO: 94)*,
-Gly-Ala-Gly-Gly- (SEQ ID NO: 95)*,
-Gly-Gly-Ala-Gly- (SEQ ID NO: 96)*,
-Gly-Val-Gly-Gly- (SEQ ID NO: 97)*,
-Gly-Gly-Val-Gly- (SEQ ID NO: 98)*,
-Gly-Phe-Gly-Gly- (SEQ ID NO: 99)*, or
-Gly-Gly-Phe-Gly- (SEQ ID NO: 100)*.

56. The compound of embodiment 52, wherein -AA¹-(AA²)$_{a1}$-* is:
-L-Ala-L-Ala-*,
-L-Ala-D-Ala-*,
-L-Ala-L-Val-*,
-L-Ala-D-Val-*,
-L-Val-L-Ala-*,
-L-Val-D-Ala-*
-L-Gln-L-Leu-*,
-L-Gln-D-Leu-*,
-L-Leu-L-Gln-*,
-L-Leu-D-Gln-*,
-L-Ala-L-Ala-L-Ala-*,
-L-Ala-D-Ala-L-Ala-*,
-L-Ala-L-Ala-D-Ala-*,
-L-Ala-L-Ala-L-Ala-L-Ala- (SEQ ID NO: 94)*,
-L-Ala-D-Ala-L-Ala-L-Ala- (SEQ ID NO: 101)*,
-L-Ala-L-Ala-D-Ala-L-Ala- (SEQ ID NO: 102)*,
-L-Ala-L-Ala-L-Ala-D-Ala- (SEQ ID NO: 103)*,
-Gly-L-Ala-Gly-Gly- (SEQ ID NO: 95)*,
-Gly-Gly-L-Ala-Gly- (SEQ ID NO: 96)*,
-Gly-D-Ala-Gly-Gly- (SEQ ID NO: 104)*,
-Gly-Gly-D-Ala-Gly- (SEQ ID NO: 105)*,
-Gly-L-Val-Gly-Gly- (SEQ ID NO: 97)*,
-Gly-Gly-L-Val-Gly- (SEQ ID NO: 98)*,
-Gly-D-Val-Gly-Gly- (SEQ ID NO: 106)*,
-Gly-Gly-D-Val-Gly- (SEQ ID NO: 107)*,
-Gly-L-Phe-Gly-Gly- (SEQ ID NO: 99)*, or
-Gly-Gly-L-Phe-Gly- (SEQ ID NO: 100)*.

57. The compound of embodiment 52, wherein -AA¹-(AA²)$_{a1}$-* is:
-L-Ala-L-Ala-*,
-L-Ala-D-Ala-LAla-*,
-L-Ala-L-Ala-L-Ala-*, or
-L-Ala-L-Ala-L-Ala-L-Ala- (SEQ ID NO: 94)*.

58. The compound of any one of embodiments 27-57, wherein A is substituted with one or more polyol.

59. The compound of any one of embodiments 27-58, wherein E is substituted with one or more polyol.

60. The compound of any one of embodiments 27-59, wherein polyol is —(C$_1$-C$_6$ alkylene)-X$^5$—Y$^3$;
wherein:
X$^5$ is —NR$^{12}$C(=O)— or —C(=O)NR$^{12}$—;
Y$^3$ is —C$_1$-C$_{10}$ alkyl, where Y$^3$ is substituted with 0-10 OH groups; and
R$^{1-2}$ is —H, C$_1$-C$_6$ alkyl, C$_1$-C$_6$ fluoroalkyl, C$_3$-C$_6$ cycloalkyl, aryl, heteroaryl, or benzyl.

61. The compound of embodiment 60, wherein polyol is

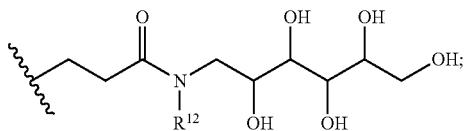

wherein R$^{1-2}$ is H or methyl.

62. The compound of any one of embodiments 27-61, wherein E is —C(=O)—(C$_1$-C$_{10}$ alkylene)-X$^3$.

63. The compound of embodiment 62, wherein E is

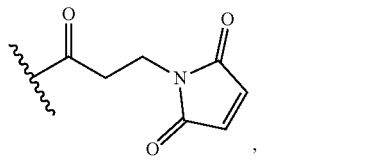,

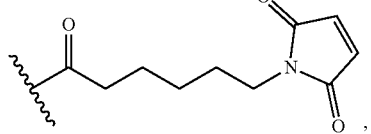,

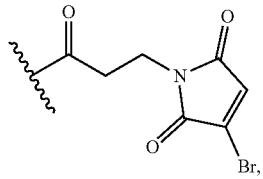,

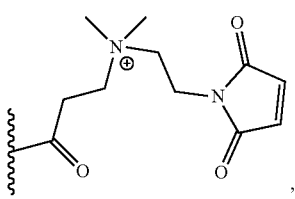,

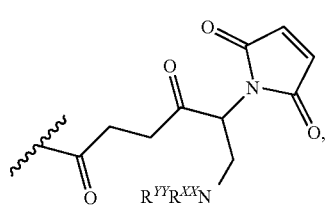,

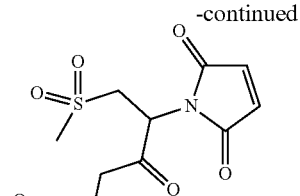,

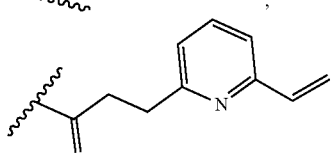,

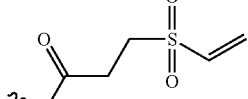,

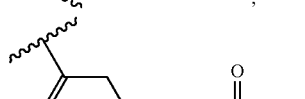,

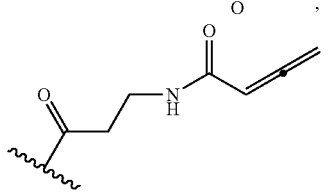,

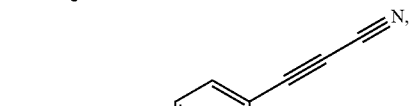,

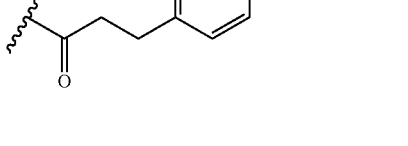,

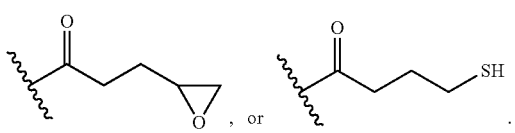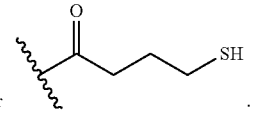.

64. The compound of any one of embodiments 27-61, wherein E is —C(=O)—Y$^1$—(C$_1$-C$_{10}$ alkylene)-X$^4$—(C$_1$-C$_{10}$ alkylene)-X$^3$;
Y$^1$ is —(CR$^a$R$^b$O)$_n$—, or —(CR$^a$R$^b$CR$^{a'}$R$^{b'}$O)$_m$—;
X$^4$ is —NR$^9$C(=O)—; and $X^3$ is

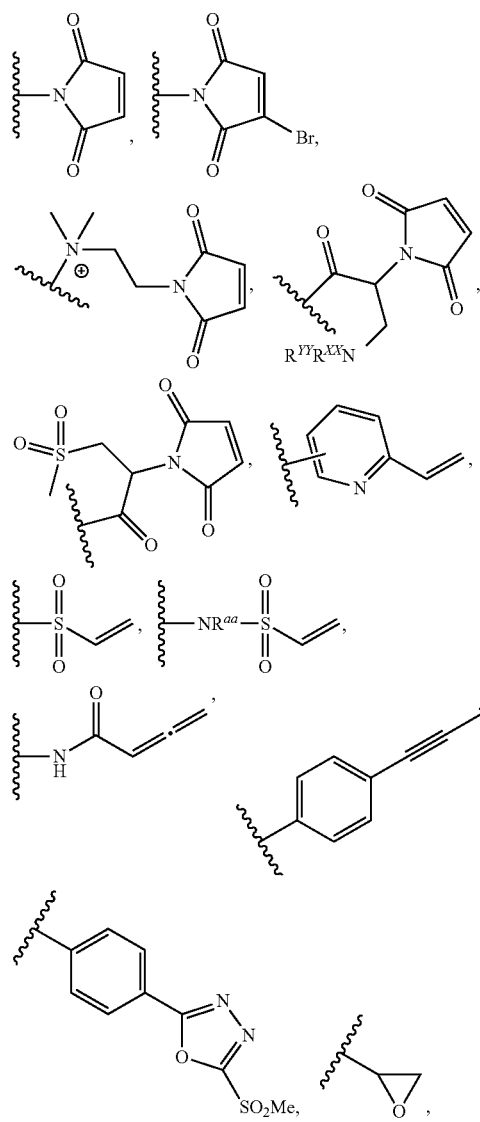

—C(=O)—CR$^{bb}$R$^{cc}$—W', NR$^{ee}$—C(=O)—CR$^{bb}$R$^{cc}$—W', or —SR$^{10}$.

65. The compound of any one of embodiments 27-61, wherein E is —C(=O)—Y$^1$—(CH$_2$)$_2$—X$^4$—(CH$_2$)$_2$—X$^3$;

Y$^1$ is —(CH$_2$O)$_n$— or —(CH$_2$CH$_2$O)$_m$—;

x$^4$ is —NHC(=O)—;

n is 2; m is 2 to 6;

X$^3$ is

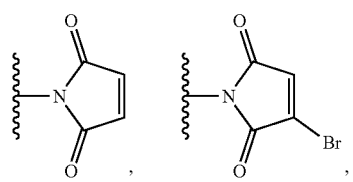

-continued

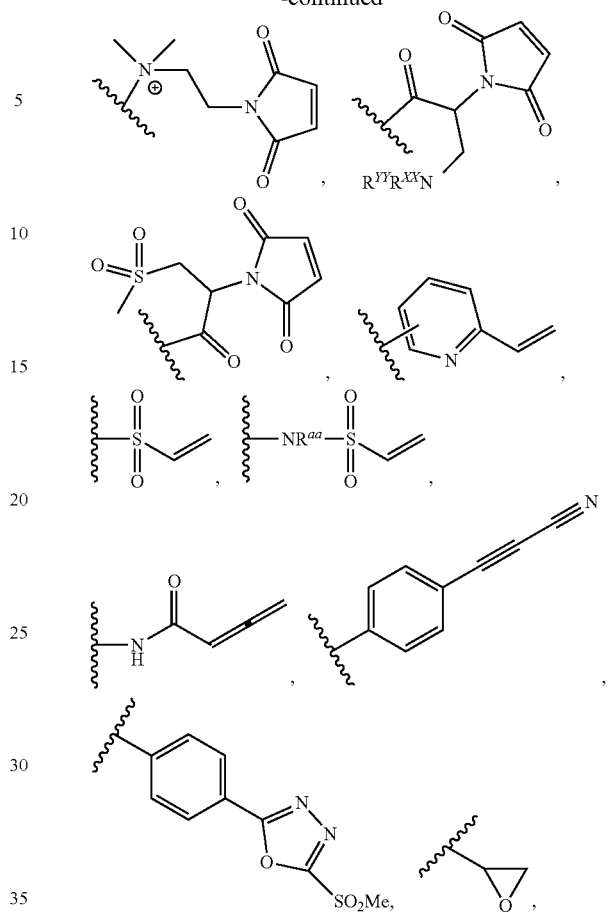

—C(=O)—CR$^{bb}$R$^{cc}$—W', NR$^{ee}$—C(=O)—CR$^{bb}$R$^{cc}$—W', or —S$^{10}$.

66. The compound of embodiment 27, wherein the compound is any one of the compounds selected from Table 2.

67. A compound of Formula III, or a pharmaceutically acceptable salt thereof:

CBA-E'-A-Z'-L$^1$-D     (Formula III)

wherein:
D is represented by the following structural formula:

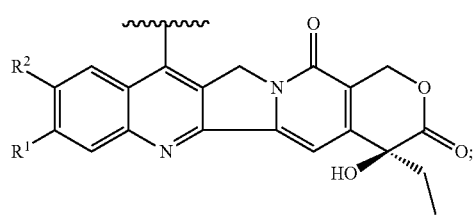

R$^1$ is —H, —F, —CH$_3$, or —CF$_3$;

R$^2$ is —H, —F, —OR$^3$, —SR$^3$, —S(O)R$^4$, —S(O)$_2$R$^4$, C$_1$-C$_6$ alkyl, or C$_1$-C$_6$ fluoroalkyl; or R$^1$ and R$^2$ taken together with the carbon atoms to which they are attached form a methylenedioxy or a difluoromethylenedioxy ring; with the proviso that both R$^1$ and R$^2$ cannot be —H;

R$^3$ is H or C$_1$-C$_6$ alkyl;

$R^4$ is $C_1$-$C_6$ alkyl;

$L^1$ is absent, —($C_1$-$C_6$ alkylene)-, —($C_1$-$C_6$ alkylene)-$X^1$—($C_1$-$C_6$ alkylene)-, $X^{1'}$—($C_1$-$C_6$ alkylene)-*, or —($C_1$-$C_6$ alkylene)-$X^1$-$L^2$-*; where * is the site covalently attached to Z';

$X^1$ is —O—, —S—, —S(O)—, —S(O)$_2$—, —C(=O)—, —NR$^5$C(=O)—, or —C(=O)NR$^5$—;

$X^{1'}$ is —O—, —S—, —S(O)—, or —S(O)$_2$—;

$L^2$ is phenylene;

each $R^5$ is independently —H, $C_1$-$C_6$ alkyl, $C_1$-$C_6$ fluoroalkyl, $C_3$-$C_6$ cycloalkyl, aryl, heteroaryl, or benzyl;

Z' is —O—CH$_2$—NR$^8$—*, —S—CH$_2$—NR$^8$—*, —NR$^8$—*; where * is the site covalently attached to A;

each $R^8$ is independently —H, $C_1$-$C_6$ alkyl, $C_1$-$C_6$ fluoroalkyl, $C_3$-$C_6$ cycloalkyl, aryl, heteroaryl, or benzyl;

$L^1$ and $L^2$ are each independently optionally substituted with 1-4 substituents selected from halogen, —CN, —OR$^7$, —SR$^7$, —N(R$^7$)$_2$, $C_1$-$C_6$ alkyl, $C_1$-$C_6$ fluoroalkyl, $C_1$-$C_6$ heteroalkyl, $C_3$-$C_6$ cycloalkyl, $C_2$-$C_{10}$ heterocycloalkyl, aryl, or heteroaryl; and each $R^7$ is independently H, $C_1$-$C_6$ alkyl, $C_1$-$C_6$ fluoroalkyl, $C_3$-$C_6$ cycloalkyl, aryl, heteroaryl, or benzyl;

A is a peptide comprising 2 to 10 amino acids; wherein A is optionally substituted with one or more polyol;

E' is —C(=O)-$L^3$-$X^6$—*; where * is the site covalently linked to CBA;

$L^3$ is —($C_1$-$C_{10}$ alkylene)- or —Y$^1$—($C_1$-$C_{10}$ alkylene)-$X^4$—Y$^2$—($C_1$-$C_{10}$ alkylene)-*; where * is the site covalently attached to $X^6$;

$Y^1$ is absent, —(CR$^a$R$^b$O)$_n$— or —(CR$^a$R$^b$CR$^{a'}$R$^{b'}$O)$_m$—;

$X^4$ is —NR$^9$C(=O)— or —C(=O)NR$^9$—;

$Y^2$ is absent, —(CR$^c$R$^d$O)$_o$—, or —(CR$^c$R$^d$CR$^{c'}$R$^{d'}$O)$_p$—;

n, m, o, and p are each independently 1-10;

each $R^a$, $R^b$, $R^{a'}$, $R^{b'}$, $R^c$, $R^d$, $R^{c'}$, and $R^{d'}$ are independently —H, $C_1$-$C_6$ alkyl, $C_1$-$C_6$ fluoroalkyl, $C_3$-$C_6$ cycloalkyl, aryl, heteroaryl, or benzyl;

wherein $L^3$ is optionally substituted with 0-4 substituents selected from halogen, —CN, —OR$^{11}$, —SR$^{11}$, —N(R$^{11}$)$_2$, $C_1$-$C_6$ alkyl, $C_1$-$C_6$ fluoroalkyl, $C_1$-$C_6$ heteroalkyl, $C_3$-$C_6$ cycloalkyl, $C_2$-$C_{10}$ heterocycloalkyl, aryl, heteroaryl, and polyol;

each R" is independently H, $C_1$-$C_6$ alkyl, $C_1$-$C_6$ fluoroalkyl, $C_3$-$C_6$ cycloalkyl, aryl, heteroaryl, or benzyl;

$X^6$ is

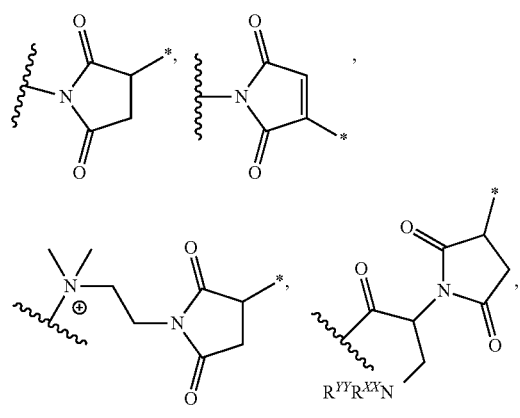

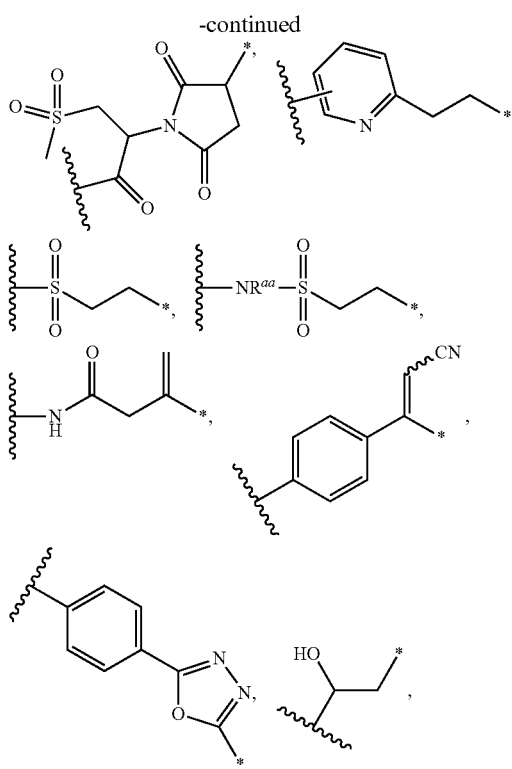

—C(=O)—CR$^{bb}$R$^{cc}$—*, or —NR$^{ee}$—C(=O)—CR$^{bb}$R$^{cc}$—*; where * is the site covalently attached to CBA;

each $R^{aa}$, $R^{bb}$, $R^{cc}$, and $R^{ee}$ are independently —H or optionally substituted $C_1$-$C_6$ alkyl;

each $R^{YY}$ and $R^{XX}$ are independently —H or $C_1$-$C_6$ alkyl;

$R^9$ is independently —H, $C_1$-$C_6$ alkyl, $C_1$-$C_6$ fluoroalkyl, $C_3$-$C_6$ cycloalkyl, aryl, heteroaryl, or benzyl; and CBA is a cell binding agent.

68. The compound of embodiment 67, wherein $R^1$ is —H or —F.

69. The compound of embodiment 67 or embodiment 68, wherein $R^1$ is —F.

70. The compound of any one of embodiments 67-69, $R^2$ is H, —F, —OCF$_3$, —CF$_3$, —OMe, —OEt, —SMe, —S(O)Me, —S(O)$_2$Me, —SEt, —S(O)Et, —S(O$_2$)Et, methyl, or ethyl.

71. The compound of any one of embodiments 67-70, wherein $R^2$ is —F.

72. The compound of any one of embodiments 67-70, wherein $R^2$ is —OMe, —SMe, —S(O)Me, or methyl.

73. The compound of any one of embodiments 67-70, wherein $R^2$ is methyl.

74. The compound of embodiment 67, wherein $R^1$ is —F and $R^2$ is —F.

75. The compound of embodiment 67, wherein $R^1$ is methyl and $R^2$ is —F.

76. The compound of embodiment 67, wherein $R^1$ is —F and $R^2$ is -methyl.

77. The compound of any one of embodiments 67-76, wherein -$L^1$-Z'—* is —($C_1$-$C_4$ alkylene)-O—CH$_2$—NR$^8$—*, —($C_1$-$C_4$ alkylene)-S—CH$_2$—NR$^8$—*, or —($C_1$-$C_4$ alkylene)-NR$^8$—*, where * is the site covalently attached to A.

78. The compound of embodiment 77, wherein -$L^1$-Z'—* is —CH$_2$O—CH$_2$NH—*, —(CH$_2$)$_{20}$—CH$_2$NH—*, —(CH$_2$)$_3$O—CH$_2$NH—*, —(CH$_2$)$_4$O—CH$_2$NH—*, —CH$_2$S—CH$_2$NH—*, —(CH$_2$)$_{25}$—CH$_2$NH—*, —(CH$_2$)$_3$S—CH$_2$NH—*, —(CH$_2$)$_4$S—CH$_2$NH—*, —CH$_2$NH—*, —(CH$_2$)$_2$NH—*, —(CH$_2$)$_3$NH—*, or —(CH$_2$)$_4$NH—.

79. The compound of any one of embodiments 67-76, wherein -L$^1$-Z'—* is —(C$_1$-C$_5$ alkylene)-NR$^5$C(=O)—(C$_1$-C$_5$ alkylene)-O—CH$_2$—NR$^8$—*, —(C$_1$-C$_5$ alkylene)-NR$^5$C(=O)—(C$_1$-C$_5$ alkylene)-S—CH$_2$—NR$^8$—*, —(C$_1$-C$_5$ alkylene)-S—(C$_1$-C$_5$ alkylene)-S—CH$_2$—NR$^8$—*, or —(C$_1$-C$_5$ alkylene)-S—(C$_1$-C$_5$ alkylene)-SS—CH$_2$—NR$^8$—*, where * is the site covalently attached to A.

80. The compound of embodiment 79, wherein -L$^1$-Z'—* is —CH$_2$NHC(=O)CH$_2$O—CH$_2$—NH—*, —CH$_2$NHC(=O)(CH$_2$)$_2$O—CH$_2$—NH—*, —CH$_2$NHC(=O)(CH$_2$)$_3$O—CH$_2$—NH—*, —CH$_2$NHC(=O)(CH$_2$)$_4$O—CH$_2$—NH—*, —CH$_2$NHC(=O)(CH$_2$)$_5$O—CH$_2$—NH—*, —CH$_2$NHC(=O)CH$_2$S—CH$_2$—NH—*, —CH$_2$NHC(=O)(CH$_2$)$_2$S—CH$_2$—NH—*, —CH$_2$NHC(=O)(CH$_2$)$_3$S—CH$_2$—NH—*, —CH$_2$NHC(=O)(CH$_2$)$_4$S—CH$_2$—NH—*, —CH$_2$NHC(=O)(CH$_2$)$_5$S—CH$_2$—NH—*, —CH$_2$SCH$_2$O—CH$_2$—NH—*, —CH$_2$S(CH$_2$)$_2$O—CH$_2$—NH—*, —CH$_2$S(CH$_2$)$_3$O—CH$_2$—NH—*, —CH$_2$S(CH$_2$)$_4$O—CH$_2$—NH—*, —CH$_2$S(CH$_2$)$_5$O—CH$_2$—NH—*, —CH$_2$SCH$_2$S—CH$_2$—NH—*, —CH$_2$S(CH$_2$)$_2$S—CH$_2$—NH—*, —CH$_2$S(CH$_2$)$_3$S—CH$_2$—NH—*, —CH$_2$S(CH$_2$)$_4$S—CH$_2$—NH—*, or —CH$_2$S(CH$_2$)$_5$S—CH$_2$—NH—*.

81. The compound of embodiment 79 or embodiment 80, wherein each R$^5$ is independently —H, methyl, or benzyl.

82. The compound of any one of embodiments 77-81, wherein each R$^8$ is independently —H, methyl, or benzyl.

83. The compound of any one of embodiments 67-76, wherein -L$^1$-Z'—* is —X$^{1'}$—(C$_1$-C$_4$ alkylene)-O—CH$_2$—NR$^8$—*, alkylene)-S—CH$_2$—NR$^8$—*, or —X$^{y'}$—(C$_1$-C$_4$ alkylene)-NR$^8$—*, 84. The compound of embodiment 83, wherein -L$^1$-Z'—* is —OCH$_2$O—CH$_2$—NH—*, —O(CH$_2$)$_{20}$—CH$_2$—NH—*, —O(CH$_2$)$_3$O—CH$_2$—NH—*, —O(CH$_2$)$_4$O—CH$_2$—NH—*, —SCH$_2$O—CH$_2$—NH—*, —S(CH$_2$)$_2$O—CH$_2$—NH—*, —S(CH$_2$)$_3$O—CH$_2$—NH—*, —S(CH$_2$)$_4$O—CH$_2$—NH—*, —S(O)CH$_2$O—CH$_2$—NH—*, —S(O)(CH$_2$)$_2$O—CH$_2$—NH—*, —S(O)(CH$_2$)$_3$O—CH$_2$—NH—*, —S(O)(CH$_2$)$_4$O—CH$_2$—NH—*, —S(O)$_2$CH$_2$O—CH$_2$—NH—*, —S(O)$_2$(CH$_2$)$_2$O—CH$_2$—NH—*, —S(O)$_2$(CH$_2$)$_3$O—CH$_2$—NH—*, —S(O)$_2$(CH$_2$)$_4$O—CH$_2$—NH—*, —OCH$_2$S—CH$_2$—NH—*, —O(CH$_2$)$_2$S—CH$_2$—NH—*, —O(CH$_2$)$_3$S—CH$_2$—NH—*, —O(CH$_2$)$_4$S—CH$_2$—NH—*, —SCH$_2$S—CH$_2$—NH—*, —S(CH$_2$)$_2$S—CH$_2$—NH—*, —S(CH$_2$)$_3$S—CH$_2$—NH—*, —S(CH$_2$)$_4$S—CH$_2$—NH—*, —S(O)CH$_2$S—CH$_2$—NH—*, —S(O)(CH$_2$)$_2$S—CH$_2$—NH—*, —S(O)(CH$_2$)$_3$S—CH$_2$—NH—*, —S(O)(CH$_2$)$_4$S—CH$_2$—NH—*, —S(O)$_2$CH$_2$S—CH$_2$—NH—*, —S(O)$_2$(CH$_2$)$_2$S—CH$_2$—NH—*, —S(O)$_2$(CH$_2$)$_3$S—CH$_2$—NH—*, —S(O)$_2$(CH$_2$)$_4$S—CH$_2$—NH—*, —OCH$_2$—NH—*, —O(CH$_2$)$_2$—NH—*, —O(CH$_2$)$_3$—NH—*, —O(CH$_2$)$_4$S—NH—*, —SCH$_2$—NH—*, —S(CH$_2$)$_2$—NH—*, —S(CH$_2$)$_3$—NH—*, —S(CH$_2$)$_4$—NH—*, —S(O)CH$_2$—NH—*, —S(O)(CH$_2$)$_2$—NH—*, —S(O)(CH$_2$)$_3$—NH—*, —S(O)(CH$_2$)$_4$—NH—*, —S(O)$_2$CH$_2$—NH—*, —S(O)$_2$(CH$_2$)$_2$—NH—*, —S(O)$_2$(CH$_2$)$_3$—NH—*, or —S(O)$_2$(CH$_2$)$_4$—NH—*.

85. The compound of any one of embodiments 67-76, wherein -L$^1$-Z'—* is —(C$_1$-C$_6$ alkylene)-X$^1$-L$^2$-Z'—*.

86. The compound of embodiment 85, wherein -L$^1$-Z'—* is

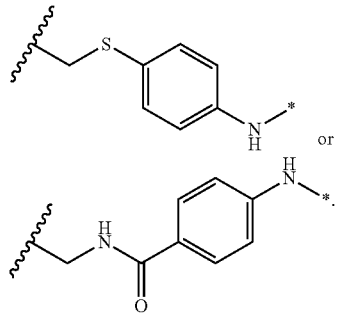

87. The compound of any one of embodiments 67-86, wherein A is a peptide comprising 2 to 8 amino acids.

88. The compound of any one of embodiments 67-87, wherein A is a peptide comprising 2 to 4 amino acids.

89. The compound of any one of embodiments 67-88, wherein at least one amino acid in said peptide is a L amino acid.

90. The compound of any one of embodiments 67-89, wherein each amino acid in said peptide is a L amino acid.

91. The compound of any one of embodiments 67-88, wherein at least one amino acid in said peptide is a D amino acid.

92. The compound of any one of embodiments 67-86, wherein A is -(AA$^1$)-(AA$^2$)$_{a1}$-*, where * is the point of attachment to E', AA' and AA$^2$ are each independently an amino acid residue; and a1 is an integer from 1-9.

93. The compound of embodiment 92, -AA1-(AA2)a1-* is -Gly-Gly-Gly-*, -Ala-Val-*, -Val-Ala-*, -Val-Cit-*, -Val-Lys-*, -Lys-Val-*, -Phe-Lys-*, -Lys-Phe-*, -Lys-Lys-*, -Ala-Lys-*, -Lys-Ala-*, -Phe-Cit-*, -Cit-Phe-*, -Leu-Cit-*, -Cit-Leu-*, -Ile -Cit-*, -Phe-Ala-*, -Ala-Phe-*, -Phe-N9-tosyl-Arg-*, —N9-tosyl-Arg-Phe-*, -Phe-N9-nitro-Arg-*, —N9-nitro-Arg-Phe *, -Phe-Phe-Lys-*, -Lys-Phe-Phe-*, -Gly-Phe-Lys-*, Lys-Phe-Gly-*, -Leu-Ala-Leu-*, -Ile-Ala-Leu-*, -Leu-Ala-Ile-*, -Val-Ala-Val-*, -Ala-Leu-Ala-Leu-(SEQ ID NO: 89)*, -Leu-Ala-Leu-Ala-(SEQ ID NO: 90)*, -β-Ala-Leu-Ala-Leu- (SEQ ID NO: 91)*, -Gly-Phe-Leu-Gly- (SEQ ID NO: 92)*, -Gly-Leu-Phe-Gly- (SEQ ID NO: 93)*, -Val-Arg-*, -Arg-Val-*, -Arg-Arg-*, -Ala-Ala-*, -Ala-Met-*, -Met-Ala-*, -Thr-Thr-*, -Thr-Met-*, -Met-Thr-*, -Leu-Ala-*, -Ala-Leu-*, -Cit-Val-*, -Gln-Val-*, -Val-Gln-*, —Ser-Val-*, -Val-Ser-*, —Ser-Ala-*, —Ser-Gly-*, -Ala-Ser-*, -Gly-Ser-*, -Leu-Gln-*, -Gln-Leu-*, -Phe-Arg-*, -Arg-Phe-*, -Tyr-Arg-*, -Arg-Tyr-*, -Phe-Gln-*, -Gln-Phe-*, -Val-Thr-*, -Thr-Val-*, -Met-Tyr-*, and -Tyr-Met-*.

94. The compound of embodiment 92, wherein -AA$^1$-(AA$^2$)$_{a1}$-* is -Val-D-Lys-*, -Val-D-Arg-*, -L-Val-Cit-*, -L-Val-Lys-*, -L-Val-Arg-*, -L-Val-D-Cit-*, -L-Phe-Phe-Lys-*, -L-Val-D-Lys-*, -L-Val-D-Arg-*, -L-Arg-D-Arg-*, -L-Ala-Ala-*, -L-Ala-D-Ala-*, -Ala-D-Ala-*, -Val-D-Cit-*, -L-Ala-L-Ala-*, -L-Ala-L-Val-*, -L-Gln-L-Val-*, -L-Gln-L-Leu-*, or -L-Ser-L-Val-*.

95. The compound of embodiment 92, wherein -AA$^1$-(AA$^2$)$_{ai}$-* is:
-Ala-Ala-*,
-Ala-Val-*,
-Val-Ala-*
-Gln-Leu-*,
-Leu-Gln-*
-Ala-Ala-Ala-*,
-Ala-Ala-Ala-Ala- (SEQ ID NO: 94)*, -Gly-Ala-Gly-Gly- (SEQ ID NO: 95)*,
-Gly-Gly-Ala-Gly- (SEQ ID NO: 96)*,
-Gly-Val-Gly-Gly- (SEQ ID NO: 97)*,
-Gly-Gly-Val-Gly- (SEQ ID NO: 98)*,
-Gly-Phe-Gly-Gly- (SEQ ID NO: 99)*, or
-Gly-Gly-Phe-Gly- (SEQ ID NO: 100)*.

96. The compound of embodiment 92, wherein -AA$^1$-(AA$^2$)$_{ai}$-* is:
-L-Ala-L-Ala-*,
-L-Ala-D-Ala-*,
-L-Ala-L-Val-*,
-L-Ala-D-Val-*,
-L-Val-L-Ala-*,
-L-Val-D-Ala-*
-L-Gln-L-Leu-*,
-L-Gln-D-Leu-*,
-L-Leu-L-Gln-*,
-L-Leu-D-Gln-*,
-L-Ala-L-Ala-L-Ala-*,
-L-Ala-D-Ala-L-Ala-*,
-L-Ala-L-Ala-D-Ala-*,
-L-Ala-L-Ala-L-Ala-L-Ala- (SEQ ID NO: 94)*,
-L-Ala-D-Ala-L-Ala-L-Ala- (SEQ ID NO: 101)*,
-L-Ala-L-Ala-D-Ala-L-Ala- (SEQ ID NO: 102)*,
-L-Ala-L-Ala-L-Ala-D-Ala- (SEQ ID NO: 103)*,
-Gly-L-Ala-Gly-Gly- (SEQ ID NO: 95)*,
-Gly-Gly-L-Ala-Gly- (SEQ ID NO: 96)*,
-Gly-D-Ala-Gly-Gly- (SEQ ID NO: 104)*,
-Gly-Gly-D-Ala-Gly- (SEQ ID NO: 105)*,
-Gly-L-Val-Gly-Gly- (SEQ ID NO: 97)*,
-Gly-Gly-L-Val-Gly- (SEQ ID NO: 98)*,
-Gly-D-Val-Gly-Gly- (SEQ ID NO: 106)*,
-Gly-Gly-D-Val-Gly- (SEQ ID NO: 107)*,
-Gly-L-Phe-Gly-Gly- (SEQ ID NO: 99)*, or
-Gly-Gly-L-Phe-Gly- (SEQ ID NO: 100)*.

97. The compound of embodiment 92, wherein -AA$^1$-(AA$^2$)$_{a1}$-* is:
-L-Ala-L-Ala-*,
-L-Ala-D-Ala-L-Ala-*,
-L-Ala-L-Ala-L-Ala-*, or
-L-Ala-L-Ala-L-Ala-L-Ala- (SEQ ID NO: 94)*.

98. The compound of any one of embodiments 67-97, wherein A is substituted with one or more polyol.

99. The compound of any one of embodiments 67-98, wherein E' is substituted with one or more polyol.

100. The compound of any one of embodiments 67-99, wherein polyol is —(C$_1$-C$_6$ alkylene)-X$^5$—Y$^3$;
wherein:
X$^5$ is —NR$^{12}$C(=O)— or —C(=O)NR$^{12}$—;
Y$^3$ is —C$_1$-C$_{10}$ alkyl, where Y$^3$ is substituted with 0-10 OH groups; and
R$^{12}$ is —H, C$_1$-C$_6$ alkyl, C$_1$-C$_6$ fluoroalkyl, C$_3$-C$_6$ cycloalkyl, aryl, heteroaryl, or benzyl.

101. The compound of embodiment 100, wherein polyol is wherein R$^{12}$ is H or methyl.

102. The compound of embodiments 63-93, wherein E' is —C(=O)—(C$_1$-C$_{10}$ alkylene)-X$^6$—*.

103. The compound of embodiment 102, wherein E' is

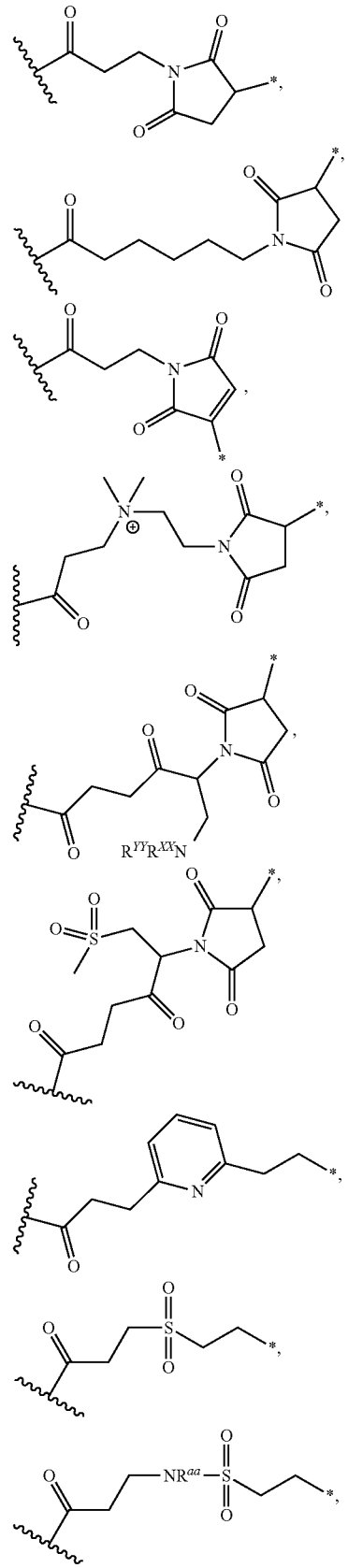

231

-continued

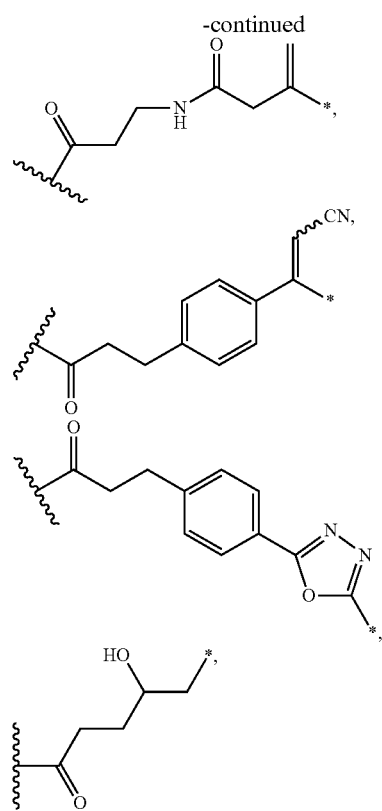

—C(=O)CH₂CH₂—C(=O)—CR$^{bb}$R$^{cc}$—*, or —C(=O)CH₂CH₂—NR$^{ee}$—C(=O)—CR$^{bb}$R$^{cc}$—*; where * is the site covalently attached to CBA.

104. The compound of embodiments any one of embodiments 63-93, wherein E' is —C(=O)—Y¹—(C₁-C₁₀ alkylene)-X⁴—(C₁-C₁₀ alkylene)-X⁶—*;
Y¹ is —(CR$^a$R$^b$O)$_n$—, or —(CR$^a$R$^b$CR$^{a'}$R$^{b'}$O)$_m$—;
X⁴ is —NR⁹C(=O)—; and
X⁶ is

232

-continued

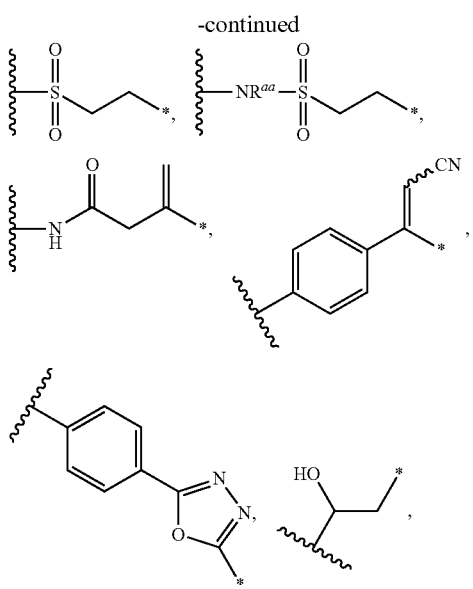

—C(=O)—CR$^{bb}$R$^{cc}$—* or —NR$^{ee}$—C(=O)—CR$^{bb}$R$^{cc}$—*; where * is the site covalently attached to CBA.

105. The compound of any one of embodiments 63-93, wherein E' is —C(=O)—Y¹—(CH₂)₂—X⁴—(CH₂)₂—X⁶—*;
Y¹ is —(CH₂O)$_n$—, or —(CH₂CH₂O)$_m$—;
X⁴ is —NHC(=O)—;
n is 2; m is 2 to 6;
X⁶ is

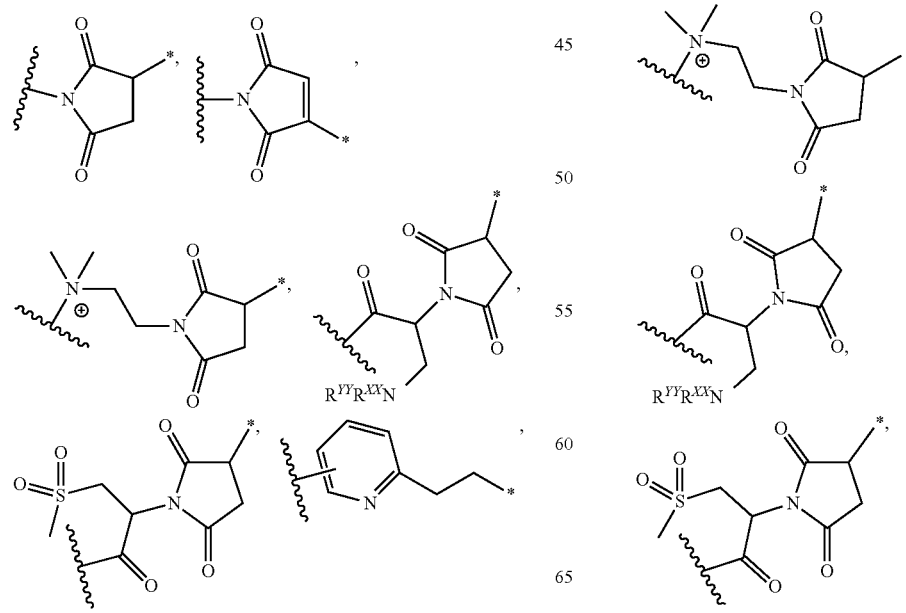

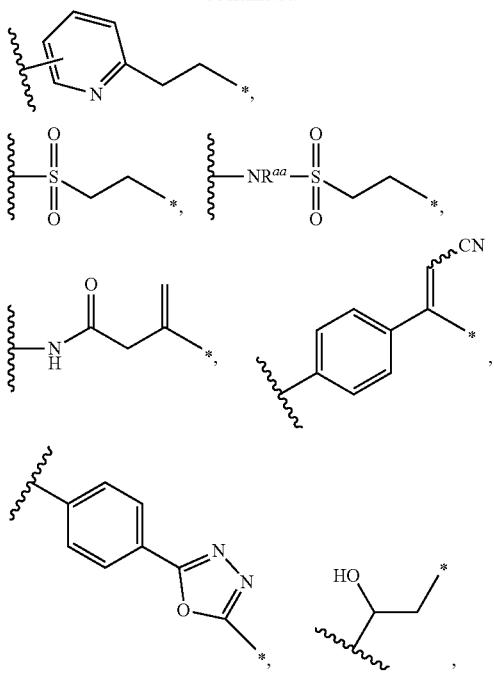

—C(=O)—CR$^{bb}$R$^{cc}$—*, or —NR$^{ee}$—C(=O)—CR$^{bb}$R$^{cc}$—*; where * is the site covalently attached to the CBA.

106. The compound of any one of embodiments 63-105, wherein the CBA comprises a —SH group that covalently links with E' to provide

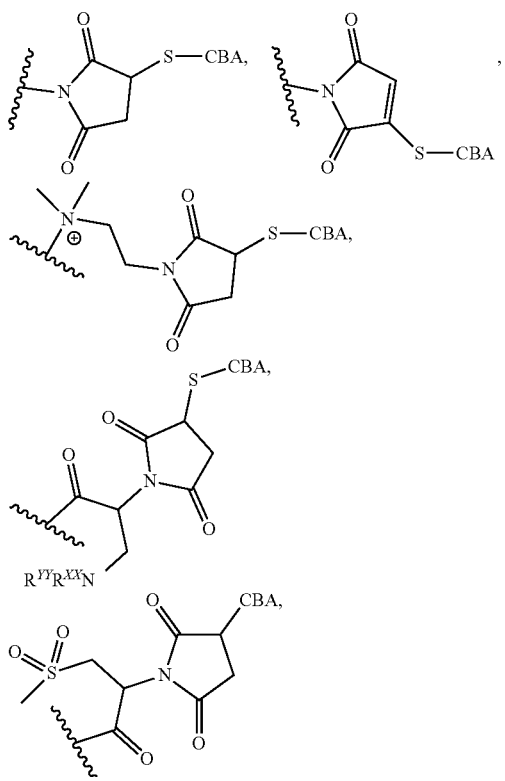

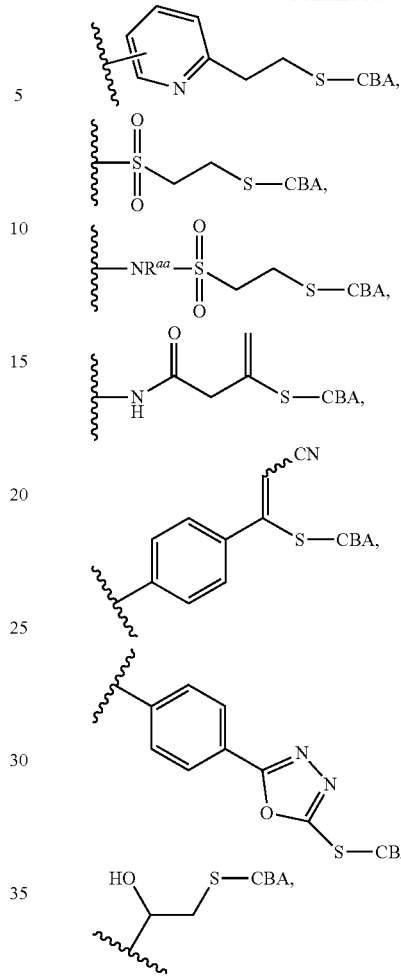

—C(=O)—CR$^{bb}$R$^{cc}$—S-CBA, or —NR$^{ee}$—C(=O)—CR$^{bb}$R$^{cc}$—S-CBA.

107. The compound of any one of embodiments 67-106, wherein CBA is an antibody and -E'-A-Z'-L$^1$-D is a drug-linker structure, the average number of drug-linker structures conjugated per antibody is in the range of from 2 to 10.

108. The compound of embodiment 107, wherein the average number of drug-linker structures conjugated per antibody is in the range of from 2 to 10.

109. The compound of embodiment 107, wherein the average number of drug-linker structures conjugated per antibody is in the range of from 6 to 8.

110. The compound of embodiment 107, wherein the average number of drug-linker structures conjugated per antibody is 8.

111. The compound of any one of embodiments 67-110, wherein the CBA is an antibody, a single chain antibody, an antibody fragment that specifically binds to the target cell, a monoclonal antibody, a single chain monoclonal antibody, or a monoclonal antibody fragment that specifically binds to a target cell, a chimeric antibody, a chimeric antibody fragment that specifically binds to the target cell, a domain antibody, a domain antibody fragment that specifically binds to the target cell, a probody, a nanobody, a hexabody, lymphokine, a hormone, a vitamin, a growth factor, a colony stimulating factor, or a nutrient-transport molecule.

112. The compound of any one of embodiments 67-111, wherein the CBA binds to target cells selected from tumor cells, virus infected cells, microorganism infected cells, parasite infected cells, autoimmune cells, activated cells, myeloid cells, activated T-cells, B cells, or melanocytes; cells expressing any one or more of 5T4, ADAM-9, ALK, AMHRII, ASCT2, Axl, B7-H3, BCMA, $C_4$.4a, CA6, CA9, CanAg, CD123, CD138, CD142, CD166, CD184, CD19, CD20, CD205, CD22, CD248, CD25, CD3, CD30, CD33, CD352, CD37, CD38, CD40L, CD44v6, CD45, CD46, CD48, CD51, CD56, CD7, CD70, CD71, CD74, CD79b, CDH6, CEACAM5, CEACAM6, cKIT, CLDN18.2, CLDN6, CLL-1, c-MET, Cripto, CSP-1, CXCRS, DLK-1, DLL3, DPEP3, Dysadherin, EFNA4, EGFR, EGFRviii, ENPP3, EpCAM, EphA2, EphA3, ETBR, FGFR2, FGFR3, FLT3, FOLR-alpha, FSH, GCC, GD2, GD3, Globo H, GPC-1, GPC3, gpNMB, HER-2, HER-3, HLA-DR, HSP90, IGF-1R, IL-13R, IL1RAP, IL7R, Interleukin-4 Receptor (IL4R), KAAG-1, LAMP-1, Lewis Y antigen, LGALS3BP, LGRS, LH/hCG, LHRH, LIV-1, LRP-1, LRRC15, Ly6E, MAGE, Mesothelin (MSLN), MET, MHC class I chain-related protein A and B (MICA and MICB), MT1-MMP, MTX3, MTXS, MUC1, MUC16, NaPi2b, Nectin-4, NOTCH3, OAcGD2, OX001L, p-Cadherin, PD-L1, Phosphatidylserine (PS), Polymorphic epithelial mucin (PEM), Prolactin Receptor (PRLR), PSMA, PTK7, RNF43, ROR1, ROR2, SAIL, SLAMF7, SLC44A4, SLITRK6, SSTR2, STEAP-1, STING, STn, TIM-1, TM4SF1, TNF-alpha, TRA, TROP-2, Tumor-associated glycoprotein 72 (TAG-72), tumor-specific epitope of mucin-1 (TA-MUC1), CDS, TIM-3, UPK2, or UPK1b antigen.

113. The compound of any one of embodiments 67-110, wherein the cell-binding agent is an anti-folate receptor antibody or an antibody fragment thereof, an anti-EGFR antibody or an antibody fragment thereof, an anti-CD33 antibody or an antibody fragment thereof, an anti-CD19 antibody or an antibody fragment thereof, an anti-Muc1 antibody or an antibody fragment thereof, an anti-CD37 antibody or an antibody fragment thereof, or an anti-EpCAM antibody or an antibody fragment thereof.

114. A pharmaceutical composition comprising a compound according to any one of embodiments 1-113, or the pharmaceutically acceptable salt thereof, and a pharmaceutically acceptable carrier.

115. A method of treating cancer in a subject in need thereof comprising administering to the subject a therapeutically effective amount of the pharmaceutical composition of embodiment 114.

116. The method of embodiment 115, wherein the cancer is a lymphoma or a leukemia.

117. The method of embodiment 116, wherein the cancer is acute myeloid leukemia (AML), chronic myelogenous leukemia (CML), myelodysplastic syndrome (MDS), acute lymphoblastic leukemia (ALL), acute B lymphoblastic leukemia or B-cell acute lymphoblastic leukemia (B-ALL), chronic lymphocytic leukemia (CLL), hairy cell leukemia (HCL), acute promyelocytic leukemia (APL), B-cell chronic lymphoproliferative disease (B-CLPD), atypical chronic lymphocytic leukemia, diffuse large B-cell lymphoma (DLBCL), blastic plasmacytoid dendritic cell neoplasm (BPDCN), non-Hodgkin lymphomas (NHL), mantel cell leukemia (MCL), small lymphocytic lymphoma (SLL), Hodgkin's lymphoma, systemic mastocytosis, and Burkitt's lymphoma.

118. The method of embodiment 115, wherein the cancer is endometrial cancer, lung cancer, colorectal cancer, bladder cancer, gastric cancer, pancreatic cancer, renal cell carcinoma, prostate cancer, esophageal cancer, breast cancer, head and neck cancer, uterine cancer, ovarian cancer, liver cancer, cervical cancer, thyroid cancer, testicular cancer, myeloid cancer, melanoma, and lymphoid cancer.

119. The method of embodiment 115, wherein the lung cancer is non-small cell lung cancer or small-cell lung cancer.

Other embodiments are set forth in the following claims.

What is claimed is:

1. A compound of Formula II, or a pharmaceutically acceptable salt thereof:

E-A-Z'-L$^1$-D   (Formula II)

wherein:

D is represented by the following structural formula:

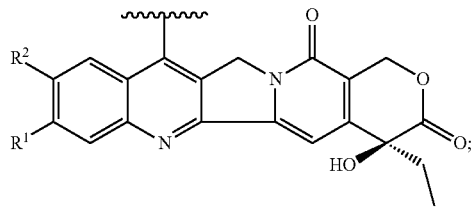

$R^1$ is F;

$R^2$ is methyl;

-L$^1$-Z'—* is —(C$_1$-C$_4$ alkylene)-O—CH$_2$—NR$^8$—*, —(C$_1$-C$_4$ alkylene)-NR$^8$—*, or —(C$_1$-C$_5$ alkylene)-NR$^5$C(=O)—(C$_1$-C$_5$ alkylene)-O—CH$_2$—NR$^8$—*, where * is the site covalently attached to A;

each R$^5$ is independently —H, methyl, or benzyl;

each R$^8$ is independently —H, methyl, or benzyl;

E is C(=O)—(C$_1$-C$_{10}$ alkylene)-X$^3$; and

303

X³ is

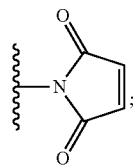

and

A is a peptide comprising 2 to 4 amino acids, wherein A is substituted with one or more polyol, wherein polyol is —(C₁-C₆ alkylene)-X⁵—Y³, wherein:

X⁵ is —NR¹²C(=O)— or —C(=O)NR¹²—;

304

Y³ is C₆ alkyl substituted with 5 OH groups; and
R¹² is —H, C₁-C₆ alkyl, C₁-C₆ fluoroalkyl, C₃-C₆ cycloalkyl, aryl, heteroaryl, or benzyl.

2. The compound of claim 1, wherein polyol is

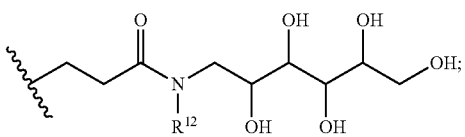

wherein R¹² is H or methyl.

3. The compound of claim 1, wherein the compound is represented by the following formula:

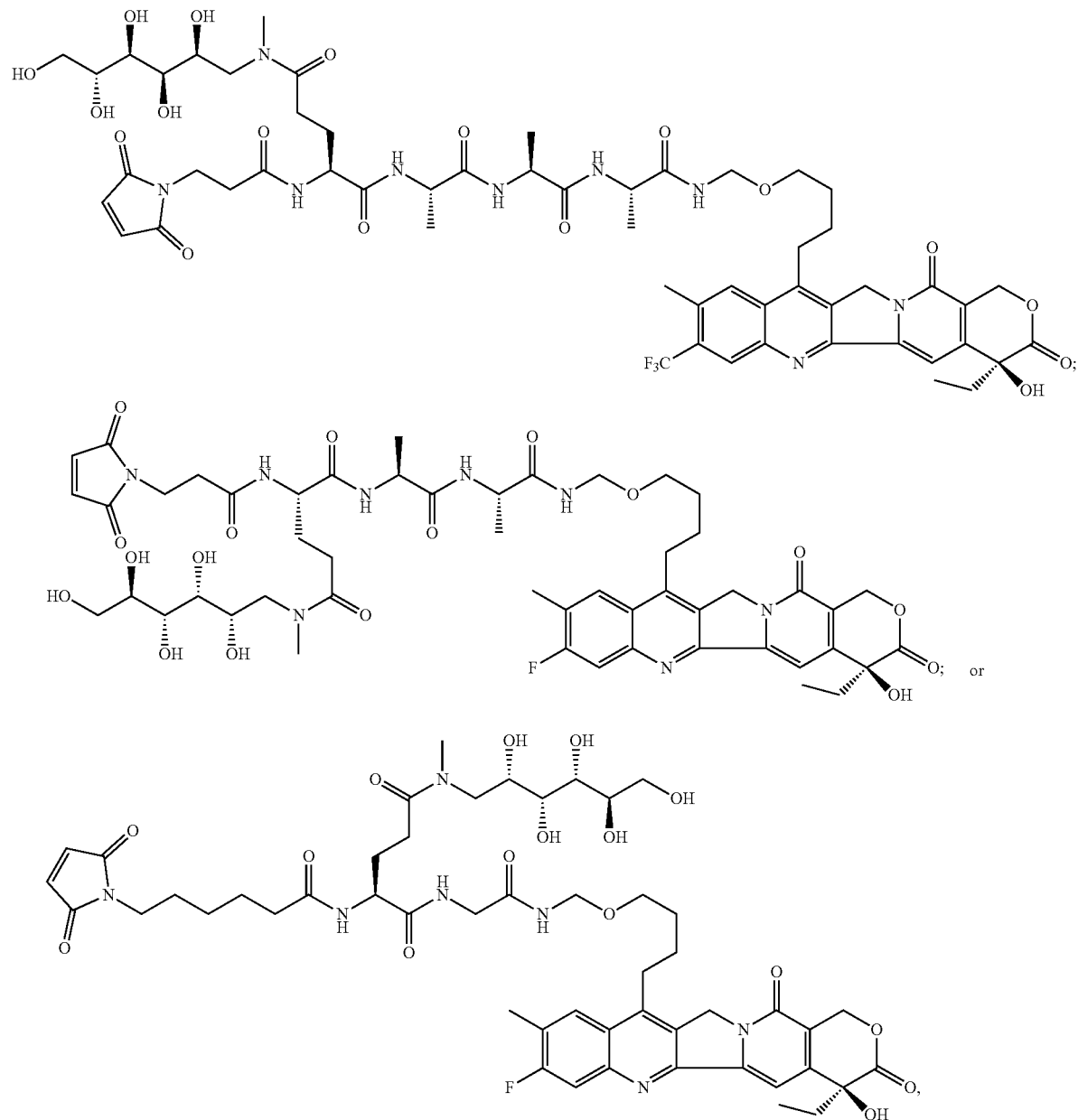

or a pharmaceutically acceptable salt thereof.

4. A compound of Formula III, or a pharmaceutically acceptable salt thereof:

CBA-E'-A-Z'-L¹-D  (Formula III)

wherein:

D is represented by the following structural formula:

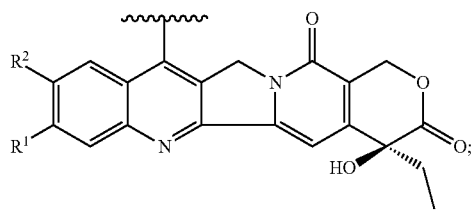

R¹ is F;
R² is methyl;
-L¹-Z'—* is —($C_1$-$C_4$ alkylene)-O—$CH_2$—$NR^8$—*, —($C_1$-$C_4$ alkylene)-$NR^8$—*, or —($C_1$-$C_5$ alkylene)-$NR^5$C(=O)—($C_1$-$C_5$ alkylene)-O—$CH_2$—$NR^8$—*, where * is the site covalently attached to A;
each $R^5$ is independently —H, methyl, or benzyl;
each $R^8$ is independently —H, methyl, or benzyl;
E' is C(=O)—($C_1$-$C_{10}$ alkylene)-$X^6$—*; where * is the site covalently linked to CBA;

$X^6$ is

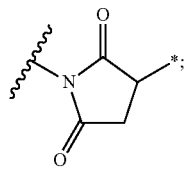

and

CBA is a cell binding agent; and

A is a peptide comprising 2 to 4 amino acids, wherein A is substituted with one or more polyol; and wherein polyol is —($C_1$-$C_6$ alkylene)-$X^5$—$Y^3$, wherein:
$X^5$ is —$NR^{12}$C(=O)— or —C(=O)$NR^{12}$—;
$Y^3$ is $C_6$ alkyl substituted with 5 OH groups; and
$R^{12}$ is —H, $C_1$-$C_6$ alkyl, $C_1$-$C_6$ fluoroalkyl, $C_3$-$C_6$ cycloalkyl, aryl, heteroaryl, or benzyl.

5. The compound of claim 4, wherein polyol is

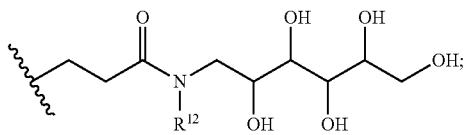

wherein $R^{12}$ is H or methyl.

6. A compound represented by the following formula:

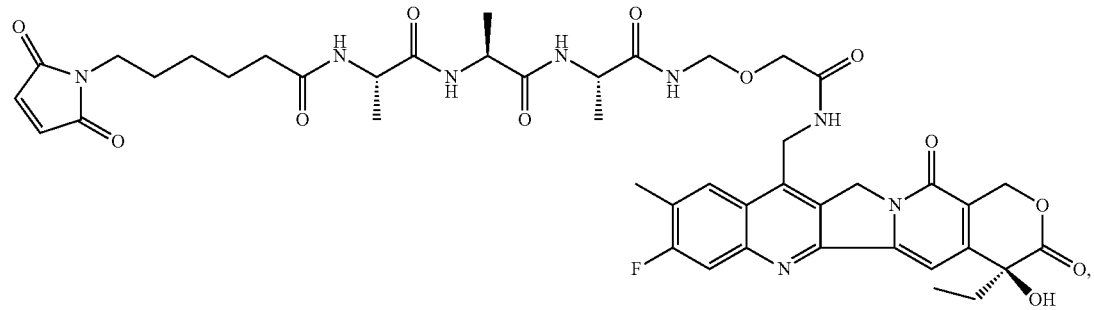 [SMILES: CC[C@@]1(O)C(=O)OCc2c1cc1n(c2=O)Cc2c-1nc1cc(F)c(C)cc1c2CNC(=O)COCNC(=O)[C@H](C)NC(=O)[C@H](C)NC(=O)[C@H](C)NC(=O)CCCCCN1C(=O)C=CC1=O]

or a pharmaceutically acceptable salt thereof.

7. A compound represented by the following formula:

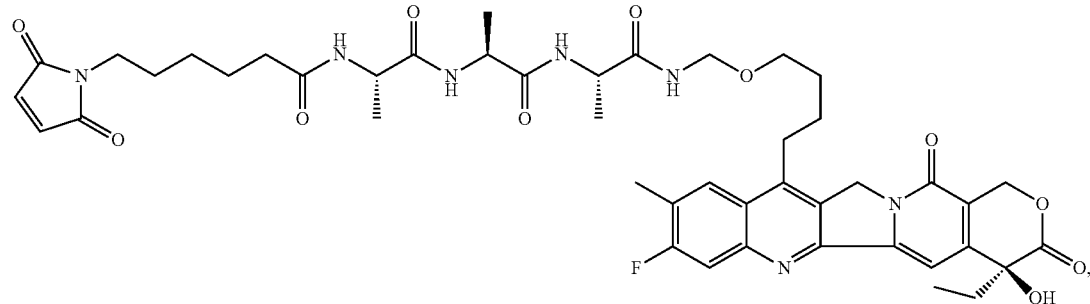 [SMILES: CC[C@@]1(O)C(=O)OCc2c1cc1n(c2=O)Cc2c-1nc1cc(F)c(C)cc1c2CCCCOCNC(=O)[C@H](C)NC(=O)[C@H](C)NC(=O)[C@H](C)NC(=O)CCCCCN1C(=O)C=CC1=O]

or a pharmaceutically acceptable salt thereof.

* * * * *

UNITED STATES PATENT AND TRADEMARK OFFICE
CERTIFICATE OF CORRECTION

PATENT NO. : 11,229,639 B2
APPLICATION NO. : 17/032219
DATED : January 25, 2022
INVENTOR(S) : Ravi V. J. Chari et al.

Page 1 of 1

It is certified that error appears in the above-identified patent and that said Letters Patent is hereby corrected as shown below:

In the Claims

At Columns 303-304, Claim number 3, Lines 16-21, Please replace the first formula:

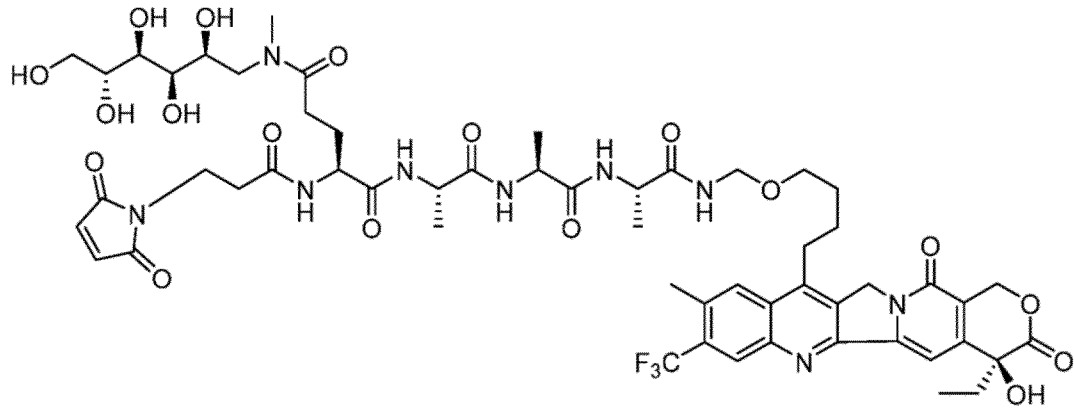

With the formula below:

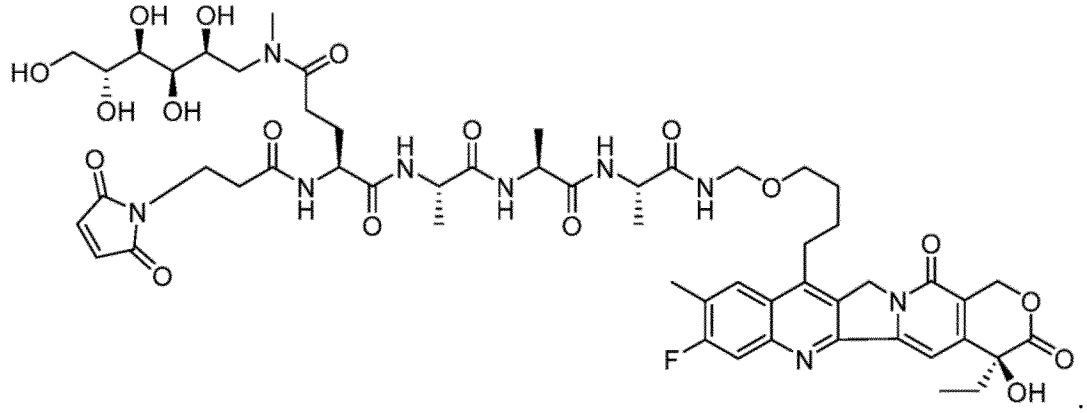

Signed and Sealed this
Seventeenth Day of September, 2024

*Katherine Kelly Vidal*

Katherine Kelly Vidal
*Director of the United States Patent and Trademark Office*